United States Patent
Kanaya et al.

(10) Patent No.: US 7,622,471 B2
(45) Date of Patent: Nov. 24, 2009

(54) PYRAZOLE DERIVATIVES HAVING A PYRIDAZINE AND PYRIDINE FUNCTIONALITY

(75) Inventors: Naoaki Kanaya, Tokyo (JP); Hiroaki Ishihara, Tokyo (JP); Youichi Kimura, Tokyo (JP); Takashi Ishiyama, Tokyo (JP); Yuichi Ochiai, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 339 days.

(21) Appl. No.: 10/543,915

(22) PCT Filed: Feb. 6, 2004

(86) PCT No.: PCT/JP2004/001259

§ 371 (c)(1),
(2), (4) Date: Jul. 29, 2005

(87) PCT Pub. No.: WO2004/069824

PCT Pub. Date: Aug. 19, 2004

(65) Prior Publication Data

US 2006/0128685 A1   Jun. 15, 2006

(30) Foreign Application Priority Data

Feb. 7, 2003   (JP)   ............... 2003-031639
Nov. 17, 2003  (JP)   ............... 2003-386515

(51) Int. Cl.
A61K 31/497   (2006.01)
C07D 237/00   (2006.01)
C07D 237/02   (2006.01)

(52) U.S. Cl. .................. 514/252.1; 544/224
(58) Field of Classification Search ........... None
See application file for complete search history.

(56) References Cited

U.S. PATENT DOCUMENTS

| | | |
|---|---|---|
| 5,134,142 A | 7/1992 | Matsuo et al. |
| 5,217,971 A | 6/1993 | Takasugi et al. |
| 5,229,386 A | 7/1993 | Takasugi et al. |
| 5,401,700 A | 3/1995 | Sohn et al. |
| 5,420,141 A | 5/1995 | Boigegrain et al. |
| 5,556,987 A | 9/1996 | Aoki et al. |
| 5,616,592 A | 4/1997 | Boigegrain et al. |
| 5,624,941 A | 4/1997 | Barth et al. |
| 5,635,526 A | 6/1997 | Boigegrain et al. |
| 5,744,491 A | 4/1998 | Boigegrain et al. |
| 5,854,265 A | 12/1998 | Anthony |
| 6,306,883 B1 | 10/2001 | Adams et al. |
| 6,407,259 B1 | 6/2002 | Harris et al. |
| 6,436,966 B1 | 8/2002 | Ohkawa et al. |
| 6,620,825 B1 | 9/2003 | Ohkawa et al. |
| 6,699,991 B2 | 3/2004 | James et al. |
| 6,962,933 B1 | 11/2005 | Ohkawa et al. |
| 2003/0144309 A1 | 7/2003 | Choon-Moon |
| 2006/0189591 A1 | 8/2006 | Okayama et al. |

FOREIGN PATENT DOCUMENTS

| | | |
|---|---|---|
| EP | 0 418 845 | 3/1991 |
| EP | 0 987 253 A1 | 3/2000 |
| EP | 1 104 758 | 6/2001 |
| EP | 1 142 889 | 10/2001 |
| HU | 44532 | 6/1986 |
| JP | 50 121269 | 9/1975 |
| JP | 61 40266 | 2/1986 |
| JP | 8 12654 | 1/1996 |
| JP | 9 227555 | 9/1997 |
| JP | 2005-022972 | 1/2005 |
| WO | 93 14062 | 7/1993 |
| WO | 97 03973 | 2/1997 |
| WO | 97 36897 | 10/1997 |
| WO | 97/49698 | 12/1997 |
| WO | 98 52937 | 11/1998 |
| WO | 98 52940 | 11/1998 |
| WO | 98 52941 | 11/1998 |
| WO | 98 56377 | 12/1998 |
| WO | 99 51580 | 10/1999 |
| WO | 99 58523 | 11/1999 |
| WO | 00 63204 | 10/2000 |
| WO | 01 16132 | 3/2001 |
| WO | WO 01/19788 | 3/2001 |

(Continued)

OTHER PUBLICATIONS

Vippagunta et al. Advanced Drug Delivery Reviews, 2001, 48, 3-26.*

(Continued)

*Primary Examiner*—James O Wilson
*Assistant Examiner*—Noble Jarrell
(74) *Attorney, Agent, or Firm*—Oblon, Spivak, McClelland, Maier & Neustadt, L.L.P.

(57) ABSTRACT

The present invention is directed to a strong platelet aggregation-inhibiting agent which does not inhibit COX-1 or COX-2. Further, the present invention provides compounds represented by formula (I), salts of the compounds, and solvates or hydrates of the compounds or the salts. Also provided are medicaments containing any of the compounds, salts, or solvates and preventive and/or therapeutic agents for ischemic diseases, containing any of the compounds, salts, or the solvates or hydrates.

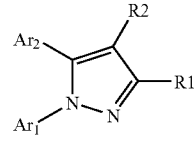

(I)

12 Claims, No Drawings

FOREIGN PATENT DOCUMENTS

| | | |
|---|---|---|
| WO | WO 01/19798 | 3/2001 |
| WO | 01 40216 | 6/2001 |
| WO | 01 58869 | 8/2001 |
| WO | 01 64642 | 9/2001 |
| WO | 01 87880 | 11/2001 |
| WO | 01 90078 | 11/2001 |
| WO | 02 04424 | 1/2002 |
| WO | 02 067683 | 9/2002 |
| WO | 02/085897 | 10/2002 |
| WO | WO 02/092593 | 11/2002 |
| WO | 03 027076 | 4/2003 |
| WO | 03 031435 | 4/2003 |
| WO | 03 037274 | 5/2003 |
| WO | 03 040110 | 5/2003 |
| WO | 03 051841 | 6/2003 |
| WO | 03 051842 | 6/2003 |
| WO | 03 051873 | 6/2003 |
| WO | WO 2004/050632 | 6/2004 |
| WO | WO 2004/089937 A1 | 10/2004 |
| WO | WO 2005/063736 A1 | 7/2005 |

OTHER PUBLICATIONS

"National library of medicine", http://www.nlm.nih.gov/cgi/mesh/2008/MB_cgi, accessed Jul. 23, 2008.*

Arnould er al. The American Journal of Pathology, 2001, 1591(1), 345-57.*

U.S. Appl. No. 10/553,982, filed Oct. 20, 2005, Okayama, et al.

U.S. Appl. No. 10/584,632, filed Jun. 26, 2006, Kanaya, et al.

U.S. Appl. No. 11/571,387, filed Dec. 28, 2006, Kanaya, et al.

U.S. Appl. No. 11/659,086, filed Feb. 1, 2007, Sato, et al.

U.S. Appl. No. 11/573,098, filed Feb. 2, 2007, Kanaya, et al.

Penning et al. "Synthesis and Biological Evaluation of the 1,5-Diarylpyrazole Class of Cyclooxygenase-2 Inhibitors: Identification of 4-[5-(4-Methylphenyl)-3-(trifluoromethyl)-1h-pyrazol-1-yl]benzenesulfonamide (SC-58635, Celecoxib)", J. Med. Chem., vol. 40, pp. 1347-1365 1997.

Lan et al. "Structure-Activity Relationships of Pyrazole Derivatives as Cannabinoid Receptor Antagonists", J. Med. Chem., vol. 42, pp. 769-776 1999.

Tanaka et al. "Antiplatelet Agents Based on Cyclooxygenase Inhibition without Ulcerogenesis. Evaluation and Synthesis of 4,5-Bis(4-methoxyphenyl)-2-substituted-thiazoles", J. Med. Chem., vol. 37, pp. 1189-1199 1994.

Dohi et al. "The anti-platelet actions of FR122047, a novel cyclooxygenase inhibitor", European Journal of Pharmacology, vol. 243, pp. 179-184 1993.

Ochi et al. "The analgesic effect profile of FR122047, a selective cyclooxygenase-1 inhibitor, in chemical nociceptive models", European Journal of Pharmacology, vol. 391, pp. 49-54 2000.

Rynbrandt et al. "Synthesis and Platelet Aggregation Inhibitory Activity of 4,5-Bis(aryl)-2-substituted-thiazoles", J. Med. Chem., vol. 24, pp. 1507-1510 1981.

Tsuji et al. "Studies on Anti-inflammatory Agents. IV. Synthesis and Pharmacological Properties of 1,5-Diarylpyrazoles and Related Derivatives", Chem. Pharm. Bull, vol. 45, No. 6, pp. 987-995 1997.

Takahashi et al. "FR167653, a p38 Mitogen-Activated Protein Kinase Inhibitor, Prevents Helicobacter pylori-Induced Gastritis in Mongolian Gerbils", Journal of Pharmacology and Experimental Therapeutics, vol. 296, No. 1, pp. 48-56 2001.

Dannhardt et al. "Cyclooxygenase inhibitors—current status and future prospects", Eur. J. Med. Chem., vol. 36, pp. 109-126 2001.

Hawkey. "COX-2 Inhibitors", The Lancet, vol. 353, pp. 307-314 1999.

Tanaka et al. "Studies on Anti-platelet Agents. V. Synthesis and Structure-Activity Relationship of 3-Substituted 5,6-Bis(4-methoxyphenyl)-1,2,4-triazines", Chem. Pharm. Bull., vol. 42, No. 9, pp. 1835-1840 1994.

Tanaka et al. "Studies on Anti-platelet Agents. IV. A Series of 2-Substituted 4,5-Bis(4-methoxyphenyl)pyrimidines as Novel Anti-platelet Agents", Chem. Pharm. Bull., vol. 42, No. 9, pp. 1828-1834 1994.

Kanebo et al. "Pamicogrel Paminate", Drugs of the Future, vol. 26, No. 2, p. 197 2001.

"2-[4,5-Bis(4-methoxypheny)thiazol-2-yl]pyrrole-1-acetic acid ethyl ester", Drugs of the Future, vol. 16, No. 2, pp. 105-107 1991.

Tanemoto et al. "Clinical Study of KBT-3022: Platelet Aggregation Effects and Pharmacokinetics in Elderly (>65 Years of Age) and Nonelderly Patients with Chronic Arterial Occlusion", Current Therapeutic Research, vol. 61, No. 12, pp. 891-900 2000.

Inoue et al. "Synthesis and Antiplatelet Activity of 2-Amino-4,5-diphenylthiazole Derivatives", Yakugaku Zasshi, vol. 115, No. 8, pp. 603-610, with English abstract 1995.

"Collaborative overview of randomiSed trials of antiplatelet therapy-I: Prevention of death, myocardial infarction, and stroke by prolonged antiplatelet therapy in various categories of patients", BMJ, vol. 308, pp. 81-106 1994.

Derry et al. "Risk of gastrointestinal haemorrhage with long term use of aspirin: meta-analysis", BMJ, vol. 321, pp. 1183-1187 2000.

Catella-Lawson. "Vascular biology of thrombosis", Neurology, vol. 57, suppl. 2, pp. S5-S7 2001.

Pairet et al. "Measurement of Differential Inhibition of COX-1 and COX-2 and the Pharmacology of Selective Inhibitors", Drugs of Today, vol. 35, pp. 251-265 1999.

New Current 12 (27), Dec. 10, 2001, Report of Research and Development (w/ English Translation).

Robert W. Hamilton, "The Antiarrhythmic and Antiinflammatory Activity of a Series of Tricyclic Pyrazoles" Journal of Heterocyclic Chemistry, Provo UT, US, vol. 13, No. 3, Jun. 1976, pp. 545-553.

* cited by examiner

PYRAZOLE DERIVATIVES HAVING A PYRIDAZINE AND PYRIDINE FUNCTIONALITY

TECHNICAL FIELD

The present invention relates to pyrazole derivatives endowed with platelet aggregation-inhibiting activity.

BACKGROUND ART

Platelets play an important role in stopping hemorrhage caused by damage to blood vessel through coagulation to form thrombi. On the other hand, it has been known that, when vascular endothelium is injured or the blood vessel is narrowed as in the case of arteriosclerosis, platelets aggregate and trigger thrombus or embolus formation, causing ischemic diseases such as myocardial infarction, angina pectoris, ischemic cerebrovascular disorder, and peripheral vascular disease. Therefore, platelet aggregation inhibitors are administered for prevention and treatment of such ischemic diseases. Aspirin is one such platelet aggregation inhibitor that has been used for a long time, and the effects of aspirin have been demonstrated by APT (Antiplatelet Trialists' Collaboration) in which clinical test results obtained by administering aspirin to 100,000 patients had been subjected to metaanalysis (BMJ, vol. 308, pages 81-106, 1994). Aspirin, however, is known to cause side effects such as hemorrhage in gastrointestine or like organs, namely, the so-called "aspirin-induced ulcer", and the side effect is not dose-dependent and occurs at a rate of about 1 per 100 patients (BMJ, vol. 321, pages 1183-1187, 2000).

The inhibitory effect of aspirin on platelet aggregation is known to be based on the activity to inhibit the action of cyclooxygenase. Cyclooxygenases include cyclooxygenase-1 (COX-1) and cyclooxygenase-2 (COX-2), and aspirin specifically inhibits COX-1 at a low dose, resulting in inhibition of platelet aggregation. The inhibition of COX-1 also causes the aspirin-induced ulcer (Neurology, vol. 57, Suppl. 2, pages S5-S7, 2001 and Drugs Today, vol. 35, pages 251-265, 1999). In addition, nonsteroidal antiinflammatory drugs are known to exhibit antiinflammatory action by selectively inhibiting COX-2.

As described above, although aspirin is useful as a platelet aggregation inhibitor, it produces a side effect of gastrointestinal dysfunction attributable to the COX-1-inhibiting action, which is an action mechanism of platelet aggregation inhibition, and there is a strong demand for new platelet aggregation inhibitors exhibiting no COX-1-inhibiting activity.

In the meanwhile, as pyrazole derivatives having antithrombotic activity, there have been known compound (A) (Japanese Patent No. 2586713 and Chem. Pharm. Bull., vol. 45, pages 987-995, 1997) and compound (B) (BMJ, vol. 321, pages 1183-1187, 2000).

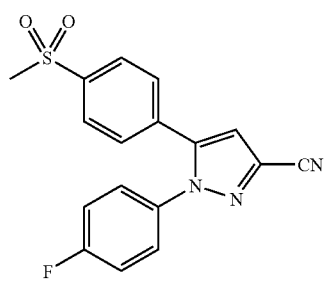

(A)

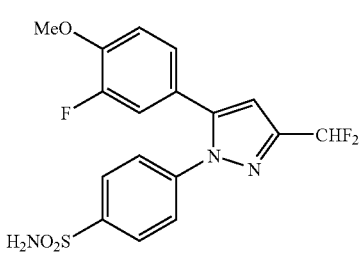

(B)

DISCLOSURE OF THE INVENTION

Compound (A), however, exhibits an $IC_{50}$ value of $5.3 \times 10^{-6}$ M against collagen-induced platelet aggregation, and even stronger inhibitory activity is exhibited against COX-2 ($IC_{50}$, $2.4 \times 10^{-7}$ M). The situation is similar to the case of compound (B). The platelet aggregation inhibitory activity of compound (B) is not so potent compared with its inhibitory activity against COX-2. As described above, inhibition of COX-2 may lead to an antiinflammatory action, and the inhibition of COX-2 is not necessarily favorable as a platelet aggregation inhibitor. In view of the situation as described above, an object of the present invention is to provide a strong inhibitor against platelet aggregation which, however, neither inhibits COX-1 nor COX-2.

The present inventors have made an extensive study in search of such a platelet aggregation inhibitor, and found that pyrazole derivatives represented by the following formulas (I) and (II) exhibit strong platelet aggregation inhibitory activity without inhibiting COX-1 or COX-2, to thereby complete the invention.

Accordingly, the present invention provides a compound represented by formula (I), a salt of the compound, or a solvate of the compound or the salt:

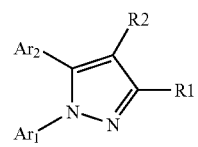

(I)

(wherein $Ar_1$ represents a 5- or 6-membered aromatic heterocyclic group having 1 to 3 substituents; $Ar_2$ represents a 5- or 6-membered aromatic heterocyclic group which may have 1 to 3 substituents or a phenyl group which may have 1 to 3 substituents; R1 is a group represented by formula (1):

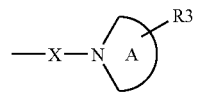

(1)

(wherein ring structure A represents a 4- to 7-membered ring which may have, other than the nitrogen atom in formula (1), one hetero atom selected from among a nitrogen atom, an oxygen atom, and a sulfur atom; X represents a carbonyl group, a thiocarbonyl group, or a methylene group that may be substituted by 1 or 2 lower alkyl groups; R3 represents 1 to 4 groups on ring structure A, R3 being selected from the group consisting of a hydrogen atom, a halogeno group, a hydroxyl group, a lower alkoxy group, a lower alkoxycarbonyl group, a carboxyl group, a sulfo group, a lower alkylsulfonyl group, a lower alkyl group which may have 1 or 2 substituents, an amino group which may have 1 or 2 substituents, a carbamoyl group which may have 1 or 2 substituents, a lower acyl group, an aminosulfonyl group which may have 1 or 2 substituents, an oxo group, a hydroxyiminocarbonyl group, a lower alkoxyiminocarbonyl group, an aralkyl group which may have 1 to 3 substituents, a 4- to 7-membered alicyclic heterocyclic group which may have 1 or 2 substituents, a phenyl group which may have 1 to 3 substituents, a 5- or 6-membered aromatic heterocyclic group which may have 1 to 3 substituents, a substituted or non-substituted 3- to 6-membered spiro alicyclic alkyl group, and a substituted or non-substituted 4- to 6-membered spiro alicyclic heterocyclic group); R2 represents a hydrogen atom, a halogeno group, a hydroxyl group, a lower alkoxy group, a lower alkyl group which may have 1 or 2 substituents, an amino group which may have 1 or 2 substituents, a carbamoyl group which may have 1 or 2 substituents, or an acyl group which may have 1 or 2 substituents).

The present invention also provides a compound represented by formula (II), a salt of the compound, or a solvate of the compound or the salt:

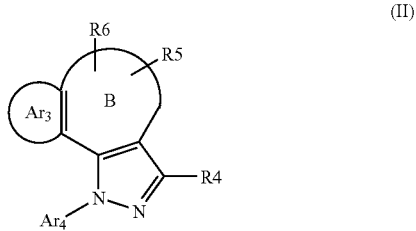

(II)

(wherein ring structure B represents a 5- to 7-membered ring which may have one hetero atom or two hetero atoms which are the same or different from each other, the hetero atom(s) being selected from among a nitrogen atom, an oxygen atom, and a sulfur atom; ring structure $Ar_3$ represents a 5- or 6-membered aromatic heterocycle which may have 1 to 3 substituents or a benzene ring which may have 1 to 3 substituents; $Ar_4$ represents a 5- or 6-membered aromatic heterocyclic group which may have 1 to 3 substituents or a phenyl group which may have 1 to 3 substituents; R4 is a group represented by formula (2):

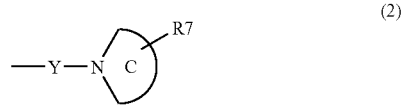

(2)

(wherein ring structure C represents a 4- to 7-membered ring which may have, other than the nitrogen atom in formula (2), one hetero atom selected from among a nitrogen atom, an oxygen atom, and a sulfur atom; Y represents a carbonyl group, a thiocarbonyl group, or a methylene group that may be substituted by 1 or 2 lower alkyl groups; R7 represents 1 to 4 groups on ring structure C, R7 being selected from the group consisting of a hydrogen atom, a halogeno group, a hydroxyl group, a lower alkoxy group, a lower alkoxycarbonyl group, a carboxyl group, a sulfo group, a lower alkylsulfonyl group, a lower alkyl group which may have 1 or 2 substituents, an amino group which may have 1 or 2 substituents, a carbamoyl group which may have 1 or 2 substituents, a lower acyl group, an aminosulfonyl group which may have 1 or 2 substituents, an oxo group, a hydroxyiminocarbonyl group, a lower alkoxyiminocarbonyl group, an aralkyl group which may have 1 to 3 substituents, a 4- to 7-membered alicyclic heterocyclic group which may have 1 or 2 substituents, a phenyl group which may have 1 to 3 substituents, a 5- or 6-membered aromatic heterocyclic group which may have 1 to 3 substituents, a substituted or non-substituted 3- to 6-membered spiro alicyclic alkyl group, and a substituted or non-substituted 4- to 6-membered spiro alicyclic heterocyclic group); each of R5 and R6 represents a group selected from the group consisting of a hydrogen atom, a halogeno group, a hydroxyl group, a lower alkoxy group, an amino group which may have 1 or 2 substituents, a lower alkyl group which may have 1 or 2 substituents, and an oxo group).

The present invention also provides a drug containing a compound represented by formula (I) or (II), a salt of the compound, or a solvate of the compound or the salt.

The present invention also provides a preventive and/or therapeutic agent for an ischemic disease, containing a compound represented by formula (I) or (II), a salt of the compound, or a solvate of the compound or the salt.

The present invention also provides a drug composition containing a compound represented by formula (I) or (II), a salt of the compound, or a solvate of the compound or the salt and a pharmacologically acceptable carrier therefor.

The present invention also provides use of a compound represented by formula (I) or (II), a salt of the compound, or a solvate of the compound or the salt in production of a drug.

The present invention also provides a method for treating an ischemic disease, characterized by comprising administering an effective amount of a compound represented by formula (I) or (II), a salt of the compound, or a solvate of the compound or the salt.

The compounds (I) and (II) of the present invention, salts of the compound, and solvates of the compounds or the salts potently inhibit platelet aggregation, and accordingly, also inhibit thrombogenesis without inhibiting COX-1 or COX-2. Therefore, they are useful as preventive and/or therapeutic agents for ischemic diseases caused by thrombus or embolus such as myocardial infarction, angina pectoris (chronic stable angina, unstable angina, etc.), ischemic cerebrovascular disorder (transient ischemic attack (TIA), cerebral infarction, etc.), peripheral vascular disease, embolism after replacement with an artificial vessel, thrombotic embolism after coronary artery intervention (coronary artery bypass grafting (CAGB), percutaneous transluminal coronary angioplasty (PTCA), stent placement, etc.), diabetic retinopathy and nephropathy, and embolism after replacement with an artificial heart valve, and are also useful as preventive and/or therapeutic agents for thrombus and embolus associated with vascular operation, blood extracorporeal circulation, and the like.

BEST MODE FOR CARRYING OUT THE INVENTION

Next will be described substituents and ring structures of the compounds represented by formula (I) and (II).

The aromatic heterocyclic group represented by $Ar_1$ or $Ar_4$ is a 5- or 6-membered aromatic heterocyclic group, and specific examples include pyridyl, pyridazinyl, pyrimidinyl, pyrazinyl, furyl, thienyl, pyrrolyl, imidazolyl, triazolyl, oxazolyl, isoxazolyl, thiazolyl, and pyrazolyl.

Examples of the substituent of the aromatic heterocyclic group $Ar_1$ or $Ar_4$ include a lower alkyl group, a halogeno group, a hydroxyl group, a cyano group, a lower alkoxy group, an aralkyloxy group, a lower thioalkoxy group, a lower alkoxycarbonyl group, a carboxyl group, a lower alkylsulfonyl group, an amino group which may have 1 or 2 substituents, a carbamoyl group which may be substituted by 1 or 2 lower alkyl groups, an aminosulfonyl group which may be substituted by 1 or 2 lower alkyl groups, and a 4- to 7-membered alicyclic heterocyclic group which may have 1 or 2 substituents. These substituents will next be described.

Among the above-mentioned substituents of aromatic heterocyclic group $Ar_1$ or $Ar_4$, the lower alkyl group refers to a linear, branched, or cyclic C1-C6 alkyl group, and examples include methyl, ethyl, propyl, isopropyl, butyl, isobutyl, t-butyl, pentyl, isopentyl, cyclopropyl, cyclopentyl, cyclohexyl, cyclopropylmethyl, and cyclopentylmethyl.

Examples of the halogeno group include fluoro, chloro, and bromo.

The lower alkoxy group refers to an alkoxy group which has a linear, branched, or cyclic C1-C6 alkyl group, and examples include methoxy, ethoxy, propoxy, isopropoxy, butoxy, isobutoxy, pentoxy, and cyclopentyloxy.

The aralkyl group of the aralkyloxy group refers to a group formed by the above lower alkyl group and a C6-C20 aryl group, and examples of the aralkyloxy group include benzyloxy and phenethyloxy.

The lower thioalkoxy refers to a thioalkoxy group having a linear, branched, or cyclic C1-C6 alkyl group, and examples include methylthio, ethylthio, propylthio, isopropylthio, butylthio, isobutylthio, pentylthio, and cyclopentylthio.

The lower alkoxycarbonyl group refers to an alkoxycarbonyl group having a linear, branched, or cyclic C1-C6 alkyl group, and examples include methoxycarbonyl, ethoxycarbonyl, propoxycarbonyl, isopropoxycarbonyl, n- to tert-butoxycarbonyl, cyclobutyloxycarbonyl, cyclopentyloxycarbonyl, cyclohexyloxycarbonyl, and cyclopentylmethyloxycarbonyl.

The lower alkylsulfonyl group refers to an alkylsulfonyl group having a linear, branched, or cyclic C1-C6 alkyl group, and examples include methanesulfonyl, ethanesulfonyl, and trifluoromethanesulfonyl.

The amino group which may have 1 or 2 substituents refers to a non-substituted amino group, an amino group substituted by 1 or 2 lower alkyl groups described above, a lower alkanoylamino group, a lower alkoxycarbonylamino group, or a ureido group which may be substituted by 1 or 2 lower alkyl groups described above. Examples of the amino group substituted by 1 or 2 lower alkyl groups described above include methylamino, ethylamino, propylamino, isopropylamino, cyclopropylamino, butylamino, isobutylamino, cyclopentylmethylamino, dimethylamino, diethylamino, dipropylamino, dibutylamino, N-methyl-N-ethylamino, N-ethyl-N-propylamino, and N-methyl-N-cyclopentylmethylamino. The lower alkanoylamino group refers to an amino group substituted by a linear or branched C2-C6 alkanoyl group, and examples include acetylamino and propionylamino. The lower alkoxycarbonylamino group refers to an amino group substituted by a linear or branched C2-C6 lower alkoxycarbonyl group, and examples include methoxycarbonylamino and ethoxycarbonylamino. Examples of the ureido group which may be substituted by 1 or 2 lower alkyl groups described above include aminocarbonylamino, N1-methylaminocarbonylamino, N1-ethylaminocarbonylamino, N3-methylaminocarbonylamino, N1,N1-dimethylaminocarbonylamino, N1,N3-dimethylaminocarbonylamino, and N1-methyl-N-3-ethylaminocarbonylamino.

The carbamoyl group which may be substituted by 1 or 2 lower alkyl groups refers to a non-substituted carbamoyl group or a carbamoyl group substituted by 1 or 2 lower alkyl group described above, and examples include methylcarbamoyl, ethylcarbamoyl, dimethylcarbamoyl, and methylethylcarbamoyl.

The aminosulfonyl group which may be substituted by 1 or 2 lower alkyl groups refers to a non-substituted aminosulfonyl group or an aminosulfonyl group substituted by 1 or 2 lower alkyl group described above, and examples include methylaminosulfonyl, ethylaminosulfonyl, propylaminosulfonyl, isopropylaminosulfonyl, n- to tert-butylaminosulfonyl, cyclopropylaminosulfonyl, cyclobutylaminosulfonyl, cyclopentylaminosulfonyl, cyclohexylaminosulfonyl, cyclopentylmethylaminosulfonyl, dimethylaminosulfonyl, and diethylaminosulfonyl.

Examples of the 4- to 7-membered alicyclic heterocyclic group of the 4- to 7-membered alicyclic heterocyclic group which may have 1 or 2 substituents include azetidinyl, pyrrolidinyl, piperidinyl, piperazinyl, hexahydropyridazinyl, hexahydropyrimidinyl, pyrazolidinyl, imidazolidinyl, homopiperazinyl, morpholinyl, and thiomorpholinyl. Examples of the alicyclic heterocyclic group substituted by 1 or 2 groups include 3-aminoazetidin-1-yl, 3-methylaminoazetidin-1-yl, 3-dimethylaminoazetidin-1-yl, 2-carbamoylazetidin-1-yl, 2-methylcarbamoylazetidin-1-yl, 2-dimethylcarbamoylazetidin-1-yl, 3-carbamoylazetidin-1-yl, 3-methylcarbamoylazetidin-1-yl, 3-dimethylcarbamoylazetidin-1-yl, 3-hydroxypyrrolidino, 3-methoxymethylpyrrolidino, 2-carbamoylpyrrolidino, 2-methylcarbamoylpyrrolidino, 2-dimethylcarbamoylpyrrolidino, 3-carbamoylpyrrolidino, 3-methylcarbamoylpyrrolidino, 3-dimethylcarbamoylpyrrolidino, 3-aminopiperidino, 4-aminopiperidino, 3-methylaminopiperidino, 4-methylaminopiperidino, 3-dimethylaminopiperidino, 4-dimethylaminopiperidino, 2-methylpiperidino, 3-methylpiperidino, 4-methylpiperidino, 2,2-dimethylpiperidino, 3,3-dimethylpiperidino, 4,4-dimethylpiperidino, 2-carbamoylpiperidino, 3-carbamoylpiperidino, 4-carbamoylpiperidino, 2-methylcarbamoylpiperidino, 3-methylcarbamoylpiperidino, 4-methylcarbamoylpiperidino, 2-dimethylcarbamoylpiperidino, 3-dimethylcarbamoylpiperidino, 4-dimethylcarbamoylpiperidino, 4-methylpiperazino, 4-cyclopropylpiperazino, 4-carbamoylpiperazino, 2,2-dimethylmorpholino, and 3,3-dimethylmorpholino.

A substituent on the aromatic heterocyclic group $Ar_1$ is preferably present at the para position with respect to the pyrazole ring.

Examples of the substituents of the phenyl group which is represented by $Ar_4$ and which may have 1 to 3 substituents include those listed above in relation to the aromatic heterocyclic group $Ar_4$. The 5- or 6-membered aromatic heterocyclic group represented by $Ar_4$ also includes non-substituted compounds.

The aromatic heterocyclic group $Ar_2$ represents a 5- or 6-membered aromatic heterocyclic group or a phenyl group, which groups may have 1 to 3 substituents. Examples of the aromatic heterocyclic group include pyridyl, pyridazinyl, pyrimidinyl, pyrazinyl, furyl, thienyl, pyrrolyl, imidazolyl, triazolyl, oxazolyl, isoxazolyl, thiazolyl, and pyrazolyl.

The aromatic heterocyclic ring $Ar_3$ represents a 5- or 6-membered aromatic heterocyclic ring or a benzene ring which rings have 1 to 3 substituents. Examples of the aromatic heterocyclic ring include pyridine ring, pyridazine ring, pyrimidine ring, pyrazine ring, furan ring, thiophene ring, pyrrole ring, imidazole ring, triazole ring, oxazole ring, isoxazole ring, thiazole ring, and pyrazole ring.

Examples of the substituent of the aromatic heterocyclic group $Ar_2$ or the aromatic heterocyclic ring $Ar_3$ include those listed above in relation to $Ar_1$ and $Ar_4$.

When the aromatic heterocyclic group $Ar_1$ has a substituent at the para position with respect to the pyrazole ring, preferably, $Ar_2$, which is an aromatic heterocyclic group or a phenyl group is not substituted or has a substituent at the meta position with respect to the pyrazole ring.

Each of the ring structures A and C is a 4- to 7-membered ring which may have, as a structural atom thereof and in addition to the nitrogen atom shown in formulas (1) and (2), a single "hetero" atom selected from among nitrogen atom, oxygen atom, and sulfur atom, and the "hetero" atom may be the same or different from the nitrogen atom. Examples of the 4- to 7-membered ring include saturated heterocyclic rings such as azetidine ring, pyrrolidine ring, imidazolidine ring, pyrazoline ring, piperidine ring, piperazine ring, morpholine ring, thiomorpholine ring, hexahydropyridazine ring, hexahydropyrimidine ring, homopiperazine ring, and azepane ring; and unsaturated heterocyclic rings pyrrole ring, dihydropyrrole ring, imidazole ring, dihydroimidazole ring, pyrazole ring, dihydropyridine ring, dihydropyrimidine ring, and dihydropyrazine ring.

The ring structure B is a 5- to 7-membered ring which may have one hetero atom or two hetero atoms which are the same or different from each other, the hetero atom(s) being selected from among nitrogen atom, oxygen atom, and sulfur atom. For example, when the ring structure B is fused with $Ar_3$ and the pyrazole ring, there may be formed 1,4-dihydroindeno[1,2-c]pyrazole ring, 1,4-dihydro-4-oxoindeno[1,2-c]pyrazole ring, 4,5-dihydro-1H-benzo[g]indazole ring, 1,4-dihydrochromeno[4,3-c]pyrazole ring, or similar rings.

Next will be described the substituents R2, R3, R5, R6, and R7.

Examples of the halogeno group include fluoro, chloro, and bromo.

The lower alkoxy group refers to an alkoxy group having a linear, branched, or cyclic C1-C6 alkyl group, and examples include methoxy, ethoxy, propoxy, isopropoxy, n- to tert-butoxy, cyclobutyloxy, cyclopentyloxy, cyclohexyloxy, and cyclopentylmethyloxy.

The lower alkoxycarbonyl group refers to an alkoxycarbonyl group having a linear, branched, or cyclic C1-C6 alkyl group, and examples include methoxycarbonyl, ethoxycarbonyl, propoxycarbonyl, isopropoxycarbonyl, n- to tert-butoxycarbonyl, cyclobutyloxycarbonyl, cyclopentyloxycarbonyl, cyclohexyloxycarbonyl, and cyclopentylmethyloxycarbonyl.

The lower alkylsulfonyl refers to a sulfonyl group having a linear, branched, or cyclic C1-C6 alkyl group, and examples include methylsulfonyl, ethylsulfonyl, propylsulfonyl, isopropylsulfonyl, n- to tert-butylsulfonyl, cyclopropylsulfonyl, cyclobutylsulfonyl, cyclopentylsulfonyl, cyclohexylsulfonyl, and cyclopentylmethylsulfonyl.

The lower alkyl group which may have 1 or 2 substituents refers to a linear, branched, or cyclic C1-C6 alkyl group which may have one substituent or two substituents which are the same or different from each other, the substituent(s) being selected from the group consisting of a hydroxyl group; a halogeno group; a carboxyl group; a sulfo group; a C1-C3 linear, branched, or cyclic alkoxy group; an alkoxycarbonyl group having a C1-C3 linear, branched, or cyclic alkyl group; an amino which may be substituted by one or two C1-C3 linear, branched, or cyclic alkyl groups; a carbamoyl group which may be substituted by one or two C1-C3 linear, branched, or cyclic alkyl groups; and a ureido group which may be substituted by one or two C1-C3 linear, branched, or cyclic alkyl groups.

Specific examples include methyl, ethyl, propyl, isopropyl, n- to tert-butyl, pentyl, hexyl, cyclopropyl, cyclobutyl, cyclopentyl, cyclohexyl, cyclopropylmethyl, cyclopentylmethyl, hydroxymethyl, 2-hydroxyethyl, 3-hydroxypropyl, 2-hydroxypropyl, 2-fluoroethyl, 3-fluoropropyl, 2-fluoropropyl, 2-fluorocyclopropyl, 2-chloroethyl, 3-chloropropyl, 2-chloropropyl, trifluoromethyl, carboxymethyl, 2-carboxyethyl, 3-carboxypropyl, 2-carboxypropyl, sulfomethyl, 2-sulfoethyl, 1-sulfoethyl, 3-sulfopropyl, 2-sulfopropyl, methoxymethyl, ethoxymethyl, propoxymethyl, isopropoxymethyl, 2-methoxyethyl, 3-methoxypropyl, methoxycarbonylmethyl, ethoxycarbonylmethyl, propoxycarbonylmethyl, 2-methoxycarbonylethyl, 2-ethoxycarbonylethyl, 2-propoxycarbonylethyl, aminomethyl, 2-aminoethyl, 1-aminoethyl, 3-aminopropyl, 2-aminopropyl, methylaminomethyl, 2-(methylamino)ethyl, 1-(methylamino) ethyl, 3-(methylamino)propyl, 2-(methylamino)propyl, dimethylaminomethyl, 2-(dimethylamino)ethyl, 1-(dimethylamino)ethyl, 3-(dimethylamino)propyl, 2-(dimethylamino)propyl, 2-(methylethylamino)ethyl, 1-(methylethylamino)ethyl, carbamoylmethyl, methylcarbamoylmethyl, ethylcarbamoylmethyl, dimethylcarbamoylmethyl, methylethylcarbamoylmethyl, carbamoylethyl, methylcarbamoylethyl, ethylcarbamoylethyl, dimethylcarbamoylethyl, methylethylcarbamoylethyl, carbamoylpropyl, 2-carbamoylcyclopropyl, ureidomethyl, N3-methylureidomethyl, N3-ethylureidomethyl, N3,N3-dimethylureidomethyl, N3-methyl-N-3-ethylureidomethyl, 2-(ureido)ethyl, 2-(N-3-methylureido)ethyl, 2-(N-3-ethylureido)ethyl, 2-(N3,N3-dimethylureido)ethyl, 2-(N-3-methyl-N-3-ethylureido)ethyl, 3-(ureido)propyl, 2-(ureido)cyclopropyl, N1-methylureidomethyl, N1-ethylureidomethyl, N1,N1-dimethylureidomethyl, N1-methyl-N1-ethylureidomethyl, 2-(ureido)ethyl, 2-(N1-methylureido)ethyl, 2-(N1-ethylureido)ethyl, 2-(N1,N1-dimethylureido)ethyl, 2-(N1-methyl-N1-ethylureido)ethyl, N1,N3-dimethylureidomethyl, N1-methyl-N-3-ethylureidomethyl, 2-(N-3-methyl-N1-ethyl)ureidoethyl, 2-(N1,N3-diethylureido)ethyl, 1-carbamoyl-2-hydroxyethyl, and 1,2-dicarbamoylethyl.

The amino group which may have 1 or 2 substituents refers to an amino group which may be substituted by one or two C1-C6 linear, branched, or cyclic alkyl groups, and examples include non-substituted amino, methylamino, ethylamino, propylamino, isopropylamino, n- to tert-butylamino, pentylamino, hexylamino, cyclopropylamino, cyclobutylamino, cyclopentylamino, cyclohexylamino, cyclopropylmethylamino, cyclopentylmethylamino, dimethylamino, methylethylamino, diethylamino, methylpropylamino, methylisopropylamino, methylcyclopropylamino, methylcyclopropylmethylamino, and methyl-tert-butoxycarbonylamino.

The carbamoyl group which may have 1 or 2 substituents refers to a carbamoyl group which may be substituted by one or two C1-C6 linear, branched, or cyclic alkyl groups, and examples include non-substituted carbamoyl, methylcarbamoyl, ethylcarbamoyl, propylcarbamoyl, isopropylcarbamoyl, n- to tert-butylcarbamoyl, pentylcarbamoyl, hexylcarbamoyl, cyclopropylcarbamoyl, cyclobutylcarbamoyl, cyclopentylcarbamoyl, cyclohexylcarbamoyl, cyclopropylmethylcarbamoyl, cyclopentylmethylcarbamoyl, dimethylcarbamoyl, methylethylcarbamoyl, diethylcarbamoyl, methylpropylcarbamoyl, methylisopropylcarbamoyl, methylcyclopropylcarbamoyl, and methylcyclopropylmethylcarbamoyl.

The lower acyl refers to an acyl group having a linear, branched, or cyclic C1-C6 alkyl group, and examples include formyl, acetyl, propionyl, n- and iso-butyryl, pivaloyl, cyclopropylcarbonyl, cyclobutyrylcarbonyl, cyclopentylcarbonyl, cyclohexylcarbonyl, cyclopropylmethylcarbonyl, cyclobutylmethylcarbonyl, and cyclopentylmethylcarbonyl.

The aminosulfonyl group which may have 1 or 2 substituents refers to an aminosulfonyl group which may be substituted by one or two C1-C3 alkyl groups, and examples include non-substituted aminosulfonyl, aminosulfonyl, methylaminosulfonyl, ethylaminosulfonyl, propylaminosulfonyl, isopropylaminosulfonyl, cyclopropylaminosulfonyl, dimethylaminosulfonyl, diethylaminosulfonyl, methylethylaminosulfonyl, methylpropylaminosulfonyl, dimethylaminosulfonyl, and diethylaminosulfonyl.

The lower alkoxyiminocarbonyl group refers to an iminocarbonyl group substituted by an alkoxy group having a linear, branched, or cyclic C1-C6 alkyl group, and examples include methoxyiminocarbonyl, ethoxyiminocarbonyl, propoxyiminocarbonyl, isopropoxyiminocarbonyl, n- to tert-butoxyiminocarbonyl, cyclobutyloxyiminocarbonyl, cyclopentyloxyiminocarbonyl, cyclohexyloxyiminocarbonyl, and cyclopentylmethyloxyiminocarbonyl.

The aralkyl group which may have 1 to 3 substituents refers to an aralkyl group which is formed of a linear, branched, or cyclic C1-C6 alkyl group and a C6-C20 aryl group and which may have 1 to 3 substituents. Examples include benzyl and phenethyl.

Examples of the substituents of the aralkyl group include hydroxyl, carboxyl, sulfo, cyano, and nitro. Examples of the substituents referred to in connection with the "phenyl group which may have 1 to 3 substituents" also include these groups.

Examples of the 5- or 6-membered aromatic heterocyclic group which may have 1 to 3 substituents include pyridyl, pyridazinyl, pyrimidinyl, pyrazinyl, furyl, thienyl, pyrrolyl, imidazolyl, triazolyl, oxazolyl, isoxazolyl, thiazolyl, and pyrazolyl.

Examples of the substituents include those listed above in relation to $Ar_1$ and $Ar_4$.

Examples of the 4- to 7-membered alicyclic heterocyclic group which may have 1 or 2 substituents include azetidinyl, pyrrolidinyl, piperidinyl, piperazinyl, hexahydropyridazinyl, hexahydropyrimidinyl, pyrazolidinyl, imidazolidinyl, homopiperazinyl, morpholinyl, and thiomorpholinyl.

The alicyclic heterocyclic group may be substituted, and examples of the substituents include a hydroxyl group, an oxo group, a carboxyl group, a sulfo group, a cyano group, a nitro group, the above-described halogeno group, the above-described lower alkoxy group, alkylsulfonyl group, the above-described lower alkyl group which may have 1 or 2 substituents, the above-described amino group which may have 1 or 2 substituents, the above-described carbamoyl group which may have 1 or 2 substituents, the above-described lower acyl group, and the above-described aminosulfonyl group which may have 1 or 2 substituents.

Examples of the substituted or non-substituted 3- to 6-membered spiro alicyclic alkyl group include cyclopropanespiro, cyclobutanespiro, cyclopentanespiro, and cyclohexanespiro.

The spiro alicyclic alkyl group may be substituted, and examples of the substituent include a hydroxyl group, an oxo group, the above-described lower alkoxy group, the above-described lower alkyl group which may have 1 or 2 substituents, the above-described amino group which may have 1 or 2 substituents, the above-described carbamoyl group which may have 1 or 2 substituents, the above-described lower acyl group, and the above-described aminosulfonyl group which may have 1 or 2 substituents.

The substituted or non-substituted 4- to 6-membered spiro alicyclic heterocyclic group refers to a spiro heterocyclic group which may have a single double bond, and examples include azetidinespiro, pyrrolidinespiro, piperidinespiro, piperazinespiro, pyrazolidinespiro, imidazolinespiro, morpholinespiro, and thiomorpholinespiro.

Examples of the substituent of the spiro alicyclic heterocyclic group include a hydroxyl group, an oxo group, a carboxyl group, the above-described lower alkoxy group, the above-described lower alkyl group which may have 1 or 2 substituents, the above-described amino group which may have 1 or 2 substituents, the above-described carbamoyl group which may have 1 or 2 substituents, the above-described acyl group which may have 1 or 2 substituents, and the above-described aminosulfonyl group which may have 1 or 2 substituents.

The compounds (I) and (II) of the present invention will next be described in more detail.

$Ar_1$ in formula (I) is preferably a 6-membered aromatic heterocyclic group which has 1 to 3 substituents, more preferably a pyridyl group having 1 to 3 substituents, a pyridazinyl group having 1 to 3 substituents, or a pyrazinyl group having 1 to 3 substituents, still more preferably a pyridyl group having 1 to 3 substituents or a pyridazinyl group having 1 to 3 substituents.

$Ar_4$ in formula (I) is preferably a 6-membered aromatic heterocyclic group which may have 1 to 3 substituents or a phenyl group which may have 1 to 3 substituents, more preferably a pyridyl group which may have 1 to 3 substituents, a pyridazinyl group which may have 1 to 3 substituents, a pyrazinyl group which may have 1 to 3 substituents, or a phenyl group which may have 1 to 3 substituents.

As mentioned above, the aromatic heterocyclic group represented by $Ar_1$ or $Ar_4$ has one to three substituents. Examples of preferred ones of the substituents include a $C_{1-6}$ alkyl group, a halogeno group, a $C_{1-6}$ alkoxy group, a $C_{1-6}$ alkylamino group, and a di($C_{1-6}$ alkyl)amino group.

$Ar_2$ in formula (I) is preferably a pyridyl group which may have 1 to 3 substituents, a pyridazinyl group which may have 1 to 3 substituents, a pyrazinyl group which may have 1 to 3 substituents, a pyrrolyl group which may have 1 to 3 substituents, or a phenyl group which may have 1 to 3 substituents.

$Ar_3$ in formula (II) is preferably a 6-membered aromatic heterocyclic ring which may have 1 to 3 substituents or a benzene ring which may have 1 to 3 substituents. Moreover, $Ar_3$ is preferably a pyridine ring which may have 1 to 3 substituents or a benzene ring which may have 1 to 3 substituents.

Each of $Ar_1$ in formula (I) and $Ar_4$ in formula (II) is preferably 3-pyridyl, 6-methoxy-3-pyridyl, 6-methyl-3-pyridyl, 6-ethyl-3-pyridyl, 6-chloro-3-pyridyl, 6-ethoxy-3-pyridyl, 6-isopropyloxy-3-pyridyl, 6-methylamino-3-pyridyl, 6-cyclopropylamino-3-pyridyl, 5-methoxy-2-pyridyl, 6-methoxy-3-pyridazinyl, 6-methyl-3-pyridazinyl, 5-methoxy-2-pyrimidinyl, 5-methyl-2-pyrimidinyl, 2-methoxy-5-pyrimidinyl, 2-methyl-5-pyrimidinyl, 5-methoxy-2-pyrazinyl, or 5-methoxy-2-pyrazinyl. Among them, 6-methoxy-3-pyridyl, 6-methyl-3-pyridyl, 5-methoxy-2-pyridyl, 6-methoxy-3-pyridazinyl, 6-methyl-3-pyridazinyl, 5-methoxy-2-pyrimidinyl, 5-methyl-2-pyrimidinyl, 5-methoxy-2-pyrazinyl, 5-methyl-2-pyrazinyl are more preferred. Of these, 6-methoxy-3-pyridyl, 6-methyl-3-pyridyl, 5-methoxy-2-pyridyl, 6-methoxy-3-pyridazinyl are still more preferred.

$Ar_2$ is preferably phenyl, 2-fluorophenyl, 2-chlorophenyl, 2-methylphenyl, 2-methoxyphenyl, 2-hydroxyphenyl, 3-fluorophenyl, 3-chlorophenyl, 3-methylphenyl, 3-methoxyphenyl, 3-hydroxyphenyl, 4-fluorophenyl, 4-chlorophenyl, 4-methylphenyl, 4-ethylphenyl, 4-methoxyphenyl, 4-hydroxyphenyl, 4-trifluoromethylphenyl, 4-benzyloxyphenyl, 2-pyridyl, 3-pyridyl, 4-pyridyl, 6-methoxy-2-pyridyl, 6-methyl-2-pyridyl, 6-methoxy-3-pyridyl, 6-methyl-2-pyridyl, 6-methoxy-2-pyridyl, 6-methyl-2-pyridyl, 3-methoxy-2-pyridyl, 3-methyl-2-pyridyl, 3-fluoro-2-pyridyl, 4-fluoro-2-pyridyl, 5-fluoro-2-pyridyl, 6-fluoro-2-pyridyl, 4-methyl-2-pyridyl, 4-ethyl-2-pyridyl, 4-methoxy-2-pyridyl, 4-ethoxy-2-pyridyl, 4-cyano-2-pyridyl, 4-carbamoyl-2-pyridyl, 4-pyrrolidinyl-2-pyridyl, 4-methylthio-2-pyridyl, 4-methanesulfonyl-2-pyridyl, 4-carboxy-2-pyridyl, 6-methoxy-3-pyridazinyl, 6-methyl-3-pyridazinyl, 5-methoxy-2-pyrimidinyl, 5-methyl-2-pyrimidinyl, 5-methoxy-2-pyrazinyl, 5-methyl-2-pyrazinyl, pyrrol-1-yl, pyrrol-2-yl, pyrrol-3-yl, 1-methylpyrrol-2-yl, 1-methylpyrrol-3-yl, 1-ethylpyrrol-2-yl, or 1-ethylpyrrol-3-yl. Among them, phenyl, 2-fluorophenyl, 2-chlorophenyl, 2-methylphenyl, 2-methoxyphenyl, 2-hydroxyphenyl, 3-fluorophenyl, 3-chlorophenyl, 3-methylphenyl, 3-methoxyphenyl, 3-hydroxyphenyl, 4-fluorophenyl, 4-chlorophenyl, 4-methylphenyl, 4-methoxyphenyl, 4-hydroxyphenyl, 2-pyridyl, 3-pyridyl, 4-pyridyl, 6-methoxy-3-pyridyl, 6-methyl-3-pyridyl, 6-methoxy-2-pyridyl, 6-methyl-2-pyridyl, 3-fluoro-2-pyridyl, 4-fluoro-2-pyridyl, 5-fluoro-2-pyridyl, 6-fluoro-2-pyridyl, 4-methyl-2-pyridyl, 4-ethyl-2-pyridyl, 4-methoxy-2-pyridyl, 4-cyano-2-pyridyl, 4-carbamoyl-2-pyridyl, 4-pyrrolidinyl-2-pyridyl, 3-methoxy-2-pyridyl, 3-methyl-2-pyridyl, 6-methoxy-3-pyridazinyl, 6-methyl-3-pyridazinyl, 5-methoxy-2-pyrimidinyl, 5-methyl-2-pyrimidinyl, 5-methoxy-2-pyrazinyl, 5-methyl-2-pyrazinyl, pyrrol-1-yl, pyrrol-2-yl, pyrrol-3-yl, 1-methylpyrrol-2-yl, 1-methylpyrrol-3-yl, 1-ethylpyrrol-2-yl, and 1-ethylpyrrol-3-yl are more preferred.

$Ar_3$ is preferably a benzene ring or a pyridine ring, more preferably a benzene ring.

As already mentioned above, R1 represents a group represented by the following formula (1):

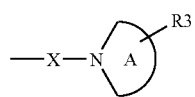
(1)

and X represents a carbonyl group; a thiocarbonyl group, or a methylene group which may be substituted by 1 or 2 lower alkyl groups. The group represented by X is preferably a carbonyl group or methylene group which may be substituted by 1 or 2 lower alkyl groups, more preferably a carbonyl group.

Also already described above, R4 represents a group represented by the following formula (2):

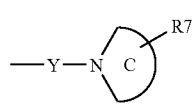
(2)

and Y represents a carbonyl group, a thiocarbonyl group, or a methylene group which may be substituted by 1 or 2 lower alkyl groups. The group represented by Y is preferably a carbonyl group or a methylene group which may be substituted by 1 or 2 lower alkyl groups, more preferably a carbonyl group.

Examples of the ring structures A and C in the above formulas (1) and (2) include saturated heterocyclic rings such as azetidine ring, pyrrolidine ring, imidazolidine ring, pyrazoline ring, piperidine ring, piperazine ring, morpholine ring, thiomorpholine ring, hexahydropyridazine ring, hexahydropyrimidine ring, homopiperazine ring, and azepane ring, and unsaturated heterocyclic rings such as pyrrole ring, dihydropyrrole ring, imidazole ring, dihydroimidazole ring, pyrazole ring, dihydropyridine ring, dihydropyrimidine ring, and dihydropyrazine ring. Of these, preferred are saturated rings such as azetidine ring, pyrrolidine ring, imidazolidine ring, pyrazoline ring, piperidine ring, piperazine ring, morpholine ring, thiomorpholine ring, hexahydropyridazine ring, hexahydropyrimidine ring, homopiperazine ring, and azepane ring.

Typical substituents represented by the following formulas:

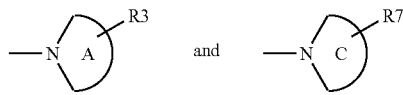

in formulas (1) or (2) include the following:

Azetidin-1-yl, 3-oxoazetidin-1-yl, 2-oxoazetidin-1-yl, 3-aminoazetidin-1-yl, 3-methylaminoazetidin-1-yl, 3-dimethylaminoazetidin-1-yl, 2-methylazetidin-1-yl, 3-methylazetidin-1-yl, 2,2-dimethylazetidin-1-yl, 3,3-dimethylazetidin-1-yl, 2,2-dimethyl-3-dimethylaminoazetidin-1-yl, 3-dimethylaminomethylazetidin-1-yl, 3-methoxyazetidin-1-yl, 2-hydroxymethylazetidin-1-yl, 3-hydroxymethylazetidin-1-yl, 3-hydroxyazetidin-1-yl, 2-carboxyazetidin-1-yl, 3-carboxyazetidin-1-yl, 2-carbamoylazetidin-1-yl, 2-methylcarbamoylazetidin-1-yl, 2-dimethylcarbamoylazetidin-1-yl, 3-carbamoylazetidin-1-yl, 3-methylcarbamoylazetidin-1-yl, 3-dimethylcarbamoylazetidin-1-yl, pyrrolidino, 2-oxopyrrolidino, 3-oxopyrrolidino, 2,5-dioxopyrrolidino, 3-aminopyrrolidino, 3-methylaminopyrrolidino, 2-dimethylaminomethylpyrrolidino, 3-dimethylaminopyrrolidino, 2-methylpyrrolidino, 3-methylpyrrolidino, 2,2-dimethylpyrrolidino, 3,3-dimethylpyrrolidino, 2,2-dimethyl-3-dimethylaminopyrrolidino, 2-hydroxymethylpyrrolidino, 3-hydroxymethylpyrrolidino, 3-methoxypyrrolidino, 2-methoxymethylpyrrolidino, 3-methoxymethylpyrrolidino, 2-carboxypyrrolidino, 3-carboxypyrrolidino, 2-carbamoylpyrrolidino, 2-methylcarbamoylpyrrolidino, 2-dimethylcarbamoylpyrrolidino, 3-carbamoylpyrrolidino, 3-methylcarbamoylpyrrolidino, 3-dimethylcarbamoylpyrrolidino, imidazolidin-1-yl, 3-methylimidazolidin-1-yl, 2-oxoimidazolidin-1-yl, 4-oxoimidazolidin-1-yl, 3-methyl-2-oxoimidazolidin-1-yl, 3-methyl-4-oxoimidazolidin-1-yl, 2,2-dimethylimidazolin-1-yl, pyrazolidin-1-yl, 2-methylpyrazolidin-1-yl, 3-oxopyrazolidin-1-yl, 3,5-dioxopyrazolidin-1-yl, piperidino, 2-oxopiperidino, 3-oxopiperidino, 4-oxopiperidino, 3-hydroxypiperidino, 4-hydroxypiperidino, 2-hydroxyiminopiperidino, 3-hydroxyiminopiperidino, 4-hydroxyiminopiperidino, 2-methoxypiperidino, 3-methoxypiperidino, 4-methoxypiperidino, 2-methoxyiminopiperidino, 3-methoxyiminopiperidino, 4-methoxyiminopiperidino, 3-aminopiperidino, 4-aminopiperidino, 3-methylaminopiperidino, 4-methylaminopiperidino, 3-dimethylaminopiperidino, 4-dimethylaminopiperidino, 2-methylpiperidino, 3-methylpiperidino, 4-methylpiperidino, 2,2-dimethylpiperidino, 3,3-dimethylpiperidino, 4,4-dimethylpiperidino, 4-fluoropiperidino, 4-chloropiperidino, 3,3-difluoropiperidino, 4,4-difluoropiperidino, 3,3-dichloropiperidino, 4,4-dichloropiperidino, 2-hydroxymethylpiperidino, 3-hydroxymethylpiperidino, 4-hydroxymethylpiperidino, 2-carboxypiperidino, 3-carboxypiperidino, 4-carboxypiperidino, 2-carbamoylpiperidino, 3-carbamoylpiperidino, 4-carbamoylpiperidino, 2-methylcarbamoylpiperidino, 3-methylcarbamoylpiperidino, 4-methylcarbamoylpiperidino, 2-dimethylcarbamoylpiperidino, 3-dimethylcarbamoylpiperidino, 4-dimethylcarbamoylpiperidino, 2-carboxymethylpiperidino, 3-carboxymethylpiperidino, 4-carboxymethylpiperidino, 2-methoxymethylpiperidino, 3-methoxymethylpiperidino, 4-methoxymethylpiperidino, 2-aminomethylpiperidino, 3-aminomethylpiperidino, 4-aminomethylpiperidino, 2-methylaminomethylpiperidino, 3-methylaminomethylpiperidino, 4-methylaminomethylpiperidino, 2-dimethylaminomethylpiperidino, 3-dimethylaminomethylpiperidino, 4-dimethylaminomethylpiperidino, 2-aminoethylpiperidino, 3-aminoethylpiperidino, 4-aminoethylpiperidino, 2-methylaminoethylpiperidino, 3-methylaminoethylpiperidino, 4-methylaminoethylpiperidino, 2-dimethylaminoethylpiperidino, 3-dimethylaminoethylpiperidino, 4-dimethylaminoethylpiperidino, piperazino, 2-oxopiperazino, 3-oxopiperazino, 2-oxo-4-methylpiperazino, 3-oxo-4-methylpiperazino, 4-formylpiperazino, 2,3-dioxopiperazino, 3,5-dioxopiperazino, 2,6-dioxopiperazino, 2,3-dioxo-4-methylpiperazino, 3,5-dioxo-4-methylpiperazino, 2,6-dioxo-4-methylpiperazino, 2-methylpiperazino, 3-methylpiperazino, 4-methylpiperazino, 2-ethylpiperazino, 3-ethylpiperazino, 4-ethylpiperazino, 2-isopropylpiperazino, 3-isopropylpiperazino, 4-isopropylpiperazino, 2-cyclopropylpiperazino, 3-cyclopropylpiperazino, 4-cyclopropylpiperazino, 4-cyclobutylpiperazino, 2-cyclopropanespiropiperazino, 3-cyclopropanespiropiperazino, 2,2-dimethylpiperazino, 3,3-dimethylpiperazino, 2,3-dimethylpiperazino, 2,4-dimethylpiperazino, 3,4-dimethylpiperazino, 3,5-dimethylpiperazino, 2,6-dimethylpiperazino, 2-ethyl-4-methylpiperazino, 3-ethyl-4-methylpiperazino, 2-isopropyl-4-methylpiperazino, 3-isopropyl-4-methylpiperazino, 2-cyclopropyl-4-methylpiperazino, 3-cyclopropyl-4-methylpiperazino, 3-methyl-4-benzylpiperazino, 4-phenylpiperazino, 4-(2-pyridyl)piperazino, 1,2,6-trimethylpiperazino, 3,4,5-trimethylpiperazino, 2,2,4-trimethylpiperazino, 3,3,4-trimethylpiperazino, 3,3,4-trimethyl-5-oxopiperazino, 2,2,4-trimethyl-3-oxopiperazino, 2-cyclopropanespiro-4-methylpiperazino, 3-cyclopropanespiro-4-methylpiperazino, 2-cyclopropanespiro-4-methyl-3-oxopiperazino, 3-cyclopropanespiro-4-methyl-5-oxopiperazino, 4-acetylpiperazino, 4-acetyl-3-cyclopropanespiropiperazino, 2-hydroxymethylpiperazino, 3-hydroxymethylpiperazino, 2-methoxymethylpiperazino, 3-methoxymethylpiperazino, 2-hydroxyethylpiperazino, 3-hydroxyethylpiperazino, 4-hydroxyethylpiperazino, 2-hydroxymethyl-4-methylpiperazino, 3-hydroxymethyl-4-methylpiperazino, 2-methoxymethyl-4-methylpiperazino, 3-methoxymethyl-4-methylpiperazino, 2-hydroxyethyl-4-methylpiperazino, 3-hydroxyethyl-4-methylpiperazino, 2-methoxyethyl-4-methylpiperazino, 3-methoxyethyl-4-methylpiperazino, 2-carbamoylpiperazino, 3-carbamoylpiperazino, 4-carbamoylpiperazino, 2-methylcarbamoylpiperazino, 3-methylcarbamoylpiperazino, 4-methylcarbamoylpiperazino, 2-dimethylcarbamoylpiperazino, 3-dimethylcarbamoylpiperazino, 4-dimethylcarbamoylpiperazino, 2-carbamoylmethylpiperazino, 3-carbamoylmethylpiperazino, 4-carbamoylmethylpiperazino, 2-methylcarbamoylmethylpiperazino, 3-methylcarbamoylmethylpiperazino, 4-methylcarbamoylpiperazino, 2-dimethylcarbamoylmethylpiperazino, 3-dimethylcarbamoylmethylpiperazino, 2-carbamoyl-4-methylpiperazino, 3-carbamoyl-4-methylpiperazino, 4-carbamoylpiperazino, 2-methylcarbamoyl-4-methylpiperazino, 3-methylcarbamoyl-4-methylpiperazino, 4-methylcarbamoylpiperazino, 2-dimethylcarbamoyl-4-methylpiperazino, 3-dimethylcarbamoyl-4-methylpiperazino, 4-dimethylcarbamoylpiperazino, 2-carbamoylmethyl-4-methylpiperazino, 3-carbamoylmethyl-4-methylpiperazino, 4-carbamoylmethylpiperazino, 2-methylcarbamoylmethyl-4-methylpiperazino, 3-methylcarbamoylmethyl-4-methylpiperazino, 4-methylcarbamoylpiperazino, 2-dimethylcarbamoylmethyl-4-methylpiperazino, 3-dimethylcarbamoylmethyl-4-methylpiperazino, 2-carboxypiperazino, 3-carboxypiperazino, 2-methoxycarboxypiperazino, 3-methoxycarboxypiperazino, 2-ethoxycarboxypiperazino, 3-ethoxycarboxypiperazino, 2-carboxymethylpiperazino, 3-carboxymethylpiperazino, 4-carboxymethylpiperazino, 2-carboxyethylpiperazino, 3-carboxyethylpiperazino, 4-carboxyethylpiperazino, 4-carboxy-tert-butylpiperazino, 2-methoxycarbonylmethylpiperazino, 3-methoxycarbonylmethylpiperazino, 2-methoxycarbonylmethylpiperazino, 3-methoxycarbonylmethylpiperazino, 4-methoxycarbonylmethylpiperazino, 2-ethoxycarbonylmethylpiperazino, 3-ethoxycarbonylmethylpiperazino, 4-ethoxycarbonylmethylpiperazino, 2-carboxy-4-methylpiperazino, 3-carboxy-4-methylpiperazino, 2-carboxymethyl-4-methylpiperazino, 3-carboxymethyl-4-methylpiperazino, 2-methoxycarbonylmethyl-4-methylpiperazino, 3-methoxycarbonylmethyl-4-methylpiperazino, 2-methoxycarbonylmethyl-4-methylpiperazino, 3-methoxycarbonylmethyl-4-methylpiperazino, 2-ethoxycarbonylmethyl-4-methylpiperazino, 3-ethoxycarbonylmethyl-4-methylpiperazino, 2-aminomethylpiperazino, 3-aminomethylpiperazino, 2-methylaminomethylpiperazino, 3-methylaminomethylpiperazino, 2-dimethylaminomethylpiperazino, 3-dimethylaminomethylpiperazino, 2-aminoethylpiperazino, 3-aminoethylpiperazino, 4-aminoethylpiperazino, 2-methylaminoethylpiperazino, 3-methylaminoethylpiperazino, 4-methylaminoethylpiperazino, 2-dimethylaminoethylpiperazino, 3-dimethylaminoethylpiperazino, 4-dimethylaminoethylpiperazino, 2-aminomethyl-4-methylpiperazino, 3-aminomethyl-4-methylpiperazino, 2-methylaminomethyl-4-methylpiperazino, 3-methylaminomethyl-4-methylpiperazino, 2-dimethylaminomethyl-4-methylpiperazino, 3-dimethylaminomethyl-4-methylpiperazino, 2-aminoethyl-4-methylpiperazino, 3-aminoethyl-4-methylpiperazino, 2-methylaminoethyl-4-methylpiperazino, 3-methylaminoethyl-4-methylpiperazino, 2-dimethylaminoethyl-4-methylpiperazino, 3-dimethylaminoethyl-4-methylpiperazino, 4-methanesulfonylpiperazino, 4-aminosulfonylpiperazino, 4-(azetidin-1-yl)piperazino, 4-pyrrolidinopiperazino, 4-piperidinopiperazino, morpholino, 2-methylmorpholino, 3-methylmorpholino, 2-ethylmorpholino, 3-ethylmorpholino, 2-cyclopropanespiromorpholino, 3-cyclopropanespiromorpholino, 2,2-dimethylmorpholino, 3,3-dimethylmorpholino, 2-hydroxymethylmorpholino, 3-hydroxymethylmorpholino, 2-methoxymethylmorpholino, 3-methoxymethylmorpholino, 2-hydroxyethylmorpholino, 3-hydroxyethylmorpholino, 2-methoxyethylmorpholino, 3-methoxyethylmorpholino, 2-carbamoylmorpholino, 3-carbamoylmorpholino, 2-methylcarbamoylmorpholino, 3-methylcarbamoylmorpholino, 2-dimethylcarbamoylmorpholino, 3-dimethylcarbamoylmorpholino, 2-carbamoylmethylmorpholino, 3-carbamoylmethylmorpholino, 2-methylcarbamoylmethylmorpholino, 3-methylcarbamoylmethylmorpholino, 2-dimethylcarbamoylmethylmorpholino, 3-dimethylcarbamoylmethylmorpholino, 2-carbamoylethylmorpholino, 3-carbamoylethylmorpholino, 2-methylcarbamoylethylmorpholino, 3-methylcarbamoylethylmorpholino, 2-dimethylcarbamoylethylmorpholino, 3-dimethylcarbamoylethylmorpholino, 2-carboxymorpholino, 3-carboxymorpholino, 2-methoxycarbonylmorpholino, 3-methoxycarbonylmorpholino, 2-carboxymethylmorpholino, 3-carboxymethylmorpholino, 2-methoxycarbonylmethylmorpholino, 3-methoxycarbonylmethylmorpholino, 2-ethoxycarbonylmethylmorpholino, 3-ethoxycarbonylmethylmorpholino, 2-aminomethylmorpholino, 3-aminomethylmorpholino, 2-methylaminomethylmorpholino, 3-methylaminomethylmorpholino, 2-dimethylaminomethylmorpholino, 3-dimethylaminomethylmorpholino, 2-aminoethylmorpholino, 3-aminoethylmorpholino, 2-methylaminoethylmorpholino, 3-methylaminoethylmorpholino, 2-dimethylaminoethylmorpholino, 3-dimethylaminoethylmorpholino, thiomorpholino, 3-oxothiomorpholino, 1,1-dioxothiomorpholino, 2-methylthiomorpholino, 3-methylthiomorpholino, 2-ethylthiomorpholino, 3-ethylthiomorpholino, 2-cyclopropanespirothiomorpholino, 3-cyclopropanespirothiomorpholino, 2,2-dimethylthiomorpholino, 3,3-dimethylthiomorpholino, 2-hydroxymethylthiomorpholino, 3-hydroxymethylthiomorpholino, 2-methoxymethylthiomorpholino, 3-methoxymethylthiomorpholino, 2-hydroxyethylthiomorpholino, 3-hydroxyethylthiomorpholino, 2-methoxyethylthiomorpholino, 3-methoxyethylthiomorpholino, 2-carbamoylthiomorpholino, 3-carbamoylthiomorpholino, 2-methylcarbamoylthiomorpholino, 3-methylcarbamoylthiomorpholino, 2-dimethylcarbamoylthiomorpholino, 3-dimethylcarbamoylthiomorpholino, 2-carbamoylmethylthiomorpholino, 3-carbamoylmethylthiomorpholino, 2-methylcarbamoylmethylthiomorpholino, 3-methylcarbamoylmethylthiomorpholino, 2-dimethylcarbamoylmethylthiomorpholino, 3-dimethylcarbamoylmethylthiomorpholino, 2-carbamoylethylthiomorpholino, 3-carbamoylethylthiomorpholino, 2-methylcarbamoylethylthiomorpholino, 3-methylcarbamoylethylthiomorpholino, 2-dimethylcarbamoylethylthiomorpholino, 3-dimethylcarbamoylethylthiomorpholino, 2-carboxythiomorpholino, 3-carboxythiomorpholino, 2-methoxycarbonylthiomorpholino, 3-methoxycarbonylthiomorpholino, 2-carboxymethylthiomorpholino, 3-carboxymethylthiomorpholino, 2-methoxycarbonylmethylthiomorpholino, 3-methoxycarbonylmethylthiomorpholino, 2-ethoxycarbonylmethylthiomorpholino, 3-ethoxycarbonylmethylthiomorpholino, 2-aminomethylthiomorpholino, 3-aminomethylthiomorpholino, 2-methylaminomethylthiomorpholino, 3-methylaminomethylthiomorpholino, 2-dimethylaminomethylthiomorpholino, 3-dimethylaminomethylthiomorpholino, 2-aminoethylthiomorpholino, 3-aminoethylthiomorpholino, 2-methylaminoethylthiomorpholino, 3-methylaminoethylthiomorpholino, 2-dimethylaminoethylthiomorpholino, 3-dimethylaminoethylthiomorpholino, hexahydropyridazin-1-yl, 2-acetylhexahydropyridazin-1-yl, 2-formylhexahydropyridazin-1-yl, 3-oxohexahydropyridazin-1-yl, 6-oxohexahydropyridazin-1-yl, 4-aminohexahydropyridazin-1-yl, 4-methylaminohexahydropyridazin-1-yl, 4-dimethylaminohexahydropyridazin-1-yl, 2-methylhexahydropyridazin-1-yl, 3-methylhexahydropyridazin-1-yl, 4-methylhexahydropyridazin-1-yl, 2,3-dimethylhexahydropyridazin-1-yl, 3,3-dimethylhexahydropyridazin-1-yl, 4,4-dimethylhexahydropyridazin-1-yl, 3-hydroxymethylhexahydropyridazin-1-yl, 4-hydroxymethylhexahydropyridazin-1-yl, 5-hydroxymethylhexahydropyridazin-1-yl, 6-hydroxymethylhexahydropyridazin-1-yl, 2-carbamoylhexahydropyridazin-1-yl, 3-carbamoylhexahydropyridazin-1-yl, 4-carbamoylhexahydropyridazin-1-yl, 5-carbamoylhexahydropyridazin-1-yl, 6-carbamoylhexahydropyridazin-1-yl, 2-methylcarbamoylhexahydropyridazin-1-yl, 3-methylcarbamoylhexahydropyridazin-1-yl, 4-methylcarbamoylhexahydropyridazin-1-yl, 5-methylcarbamoylhexahydropyridazin-1-yl, 6-methylcarbamoylhexahydropyridazin-1-yl, 2-dimethylcarbamoylhexahydropyridazin-1-yl, 3-dimethylcarbamoylhexahydropyridazin-1-yl, 4-dimethylcarbamoylhexahydropyridazin-1-yl, 5-dimethylcarbamoylhexahydropyridazin-1-yl, 6-dimethylcarbamoylhexahydropyridazin-1-yl, 3-carboxyhexahydropyridazin-1-yl, 4-carboxyhexahydropyridazin-1-yl, 5-carboxyhexahydropyridazin-1-yl, 6-carboxyhexahydropyridazin-1-yl, 2-carboxymethylhexahydropyridazin-1-yl, 3-carboxymethylhexahydropyridazin-1-yl, 4-carboxymethylhexahydropyridazin-1-yl, 5-carboxymethylhexahydropyridazin-1-yl, 6-carboxymethylhexahydropyridazin-1-yl, 3-methoxycarboxyhexahydropyridazin-1-yl, 4-methoxycarboxyhexahydropyridazin-1-yl, 5-methoxycarboxyhexahydropyridazin-1-yl, 6-methoxycarboxyhexahydropyridazin-1-yl, 2-methoxycarbonylmethylhexahydropyridazin-1-yl, 3-methoxycarbonylmethylhexahydropyridazin-1-yl, 4-methoxycarbonylmethylhexahydropyridazin-1-yl, 5-methoxycarbonylmethylhexahydropyridazin-1-yl, 6-methoxycarbonylmethylhexahydropyridazin-1-yl, 3-methoxymethylhexahydropyridazin-1-yl, 4-methoxymethylhexahydropyridazin-1-yl, 5-methoxymethylhexahydropyridazin-1-yl, 6-methoxymethylhexahydropyridazin-1-yl, 2-aminoethylhexahydropyridazin-1-yl, 3-aminoethylhexahydropyridazin-1-yl, 4-aminoethylhexahydropyridazin-1-yl, 5-aminoethylhexahydropyridazin-1-yl, 6-aminoethylhexahydropyridazin-1-yl, 2-methylaminoethylhexahydropyridazin-1-yl, 3-methylaminoethylhexahydropyridazin-1-yl, 4-methylaminoethylhexahydropyridazin-1-yl, 5-methylaminoethylhexahydropyridazin-1-yl, 6-methylaminoethylhexahydropyridazin-1-yl, 3-aminomethylhexahydropyridazin-1-yl, 4-aminomethylhexahydropyridazin-1-yl, 5-aminomethylhexahydropyridazin-1-yl, 6-aminomethylhexahydropyridazin-1-yl, 3-methylaminomethylhexahydropyridazin-1-yl, 4-methylaminomethylhexahydropyridazin-1-yl, 5-methylaminomethylhexahydropyridazin-1-yl, 6-methylaminomethylhexahydropyridazin-1-yl, 3-dimethylaminomethylhexahydropyridazin-1-yl, 4-dimethylaminomethylhexahydropyridazin-1-yl, 5-dimethylaminomethylhexahydropyridazin-1-yl, 6-dimethylaminomethylhexahydropyridazin-1-yl, 2-dimethylaminoethylhexahydropyridazin-1-yl, 3-dimethylaminoethylhexahydropyridazin-1-yl, 4-dimethylaminoethylhexahydropyridazin-1-yl, 5-dimethylaminoethylhexahydropyridazin-1-yl, 6-dimethylaminoethylhexahydropyridazin-1-yl, hexahydropyrimidin-1-yl, 2-oxohexahydropyrimidin-1-yl, 4-oxohexahydropyrimidin-1-yl, 5-oxohexahydropyrimidin-1-yl, 6-oxohexahydropyrimidin-1-yl, 2-methylhexahydropyrimidin-1-yl, 3-methylhexahydropyrimidin-1-yl, 4-methylhexahydropyrimidin-1-yl, 4-methylhexahydropyrimidin-1-yl, 2,2-dimethylhexahydropyrimidin-1-yl, 4,4-dimethylhexahydropyrimidin-1-yl, 5,5-dimethylhexahydropyrimidin-1-yl, 6,6-dimethylhexahydropyrimidin-1-yl, 2-hydroxymethylhexahydropyrimidin-1-yl, 4-hydroxymethylhexahydropyrimidin-1-yl, 5-hydroxymethylhexahydropyrimidin-1-yl, 6-hydroxymethylhexahydropyrimidin-1-yl, 2-carboxyhexahydropyrimidin-1-yl, 4-carboxyhexahydropyrimidin-1-yl, 5-carboxyhexahydropyrimidin-1-yl, 6-carboxyhexahydropyrimidin-1-yl, 2-carbamoylhexahydropyrimidin-1-yl, 3-carbamoylhexahydropyrimidin-1-yl, 4-carbamoylhexahydropyrimidin-1-yl, 5-carbamoylhexahydropyrimidin-1-yl, 6-carbamoylhexahydropyrimidin-1-yl, 2-methylcarbamoylhexahydropyrimidin-1-yl, 3-methylcarbamoylhexahydropyrimidin-1-yl, 4-methylcarbamoylhexahydropyrimidin-1-yl, 5-methylcarbamoylhexahydropyrimidin-1-yl, 6-methylcarbamoylhexahydropyrimidin-1-yl, 2-dimethylcarbamoylhexahydropyrimidin-1-yl, 3-dimethylcarbamoylhexahydropyrimidin-1-yl, 4-dimethylcarbamoylhexahydropyrimidin-1-yl, 5-dimethylcarbamoylhexahydropyrimidin-1-yl, 6-dimethylcarbamoylhexahydropyrimidin-1-yl, 2-carboxymethylhexahydropyrimidin-1-yl, 3-carboxymethylhexahydropyrimidin-1-yl, 4-carboxymethylhexahydropyrimidin-1-yl, 5-carboxymethylhexahydropyrimidin-1-yl, 6-carboxymethylhexahydropyrimidin-1-yl, 2-methoxycarbonylmethylhexahydropyrimidin-1-yl, 3-methoxycarbonylmethylhexahydropyrimidin-1-yl, 4-methoxycarbonylmethylhexahydropyrimidin-1-yl, 5-methoxycarbonylmethylhexahydropyrimidin-1-yl, 6-methoxycarbonylmethylhexahydropyrimidin-1-yl, 3-methoxymethylhexahydropyrimidin-1-yl, 4-methoxymethylhexahydropyrimidin-1-yl, 5-methoxymethylhexahydropyrimidin-1-yl, 6-methoxymethylhexahydropyrimidin-1-yl, 2-aminoethylhexahydropyrimidin-1-yl, 3-aminoethylhexahydropyrimidin-1-yl, 4-aminoethylhexahydropyrimidin-1-yl, 5-aminoethylhexahydropyrimidin-1-yl, 6-aminoethylhexahydropyrimidin-1-yl, 2-methylaminoethylhexahydropyrimidin-1-yl, 3-methylaminoethylhexahydropyrimidin-1-yl, 4-methylaminoethylhexahydropyrimidin-1-yl, 5-methylaminoethylhexahydropyrimidin-1-yl, 6-methylaminoethylhexahydropyrimidin-1-yl, 2-dimethylaminoethylhexahydropyrimidin-1-yl, 3-dimethylaminoethylhexahydropyrimidin-1-yl, 4-dimethylaminoethylhexahydropyrimidin-1-yl, 5-dimethylaminoethylhexahydropyrimidin-1-yl, 6-dimethylaminoethylhexahydropyrimidin-1-yl, homopiperazino, 2-oxohomopiperazino, 3-oxohomopiperazino, 5-oxohomopiperazino, 6-oxohomopiperazino, 7-oxohomopiperazino, 2-oxo-4-methylhomopiperazino, 3-oxo-4-methylhomopiperazino, 5-oxo-4-methylhomopiperazino, 6-oxo-4-methylhomopiperazino, 7-oxo-4-methylhomopiperazino, 2,3-dioxohomopiperazino, 2,7-dioxohomopiperazino, 3,5-dioxohomopiperazino, 3,7-dioxohomopiperazino, 2,3-dioxo-4-methylhomopiperazino, 2,7-dioxo-4-methylhomopiperazino, 3,5-dioxo-4-methylhomopiperazino, 3,7-dioxo-4-methylhomopiperazino, 2-methylhomopiperazino, 3-methylhomopiperazino, 4-methylhomopiperazino, 5-methylhomopiperazino, 6-methylhomopiperazino, 7-methylhomopiperazino, 2-ethylhomopiperazino, 3-ethylhomopiperazino, 4-ethylhomopiperazino, 5-ethylhomopiperazino, 6-ethylhomopiperazino, 7-ethylhomopiperazino, 4-cyclopropylhomopiperazino, 2-cyclopropanespirohomopiperazino, 3-cyclopropanespirohomopiperazino, 5 cyclopropanespirohomopiperazino, 6-cyclopropanespirohomopiperazino, 7-cyclopropanespirohomopiperazino, 2-cyclapropanespiro-4-methylhomopiperazino, 3-cyclopropanespiro-4-methylhomopiperazino, 5-cyclopropanespiro-4-methylhomopiperazino, 6-cyclopropanespiro-4-methylhomopiperazino, 7-cyclopropanespiro-4-methylhomopiperazino, 2-cyclopropanespiro-4-methyl-3-oxohomopiperazino, 2-cyclopropanespiro-4-methyl-5-oxohomopiperazino, 2-cyclopropanespiro-4-methyl-7-oxohomopiperazino, 3-cyclopropanespiro-4-methyl-2-oxohomopiperazino, 3-cyclopropanespiro-4-methyl-5-oxohomopiperazino, 3-cyclopropanespiro-4-methyl-7-oxohomopiperazino, 5-cyclopropanespiro-4-methyl-2-oxohomopiperazino, 5-cyclopropanespiro-4-methyl-3-oxohomopiperazino, 5-cyclopropanespiro-4-methyl-7-oxohomopiperazino, 6-cyclopropanespiro-4-methyl-2-oxohomopiperazino, 6-cyclopropanespiro-4-methyl-3-oxohomopiperazino, 6-cyclopropanespiro-4-methyl-5-oxohomopiperazino, 6-cyclopropanespiro-4-methyl-7-oxohomopiperazino, 7-cyclopropanespiro-4-methyl-2-oxohomopiperazino, 7-cyclopropanespiro-4-methyl-3-oxohomopiperazino, 7-cyclopropanespiro-4-methyl-5-oxohomopiperazino, 2,2-dimethylhomopiperazino, 3,3-dimethylhomopiperazino, 5,5-dimethylhomopiperazino, 6,6-dimethylhomopiperazino, 7,7-dimethylhomopiperazino, 2,3-dimethylhomopiperazino, 2,4-dimethylhomopiperazino, 3,4-dimethylhomopiperazino, 3,5-dimethylhomopiperazino, 3,4,5-trimethylhomopiperazino, 2-hydroxymethylhomopiperazino, 3-hydroxymethylhomopiperazino, 5-hydroxymethylhomopiperazino, 6-hydroxymethylhomopiperazino, 7-hydroxymethylhomopiperazino, 2-hydroxymethyl-4-methylhomopiperazino, 3-hydroxymethyl-4-methylhomopiperazino, 5-hydroxymethyl-4-methylhomopiperazino, 6-hydroxymethyl-4-methylhomopiperazino, 7-hydroxymethyl-4-methylhomopiperazino, 2-methoxymethylhomopiperazino, 3-methoxymethylhomopiperazino, 5-methoxymethylhomopiperazino, 6-methoxymethylhomopiperazino, 7-methoxymethylhomopiperazino, 2-methoxymethyl-4-methylhomopiperazino, 3-methoxymethyl-4-methylhomopiperazino, 5-methoxymethyl-4-methylhomopiperazino, 6-methoxymethyl-4-methylhomopiperazino, 7-methoxymethyl-4-methylhomopiperazino, 2-hydroxyethylhomopiperazino, 3-hydroxyethylhomopiperazino, 4-hydroxyethylhomopiperazino, 5-hydroxyethylhomopiperazino, 6-hydroxyethylhomopiperazino, 7-hydroxyethylhomopiperazino, 2-hydroxyethyl-4-methylhomopiperazino, 3-hydroxyethyl-4-methylhomopiperazino, 5-hydroxyethyl-4-methylhomopiperazino, 6-hydroxyethyl-4-methylhomopiperazino, 7-hydroxyethyl-4-methylhomopiperazino, 2-methoxyethylhomopiperazino, 3-methoxyethylhomopiperazino, 4-methoxyethylhomopiperazino, 5-methoxyethylhomopiperazino, 6-methoxyethylhomopiperazino, 7-methoxyethylhomopiperazino, 2-methoxyethyl-4-methylhomopiperazino, 3-methoxyethyl-4-methylhomopiperazino, 5-methoxyethyl-4-methylhomopiperazino, 6-methoxyethyl-4-methylhomopiperazino, 7-methoxyethyl-4-methylhomopiperazino, 2-carbamoylhomopiperazino, 3-carbamoylhomopiperazino, 4-carbamoylhomopiperazino, 5-carbamoylhomopiperazino, 6-carbamoylhomopiperazino, 7-carbamoylhomopiperazino, 2-carbamoyl-4-methylhomopiperazino, 3-carbamoyl-4-methylhomopiperazino, 4-carbamoylhomopiperazino, 5-carbamoyl-4-methylhomopiperazino, 6-carbamoyl-4-methylhomopiperazino, 7-carbamoyl-4-methylhomopiperazino, 2-methylcarbamoylhomopiperazino, 3-methylcarbamoylhomopiperazino, 4-methylcarbamoylhomopiperazino, 5-methylcarbamoylhomopiperazino, 6-methylcarbamoylhomopiperazino, 7-methylcarbamoylhomopiperazino, 2-methylcarbamoyl-4-methylhomopiperazino, 3-methylcarbamoyl-4-methylhomopiperazino, 5-methylcarbamoyl-4-methylhomopiperazino, 6-methylcarbamoyl-4-methylhomopiperazino, 7-methylcarbamoyl-4-methylhomopiperazino, 2-dimethylcarbamoylhomopiperazino, 3-dimethylcarbamoylhomopiperazino, 4-dimethylcarbamoylhomopiperazino, 5-dimethylcarbamoylhomopiperazino, 6-dimethylcarbamoylhomopiperazino, 7-dimethylcarbamoylhomopiperazino, 2-dimethylcarbamoyl-4-methylhomopiperazino, 3-dimethylcarbamoyl-4-methylhomopiperazino, 5-dimethylcarbamoyl-4-methylhomopiperazino, 6-dimethylcarbamoyl-4-methylhomopiperazino, 7-dimethylcarbamoyl-4-methylhomopiperazino, 2-carboxyhomopiperazino, 3-carboxyhomopiperazino, 5-carboxyhomopiperazino, 6-carboxyhomopiperazino, 7-carboxyhomopiperazino, 2-carboxy-4-methylhomopiperazino, 3-carboxy-4-methylhomopiperazino, 5-carboxy-4-methylhomopiperazino, 6-carboxy-4-methylhomopiperazino, 7-carboxy-4-methylhomopiperazino, 2-carboxymethylhomopiperazino, 3-carboxymethylhomopiperazino, 4-carboxymethylhomopiperazino, 5-carboxymethylhomopiperazino, 6-carboxymethylhomopiperazino, 7-carboxymethylhomopiperazino, 2-carboxymethyl-4-methylhomopiperazino, 3-carboxymethyl-4-methylhomopiperazino, 5-carboxymethyl-4-methylhomopiperazino, 6-carboxymethyl-4-methylhomopiperazino, 7-carboxymethyl-4-methylhomopiperazino, 2-methoxycarbonylmethylhomopiperazino, 3-methoxycarbonylmethylhomopiperazino, 4-methoxycarbonylmethylhomopiperazino, 5-methoxycarbonylmethylhomopiperazino, 6-methoxycarbonylmethylhomopiperazino, 7-methoxycarbonylmethylhomopiperazino, 2-methoxycarbonylmethyl-4-methylhomopiperazino, 3-methoxycarbonylmethyl-4-methylhomopiperazino, 5-methoxycarbonylmethyl-4-methylhomopiperazino, 6-methoxycarbonylmethyl-4-methylhomopiperazino, 7-methoxycarbonylmethyl-4-methylhomopiperazino, 2-ethoxycarbonylmethylhomopiperazino, 3-ethoxycarbonylmethylhomopiperazino, 4-ethoxycarbonylmethylhomopiperazino, 5-ethoxycarbonylmethylhomopiperazino, 6-ethoxycarbonylmethylhomopiperazino, 7-ethoxycarbonylmethylhomopiperazino, 2-ethoxycarbonylmethyl-4-methylhomopiperazino, 3-ethoxycarbonylmethyl-4-methylhomopiperazino, 5-ethoxycarbonylmethyl-4-methylhomopiperazino, 6-ethoxycarbonylmethyl-4-methylhomopiperazino, 7-ethoxycarbonylmethyl-4-methylhomopiperazino, 2-carbamoylmethylhomopiperazino, 3-carbamoylmethylhomopiperazino, 4-carbamoylmethylhomopiperazino, 5-carbambylmethylhomopiperazino, 6-carbamoylmethylhomopiperazino, 7-carbamoylmethylhomopiperazino, 2-carbamoylmethyl-4-methylhomopiperazino, 3-carbamoylmethyl-4-methylhomopiperazino, 5-carbamoylmethyl-4-methylhomopiperazino, 6-carbamoylmethyl-4-methylhomopiperazino, 7-carbamoylmethyl-4-methylhomopiperazino, 2-methylcarbamoylmethylhomopiperazino, 3-methylcarbamoylmethylhomopiperazino, 4-methylcarbamoylhomopiperazino, 5-methylcarbamoylhomopiperazino, 6-methylcarbamoylhomopiperazino, 7-methylcarbamoylhomopiperazino, 2-methylcarbamoylmethyl-4-methylhomopiperazino, 3-methylcarbamoylmethyl-4-methylhomopiperazino, 5-methylcarbamoyl-4-methylhomopiperazino, 6-methylcarbamoyl-4-methylhomopiperazino, 7-methylcarbamoyl-4-methylhomopiperazino, 2-dimethylcarbamoylmethylhomopiperazino, 3-dimethylcarbamoylmethylhomopiperazino, 4-dimethylcarbamoylmethylhomopiperazino, 5-dimethylcarbamoylmethylhomopiperazino, 6-dimethylcarbamoylmethylhomopiperazino, 7-dimethylcarbamoylmethylhomopiperazino, 2-dimethylcarbamoylmethyl-4-methylhomopiperazino, 3-dimethylcarbamoylmethyl-4-methylhomopiperazino, 5-dimethylcarbamoylmethyl-4-methylhomopiperazino, 6-dimethylcarbamoylmethyl-4-methylhomopiperazino, 7-dimethylcarbamoylmethyl-4-methylhomopiperazino, 2-aminomethylhomopiperazino, 3-aminomethylhomopiperazino, 5-aminomethylhomopiperazino, 6-aminomethylhomopiperazino, 7-aminomethylhomopiperazino, 2-aminomethyl-4-methylhomopiperazino, 3-aminomethyl-4-methylhomopiperazino, 5-aminomethyl-4-methylhomopiperazino, 6-aminomethyl-4-methylhomopiperazino, 7-aminomethyl-4-methylhomopiperazino, 2-methylaminomethylhomopiperazino, 3-methylaminomethylhomopiperazino, 4-methylaminomethylhomopiperazino, 5-methylaminomethylhomopiperazino, 6-methylaminomethylhomopiperazino, 7-methylaminomethylhomopiperazino, 2-methylaminomethyl-4-methylhomopiperazino, 3-methylaminomethyl-4-methylhomopiperazino, 5-methylaminomethyl-4-methylhomopiperazino, 6-methylaminomethyl-4-methylhomopiperazino, 7-methylaminomethyl-4-methylhomopiperazino, 2-dimethylaminomethylhomopiperazino, 3-dimethylaminomethylhomopiperazino, 4-dimethylaminomethylhomopiperazino, 5-dimethylaminomethylhomopiperazino, 6-dimethylaminomethylhomopiperazino, 7-dimethylaminomethylhomopiperazino, 2-dimethylaminomethyl-4-methylhomopiperazino, 3-dimethylaminomethyl-4-methylhomopiperazino, 5-dimethylaminomethyl-4-methylhomopiperazino, 6-dimethylaminomethyl-4-methylhomopiperazino, 7-dimethylaminomethyl-4-methylhomopiperazino, 2-aminoethylhomopiperazino, 3-aminoethylhomopiperazino, 4-aminoethylhomopiperazino, 5-aminoethylhomopiperazino, 6-aminoethylhomopiperazino, 7-aminoethylhomopiperazino, 2-aminoethyl-4-methylhomopiperazino, 3-aminoethyl-4-methylhomopiperazino, 5-aminoethyl-4-methylhomopiperazino, 6-aminoethyl-4-methylhomopiperazino, 7-aminoethyl-4-methylhomopiperazino, 2-methylaminoethylhomopiperazino, 3-methylaminoethylhomopiperazino, 4-methylaminoethylhomopiperazino, 5-methylaminoethylhomopiperazino, 6-methylaminoethylhomopiperazino, 7-methylaminoethylhomopiperazino, 2-methylaminoethyl-4-methylhomopiperazino, 3-methylaminoethyl-4-methylhomopiperazino, 5-methylaminoethyl-4-methylhomopiperazino, 6-methylaminoethyl-4-methylhomopiperazino, 7-methylaminoethyl-4-methylhomopiperazino, 2-dimethylaminoethylhomopiperazino, 3-dimethylaminoethylhomopiperazino, 4-dimethylaminoethylhomopiperazino, 5-dimethylaminoethylhomopiperazino, 6-dimethylaminoethylhomopiperazino, 7-dimethylaminoethylhomopiperazino, 2-dimethylaminoethyl-4-methylhomopiperazino, 3-dimethylaminoethyl-4-methylhomopiperazino, 5-dimethylaminoethyl-4-methylhomopiperazino, 6-dimethylaminoethyl-4-methylhomopiperazino, 7-dimethylaminoethyl-4-methylhomopiperazino, 4-methanesulfonylhomopiperazino, 4-methanesulfonylaminohomopiperazino, 4-(azetidin-1-yl)homopiperazino, 4-pyrrolidinohomopiperazino, 0.4-piperidinohomopiperazino, 1,4-oxazepan-4-yl, spiro[azetidine-3,2'-1'-methylazetidin]-1-yl, spiro[piperidine-4,2'-1'-methylazetidin]-1-yl, spiro[piperidine-2,3'-1'-methylazetidin]-1-yl, spiro[piperidine-2,3'-1'-methylpyrrolidin]-1-yl, spiro[morpholine-3,3'-1'-methylazetidin]-4-yl, spiro[morpholine-3,3'-1'-methylpyrrolidin]-4-yl, spiro[piperazine-3-cyclopropan]-1-yl, and spiro[4-methylpiperazine-3-cyclopropan]-1-yl.

Of these, preferred groups are the following:

Azetidin-1-yl, 3-dimethylaminoazetidin-1-yl, 2-methylazetidin-1-yl, 3-methylazetidin-1-yl, 2,2-dimethylazetidin-1-yl, 3,3-dimethylazetidin-1-yl, 2,2-dimethyl-3-dimethylaminoazetidin-1-yl, 2-hydroxymethylazetidin-1-yl, 3-hydroxymethylazetidin-1-yl, 2-carbamoylazetidin-1-yl, 2-methylcarbamoylazetidin-1-yl, 2-dimethylcarbamoylazetidin-1-yl, pyrrolidino, 2-oxopyrrolidino, 2-dimethylaminomethylpyrrolidino, 3-dimethylaminomethylpyrrolidino, 2,5-dioxopyrrolidino, 2-methylpyrrolidino, 3-methylpyrrolidino, 2,2-dimethylpyrrolidino, 3,3-dimethylpyrrolidino, 2-hydroxymethylpyrrolidino, 3-hydroxymethylpyrrolidino, 3-methoxypyrrolidino, 2-methoxymethylpyrrolidino, 3-methoxymethylpyrrolidino, 2-carbamoylpyrrolidino, 2-methylcarbamoylpyrrolidino, 2-dimethylcarbamoylpyrrolidino, 2-oxoimidazolidin-1-yl, 4-oxoimidazolidin-1-yl, 3-methyl-2-oxoimidazolidin-1-yl, 3-methyl-4-oxoimidazolidin-1-yl, 2-methylpyrazolidin-1-yl, 3-oxopyrazolidin-1-yl, 3,5-dioxopyrazolidin-1-yl, piperidino, 2-oxopiperidino, 3-oxopiperidino, 4-oxopiperidino, 2-hydroxyiminopiperidino, 3-hydroxyiminopiperidino, 4-hydroxyiminopiperidino, 2-methoxypiperidino, 3-methoxypiperidino, 4-methoxypiperidino, 2-methoxyiminopiperidino, 3-methoxyiminopiperidino, 4-methoxyiminopiperidino, 2-methylpiperidino, 3-methylpiperidino, 4-methylpiperidino, 2,2-dimethylpiperidino, 3,3-dimethylpiperidino, 4,4-dimethylpiperidino, 4-fluoropiperidino, 4-chloropiperidino, 3,3-difluoropiperidino, 4,4-difluoropiperidino, 3,3-dichloropiperidino, 4,4-dichloropiperidino, 2-hydroxymethylpiperidino, 2-carbamoylpiperidino, 2-methylcarbamoylpiperidino, 2-dimethylcarbamoylpiperidino, 2-carboxymethylpiperidino, 2-methoxymethylpiperidino, 2-aminomethylpiperidino, 2-methylaminomethylpiperidino, 2-dimethylaminomethylpiperidino, 2-aminoethylpiperidino, 2-methylaminoethylpiperidino, 2-dimethylaminoethylpiperidino, 2-oxo-4-methylpiperazino, 3-oxo-4-methylpiperazino, 4-formylpiperazino, 2,3-dioxo-4-methylpiperazino, 3,5-dioxo-4-methylpiperazino, 2,6-dioxo-4-methylpiperazino, 4-methylpiperazino, 4-ethylpiperazino, 4-isopropylpiperazino, 2,4-dimethylpiperazino, 3,4-dimethylpiperazino, 2-ethyl-4-methyl-piperazino, 3-ethyl-4-methylpiperazino, 2-isopropyl-4-methylpiperazino, 3-isopropyl-4-methylpiperazino, 2-cyclopropyl-4-methylpiperazino, 3-cyclopropyl-4-methylpiperazino, 3,4,5-trimethylpiperazino, 2,2,4-trimethylpiperazino, 3,3,4-trimethylpiperazino, 3,3,4-trimethyl-5-oxopiperazino, 2,2,4-trimethyl-3-oxopiperazino, 2-cyclopropanespiro-4-methylpiperazino, 3-cyclopropanespiro-4-methylpiperazino, 2-cyclopropanespiro-4-methyl-3-oxopiperazino, 3-cyclopropanespiro-4-methyl-5-oxopiperazino, 4-acetyl-3-cyclopropanespiropiperazino, 2-hydroxymethyl-4-methylpiperazino, 3-hydroxymethyl-4-methylpiperazino, 2-methoxymethyl-4-methylpiperazino, 3-methoxymethyl-4-methylpiperazino, 2-hydroxyethyl-4-methylpiperazino, 3-hydroxyethyl-4-methylpiperazino, 2-methoxyethyl-4-methylpiperazino, 3-methoxyethyl-4-methylpiperazino, 2-carbamoyl-4-methylpiperazino, 3-carbamoyl-4-methylpiperazino, 4-carbamoylpiperazino, 2-methylcarbamoyl-4-methylpiperazino, 3-methylcarbamoyl-4-methylpiperazino, 4-methylcarbamoylpiperazino, 2-dimethylcarbamoyl-4-methylpiperazino, 3-dimethylcarbamoyl-4-methylpiperazino, 4-dimethylcarbamoylpiperazino, 2-carboxymethyl-4-methylpiperazino, 3-carbamoylmethyl-4-methylpiperazino, 4-carbamoylmethylpiperazino, 2-methylcarbamoylmethyl-4-methylpiperazino, 3-methylcarbamoylmethyl-4-methylpiperazino, 4-methylcarbamoylpiperazino, 2-dimethylcarbamoylmethyl-4-methylpiperazino, 3-dimethylcarbamoylmethyl-4-methylpiperazino, 2-carboxy-4-methylpiperazino, 2-carboxymethyl-4-methylpiperazino, 2-methoxycarbonylmethyl-4-methylpiperazino, 3-methoxycarbonylmethyl-4-methylpiperazino, 2-ethoxycarbonylmethyl-4-methylpiperazino, 3-ethoxycarbonylmethyl-4-methylpiperazino, 2-aminomethyl-4-methylpiperazino, 2-methylaminomethyl-4-methylpiperazino, 2-dimethylaminomethyl-4-methylpiperazino, 2-aminoethyl-4-methylpiperazino, 2-methylaminoethyl-4-methylpiperazino, 2-dimethylaminoethyl-4-methylpiperazino, morpholino, 2-methylmorpholino, 3-methylmorpholino, 2-ethylmorpholino, 3-ethylmorpholino, 2-cyclopropanespiromorpholino, 3-cyclopropanespiromorpholino, 2,2-dimethylmorpholino, 3,3-dimethylmorpholino, 3-hydroxymethylmorpholino, 3-methoxymethylmorpholino, 3-hydroxyethylmorpholino, 3-methoxyethylmorpholino, 3-carbamoylmorpholino, 3-methylcarbamoylmorpholino, 3-dimethylcarbamoylmorpholino, 3-carbamoylmethylmorpholino, 3-methylcarbamoylmethylmorpholino, 3-dimethylcarbamoylmethylmorpholino, 3-carbamoylethylmorpholino, 3-methylcarbamoylethylmorpholino, 3-dimethylcarbamoylethylmorpholino, 3-methoxycarbonylmorpholino, 3-methoxycarbonylmethylmorpholino, 3-ethoxycarbonylmethylmorpholino, 3-aminomethylmorpholino, 3-methylaminomethylmorpholino, 3-dimethylaminomethylmorpholino, 3-aminoethylmorpholino, 3-methylaminoethylmorpholino, 3-dimethylaminoethylmorpholino, thiomorpholino, 3-oxothiomorpholino, 1,1-dioxothiomorpholino, 2-methylthiomorpholino, 3-methylthiomorpholino, 2-ethylthiomorpholino, 3-ethylthiomorpholino, 2-cyclopropanespirothiomorpholino, 3-cyclopropanespirothiomorpholino, 2,2-dimethylthiomorpholino, 3,3-dimethylthiomorpholino, 3-hydroxymethylthiomorpholino, 3-methoxymethylthiomorpholino, 3-hydroxyethylthiomorpholino, 3-methoxyethylthiomorpholino, 3-carbamoylthiomorpholino, 3-methylcarbamoylthiomorpholino, 3-dimethylcarbamoylthiomorpholino, 3-carbamoylmethylthiomorpholino, 3-methylcarbamoylmethylthiomorpholino, 3-dimethylcarbamoylmethylthiomorpholino, 3-carbamoylethylthiomorpholino, 3-methylcarbamoylethylthiomorpholino, 3-dimethylcarbamoylethylthiomorpholino, 3-methoxycarbonylthiomorpholino, 3-methoxycarbonylmethylthiomorpholino, 3-ethoxycarbonylmethylthiomorpholino, 2-acetylhexahydropyridazin-1-yl, 2-formylhexahydropyridazin-1-yl, 3-oxohexahydropyridazin-1-yl, 6-oxohexahydropyridazin-1-yl, 2,3-dimethylhexahydropyridazin-1-yl, 3-hydroxymethylhexahydropyridazin-1-yl, 5-hydroxymethylhexahydropyridazin-1-yl, 6-hydroxymethylhexahydropyridazin-1-yl, 2-carbamoylhexahydropyridazin-1-yl, 2-methylcarbamoylhexahydropyridazin-1-yl, 2-dimethylcarbamoylhexahydropyridazin-1-yl, 2-oxohexahydropyrimidin-1-yl, 4-oxohexahydropyrimidin-1-yl, 6-oxohexahydropyrimidin-1-yl, 2-methylhexahydropyrimidin-1-yl, 3-methylhexahydropyrimidin-1-yl, 3-carbamoylhexahydropyrimidin-1-yl, 3-methylcarbamoylhexahydropyrimidin-1-yl, 3-dimethylcarbamoylhexahydropyrimidin-1-yl, 2-oxo-4-methylhomopiperazino, 3-oxo-4-methylhomopiperazino, 5-oxo-4-methylhomopiperazino, 6-oxo-4-methylhomopiperazino, 7-oxo-4-methylhomopiperazino, 2,3-dioxohomopiperazino, 2,7-dioxohomopiperazino, 3,5-dioxohomopiperazino, 3,7-dioxohomopiperazino, 2,3-dioxo-4-methylhomopiperazino, 2,7-dioxo-4-methylhomopiperazino, 3,5-dioxo-4-methylhomopiperazino, 3,7-dioxo-4-methylhomopiperazino, 4-methylhomopiperazino, 4-ethylhomopiperazino, 4-cyclopropylhomopiperazino, 2-cyclopropanespirohomopiperazino, 3-cyclopropanespirohomopiperazino, 5-cyclopropanespirohomopiperazino, 6-cyclopropanespirohomopiperazino, 7-cyclopropanespirohomopiperazino, 2,4-dimethylhomopiperazino, 3,4-dimethylhomopiperazino, 3,4,5-trimethylhomopiperazino, 2-hydroxymethyl-4-methylhomopiperazino, 7-hydroxymethyl-4-methylhomopiperazino, 2-methoxymethyl-4-methylhomopiperazino, 3-methoxymethyl-4-methylhomopiperazino, 5-methoxymethyl-4-methylhomopiperazino, 6-methoxymethyl-4-methylhomopiperazino, 7-methoxymethyl-4-methylhomopiperazino, 2-hydroxyethyl-4-methylhomopiperazino, 7-hydroxyethyl-4-methylhomopiperazino, 2-methoxyethyl-4-methylhomopiperazino, 3-methoxyethyl-4-methylhomopiperazino, 5-methoxyethyl-4-methylhomopiperazino, 6-methoxyethyl-4-methylhomopiperazino, 7-methoxyethyl-4-methylhomopiperazino, 2-carbamoyl-4-methylhomopiperazino, 7-carbamoyl-4-methylhomopiperazino, 2-methylcarbamoyl-4-methylhomopiperazino, 7-methylcarbamoyl-4-methylhomopiperazino, 2-dimethylcarbamoylhomopiperazino, 7-dimethylcarbamoylhomopiperazino, 2-carboxyhomopiperazino, 7-carboxyhomopiperazino, 2-carboxy-4-methylhomopiperazino, 7-carboxy-4-methylhomopiperazino, 2-carboxymethyl-4-methylhomopiperazino, 7-carboxymethyl-4-methylhomopiperazino, and 1,4-oxazepan-4-yl.

Among them, particularly preferred groups are the following.

Azetidin-1-yl, 3-dimethylaminoazetidin-1-yl, 2,2-dimethyl-3-dimethylaminoazetidin-1-yl, 2-hydroxymethylazetidin-1-yl, 2-carbamoylazetidin-1-yl, 2-methylcarbamoylazetidin-1-yl, 2-dimethylcarbamoylazetidin-1-yl, pyrrolidino, 2-oxopyrrolidino, 2,5-dioxopyrrolidino, 2-methylpyrrolidino, 3-methylpyrrolidino, 2,2-dimethylpyrrolidino, 3,3-dimethylpyrrolidino, 2-dimethylaminomethylpyrrolidino, 3-dimethylaminomethylpyrrolidino, 2-hydroxymethylpyrrolidino, 3-methoxymethylpyrrolidino, 2-carbamoylpyrrolidino, 2-methylcarbamoylpyrrolidino, 2-dimethylcarbamoylpyrrolidino, 3-methyl-2-oxoimidazolidin-1-yl, 3-methyl-4-oxoimidazolidin-1-yl, piperidino, 2-oxopiperidino, 2-methoxypiperidino, 3-methoxypiperidino, 4-methoxypiperidino, 2-hydroxymethylpiperidino, 2-carbamoylpiperidino, 2-methylcarbamoylpiperidino, 2-dimethylcarbamoylpiperidino, 2-methoxymethylpiperidino, 2-aminomethylpiperidino, 2-methylaminomethylpiperidino, 2-dimethylaminomethylpiperidino, 2-aminoethylpiperidino, 2-methylaminoethylpiperidino, 2-dimethylaminoethylpiperidino, 4-fluoropiperidino, 3,3-difluoropiperidino, 4,4-difluoropiperidino, 2-oxo-4-methylpiperazino, 3-oxo-4-methylpiperazino, 4-formylpiperazino, 2,3-dioxopiperazino, 3,5-dioxopiperazino, 2,6-dioxopiperazino, 4-methylpiperazino, 4-ethylpiperazino, 4-isopropylpiperazino, 4-cyclopropylpiperazino, 2,4-dimethylpiperazino, 3,4-dimethylpiperazino, 2-methyl-4-methylpiperazino, 3-methyl-4-methylpiperazino, 3,4,5-trimethylpiperazino, 2,2,4-trimethylpiperazino, 3,3,4-trimethylpiperazino, 3,3,4-trimethyl-5-oxopiperazino, 2,2,4-trimethyl-3-oxopiperazino, 2-cyclopropanespiro-4-methylpiperazino, 3-cyclopropanespiro-4-methylpiperazino, 2-cyclopropanespiro-4-methyl-3-oxopiperazino, 3-cyclopropanespiro-4-methyl-5-oxopiperazino, 4-acetyl-3-cyclopropanespiropiperazino, 2-hydroxymethyl-4-methylpiperazino, 3-hydroxymethyl-4-methylpiperazino, 2-methoxymethyl-4-methyl-piperazino, 3-methoxymethyl-4-methylpiperazino, 2-hydroxyethyl-4-methylpiperazino, 3-hydroxyethyl-4-methylpiperazino, 2-methoxyethyl-4-methylpiperazino, 3-methoxyethyl-4-methylpiperazino, 2-carbamoyl-4-methylpiperazino, 2-methylcarbamoyl-4-methylpiperazino, 2-dimethylcarbamoyl-4-methylpiperazino, 2-carbamoylmethyl-4-methylpiperazino, 2-methylcarbamoylmethyl-4-methylpiperazino, 2-dimethylcarbamoylmethyl-4-methylpiperazino, 2-methoxycarbonylmethyl-4-methylpiperazino, 2-ethoxycarbonylmethyl-4-methylpiperazino, 2-aminomethyl-4-methylpiperazino, 2-methylaminomethyl-4-methylpiperazino, 2-dimethylaminomethyl-4-methylpiperazino, 2-aminoethyl-4-methylpiperazino, 2-methylaminoethyl-4-methylpiperazino, 2-dimethylaminoethyl-4-methylpiperazino, morpholino, 2-cyclopropanespiromorpholino, 3-cyclopropanespiromorpholino, 2,2-dimethylmorpholino, 3,3-dimethylmorpholino, 3-hydroxymethylmorpholino, 3-methoxymethylmorpholino, 3-hydroxyethylmorpholino, 3-methoxyethylmorpholino, 3-carbamoylmorpholino, 3-methylcarbamoylmorpholino, 3-dimethylcarbamoylmorpholino, 3-aminomethylmorpholino, 3-methylaminomethylmorpholino, 3-dimethylaminomethylmorpholino, 3-aminoethylmorpholino, 3-methylaminoethylmorpholino, 3-dimethylaminoethylmorpholino, thiomorpholino, 3-oxothiomorpholino, 1,1-dioxothiomorpholino, 3-hydroxymethylthiomorpholino, 3-hydroxyethylthiomorpholino, 2-acetylhexahydropyridazin-1-yl, 2-formylhexahydropyridazin-1-yl, 3-oxohexahydropyridazin-1-yl, 2-methylhexahydropyridazin-1-yl, 2-carbamoylhexahydropyridazin-1-yl, 2-oxohexahydropyrimidin-1-yl, 4-oxohexahydropyrimidin-1-yl, 3-methylhexahydropyrimidin-1-yl, 6-hydroxymethylhexahydropyrimidin-1-yl, 2-oxo-4-methylhomopiperazino, 3-oxo-4-methylhomopiperazino, 5-oxo-4-methylhomopiperazino, 7-oxo-4-methylhomopiperazino, 2,3-dioxohomopiperazino, 2,7-dioxohomopiperazino, 3,5-dioxohomopiperazino, 3,7-dioxohomopiperazino, 4-methylhomopiperazino, 4-ethylhomopiperazino, 4-cyclopropylhomopiperazino, 2-cyclopropanespiro-4-methylhomopiperazino, 3-cyclopropanespiro-4-methylhomopiperazino, 5-cyclopropanespiro-4-methylhomopiperazino, 7-cyclopropanespiro-4-methylhomopiperazino, and 1,4-oxazepan-4-yl.

Still more preferred examples include 3-dimethylaminoazetidin-1-yl, 2,2-dimethyl-3-dimethylaminoazetidin-1-yl, 2-hydroxymethylazetidin-1-yl, 2-carbamoylazetidin-1-yl, 2-oxopyrrolidino, 2-hydroxymethylpyrrolidino, 2-carbamoylpyrrolidino, 2-hydroxymethylpiperidino, 2-carbamoylpiperidino, 2-methylcarbamoylpiperidino, 2-dimethylcarbamoylpiperidino, 3-oxo-4-methylpiperazino, 4-methylpiperazino, 4-ethylpiperazino, 4-isopropylpiperazino, 4-cyclopropylpiperazino, 2,4-dimethylpiperazino, 3,4-dimethylpiperazino, 3-cyclopropyl-4-methylpiperazino, 3,4,5-trimethylpiperazino, 2,2,4-trimethylpiperazino, 3,3,4-trimethylpiperazino, 2-cyclopropanespiro-4-methylpiperazino, morpholino, 3-carbamoylmorpholino, 1,1-dioxothiomorpholino, 2-methylhexahydropyridazin-1-yl, 3-methylhexahydropyridazin-1-yl, 3-oxo-4-methylhomopiperazino, 5-oxo-4-methylhomopiperazino, 4-methylhomopiperazino, 4-ethylhomopiperazino, 4-cyclopropylhomopiperazino, 1,4-oxazepan-4-yl, piperidino, 4-methoxypiperidino, thiomorpholino, 4,4-difluoropiperidino, 3,3-difluoropiperidino, 4-fluoropiperidino, 2-dimethylaminomethylpyrrolidino, 3-dimethylaminopyrrolidino, 3-methyl-4-oxoimidazolidin-1-yl, 3-methoxypyrrolidino, 2-acetylhexahydropyridazin-1-yl, and 2-carbamoylhexahydropyridazin-1-yl.

All the compounds (I) and (II) of the present invention do not necessarily form salts. However, when the compound (I) or (II) has a carboxyl group, an amino group, or a like group, and/or when $Ar_1$, $Ar_2$, $Ar_3$, or $Ar_4$ is a pyridine ring or an analogous ring, the compound can form a salt, and in some cases, the salt may form a solvate. Examples of the salt include salts of inorganic acids such as hydrochloric acid, hydrobromic acid, sulfuric acid, and nitric acid; salts of organic acids such as methanesulfonic acid, p-toluenesulfonic acid, fumaric acid, and trifluoroacetic acid; and salts of alkali metal ions or alkaline earth metal ions, such as sodium ion, potassium ion, or calcium ion.

The solvate of the present compound (I) or (II) and the solvate of a salt of the present compound (I) or (II) include those formed through addition of a solvent employed in a crystallization step and those formed through absorption of moisture in air. Examples of the solvent include lower alcohols such as methanol and ethanol; other organic solvents such as acetone and acetonitrile; and water.

The compound (I) of the present invention may be produced through the following process:

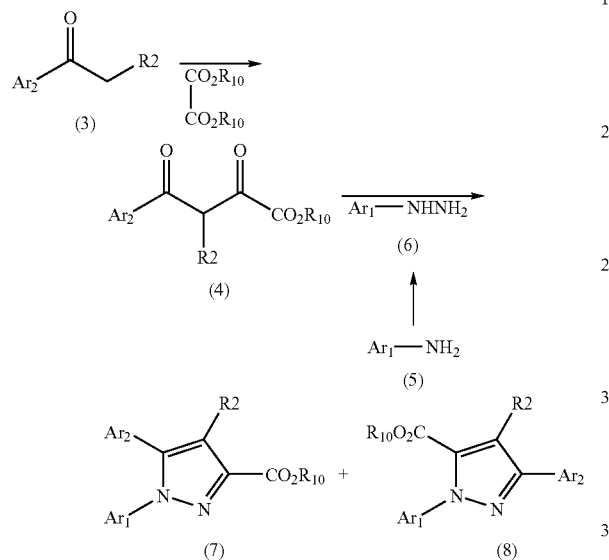

(wherein $Ar_1$, $Ar_2$, and R2 have the same meanings as described above, and R10 represents a methyl group or an ethyl group).

Specifically, a compound (3) and dialkyl oxalate are dissolved or suspended in a suitable solvent such as N,N-dimethylformamide, and sodium hydride is added to the solution under argon flow at a temperature of −20 to 20° C., and the mixture is stirred, thereby producing a compound (4).

Alternatively, the compound (4) may be produced by treating a compound (3) and dialkyl oxalate in the presence of sodium alkoxide (methoxide or ethoxide) in an alcohol (methanol or ethanol) solution. The reaction temperature is preferably −10 to 100° C.

The compound (4) is dissolved in an alcohol (methanol or ethanol), and a hydrazine derivative (6) or a salt thereof is added to the solution at room temperature. A suitable amount of acetic acid is added to the mixture, and the mixture is refluxed under heat, thereby yielding a compound (7) and the position isomer (8) as a byproduct. The compound (7) can be readily separated and purified through silica gel column chromatography.

In the pyrazole ring formation reaction, instead of acetic acid, an appropriate amount of triethylamine or concentrated hydrochloric acid may be added prior to reflux under heat. In some cases, the compound (7) can be obtained without addition of any of acetic acid, triethylamine, or concentrated hydrochloric acid.

The hydrazine derivative (6) or a salt thereof employed in the above pyrazole ring formation reaction may be produced by dissolving an aromatic amine (5) in concentrated hydrochloric acid, adding sodium nitrite to the solution under ice cooling to form a diazo compound, and treating the diazo compound with tin(II) chloride. The reaction temperature is preferably −10 to 20° C.

The hydrazine derivative (6) may be a commercially available hydrazine derivative product. Alternatively, the hydrazine derivative (6) may be produced by reacting a halogenated compound of $Ar_1$ with hydrazine, as described in Referential Examples, or through a similar method.

The aromatic amine (5) may be a commercially available product. Alternatively, the aromatic amine (5) may be produced through a method described in Referential Examples or a similar method.

When the thus-produced compound (7) is treated through the following process:

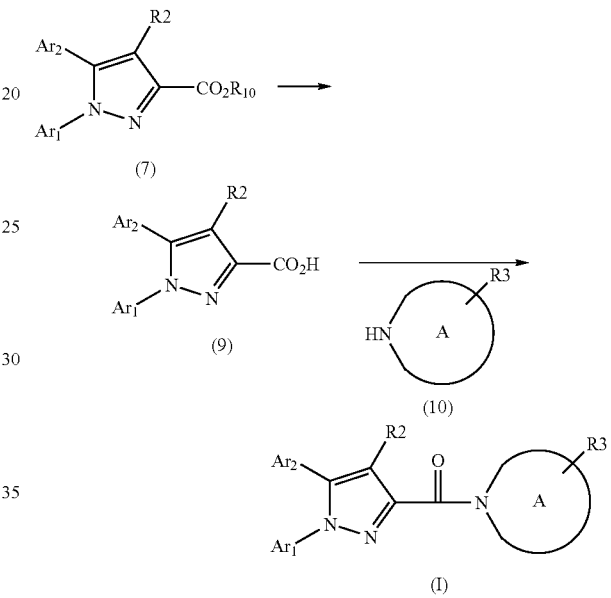

(wherein R2, R3, R10, $Ar_1$, $Ar_2$, and ring structure A have the same meanings as described above), a compound (I) of the present invention can be obtained.

Specifically, the compound (7) is hydrolyzed through a common process to form a carboxylic acid (9), and the carboxylic acid (9) is fused with an amine compound (10), to thereby give the compound (I) of the present invention.

The above hydrolysis reaction may be performed in the presence of a base or a Lewis acid. Examples of the base include a hydroxide of an alkali metal (such as lithium, sodium, or potassium). Examples of the Lewis acid include boron tribromide. The reaction temperature is preferably −20 to 100° C., more preferably −5 to 50° C.

When the compound (7) has, as a substituent of $Ar_1$, a halogeno group such as chloro or bromo, the substituent of $Ar_1$ can be substituted by a methoxy group by dissolving the compound (7) in methanol, and adding sodium methoxide to the solution, followed by reflux under heat, or by dissolving the compound (7) in a solvent mixture of methanol and toluene, and adding sodium methoxide and a catalyst such as copper(I) bromide, followed by reflux under heat. Thus, a compound (7) having, as a substituent of $Ar_1$, a methoxy group (R10 is methyl) can be produced.

The fusion process described above may be performed through a method generally used for peptide synthesis. Examples of the method for peptide synthesis include the azide method, the acid chloride method, the acid anhydride method, the DCC (dicyclohexylcarbodiimide) method, the active ester method, the carbodiimidazole method, the DCC/HOBT(1-hydroxybenzotriazole) method, a method using water-soluble carbodiimide, and a method using diethyl cyanophosphate. These methods are described in, for example, M. Bodanszky, Y. S. Klausner, and M. A. Ondetti, "Peptide Synthesis", A Wiley-interscience publication, New York, 1976; G. R. Pettit, "Synthetic Peptides", Elsevier Scientific Publication Company, New York, 1976; and Japanese Society of Chemistry ed. "Lectures on Experimental Chemistry 4th ed., vol. 22, Organic Synthesis IV", Maruzen Publishing, 1991. Examples of a solvent used in the fusion reaction include N,N-dimethylformamide, pyridine, chloroform, methylene chloride, tetrahydrofuran, dioxane, acetonitrile, and a solvent mixture thereof. The reaction temperature is preferably −20 to 5° C., more preferably −10 to 30° C. The amine compound (10) may be a commercially available product or may be produced through a method described in documents or Referential Example or a similar method.

When the amine compound (10) used in the fusion reaction described above has a functional group such as a hydroxyl group, an amino group, or a carboxyl group, the functional group may have to be protected in advance by use of a suitable protective group. Examples of a typical protective group for a hydroxyl group include a tert-butyl group and a benzyl group. Examples of a typical protective group for an amino group include a trifluoroacetyl group, a tert-butoxycarbonyl group, and a benzyloxycarbonyl group. When the functional group is a carboxyl group, the amine compound (10) may be transformed to a methyl ester or a tert-butyl ester prior to the fusion reaction. Such protective groups can be removed under suitable conditions, which vary depending on the type of protective group.

The compound (II) of the present invention may be produced through the following process:

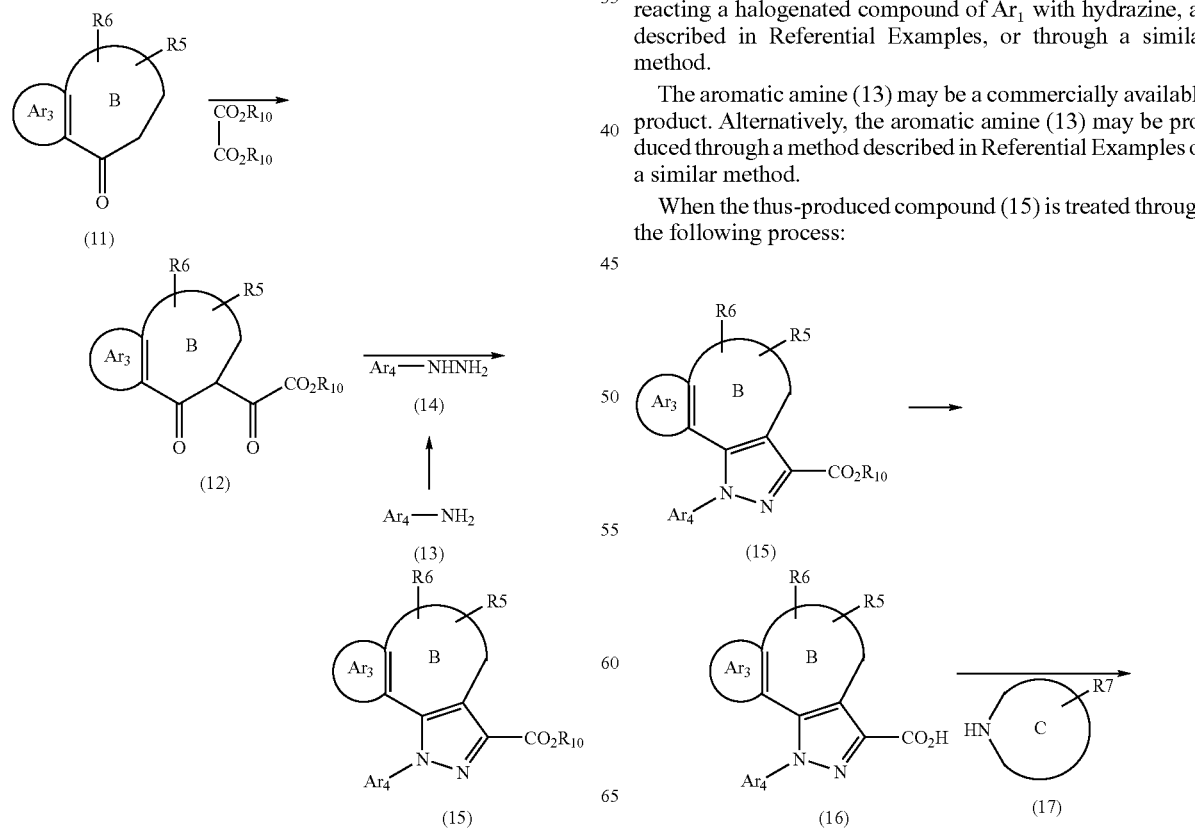

(wherein $Ar_3$, $Ar_4$, R5, R6, ring structure $Ar_3$, and ring structure B have the same meanings as described above, and R10 represents a methyl group or an ethyl group).

Specifically, a commercially available compound (11) and dialkyl oxalate are dissolved or suspended in a suitable solvent such as N,N-dimethylformamide, and sodium hydride is added to the solution under argon flow at a temperature of −20 to 20° C., followed by stirring, thereby yielding a compound (12).

Alternatively, the compound (12) may be produced by treating a compound (11) and diethyl oxalate with lithium bis(trimethylsilyl)amide in an inert solvent such as tetrahydrofuran. The reaction temperature is preferably −78 to 50° C.

Subsequently, the compound (12) is dissolved in ethanol, and a hydrazine derivative (14) or a salt thereof is added to the solution at room temperature. A suitable amount of acetic acid is added to the mixture and then refluxed under heat, to thereby give a compound (15).

In the pyrazole ring formation reaction, instead of acetic acid, an appropriate amount of triethylamine may be added prior to reflux under heat. In some cases, the compound (15) can be obtained without addition of any of acetic acid and triethylamine.

The hydrazine derivative (14) or a salt thereof employed in the above pyrazole ring formation reaction may be produced by dissolving an aromatic amine (13) in concentrated hydrochloric acid, adding sodium nitrite to the solution under ice cooling to form a diazo compound, and treating the diazo compound with tin(II) chloride. The reaction temperature is preferably −10 to 20° C.

Alternatively, the hydrazine derivative (14) may be a commercially available hydrazine derivative product. Alternatively, the hydrazine derivative (14) may be produced by reacting a halogenated compound of $Ar_1$ with hydrazine, as described in Referential Examples, or through a similar method.

The aromatic amine (13) may be a commercially available product. Alternatively, the aromatic amine (13) may be produced through a method described in Referential Examples or a similar method.

When the thus-produced compound (15) is treated through the following process:

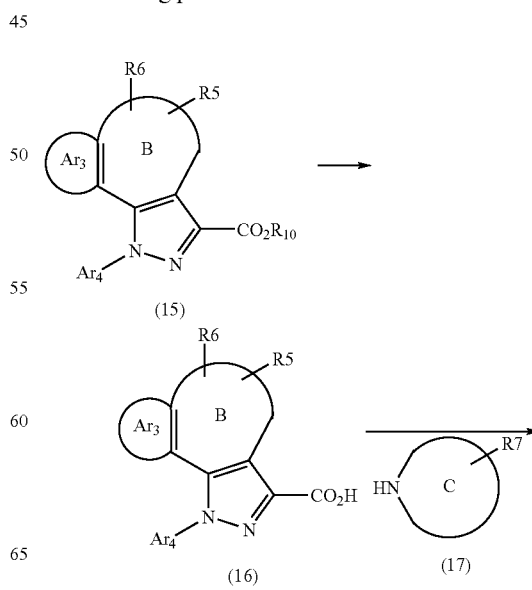

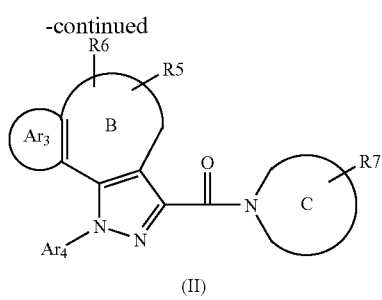

(wherein R5, R6, R7, R10, Ar$_4$, ring structure Ar$_3$, and ring structures B and C have the same meanings as described above), a compound (II) of the present invention can be obtained.

Specifically, the compound (15) is hydrolyzed through a process known per se to form a carboxylic acid (16), and the carboxylic acid (16) is fused with an amine compound (17), to thereby give the compound (II) of the present invention.

The above hydrolysis reaction and fusion reaction may be performed under conditions similar to those described in relation to production of the compound (I).

Alternatively, the compound (I) of the present invention may be produced through the following process:

The reduction reaction of reducing the ester (7) into alcohol (18) may be performed by, for example, treating the ester (7) with aluminum lithium hydride, lithium boron hydride, or a similar compound in an inert solvent such as tetrahydrofuran at −78 to 50° C., preferably at −20 to 30° C.

The alcohol (18) may be produced by treating a carboxylic acid (9) in an inert solvent such as tetrahydrofuran by use of aluminum lithium hydride, a boran-tetrahydrofuran complex, or a similar compound, at −78 to 50° C., preferably at −20 to 30° C.

Subsequently, the alcohol compound (18) may be transformed to the compound (19) as follows. When the group Z is a methanesulfonyloxy group, the alcohol compound (18) is reacted with methanesulfonyl chloride in the presence of a base such as pyridine at −50 to 50° C. When the group Z is a p-toluenesulfonyloxy group, a trifluoromethanesulfonyloxy group, or a similar group, the transformation to the compound (19) may be performed under similar conditions. When the group Z is a chloro group or a bromo group, the alcohol compound (18) is transformed to a chloro derivative (19) or a bromo derivative (19) through use of thionyl chloride, thionyl bromide, or a similar compound. When the group Z is an iodo group or a similar group, the thus-obtained chloro or bromo derivative (19) is treated with sodium iodide, thereby yielding an iodo derivative (19). Conditions and reagents employed in

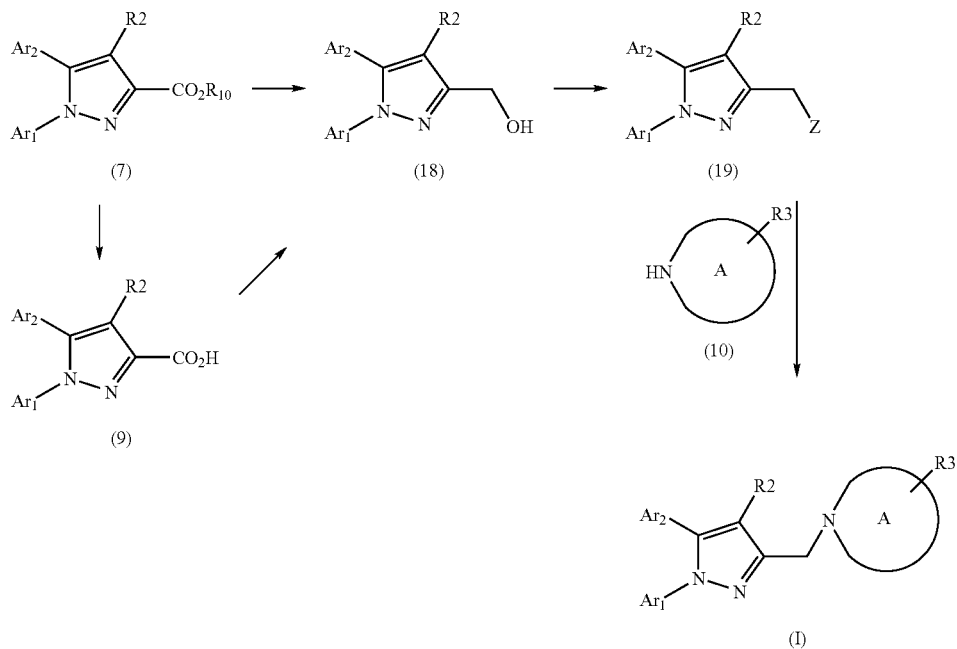

(wherein R2, R3, R10, Ar$_1$, Ar$_2$, and ring structure A have the same meanings as described above, and Z represents a releasing group).

Specifically, an ester (7) is reduced to form an alcohol (18), and the alcohol (18) is transformed to a compound (19) having a releasing group Z (such as a p-toluenesulfonyloxy group, a methanesulfonyloxy group, a trifluoromethanesulfonyloxy group, a chloro group, a bromo group, or an iodo group). The compound (19) is reacted with an amine compound (10), thereby yielding a compound (I) of the present invention.

these reactions may be determined appropriately based on a common knowledge of organic chemistry.

The transformation from the compound (19) to the compound (I) of the present invention may be performed by reacting the compound (19) with the amine (10) in a suitable solvent such as tetrahydrofuran or N,N-dimethylformamide by use of a base such as triethylamine or diisopropylethylamine or an inorganic base such as potassium carbonate and by use of a base such as sodium hydride. The reaction temperature, which differs depending on the type of the group Z, is preferably −79 to 100° C.

In the above reaction, in some cases, functional groups are required to be protected. Protection groups and conditions employed for removal of the protecting groups may be determined appropriately based on a common knowledge of organic chemistry.

A compound (I) of the present invention produced through any of the above three processes can be transformed to another compound (I) of the present invention through chemical modifications based on a common knowledge of organic chemistry.

The compounds (I) and (II) of the present invention, salts or solvates thereof, and solvates of the salts are endowed with potent anti-platelet aggregation activity, and they exhibited effectiveness in a high shear stress-induced thrombosis model. Therefore, the compounds (I) and (II) of the present invention, salts or solvates thereof, or solvates of the salts are useful in humans and other mammals as preventive and/or therapeutic agents for ischemic diseases caused by thrombus or embolus such as myocardial infarction, angina pectoris (chronic stable angina, unstable angina, etc.), ischemic cerebrovascular disorder (transient ischemic attack (TIA), cerebral infarction, etc.), peripheral vascular disease, embolism after replacement with an artificial vessel, thrombotic embolism after coronary artery intervention (coronary artery bypass grafting (CABG), percutaneous transluminal coronary angioplasty (PTCA), stent placement, etc.), diabetic retinopathy and nephropathy, and embolism after replacement with an artificial heart valve, and also, as a preventive and/or therapeutic agent for thrombus and embolus associated with vascular operation, blood extracorporeal circulation, and the like.

When the compound (I) or (II) of the present invention, a salt of the compound, or a solvate of the compound or the salt is used as a drug, the daily dose for an adult, which varies depending on the age, sex, symptoms of the patient, etc., is preferably 0.1 mg to 1 g, more preferably 0.5 mg to 500 mg. The drug may be administered once a day or several times a day in a divided manner. If necessary, the compound/salt/solvate may be administered at a dose exceeding the above daily dose.

No particular limitation is imposed on the administration route and the dosage form of a drug containing a compound (I) or (II) of the present invention, a salt of the compound, or a solvate of the compound or the salt, and the drug may be administered via any route and in any dosage form as desired. The dosage form may be determined appropriately depending on the administration route. The drug preparation may be produced through a common drug preparation method by incorporating a pharmacologically acceptable carrier as desired.

Examples of oral preparations include solid preparations such as tablets, powders, granules, pills, and capsules, as well as liquid preparations such as solution, syrup, elixir, suspension, and emulsion.

An injection may be prepared by filling a container with a solution of a compound (I), a salt of the compound, or a solvate of the compound or the salt. A solid prepared by, for example, freeze-drying such a solution may also be used as an injection which is rehydrated before use.

In the production of such drug preparation, one or more pharmaceutically acceptable additives selected, in accordance with needs, from among a binder, a disintegrant, a dissolution promoter, a lubricant, a filler, an excipient, and similar additives may be incorporated into the drug preparation.

EXAMPLES

Next will be described processes for producing typical compounds of the present invention. Also, descriptions will be given of specific tests conducted to demonstrate strong platelet aggregation inhibitory action, without inhibiting COX-1 or COX-2, of the produced compounds.

Referential Example 1

5-Hydrazino-2-methoxypyridine hydrochloride

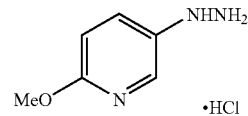

A solution of sodium nitrite (3.795 g) in water (20 mL) was added dropwise to 5-amino-2-methoxypyridine (6.21 g) in concentrated hydrochloric acid (50 mL) over a period of 60 minutes with ice cooling, and the resultant mixture was stirred at a constant temperature for 30 minutes. Tin(II) chloride dihydrate (39.5 g) in concentrated hydrochloric acid (30 mL) was added dropwise to the reaction mixture at an internal temperature of about 10° C. for 30 minutes, followed by stirring for 2 hours at room temperature. Under cooling with ice, the reaction mixture was partitioned between sodium hydroxide (75 g) in water (300 mL) and diethyl ether. The aqueous layer was extracted with diethyl ether twice. Subsequently, the aqueous layer was saturated with sodium chloride, followed by extraction with diethyl ether. The organic layers were combined, and dried over sodium sulfate anhydrate, followed by filtration. 1M HCl in ethanol (50 mL) was added to the filtrate and the mixture was stirred. The solid that precipitated was collected by filtration, washed with diethyl ether, and dried, to thereby give the title compound (5.02 g, 57%).

$^1$H-NMR (400 MHz, DMSO-$d_6$) δ: 3.81 (3H, s), 6.82 (1H, d, J=8.8 Hz), 7.57 (1H, dd, J=8.8, 2.9 Hz), 7.97 (1H, d, J=2.9 Hz), 8.55-9.20 (1H, br), 10.13-10.50 (3H, br).

MS (ESI) m/z: 140(M+H)$^+$.

Referential Example 2

5-Hydrazino-2-methoxypyridine

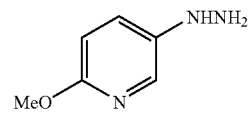

Sodium nitrite (3.795 g) in water (20 mL) was added dropwise to 5-amino-2-methoxypyridine (6.207 g) in concentrated hydrochloric acid (50 mL) for 80 minutes with ice cooling, followed by stirring at a constant temperature for 30 minutes. Tin(II) chloride dihydrate (39.5 g) in concentrated hydrochloric acid (30 mL) was added dropwise to the reaction mixture at an internal temperature of about 10° C. for 60 minutes, followed by stirring at room temperature for 12.5 hours. Under cooling with ice, sodium hydroxide (54 g) in water (200 mL) and chloroform were added to the reaction mixture. After insoluble substances in the resultant mixture were removed by filtration, the mixture was partitioned. The aqueous layer was extracted with chloroform twice. The organic layers were combined, and dried over sodium sulfate anhydrate, followed by filtration. The solvent was evaporated under reduced pressure, to thereby give the title compound as crystals (4.23 g, 60%).

$^1$H-NMR (400 MHz, CDCl$_3$) δ: 3.50-3.68 (2H, br), 3.88 (3H, s), 4.86-5.03 (1H, br), 6.66 (1H, d, J=8.8 Hz), 7.20 (1H, dd, J=8.8, 2.9 Hz), 7.77 (1H, d, J=2.9 Hz).

MS (ESI) m/z: 140(M+H)$^+$.

Referential Example 3

5-(4-Chlorophenyl)-1-(6-methoxy-3-pyridyl)pyrazole-3-carboxylic acid ethyl ester

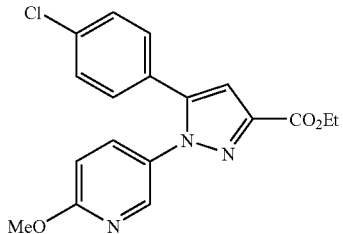

1) 4-(4-Chlorophenyl)-2,4-dioxobutanoic acid ethyl ester

Sodium hydride (which was used after having been washed with pentane and then dried; 0.474 g) was added to 4'-chloroacetophenone (1.535 g) in N,N-dimethylformamide (25 mL) at 0° C., followed by stirring at room temperature for 0.5 hours. Diethyl oxalate (2.6 mL) was added to the reaction mixture, followed by stirring at room temperature for 17 hours. The reaction mixture was partitioned between water and diethyl ether. The aqueous layer was acidified to pH 3 with 1M aqueous hydrochloric acid, followed by extraction with diethyl ether. Subsequently, the aqueous layer was further extracted with diethyl ether. The organic layer was washed with saturated brine, and dried with sodium sulfate anhydrate, followed by filtration. The solvent was evaporated under reduced pressure, to thereby give 4-(4-chlorophenyl)-2,4-dioxobutanoic acid ethyl ester (1.952 g, 77%).

$^1$H-NMR (400 MHz, CDCl$_3$) δ: 1.41 (3H, t, J=7.0 Hz), 4.40 (2H, q, J=7.0 Hz), 7.03 (1H, s), 7.48 (2H, d-like, J=8.6 Hz), 7.94 (2H, d-like, J=8.6 Hz).

MS (ESI) m/z: 255(M+H)$^+$.

2) The Title Compound

A hydrazine compound (0.250 g) obtained from Referential Example 2 was added to a solution of the above-obtained 4-(4-chlorophenyl)-2,4-dioxobutanoic acid ethyl ester (0.930 g) dissolved in ethanol (20 mL) at room temperature. The mixture was refluxed under heat for 12 hours, and then cooled in air. The solvent was evaporated under reduced pressure, and the residue was partitioned between water and chloroform. Subsequently, the aqueous layer was extracted with chloroform. The organic layer was washed with saturated brine, and dried with sodium sulfate anhydrate, followed by filtration. The solvent was evaporated under reduced pressure, and the residue was purified by silica gel column chromatography (hexane-ethyl acetate: 17 to 50%), to thereby give the title compound as an oily substance (0.543 g, 85%).

$^1$H-NMR (400 MHz, CDCl$_3$) δ: 1.42 (3H, t, J=7.1 Hz), 3.94 (3H, s), 4.45 (2H, q, J=7.1 Hz), 6.75 (1H, d, J=8.8 Hz), 7.03 (1H, s), 7.15 (2H, d-like, J=8.3 Hz), 7.32 (2H, d-like, J=8.3 Hz), 7.57 (1H, dd, J=8.8, 2.9 Hz), 8.08 (1H, d, J=2.9 Hz).

MS (FAB) m/z: 358(M+H)$^+$.

Referential Example 4

5-(4-Chlorophenyl)-1-(6-methoxy-3-pyridyl)pyrazole-3-carboxylic acid

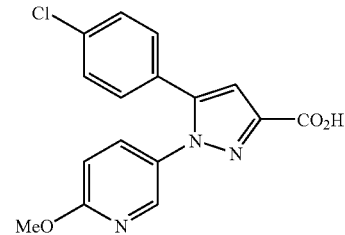

Lithium hydroxide monohydrate (69.4 mg) was added to pyrazole-3-carboxylic acid ethyl ester (0.543 g) described in relation to step 2) of Referential Example 3 in tetrahydrofuran (6 mL)-water (2 mL) and methanol (1.5 mL), followed by stirring at room temperature for 2 hours. The solvent was evaporated under reduced pressure, and the residue was partitioned between water and diethyl ether. The aqueous layer was acidified to pH 3 with 1M aqueous hydrochloric acid, followed by stirring at 0° C. The resultant solid was collected by filtration. The solid was sequentially washed with water, isopropyl alcohol, and diethyl ether. Subsequently, the solid was dried, to thereby give the title compound as a solid substance (0.240 g, 48%).

$^1$H-NMR (400 MHz, CDCl$_3$) δ: 3.95 (3H, s), 6.77 (1H, d, J=8.8 Hz), 7.09 (1H, s), 7.17 (2H, d-like, J=8.6 Hz), 7.34 (2H, d-like, J=8.6 Hz), 7.56 (1H, dd, J=8.8, 2.9 Hz), 8.09 (1H, d, J=2.9 Hz).

MS (ESI) m/z: 330(M+H)$^+$.

Referential Example 5

5-(4-Ethylphenyl)-1-(6-methoxy-3-pyridyl)pyrazole-3-carboxylic acid ethyl ester

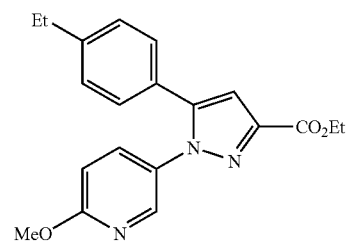

1) 4-(4-Ethylphenyl)-2,4-dioxobutanoic acid ethyl ester

In a manner similar to that described in relation to step 1) of Referential Example 3,4-(4-ethylphenyl)-2,4-dioxobutanoic acid ethyl ester (2.577 g, 97%) was produced by use of 4'-ethylacetophenone (1.599 g) and diethyl oxalate (2.9 mL).

$^1$H-NMR (400 MHz, CDCl$_3$) δ: 1.27 (3H, t, J=7.5 Hz), 1.41 (3H, t-like, J=7.4 Hz), 2.73 (2H, q, J=7.4 Hz), 4.30-4.50 (2H, m), 7.05 (1H, s), 7.32 (2H, d-like, J=7.1 Hz), 7.92 (2H, d-like, J=7.1 Hz).

MS (ESI) m/z: 249(M+H)$^+$.

2) The Title Compound

In a manner similar to that described in relation to step 2) of Referential Example 3, the title compound was produced as an oily substance (0.589 g, 83%) by use of the above-obtained 4-(4-ethylphenyl)-2,4-dioxobutanoic acid ethyl ester (1.012 g) and 5-hydrazino-2-methoxypyridine (0.280 g) obtained from Referential Example 2.

$^1$H-NMR (400 MHz, CDCl$_3$) δ: 1.22 (3H, t, J=7.6 Hz), 1.41 (3H, t, J=7.0 Hz), 2.63 (2H, q, J=7.6 Hz), 3.92 (3H, s), 4.44 (2H, q, J=7.0 Hz), 6.73 (1H, d, J=8.8 Hz), 7.01 (1H, s), 7.08-7.20 (4H, m), 7.57 (1H, dd, J=8.8, 2.7 Hz), 8.12 (1H, d, J=2.7 Hz).

MS (FAB) m/z: 352(M+H)$^+$.

Referential Example 6

5-(4-Ethylphenyl)-1-(6-methoxy-3-pyridyl)pyrazole-3-carboxylic acid

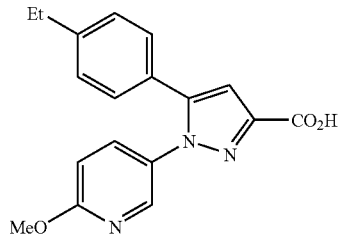

In a manner similar to that described in relation to Referential Example 4, the title compound was produced as a solid substance (0.457 g, 84%) by use of pyrazole-3-carboxylic acid ethyl ester (0.589 g) obtained from step 2) of Referential Example 5.

$^1$H-NMR (400 MHz, CDCl$_3$) δ: 1.23 (3H, t, J=7.6 Hz), 2.64 (2H, q, J=7.6 Hz), 3.94 (3H, s), 6.75 (1H, d, J=8.8 Hz), 7.07 (1H, s), 7.10-7.20 (5H, m), 7.60 (1H, dd, J=8.8, 2.7 Hz), 8.15 (1H, d, J=2.7 Hz), 10.20 (1H, br).

MS (FAB) m/z: 324(M+H)$^+$.

Referential Example 7

1-(6-Methoxy-3-pyridyl)-5-(3-methylphenyl)pyrazole-3-carboxylic acid ethyl ester

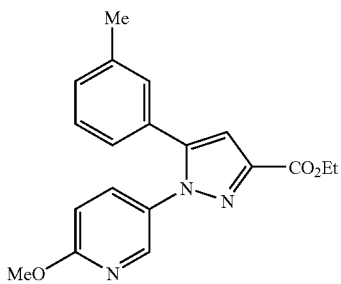

1) 4-(3-Methylphenyl)-2,4-dioxobutanoic acid ethyl ester

In a manner similar to that described in relation to step 1) of Referential Example 3,4-(3-methylphenyl)-2,4-dioxobutanoic acid ethyl ester (2.71 g, quantitative amount) was produced by use of 3'-methylacetophenone (1.557 g) and diethyl oxalate (3.1 mL).

$^1$H-NMR (400 MHz, CDCl$_3$) δ: 1.41 (3H, t, J=7.1 Hz), 2.43 (3H, s), 4.40 (2H, q, J=7.1 Hz), 7.06 (1H, s), 7.35-7.45 (2H, m), 7.75-7.82 (2H, m).

MS (ESI) m/z: 235(M+H)$^+$.

2) The Title Compound

5-Hydrazino-2-methoxypyridine hydrochloride (0.380 g) obtained from Referential Example 1 and triethylamine (0.30 mL) were added to a solution of the above-obtained 4-(3-methylphenyl)-2,4-dioxobutanoic acid ethyl ester (1.014 g) dissolved in ethanol (20 mL) at room temperature. The resultant mixture was refluxed under heat for 14 hours, and then cooled in air. The solvent was evaporated under reduced pressure, and the residue was partitioned between chloroform and water. The aqueous layer was extracted with chloroform. The organic layer was washed with saturated brine and dried over sodium sulfate anhydrate, followed by filtration. The solvent was evaporated under reduced pressure, and the residue was subjected to silica gel column chromatography (hexane-ethyl acetate: 20%), to thereby give the title compound as an oily substance (0.451 g, 62%).

$^1$H-NMR (400 MHz, CDCl$_3$) δ: 1.42 (3H, t, J=7.1 Hz), 2.30 (3H, s), 3.92 (3H, s), 4.45 (2H, q, J=7.1 Hz), 6.68-6.76 (1H, m), 6.92-7.25 (4H, m), 7.02 (1H, s), 7.53-7.61 (1H, m), 8.08-8.15 (1H, m).

MS (FAB) m/z: 338(M+H)$^+$.

Referential Example 8

1-(6-Methoxy-3-pyridyl)-5-(3-methylphenyl)pyrazole-3-carboxylic acid

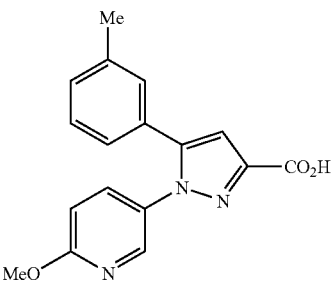

In a manner similar to that described in relation to Referential Example 4, the title compound was produced as a solid substance (0.353 g, 86%) by use of pyrazole-3-carboxylic acid ethyl ester (0.451 g) obtained from step 2) of Referential Example 7.

$^1$H-NMR (400 MHz, CDCl$_3$) δ: 2.31 (3H, s), 3.94 (3H, s), 6.74 (1H, d, J=8.8 Hz), 6.96 (1H, d-like, J=7.3 Hz), 7.05-7.25 (4H, m), 7.60 (1H, dd, J=8.8, 2.7 Hz), 8.14 (1H, d, J=2.7 Hz), 9.65 (1H, br).

Referential Example 9

1-(6-Methoxy-3-pyridyl)-5-(2-methylphenyl)pyrazole-3-carboxylic acid ethyl ester

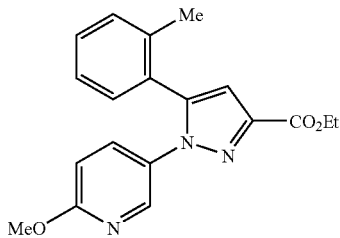

1) 4-(2-Methylphenyl)-2,4-dioxobutanoic acid ethyl ester

In a manner similar to that described in relation to step 1) of Referential Example 3, 4-(2-methylphenyl)-2,4-dioxobutanoic acid ethyl ester was produced as an oily substance (2.54 g, 95%) by use of 2'-methylacetophenone (1.543 g) and diethyl oxalate (3.1 mL).

$^1$H-NMR (400 MHz, CDCl$_3$) δ: 1.39 (3H, t-like, J=7.1 Hz), 2.55 (3H, s), 4.38 (2H, q-like, J=7.1 Hz), 6.83 (1H, s), 7.20-7.30 (2H, m), 7.41 (1H, t-like, J=7.6 Hz), 7.62 (1H, d-like, J=7.6 Hz).

LC-MS m/z: 235(M+H)$^+$.

2) The Title Compound

In a manner similar to that described in relation to step 2) of Referential Example 7, the title compound was produced as an oily substance (0.542 g, 69%) by use of the above-obtained 4-(2-methylphenyl)-2,4-dioxobutanoic acid ethyl ester (1.074 g) and 5-hydrazino-2-methoxypyridine hydrochloride (0.407 g) obtained from Referential Example 1.

$^1$H-NMR (400 MHz, CDCl$_3$) δ: 1.42 (3H, t, J=7.1 Hz), 2.04 (3H, s), 3.86 (3H, s), 4.45 (2H, q, J=7.1 Hz), 6.65 (1H, d, J=8.8 Hz), 6.94 (1H, s), 7.10-7.35 (4H, m), 7.56 (1H, dd, J=8.8, 2.2 Hz), 8.01 (1H, d, J=2.2 Hz).

MS (FAB) m/z: 338(M+H)$^+$.

Referential Example 10

1-(6-Methoxy-3-pyridyl)-5-(2-methylphenyl)pyrazole-3-carboxylic acid

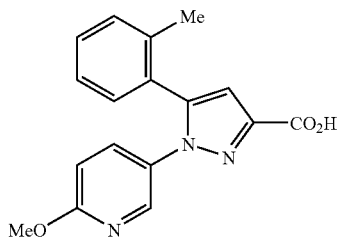

In a manner similar to that described in relation to Referential Example 4, the title compound was produced as a solid substance (0.479 g, 96%) by use of pyrazole-3-carboxylic acid ethyl ester (0.542 g) obtained from step 2) of Referential Example 9.

$^1$H-NMR (400 MHz, CDCl$_3$) δ: 2.06 (3H, s), 3.91 (3H, s), 6.68 (1H, d, J=9.0 Hz), 7.00 (1H, s), 7.15-7.38 (4H, m), 7.50-7.60 (1H, m), 8.03 (1H, d, J=2.5 Hz).

MS (ESI) m/z: 310(M+H)$^+$.

Referential Example 11

5-(3-Fluorophenyl)-1-(6-methoxy-3-pyridyl)pyrazole-3-carboxylic acid ethyl ester

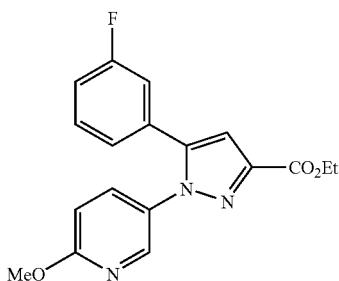

1) 4-(3-Fluorophenyl)-2,4-dioxobutanoic acid ethyl ester

In a manner similar to that described in relation to step 1) of Referential Example 3, 4-(3-fluorophenyl)-2,4-dioxobutanoic acid ethyl ester was produced as a solid substance (2.26 g, 86%) by use of 3'-fluoroacetophenone (1.530 g) and diethyl oxalate (3.0 mL).

$^1$H-NMR (400 MHz, CDCl$_3$) δ: 1.39 (3H, t, J=7.1 Hz), 4.38 (2H, q, J=7.1 Hz), 7.01 (1H, s), 7.20-7.32 (1H, m), 7.40-7.50 (1H, m), 7.60-7.68 (1H, m), 7.70-7.77 (1H, m).

MS (ESI) m/z: 239(M+H)$^+$.

2) The Title Compound

In a manner similar to that described in relation to step 2) of Referential Example 7, the title compound (0.362 g, 52%) was produced as an oily substance by use of the above-obtained 4-(3-fluorophenyl)-2,4-dioxobutanoic acid ethyl ester (0.978 g) and 5-hydrazino-2-methoxypyridine hydrochloride (0.358 g) obtained from Referential Example 1.

$^1$H-NMR (400 MHz, CDCl$_3$) δ: 1.42 (3H, t, J=7.1 Hz), 3.94 (3H, s), 4.45 (2H, q, J=7.1 Hz), 6.76 (1H, d, J=8.8 Hz), 6.92-7.10 (3H, m), 7.06 (1H, s), 7.58 (1H, dd, J=8.8, 2.9 Hz), 8.09 (1H, d, J=2.9 Hz).

MS (FAB) m/z: 342(M+H)$^+$.

Referential Example 12

5-(3-Fluorophenyl)-1-(6-methoxy-3-pyridyl)pyrazole-3-carboxylic acid

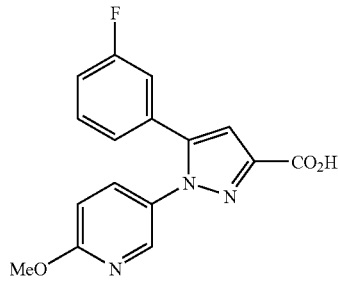

In a manner similar to that described in relation to Referential Example 4, the title compound (0.302 g, 91%) was produced as a solid substance by use of the pyrazole-3-carboxylic acid ethyl ester compound (0.362 g) obtained from step 2) of Referential Example 11.

$^1$H-NMR (400 MHz, CDCl$_3$) δ: 3.95 (3H, s), 6.78 (1H, d, J=8.8 Hz), 6.93-7.12 (3H, m), 7.12 (1H, s), 7.28-7.38 (1H, m), 7.60 (1H, dd, J=8.8, 2.7 Hz), 8.12 (1H, d, J=2.7 Hz).

MS (ESI) m/z: 314(M+H)$^+$.

Referential Example 13

5-(4-Benzyloxyphenyl)-1-(6-methoxy-3-pyridyl) pyrazole-3-carboxylic acid ethyl ester

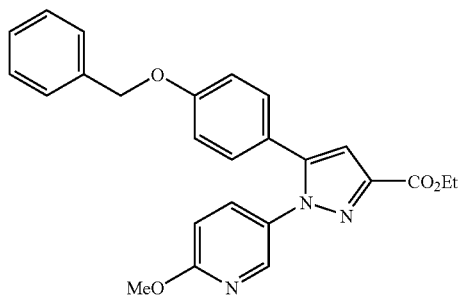

1) 4-(4-Benzyloxyphenyl)-2,4-dioxobutanoic acid ethyl ester

In a manner similar to that described in relation to step 1) of Referential Example 3,4-(4-benzyloxyphenyl)-2,4-dioxobutanoic acid ethyl ester (3.18 g, quantitative amount) was produced as an oily substance by use of 4'-benzyloxyacetophenone (2.07 g) and diethyl oxalate (2.5 mL).

MS (ESI) m/z: 327(M+H)$^+$.

2) The Title Compound

In a manner similar to that described in relation to step 2) of Referential Example 3, the title compound (1.026 g, 35%) was produced as a solid substance by use of the above-obtained 4-(4-benzyloxyphenyl)-2,4-dioxobutanoic acid ethyl ester (3.21 g) and 5-hydrazino-2-methoxypyridine (0.952 g) obtained from Referential Example 2.

$^1$H-NMR (400 MHz, CDCl$_3$) δ: 1.42 (3H, t, J=7.3 Hz), 3.94 (3H, s), 4.44 (2H, q, J=7.3 Hz), 5.05 (2H, s), 6.73 (1H, d, J=8.8 Hz), 6.92 (2H, d-like, J=8.6 Hz), 6.97 (1H, s), 7.13 (2H, d-like, J=8.6 Hz), 7.30-7.46 (5H, m), 7.56 (1H, dd, J=8.8, 2.7 Hz), 8.10 (1H, d, J=2.7 Hz).

MS (FAB) m/z: 430(M+H)$^+$.

Referential Example 14

5-(4-Benzyloxyphenyl)-1-(6-methoxy-3-pyridyl) pyrazole-3-carboxylic acid

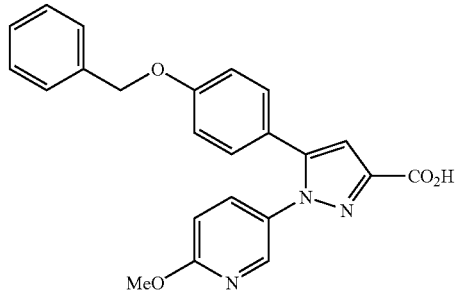

In a manner similar to that described in relation to Referential Example 4, the title compound (0.973 g, quantitative amount) was produced as an oily substance by use of 5-(4-benzyloxyphenyl)-1-(6-methoxy-3-pyridyl)pyrazole-3-carboxylic acid ethyl ester (0.991 g) obtained from Referential Example 13.

$^1$H-NMR (400 MHz, CDCl$_3$) δ: 3.94 (3H, s), 5.05 (2H, s), 6.74 (1H, d, J=8.8 Hz), 6.93 (2H, d-like, J=8.8 Hz), 7.02 (1H, s), 7.12 (2H, d-like, J=8.8 Hz), 7.30-7.45 (5H, m), 7.56 (1H, dd, J=8.8, 2.7 Hz), 8.12 (1H, d, J=2.7 Hz).

MS (FAB) m/z: 402(M+H)$^+$.

Referential Example 15

4-Methoxypyridine-2-carbonitrile

In an argon atmosphere, triethylamine (17.8 mL) was added to 4-methoxypyridine-N-oxide (8.0 g) in acetonitrile (160 mL) at room temperature. Trimethylsilyl cyanide (24.1 mL) was added dropwise to the mixture, followed by stirring for 20 minutes. Subsequently, the mixture was stirred at 95° C. for 14 hours, and then cooled in air. The solvent was evaporated under reduced pressure. The residue was partitioned between saturated aqueous solution of sodium hydrogencarbonate and ethyl acetate. The organic layer was dried over sodium hydrogensulfate anhydrate, followed by filtration. The solvent was evaporated under reduced pressure, and the residue was purified by silica gel column chromatography (hexane-ethyl acetate), to thereby give the title compound as a solid substance (1.57 g, 18%).

$^1$H-NMR (400 MHz, CDCl$_3$) δ: 3.91 (3H, s), 7.00-7.02 (1H, m), 7.22 (1H, d, J=2.4 Hz), 8.51 (1H, d, J=6.0 Hz).

MS (EI) m/z: 134(M$^+$).

Referential Example 16

1-(4-Methoxy-2-pyridyl)ethanone

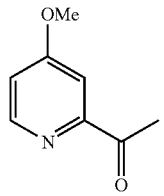

In an argon atmosphere, 0.93M methylmagnesium bromide in tetrahydrofuran (13.8 mL) was added dropwise to 4-methoxypyridine-2-carbonitrile (1.56 g) in tetrahydrofuran (31 mL) at −78° C., followed by stirring for 15 minutes. Subsequently, the reaction mixture was stirred at 0° C. for 15 minutes, and then at room temperature for 5 hours. Water was added dropwise to the reaction mixture. The resultant mixture was partitioned between water and ethyl acetate. The organic layer was dried over sodium sulfate anhydrate, followed by filtration. The solvent was evaporated under reduced pressure, and the residue was purified by silica gel column chromatography (hexane-ethyl acetate), to thereby give the title compound as a solid substance (1.30 g, 73%).

$^1$H-NMR (400 MHz, CDCl$_3$) δ: 2.72 (3H, s), 3.91 (3H, s), 6.97-6.99 (1H, m), 7.57-7.58 (1H, m), 8.48-8.50 (1H, m).

MS (ESI) m/z: 152(M+H)$^+$.

Referential Example 17

4-(4-Methoxy-2-pyridyl)-2,4-dioxobutanoic acid ethyl ester

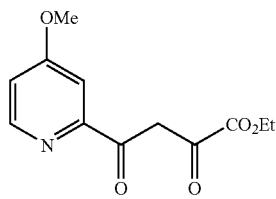

In a manner similar to that described in relation to step 1) of Referential Example 3, the title compound was produced as a solid substance (0.713 g, 33%) by use of 1-(4-methoxy-2-pyridyl)ethanone (1.28 g) and diethyl oxalate (2.30 mL).

$^1$H-NMR (400 MHz, CDCl$_3$) δ: 1.39-1.43 (3H, m), 3.96 (3H, s), 4.37-4.42 (2H, m), 7.03-7.05 (1H, m), 7.72 (1H, d, J=2.8 Hz), 8.02 (1H, s), 8.50 (1H, d, J=5.6 Hz).

MS (EI) m/z: 251(M$^+$).

Referential Example 18

1-(6-Methoxy-3-pyridyl)-5-(4-methoxy-2-pyridyl) pyrazole-3-carboxylic acid ethyl ester

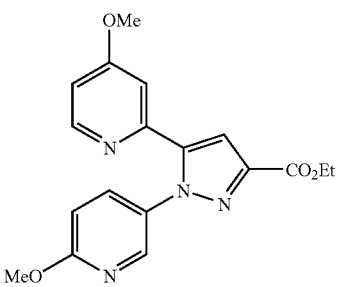

In a manner similar to that described in relation to step 2) of Referential Example 3, the title compound was produced as a solid substance (0.473 g, 49%) by use of 4-(4-methoxy-2-pyridyl)-2,4-dioxobutanoic acid ethyl ester (0.691 g) obtained from Referential Example 17 and 5-hydrazino-2-methoxypyridine (0.383 g) obtained from Referential Example 2.

$^1$H-NMR (400 MHz, CDCl$_3$) δ: 1.41-1.44 (3H, m), 3.82 (3H, s), 3.95 (3H, s), 4.43-4.48 (2H, m), 6.75-6.78 (2H, m), 6.89 (1H, d, J=2.4 Hz), 7.25 (1H, s), 7.68 (1H, dd, J=8.8, 2.4 Hz), 8.11 (1H, d, J=2.4 Hz), 8.33 (1H, d, J=5.6 Hz).

MS (FAB) m/z: 355(M+H)$^+$.

Referential Example 19

1-(6-Methoxy-3-pyridyl)-5-(4-methoxy-2-pyridyl) pyrazole-3-carboxylic acid

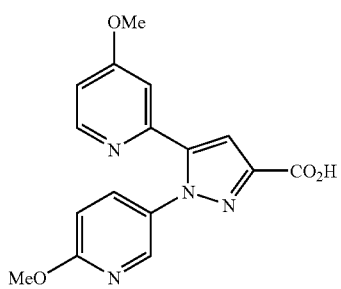

1N Aqueous solution of sodium hydroxide (2.23 mL) was added to 1-(6-Methoxy-3-pyridyl)-5-(4-methoxy-2-pyridyl) pyrazole-3-carboxylic acid ethyl ester (0.416 g) obtained from Referential Example 18 in a mixture of methanol (6.3 mL) and tetrahydrofuran (6.3 mL) at room temperature, followed by stirring for 5 hours. The reaction mixture was neutralized with 1N aqueous solution of hydrochloric acid (2.23 mL), and then partitioned between water and chloroform. Subsequently, the aqueous layer was extracted with chloroform twice. The organic layer was dried over sodium sulfate anhydrate, followed by filtration. The solvent was evaporated under reduced pressure, to thereby give the title compound as a solid substance (0.353 g, 92%).

$^1$H-NMR (400 MHz, DMSO-d$_6$) δ: 3.86 (3H, s), 3.89 (3H, s), 6.88 (1H, d, J=8.8 Hz), 6.93 (1H, dd, J=5.6, 2.7 Hz), 7.29

(1H, d, J=5.6 Hz), 7.37 (1H, s), 7.69-7.72 (1H, m), 8.14 (1H, d, J=2.8 Hz), 8.24 (1H, d, J=5.6 Hz), 13.05 (1H, br).

MS (FAB) m/z: 327(M+H)$^+$.

Referential Example 20

2-Bromo-6-methoxypyridine

In an argon atmosphere, sodium methoxide (1.82 g) was added to 2,6-dibromopyridine (8.0 g) in toluene (120 mL), followed by stirring at 120° C. for 13 hours. Subsequently, sodium methoxide (0.728 g) was added to the mixture, followed by stirring at 120° C. for 6 hours. The mixture was cooled in air. The reaction mixture was partitioned between water and ethyl acetate. The organic layer was dried over sodium sulfate anhydrate, followed by filtration. The solvent was evaporated under reduced pressure. The residue was purified by silica gel column chromatography (hexane-ethyl acetate), to thereby give the title compound in an oily substance (5.64 g, 89%).

$^1$H-NMR (400 MHz, CDCl$_3$) δ: 3.93 (3H, s), 6.68 (1H, d, J=8.0 Hz), 7.05 (1H, d, J=7.2 Hz), 7.39-7.42 (1H, m).

Referential Example 21

6-Methoxypyridine-2-carbonitrile

Copper(I) cyanide (2.68 g) was added to 2-bromo-6-methoxypyridine (5.62 g) in N,N-dimethylformamide (112 mL) at room temperature, followed by stirring at 165° C. for 15 hours. The resultant mixture was cooled in air. Water and ethyl acetate was added to the mixture. The insoluble matter that was formed in the mixture was filtered by Celite. The filtrate was partitioned between water and ethyl acetate. The organic layer was dried over sodium sulfate anhydrate, followed by filtration. The solvent was evaporated under reduced pressure. The residue was subjected to silica gel column chromatography (hexane-ethyl acetate), to thereby give the title compound as a solid substance (1.78 g, 44%).

$^1$H-NMR (400 MHz, CDCl$_3$) δ: 3.96 (3H, s), 6.95-6.98 (1H, m), 7.29-7.31 (1H, m), 7.64-7.67 (1H, m).

MS (EI) m/z: 134(M$^+$).

Referential Example 22

1-(6-Methoxy-2-pyridyl)ethanone

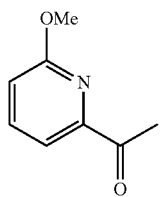

In a manner similar to that described in relation to Referential Example 16, the title compound was produced as a solid substance (0.819 g, 42%) by use of 6-methoxypyridine-2-carbonitrile (1.75 g).

$^1$H-NMR (400 MHz, CDCl$_3$) δ: 2.68 (3H, s), 4.00 (3H, s), 6.92-6.94 (1H, m), 7.62-7.72 (2H, m).

MS (ESI) m/z: 152(M+H)$^+$.

Referential Example 23

4-(6-Methoxy-2-pyridyl)-2,4-dioxobutanoic acid ethyl ester

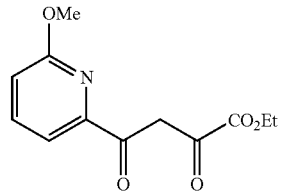

In a manner similar to that described in relation to step 1) of Referential Example 3, the title compound was produced as an oily substance (1.16 g, 87%) by use of 1-(6-methoxy-2-pyridyl)ethanone (0.80 g) and diethyl oxalate (1.44 mL).

$^1$H-NMR (400 MHz, CDCl$_3$) δ: 1.40-1.43 (3H, m), 4.03 (3H, s), 4.38-4.43 (2H, m), 6.95-6.98 (1H, m), 7.63 (1H, m), 7.74-7.76 (1H, m), 8.02 (1H, s).

MS (EI) m/z: 251(M$^+$).

Referential Example 24

1-(6-Methoxy-3-pyridyl)-5-(6-methoxy-2-pyridyl) pyrazole-3-carboxylic acid ethyl ester

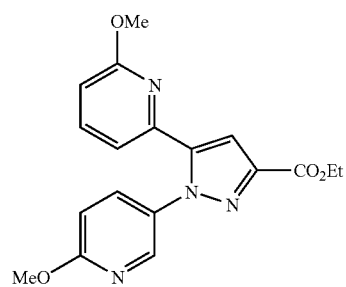

In a manner similar to that described in relation to step 2) of Referential Example 3, the title compound was produced as an oily substance (0.740 g, 46%) by use of 4-(6-methoxy-2-pyridyl)-2,4-dioxobutanoic acid ethyl ester (1.15 g) obtained from Referential Example 23 and 5-hydrazino-2-methoxypyridine (0.637 g) obtained from Referential Example 2.

$^1$H-NMR (400 MHz, CDCl$_3$) δ: 1.41-1.45 (3H, m), 3.43 (3H, s), 3.95 (3H, s), 4.44-4.49 (2H, m), 6.64-6.67 (1H, m), 6.77-6.79 (1H, m), 7.08-7.10 (1H, m), 7.27 (1H, s), 7.56-7.60 (1H, m), 7.64-7.66 (1H, m), 8.16-8.17 (1H, m).

MS (EI) m/z: 354(M$^+$).

Referential Example 25

1-(6-Methoxy-3-pyridyl)-5-(6-methoxy-2-pyridyl)pyrazole-3-carboxylic acid

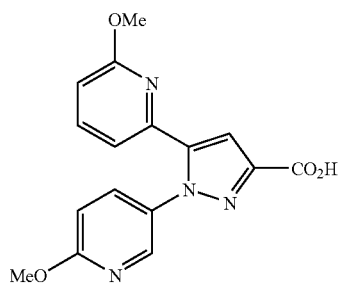

In a manner similar to that described in relation to Referential Example 19, the title compound was produced as a solid substance (0.584 g, 91%) by use of the pyrazole-3-carboxylic acid ethyl ester compound (0.694 g) obtained from Referential Example 24.

$^1$H-NMR (400 MHz, CDCl$_3$) δ: 3.44 (3H, s), 3.96 (3H, s), 6.66-6.69 (1H, m), 6.80 (1H, d, J=8.8 Hz), 7.10-7.12 (1H, m), 7.33 (1H, s), 7.57-7.61 (1H, m), 7.66-7.68 (1H, m), 8.19 (1H, m).

MS (FAB) m/z: 327(M+1)$^+$.

Referential Example 26

6-Methylpyridine-2-carbonitrile

In a manner similar to that described in relation to Referential Example 21, the title compound was produced as a solid substance (2.81 g, 41%) by use of 2-bromo-6-picoline (9.87 g) and copper(I) cyanide (5.14 g).

$^1$H-NMR (400 MHz, CDCl$_3$) δ: 2.62 (3H, s), 7.39 (1H, d, J=8.0 Hz), 7.52 (1H, d, J=7.6 Hz), 7.70-7.74 (1H, m).

MS (EI) m/z: 118(M$^+$).

Referential Example 27

1-(6-Methyl-2-pyridyl)ethanone

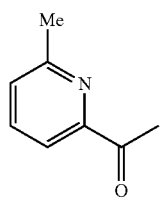

In a manner similar to that described in relation to Referential Example 16, the title compound was produced as an oily substance (1.04 g, 33%) by use of 6-methylpyridine-2-carbonitrile (2.80 g) and 0.93M methylmagnesium bromide in tetrahydrofuran (28.0 mL).

$^1$H-NMR (400 MHz, CDCl$_3$) δ: 2.62 (3H, s), 2.71 (3H, s), 7.30-7.32 (1H, m), 7.68-7.71 (1H, m), 7.82-7.85 (1H, m).

MS (FAB) m/z: 136(M+H)$^+$.

Referential Example 28

4-(6-Methyl-2-pyridyl)-2,4-dioxobutanoic acid ethyl ester

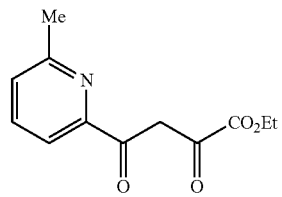

In a manner similar to step 1) of Referential Example 3, the title compound was produced as an oily substance (0.443 g, 25%) by use of 1-(6-methyl-2-pyridyl)ethanone (1.03 g) and diethyl oxalate (2.07 mL).

$^1$H-NMR (400 MHz, CDCl$_3$) δ: 1.42 (3H, t, J=7.2 Hz), 2.67 (3H, s), 4.41 (2H, q, J=7.2 Hz), 7.39 (1H, d, J=7.6 Hz), 7.49 (1H, br), 7.79-7.83 (1H, m), 8.00 (1H, d, J=7.6 Hz).

MS (EI) m/z: 235(M$^+$).

Referential Example 29

1-(6-Methoxy-3-pyridyl)-5-(6-methyl-2-pridyl)pyrazole-3-carboxylic acid ethyl ester

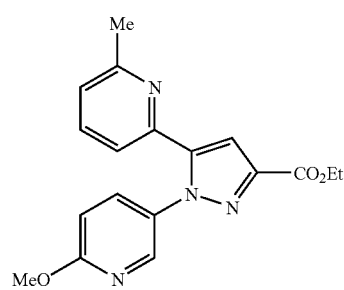

In a manner similar to that described in relation to step 2) of Referential Example 3, the title compound was produced as an oily substance (0.491 g, 79%) by use of 4-(6-methyl-2-pyridyl)-2,4-dioxobutanoic acid ethyl ester (0.431 g) obtained from Referential Example 28 and 5-hydrazino-2-methoxypyridine (0.255 g) obtained from Referential Example 2.

$^1$H-NMR (400 MHz, CDCl$_3$) δ: 1.41-1.44 (3H, m), 2.41 (3H, s), 3.95 (3H, s), 4.43-4.48 (2H, m), 6.75-6.77 (1H, m), 7.07-7.14 (2H, m), 7.27 (1H, s), 7.53-7.57 (1H, m), 7.66-7.69 (1H, m), 8.10-8.11 (1H, m).

MS (FAB) m/z: 339(M$^+$).

Referential Example 30

1-(6-Methoxy-3-pyridyl)-5-(6-methyl-2-pyridyl)pyrazole-3-carboxylic acid

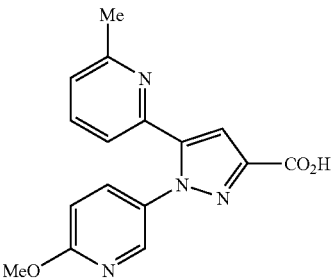

In a manner similar to that described in relation to Referential Example 19, the title compound was produced as a solid substance (0.342 g, 84%) by use of the pyrazole-3-carboxylic acid ethyl ester compound (0.444 g) obtained from Referential Example 29.

$^1$H-NMR (400 MHz, DMSO-$d_6$) δ: 2.25 (3H, s), 3.90 (3H, s), 6.90 (1H, d, J=8.8 Hz), 7.20 (1H, d, J=7.6 Hz), 7.32 (1H, s), 7.46 (1H, d, J=7.6 Hz), 7.71-7.75 (2H, m), 8.14 (1H, d, J=2.4 Hz), 13.05 (1H, br).

MS (FAB) m/z: 311(M+H)$^+$.

Referential Example 31

4-(2-Pyridyl)-2,4-dioxobutanoic acid ethyl ester

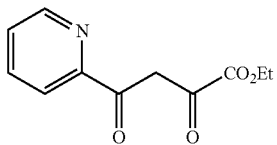

In a manner similar to that described in relation to step 1) of Referential Example 3, the title compound was produced as a solid substance (1.12 g, 41%) by use of 2-acetylpyridine (1.39 mL) and diethyl oxalate (3.36 mL).

$^1$H-NMR (400 MHz, CDCl$_3$) δ: 1.40-1.43 (3H, m), 4.38-4.43 (2H, m), 7.51-7.54 (1H, m), 7.62 (1H, s), 7.89-7.93 (1H, m), 8.18 (1H, d, J=8.0 Hz), 8.73 (1H, d, J=4.4 Hz).

MS (EI) m/z: 221(M$^+$).

Referential Example 32

1-(6-Methoxy-3-pyridyl)-5-(2-pyridyl)pyrazole-3-carboxylic acid ethyl ester

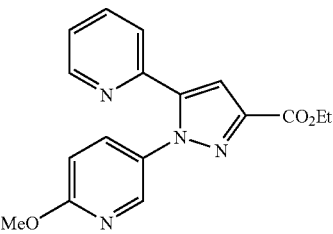

1) 5-Hydroxy-1-(6-methoxy-3-pyridyl)-5-(2-pyridyl)-4,5-dihydropyrazole-3-carboxylic acid ethyl ester 4-(2-Pyridyl)-2,4-dioxobutanoic acid ethyl ester (1.10 g) obtained from Referential Example 31 and 5-hydrazino-2-methoxypyridine (0.692 g) obtained from Referential Example 2 were dissolved in ethanol (22 mL). The resultant mixture was refluxed under heat for 14 hours, followed by cooling in air. The solvent was evaporated under reduced pressure. The residue was purified by silica gel column chromatography (hexane-ethyl acetate), followed by purification through silica gel column chromatography (toluene-acetone), to thereby give 5-hydroxy-1-(6-methoxy-3-pyridyl)-5-(2-pyridyl)-4,5-dihydropyrazole-3-carboxylic acid ethyl ester as a solid substance (0.575 g, 34%).

$^1$H-NMR (400 MHz, CDCl$_3$) δ: 1.37-1.40 (3H, m), 3.47-3.64 (2H, m), 3.81 (3H, s), 4.35-4.40 (2H, m), 6.57-6.59 (1H, m), 6.85 (1H, m), 7.34-7.38 (1H, m), 7.45-7.48 (1H, m), 7.52-7.59 (2H, m), 7.79-7.83 (1H, m), 8.55-8.57 (1H, m).

2) The Title Compound

The above-obtained 5-hydroxy-1-(6-methoxy-3-pyridyl)-5-(2-pyridyl)-4,5-dihydropyrazole-3-carboxylic acid ethyl ester (0.546 g) was dissolved in ethanol (11 mL). Acetic acid (0.456 mL) was added to the resultant mixture, followed by stirring at 105° C. for 4 hours. The mixture was cooled in air. Subsequently, the reaction mixture was partitioned by use of saturated aqueous solution of sodium hydrogencarbonate, water, and ethyl acetate. The organic layer was dried over sodium sulfate anhydrate, followed by filtration. The solvent was evaporated under reduced pressure. The residue was purified through silica gel column chromatography (hexane-ethyl acetate), to thereby give the title compound as a solid substance (0.516 g, 100%).

$^1$H-NMR (400 MHz, CDCl$_3$) δ: 1.43 (3H, t, J=7.2 Hz), 3.95 (3H, s), 4.46 (2H, q, J=7.2 Hz), 6.76-6.78 (1H, m), 7.22-7.28 (2H, m), 7.35-7.37 (1H, m), 7.66-7.71 (2H, m), 8.11 (1H, m), 8.52-8.54 (1H, m).

MS (FAB) m/z: 325(M+H)$^+$.

Referential Example 33

1-(6-Methoxy-3-pyridyl)-5-(2-pyridyl)pyrazole-3-carboxylic acid

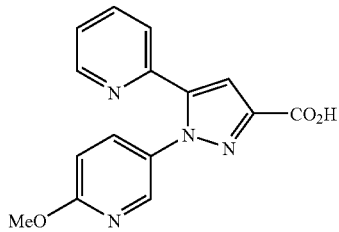

In a manner similar to that described in relation to Referential Example 19, the title compound was produced as a solid substance (0.344 g, 86%) by use of the pyrazole-3-carboxylic acid ethyl ester compound (0.438 g) obtained from step 2) of Referential Example 32.

$^1$H-NMR (400 MHz, DMSO-$d_6$) δ: 3.89 (3H, s), 6.89 (1H, d, J=8.8 Hz), 7.33-7.37 (2H, m), 7.67-7.73 (2H, m), 7.85-7.89 (1H, m), 8.14 (1H, d, J=2.4 Hz), 8.44-8.46 (1H, m), 13.06 (1H, br).

MS (FAB) m/z: 297(M+H)$^+$.

Referential Example 34

4-(4-Methylphenyl)-2,4-dioxobutanoic acid ethyl ester

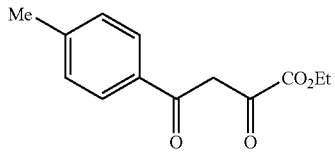

In a manner similar to that described in relation to step 1) of Referential Example 3, the title compound was produced as an oily substance (1.68 g, 64%) by use of 4'-methylacetophenone (1.50 g) and diethyl oxalate (3.04 mL).

$^1$H-NMR (400 MHz, CDCl$_3$) δ: 1.40-1.43 (3H, m), 2.44 (3H, s), 4.37-4.43 (2H, m), 7.06 (1H, s), 7.30-7.32 (2H, m), 7.89-7.91 (2H, m).

MS (EI) m/z: 234(M$^+$).

Referential Example 35

1-(6-Methoxy-3-pyridyl)-5-(4-methylphenyl)pyrazole-3-carboxylic acid ethyl ester

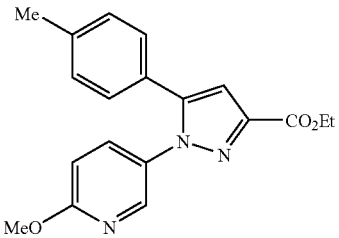

In a manner similar to that described in relation to step 2) of Referential Example 3, the title compound was produced as an oily substance (1.52 g, 63%) by use of 4-(4-methylphenyl)-2,4-dioxobutanoic acid ethyl ester (1.67 g) obtained from Referential Example 34 and 5-hydrazino-2-methoxypyridine (0.992 g) obtained from Referential Example 2.

$^1$H-NMR (400 MHz, CDCl$_3$) δ: 1.41-1.44 (3H, m), 2.35 (3H, s), 3.94 (3H, s), 4.43-4.48 (2H, m), 6.72-6.75 (1H, m), 7.01 (1H, s), 7.09-7.15 (4H, m), 7.56-7.59 (1H, m), 8.11 (1H, m).

MS (EI) m/z: 337(M$^+$).

Referential Example 36

1-(6-Methoxy-3-pyridyl)-5-(4-methylphenyl)pyrazole-3-carboxylic acid

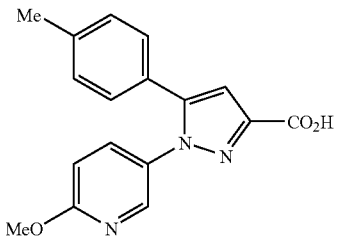

In a manner similar to that described in relation to Referential Example 19, the title compound was produced as an amorphous product (1.24 g, 90%) by use of pyrazole-3-carboxylic acid ethyl ester (1.50 g) obtained from Referential Example 35.

$^1$H-NMR (400 MHz, CDCl$_3$) δ: 2.36 (3H, s), 3.95 (3H, s), 6.75 (1H, d, J=8.8 Hz), 7.07 (1H, s), 7.11-7.16 (4H, m), 7.59 (1H, dd, J=8.8, 2.8 Hz), 8.13 (1H, d, J=2.8 Hz).

MS (EI) m/z: 309(M$^+$).

Referential Example 37

4-(2-Fluorophenyl)-2,4-dioxobutanoic acid ethyl ester

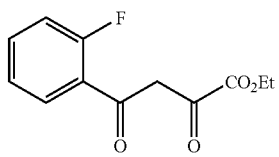

In a manner similar to that described in relation to step 1) of Referential Example 3, the title compound was produced as a solid substance (0.256 g, 37%) by use of 2'-fluoroacetophenone (0.40 g) and diethyl oxalate.

$^1$H-NMR (400 MHz, CDCl$_3$) δ: 1.39-1.43 (3H, m), 4.37-4.43 (2H, m), 6.96-7.32 (3H, m), 7.54-7.59 (1H, m), 7.90-7.99 (1H, m).

MS (FAB) m/z: 239(M+H)$^+$.

Referential Example 38

5-(2-Fluorophenyl)-1-(6-methoxy-3-pyridyl)pyrazole-3-carboxylic acid ethyl ester

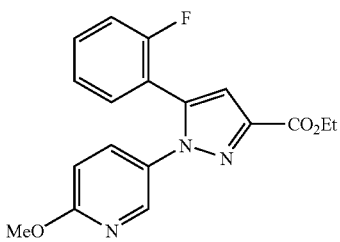

In a manner similar to that described in relation to step 2) of Referential Example 7, the title compound was produced as an oily substance (0.231 g, 65%) by use of 4-(2-fluorophenyl)-2,4-dioxobutanoic acid ethyl ester (0.248 g) obtained from Referential Example 37 and 5-hydrazino-2-methoxypyridine hydrochloride (0.219 g) obtained from Referential Example 1.

$^1$H-NMR (400 MHz, CDCl$_3$) δ: 1.41-1.45 (3H, m), 3.91 (3H, s), 4.43-4.48 (2H, m), 6.71-6.73 (1H, m), 7.03-7.41 (5H, m), 7.60-7.63 (1H, m), 8.04-8.06 (1H, m).

MS (EI) m/z: 341(M$^+$).

Referential Example 39

5-(2-Fluorophenyl)-1-(6-methoxy-3-pyridyl)pyrazole-3-carboxylic acid

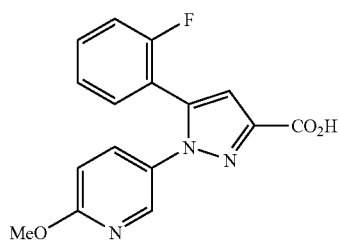

In a manner similar to that described in relation to Referential Example 19, the title compound was produced as an amorphous product (0.199 g, 98%) by use of the pyrazole-3-carboxylic acid ethyl ester compound (0.222 g) obtained from Referential Example 38.

$^1$H-NMR (400 MHz, CDCl$_3$) δ: 3.93 (3H, s), 6.75 (1H, d, J=8.8 Hz), 7.03-7.43 (5H, m), 7.63 (1H, dd, J=8.8, 2.8 Hz), 8.07 (1H, d, J=2.8 Hz).

MS (EI) m/z: 313(M$^+$).

Referential Example 40

1-(6-Methoxy-3-pyridyl)-5-phenylpyrazole-3-carboxylic acid ethyl ester

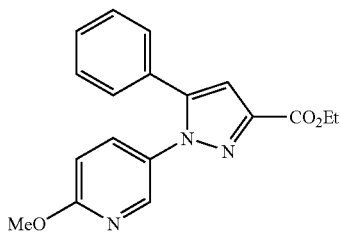

In a manner similar to that described in relation to step 1) of Referential Example 3,4-phenyl-2,4-dioxobutanoic acid ethyl ester was produced as an oily substance (22.96 g, quantitative amount) by use of acetophenone (9.85 g) and diethyl oxalate (23.97 g). Subsequently, in a manner similar to that described in relation to step 2) of Referential Example 3, the title compound was produced as an oily substance (16.37 g, 61%) by use of the above-obtained 4-phenyl-2,4-dioxobutanoic acid ethyl ester and 5-hydrazino-2-methoxypyridine (11.39 g) obtained from Referential Example 2.

$^1$H-NMR (400 MHz, CDCl$_3$) δ: 1.42 (3H, t, J=7.0 Hz), 3.93 (3H, s), 4.45 (2H, q, J=7.0 Hz), 6.73 (1H, d, J=8.8 Hz), 7.04 (1H, s), 7.19-7.26 (2H, m), 7.30-7.37 (3H, m), 7.57 (1H, dd, J=8.8, 2.6 Hz), 8.11 (1H, d, J=2.6 Hz).

MS (ESI) m/z: 324 (M+H)$^+$.

Referential Example 41

1-(6-Methoxy-3-pyridyl)-5-phenylpyrazole-3-carboxylic acid

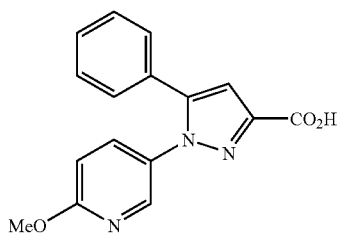

In a manner similar to that described in relation to Referential Example 19, the title compound was produced as crystals (13.88 g, 92%) by use of the pyrazole-3-carboxylic acid ethyl ester compound (16.37 g) obtained from Referential Example 40.

$^1$H-NMR (400 MHz, CDCl$_3$) δ: 3.94 (3H, s), 6.75 (1H, d, J=8.8 Hz), 7.10 (1H, s), 7.21-7.27 (2H, m), 7.32-7.39 (3H, m), 7.58 (1H, dd, J=8.8, 2.6 Hz), 8.12 (1H, d, J=2.6 Hz).

MS (ESI) m/z: 296(M+H)$^+$.

Referential Example 42

1-(6-Chloro-3-pyridazinyl)-5-phenylpyrazole-3-carboxylic acid ethyl ester

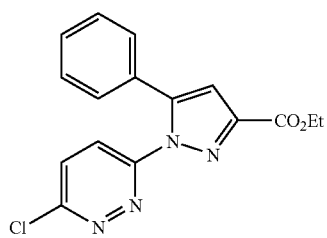

In a manner similar to that described in relation to step 2) of Referential Example 3, the title compound was produced as an amorphous product (1.93 g, 65%) by use of 3-chloro-6-hydrazinopyridazine (1.31 g) and 4-phenyl-2,4-dioxobutanoic acid ethyl ester (2.20 g) produced in a manner similar to that described in relation to Referential Example 40.

$^1$H-NMR (400 MHz, CDCl$_3$) δ: 1.43 (3H, t, J=7.0 Hz), 4.46 (2H, q, J=7.0 Hz), 7.04 (1H, s), 7.29-7.39 (5H, m), 7.64 (1H, d, J=9.1 Hz), 8.06 (1H, d, J=9.1 Hz).

LC-MS m/z: 329(M+H)$^+$.

Referential Example 43

1-(6-Methoxy-3-pyridazinyl)-5-phenylpyrazole-3-carboxylic acid

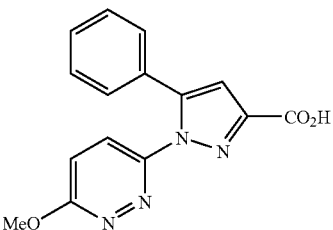

The pyrazole-3-carboxylic acid ethyl ester compound (329 mg) obtained from Referential Example 42 was dissolved in methanol (10 mL). 28% Sodium methoxide in methanol (0.6 mL) was added to the resultant mixture, followed by refluxing under heat for 2 hours. The mixture was cooled in air. Tetrahydrofuran (5 mL) and water (5 mL) were added to the reaction mixture, followed by stirring at room temperature for 30 minutes. Subsequently, 1N aqueous solution of hydrochloric acid (4 mL) was added to the reaction mixture. The resultant mixture was partitioned between water and ethyl acetate. The organic layer was sequentially washed with water and saturated brine. Subsequently, the organic layer was dried over magnesium sulfate anhydrate, followed by filtration. The solvent was evaporated under reduced pressure. Ether was added to the residue. The resultant solid was collected by filtration, and then dried, to thereby give the title compound as a solid substance (218 mg, 74%).

$^1$H-NMR (400 MHz, DMSO-$d_6$) δ: 4.03 (3H, s), 7.12 (1H, s), 7.28-7.31 (2H, m), 7.37-7.40 (3H, m), 7.51 (1H, d, J=9.2 Hz), 8.01 (1H, d, J=9.2 Hz), 13.18 (1H, br).

LC-MSm/z: 297(M+H)$^+$.

Referential Example 44

5-(4-Methoxyphenyl)-1-(6-methoxy-3-pyridyl)pyrazole-3-carboxylic acid ethyl ester

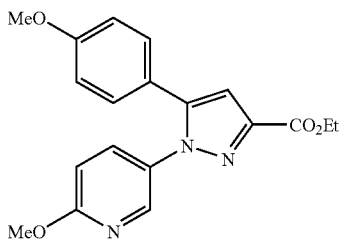

4-Methoxyacetophenone (300 mg) was dissolved in N,N-dimethylformamide (4 mL). 60% Sodium hydride (160 mg) was added to the resultant mixture at 0° C., followed by stirring at room temperature for 0.5 hours. Under cooling with ice, diethyl oxalate (542 µL) was added to the reaction mixture, followed by stirring at room temperature for 14 hours. 5-Hydrazino-2-methoxypyridine hydrochloride (406 mg) obtained from Referential Example 1 was added to the reaction mixture, followed by stirring at 80° C. for 3 hours. The mixture was cooled in air. The reaction mixture was partitioned between water and ethyl acetate. The organic layer was sequentially washed with water and saturated brine. Subsequently, the organic layer was dried over sodium sulfate anhydrate, followed by filtration. The solvent was evaporated under reduced pressure. The residue was subjected to silica gel column chromatography (hexane-ethyl acetate), to thereby give the title compound as an oily substance (517 mg, 73%).

$^1$H-NMR (400 MHz, CDCl$_3$) δ: 1.42 (3H, t, J=7.0 Hz), 3.80 (3H, s), 3.93 (3H, s), 4.44 (2H, q, J=7.0 Hz), 6.73 (1H, d, J=8.8 Hz), 6.84 (2H, d-like, J=8.8 Hz), 6.97 (1H, s), 7.13 (2H, d-like, J=8.8 Hz), 7.56 (1H, dd, J=8.8, 2.7 Hz), 8.10 (1H, d, J=2.7 Hz).

MS (ESI) m/z: 354(M+H)$^+$.

Referential Example 45

5-(4-Methoxyphenyl)-1-(6-methoxy-3-pyridyl)pyrazole-3-carboxylic acid

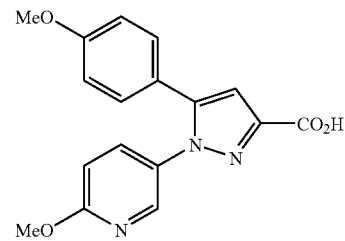

The pyrazole-3-carboxylic acid ethyl ester compound (515 mg) obtained from Referential Example 44 was dissolved in methanol (10 mL). 1M Aqueous solution of sodium hydroxide (3.64 mL) was added to the resultant mixture, followed by refluxing under heat for 1 hour. The reaction solvent was evaporated under reduced pressure. The residue was partitioned between water and ethyl acetate. The aqueous layer was acidified with 1M aqueous solution of hydrochloric acid (4.5 mL). Subsequently, the aqueous layer was extracted with ethyl acetate. The organic layer was sequentially washed with water and saturated brine. Subsequently, the organic layer was dried over sodium sulfate anhydrate, followed by filtration. The solvent was evaporated under reduced pressure, to thereby give the title compound as crystals (453 mg, 95%).

$^1$H-NMR (400 MHz, CDCl$_3$) δ: 3.81 (3H, s), 3.95 (3H, s), 6.75 (1H, d, J=8.8 Hz), 6.86 (2H, d-like, J=8.8 Hz), 7.03 (1H, s), 7.15 (2H, d-like, J=8.8 Hz), 7.57 (1H, dd, J=8.8, 2.7 Hz), 8.12 (1H, d, J=2.7 Hz).

MS (ESI) m/z: 326(M+H)$^+$.

Referential Example 46

5-(3-Methoxyphenyl)-1-(6-methoxy-3-pyridyl)pyrazole-3-carboxylic acid ethyl ester

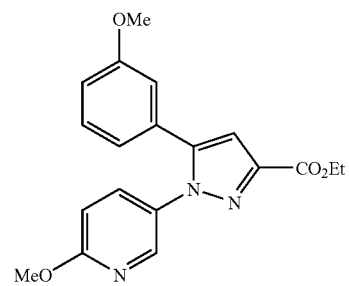

In a manner similar to that described in relation to Referential Example 44, the title compound was produced as an oily substance (495 mg, 70%) by use of 3-methoxyacetophenone (300 mg), diethyl oxalate (542 μL), and 5-hydrazino-2-methoxypyridine hydrochloride (406 mg) obtained from Referential Example 1.

$^1$H-NMR (400 MHz, CDCl$_3$) δ: 1.42 (3H, t, J=7.1 Hz), 3.72 (3H, s), 3.93 (3H, s), 4.45 (2H, q, J=7.0 Hz), 6.73 (1H, d, J=8.8 Hz), 6.73-6.80 (2H, m), 6.85-6.91 (1H, m), 7.03 (1H, s), 7.20-7.27 (1H, m), 7.58 (1H, dd, J=8.8, 2.7 Hz), 8.11 (1H, d, J=2.7 Hz).

MS (ESI) m/z: 354(M+H)$^+$.

Referential Example 47

5-(3-Methoxyphenyl)-1-(6-methoxy-3-pyridyl)pyrazole-3-carboxylic acid

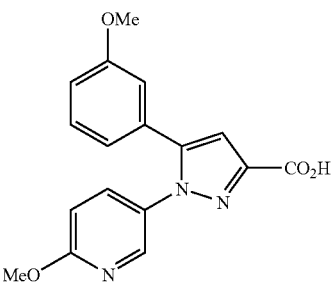

In a manner similar to that described in relation to Referential Example 45, the title compound was produced as crystals (427 mg, 94%) by use of pyrazole-3-carboxylic acid ethyl ester compound (490 mg) obtained from Referential Example 46.

$^1$H-NMR (400 MHz, CDCl$_3$) δ: 3.74 (3H, s), 3.94 (3H, s), 6.75 (1H, d, J=8.8 Hz), 6.75-6.82 (2H, m), 6.88-6.93 (1H, m), 7.09 (1H, s), 7.22-7.29 (1H, m), 7.58 (1H, dd, J=8.8, 2.7 Hz), 8.13 (1H, d, J=2.7 Hz).

MS (ESI) m/z: 326(M+H)$^+$.

Referential Example 48

5-(2-Methoxyphenyl)-1-(6-methoxy-3-pyridyl)pyrazole-3-carboxylic acid ethyl ester

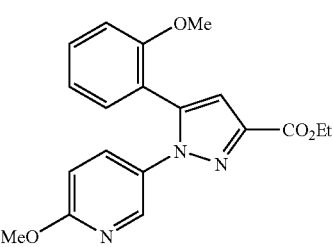

In a manner similar to that described in relation to Referential Example 44, the title compound was produced as crystals (476 mg, 67%) by use of 2-methoxyacetophenone (300 mg), diethyl oxalate (542 μL), and 5-hydrazino-2-methoxypyridine hydrochloride (421 mg) obtained from Referential Example 1.

$^1$H-NMR (400 MHz, CDCl$_3$) δ: 1.41 (3H, t, J=7.1 Hz), 3.49 (3H, s), 3.89 (3H, s), 4.44 (2H, q, J=7.1 Hz), 6.67 (1H, d, J=8.8 Hz), 6.81 (1H, d, J=8.3 Hz), 6.95-7.01 (1H, m), 6.97 (1H, s), 7.22-7.29 (1H, m), 7.33-7.40 (1H, m), 7.58 (1H, dd, J=8.8, 2.7 Hz), 8.03 (1H, d, J=2.7 Hz).

MS (ESI) m/z: 354(M+H)$^+$.

Referential Example 49

5-(2-Methoxyphenyl)-1-(6-methoxy-3-pyridyl)pyrazole-3-carboxylic acid

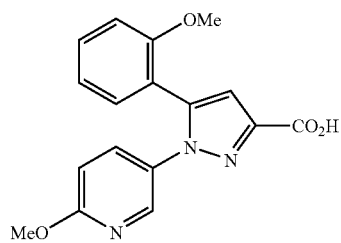

In a manner similar to that described in relation to Referential Example 45, the title compound was produced as a solid substance (454 mg, quantitative amount) by use of the pyrazole-3-carboxylic acid ethyl ester compound (473 mg) obtained from Referential Example 48.

$^1$H-NMR (400 MHz, CDCl$_3$) δ: 3.50 (3H, s), 3.91 (3H, s), 6.70 (1H, d, J=8.8 Hz), 6.83 (1H, d, J=8.3 Hz), 6.97-7.03 (1H, m), 7.04 (1H, s), 7.23-7.30 (1H, m), 7.35-7.42 (1H, m), 7.58 (1H, dd, J=8.8, 2.7 Hz), 8.05 (1H, d, J=2.7 Hz).

MS (ESI) m/z: 326(M+H)$^+$.

Referential Example 50

5-[4-(Trifluoromethyl)phenyl]-1-(6-methoxy-3-pyridyl)pyrazole-3-carboxylic acid ethyl ester

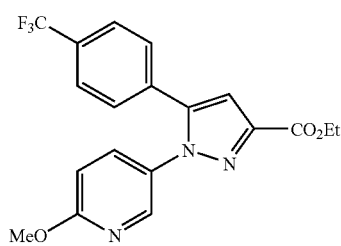

In a manner similar to that described in relation to Referential Example 44, the title compound was produced as an oily substance (332 mg, 42%) by use of 4'-(trifluoromethyl)acetophenone (376 mg), diethyl oxalate (542 μL), and 5-hydrazino-2-methoxypyridine hydrochloride (421 mg) obtained from Referential Example 1.

$^1$H-NMR (400 MHz, CDCl$_3$) δ: 1.43 (3H, t, J=7.1 Hz), 3.94 (3H, s), 4.46 (2H, q, J=7.1 Hz), 6.77 (1H, d, J=8.8 Hz), 7.10 (1H, s), 7.34 (2H, d, J=8.0 Hz), 7.56-7.64 (3H, m), 8.07 (1H, d, J=2.7 Hz).

MS (ESI) m/z: 392(M+H)$^+$.

Referential Example 51

5-[4-(Trifluoromethyl)phenyl]-1-(6-methoxy-3-pyridyl)pyrazole-3-carboxylic acid

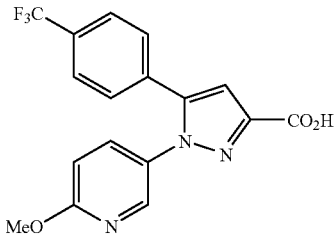

In a manner similar to that described in relation to Referential Example 45, the title compound was produced as crystals (309 mg, quantitative amount) by use of the pyrazole-3-carboxylic acid ethyl ester compound (332 mg) obtained from Referential Example 50.

$^1$H-NMR (400 MHz, CDCl$_3$) δ: 3.96 (3H, s), 6.79 (1H, d, J=8.8 Hz), 7.15 (1H, s), 7.37 (2H, d, J=8.5 Hz), 7.58 (1H, dd, J=8.8, 2.7 Hz), 7.62 (2H, d, J=8.5 Hz), 8.09 (1H, d, J=2.7 Hz).

MS (ESI) m/z: 364(M+H)$^+$.

Referential Example 52

3-Hydrazinopyridine

Sodium nitrite (4.28 g) in water (20 mL) was added dropwise to 3-aminopyridine (5.15 g) in concentrated hydrochloric acid (54 mL) at an internal temperature of 0 to 5° C. over a period of 30 minutes, followed by stirring for 5 minutes. The reaction mixture was added dropwise to tin(II) chloride dihydrate (43.68 g) in concentrated hydrochloric acid (30 mL) at an internal temperature of 0 to 10° C. over a period of 1 hour, followed by stirring for 0.5 hours. The resultant solid was collected by filtration. Subsequently, the solid was washed with diethyl ether, and then dried under reduced pressure, to thereby give the title compound (16.38 g, quantitative amount).

$^1$H-NMR (400 MHz, DMSO-d$_6$) δ: 7.93 (1H, dd, J=8.8-5.6 Hz), 8.09 (1H, dd, J=8.8, 2.7 Hz), 8.43 (1H, d, J=5.6 Hz), 8.51 (1H, d-like, J=2.7 Hz).

MS (ESI) m/z: 109(M)$^+$.

Referential Example 53

4-Methyl-5-phenyl-1-(3-pyridyl)pyrazole-3-carboxylic acid ethyl ester

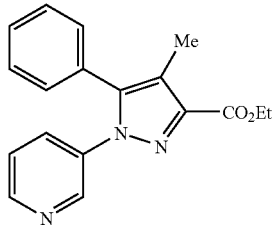

1) 3-Methyl-4-phenyl-2,4-dioxobutanoic acid ethyl ester

Propiophenone (4.0 g) in diethyl ether (5 mL) was added to 1.0 M lithium bis(trimethylsilyl)amide in tetrahydrofuran (30 mL) at −78° C., followed by stirring for 30 minutes. Diethyl oxalate (4.35 g) in diethyl ether (5 mL) was added to the reaction mixture, followed by stirring for 10 minutes. The resultant mixture was further stirred at room temperature for 16 hours. The resultant solid was collected by filtration. Subsequently, the solid was washed with diethyl ether, and then dried, to thereby give a lithium salt of 3-methyl-4-phenyl-2,4-dioxobutanoic acid ethyl ester as a solid substance (3.23 g, 47%).

MS (FAB) m/z: 235(M+H)$^+$.

2) The Title Compound

The above-obtained lithium salt of 3-methyl-4-phenyl-2,4-dioxobutanoic acid ethyl ester (1.502 g) was dissolved in ethanol (30 mL). To the resultant mixture were added 1M HCl in ethanol (8 mL) and 3-hydrazinopyridine (1.977 g) obtained from Referential Example 52, followed by refluxing for 2.5 hours. The mixture was cooled in air. The reaction mixture was alkalinized to pH 10 with an aqueous solution of sodium hydroxide. The mixture was partitioned between chloroform and water. The aqueous layer was extracted with chloroform. The organic layer was washed with saturated brine, and then dried over sodium sulfate anhydrate, followed by filtration. The solvent was evaporated under reduced pressure. The residue was purified by silica gel column chromatography (chloroform-acetone), to thereby give the title compound as an oily substance (1.428 g, 34%).

$^1$H-NMR (400 MHz, CDCl$_3$) δ: 1.44 (3H, t, J=7.1 Hz), 2.32 (3H, s), 4.47 (2H, q, J=7.1 Hz), 7.13-7.20 (2H, m), 7.22-7.30 (1H, m), 7.35-7.42 (3H, m), 7.60-7.68 (1H, m), 8.46-8.53 (2H, m).

MS (FAB) m/z: 308(M+H)$^+$.

Referential Example 54

4-Methyl-5-phenyl-1-(3-pyridyl)pyrazole-3-carboxylic acid

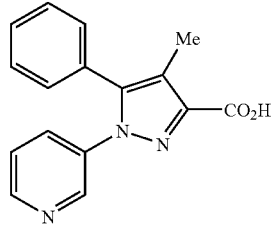

In a manner similar to that described in relation to Referential Example 45, the title compound was produced as a solid substance (0.892 g, 69%) by use of the pyrazole-3-carboxylic acid ethyl ester compound (1.428 g) obtained from Referential Example 53.

$^1$H-NMR (400 MHz, DMSO-d$_6$) δ: 2.20 (3H, s), 7.20-7.30 (2H, m), 7.37-7.50 (m, 4H), 7.66-7.74 (1H, m), 8.41 (1H, d, J=2.7 Hz), 8.52 (1H, d-like, J=4.7 Hz), 12.91 (1H, br).

LC-MS m/z: 280(M+H)$^+$.

Referential Example 55

4-Methyl-1,5-diphenylpyrazole-3-carboxylic acid ethyl ester

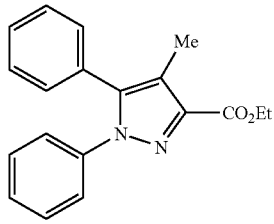

In a manner similar to that described in relation to step 2) of Referential Example 53, the title compound was produced as an oily substance (1.897 g, 62%) by use of the lithium salt of 3-methyl-4-phenyl-2,4-dioxobutanoic acid ethyl ester (3.04 g) obtained from step 1) of Referential Example 53 and phenylhydrazone (1.671 g).

$^1$H-NMR (400 MHz, CDCl$_3$) δ: 1.43 (3H, t, J=7.3 Hz), 2.32 (3H, s), 4.46 (2H, q, J=7.3 Hz), 7.10-7.18 (2H, m), 7.20-7.31 (5H, m), 7.32-7.40 (3H, m).

MS (FAB) m/z: 307(M+H)$^+$.

Referential Example 56

4-Methyl-1,5-diphenylpyrazole-3-carboxylic acid

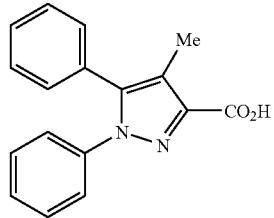

In a manner similar to that described in relation to Referential Example 4, the title compound was produced as a solid substance (1.38 g, 80%) by use of the pyrazole-3-carboxylic acid ethyl ester compound (1.897 g) obtained from Referential Example 55.

$^1$H-NMR (400 MHz, DMSO-d$_6$) δ: 2.20 (3H, s), 7.15-7.25 (4H, m), 7.30-7.45 (6H, m), 12.80 (H, br).

MS (FAB) m/z: 279(M+H)$^+$.

Referential Example 57

α-Fluoroacetophenone

A suspension of potassium fluoride (3.091 g) and 18-crown-6-ether (0.341 g) in acetonitrile (25 mL) was stirred at 55° C. for 1 hour. α-Bromoacetophenone (5.12 g) was added to the reaction mixture, followed by stirring for 20 hours. Subsequently, diethyl ether was added to the reaction mixture, and then the insoluble matter that was formed was removed by filtration. Water was added for partitioning the filtrate. The organic layer was sequentially washed with water and saturated brine. Subsequently, the organic layer was dried over sodium sulfate anhydrate, followed by filtration. The solvent was evaporated under reduced pressure, to thereby give the residue.

The similar reaction procedure was repeated, to thereby give the residue. The residues were combined, and purified through silica gel column chromatography (hexane-ethyl acetate), to thereby give the title compound as an oily substance (4.7 g, 45%).

$^1$H-NMR (400 MHz, CDCl$_3$) δ: 5.53 (2H, d, J=47.0 Hz), 7.50 (2H, t-like, J=7.9 Hz), 7.62 (1H, t-like, J=7.9 Hz), 7.89 (2H, d-like, J=7.9 Hz).

MS (ESI) m/z: 139(M+H)$^+$.

Referential Example 58

4-Fluoro-1,5-diphenylpyrazole-3-carboxylic acid ethyl ester

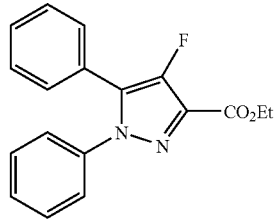

1) 3-Fluoro-4-phenyl-2,4-dioxobutanoic acid ethyl ester 1.0 M Lithium bis(trimethylsilyl)amide in tetrahydrofuran (13 mL) was added dropwise to α-fluoroacetophenone (1.64 g) in tetrahydrofuran (35 mL) at α-78° C., followed by stirring for 45 minutes. Diethyl oxalate (1.77 mL) was added to the reaction mixture, followed by stirring for 30 minutes. The mixture was further stirred at 0° C. for 1 hour. The resultant mixture was neutralized with 1M aqueous solution of hydrochloric acid. The reaction mixture was partitioned between water and chloroform. Subsequently, the aqueous layer was extracted with chloroform. The organic layers were combined, and washed with saturated brine, and then dried over sodium sulfate anhydrate. The mixture was subjected to filtration, and the solvent was evaporated under reduced pressure, to thereby give 3-fluoro-4-phenyl-2,4-dioxobutanoic acid ethyl ester as an oily substance (0.753 g, 27%).

2) The Title Compound

In a manner similar to that described in relation to step 2) of Referential Example 53, the title compound was produced (0.208 g, 15%) by use of the above-obtained lithium salt of 3-fluoro-4-phenyl-2,4-dioxobutanoic acid ethyl ester (0.753 g) and phenylhydrazine (0.350 g).

$^1$H-NMR (400 MHz, CDCl$_3$) δ: 1.27 (3H, t, J=7.1 Hz), 4.30 (2H, q, J=7.1 Hz), 7.33-7.52 (8H, m), 7.93 (2H, d-like, J=7.4 Hz).

MS (FAB) m/z: 311(M+H)$^+$.

Referential Example 59

4-Fluoro-1,5-diphenylpyrazole-3-carboxylic acid

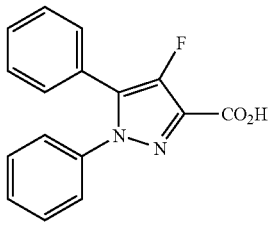

In a manner similar to that described in relation to Referential Example 4, the title compound was produced as a solid substance (0.169 g, 90%) by use of the pyrazole-3-carboxylic acid ethyl ester compound (0.208 g) obtained from Referential Example 58.

$^1$H-NMR (400 MHz, DMSO-$d_6$) δ: 7.45 (1H, t-like, J=7.6 Hz), 7.48-7.60 (7H, m), 7.83 (1H, d-like, J=7.3 Hz).

Referential Example 60

1,4-Dihydro-1-(6-methoxy-3-pyridyl)indeno[1,2-c]pyrazole-3-carboxylic acid ethyl ester

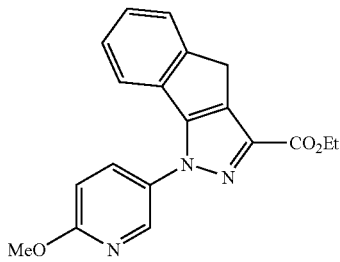

60% Sodium hydride (400 mg) was added to 1-indanone (661 mg) in N,N-dimethylformamide (10 mL) at 0° C., followed by stirring at room temperature for 0.5 hours. Diethyl oxalate (1.36 mL) was added to the reaction mixture at 0° C., followed by stirring at room temperature for 16 hours. The reaction mixture was acidified with 1M aqueous solution of hydrochloric acid (11 mL). Subsequently, the mixture was partitioned between water and ethyl acetate. The organic layer was sequentially washed with water and saturated brine, and then dried over sodium sulfate anhydrate. The mixture was subjected to filtration, and the solvent was evaporated under reduced pressure, to thereby give 2-oxo-2-(1-oxoindan-2-yl)acetic acid ethyl ester as an oily substance (1.441 g, quantitative amount). 5-Hydrazino-2-methoxypyridine (696 mg) obtained from Referential Example 2 was added to the above-obtained 2-oxo-2-(1-oxoindan-2-yl)acetic acid ethyl ester in ethanol (25 mL), followed by refluxing under heat for 16 hours. Subsequently, the resultant mixture was cooled in air. The reaction solvent was evaporated under reduced pressure. The residue was partitioned between water and ethyl acetate. The organic layer was sequentially washed with water and saturated brine, and dried over sodium sulfate anhydrate. The mixture was subjected to filtration, and the solvent was evaporated under reduced pressure. The residue was purified through silica gel column chromatography (hexane-ethyl acetate), to thereby give the title compound as crystals (890 mg, 53%).

$^1$H-NMR (400 MHz, CDCl$_3$) δ: 1.45 (3H, t, J=7.0 Hz), 3.84 (2H, s), 4.04 (3H, s), 4.47 (2H, q, J=7.0 Hz), 6.93 (1H, d, J=8.8 Hz), 7.27-7.34 (2H, m), 7.36-7.41 (1H, m), 7.57 (1H, d, J=6.6 Hz), 7.96 (1H, dd, J=8.8, 2.9 Hz), 8.54 (1H, d, J=2.9 Hz).

MS (ESI) m/z: 336(M+H)$^+$.

Referential Example 61

1,4-Dihydro-1-(6-methoxy-3-pyridyl)indeno[1,2-c]pyrazole-3-carboxylic acid

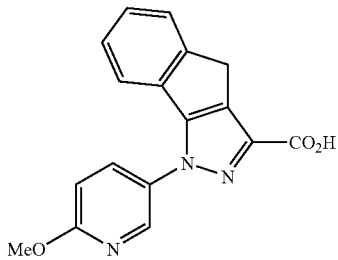

In a manner similar to that described in relation to Referential Example 45, the title compound was produced as crystals (791 mg, 97%) by use of 1,4-dihydro-1-(6-methoxy-3-pyridyl)indeno[1,2-c]pyrazole-3-carboxylic acid ethyl ester (890 mg) obtained from Referential Example 60.

$^1$H-NMR (400 MHz, CDCl$_3$) δ: 3.89 (2H, s), 4.05 (3H, s), 6.95 (1H, d, J=8.8 Hz), 7.28-7.36 (2H, m), 7.38-7.42 (1H, m), 7.58 (1H, d, J=6.6 Hz), 7.96 (1H, dd, J=8.8, 2.6 Hz), 8.56 (1H, d, J=2.6 Hz).

MS (ESI) m/z: 308(M+H)$^+$.

Referential Example 62

2-Oxo-2-(1-oxoindan-2-yl)acetic acid ethyl ester

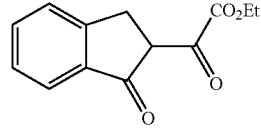

In a manner similar to that described in step 1) of Referential Example 3, the title compound was produced as crystals (3.39 g, 97%) by use of 1-indanone (1.982 g) and diethyl oxalate (4.07 mL).

$^1$H-NMR (400 MHz, CDCl$_3$) δ: 1.43 (3H, t, J=7.0 Hz), 3.99 (2H, s), 4.42 (2H, q, J=7.0 Hz), 7.44 (1H, dd, J=7.3, 7.1 Hz), 7.55 (1H, d, J=7.3 Hz), 7.64 (1H, dd, J=7.3, 7.1 Hz), 7.87 (1H, d, J=7.3 Hz).

MS (ESI) m/z: 233(M+H)$^+$.

Referential Example 63

1,4-Dihydro-1-(6-methyl-3-pyridyl)indeno[1,2-c]pyrazole-3-carboxylic acid ethyl ester

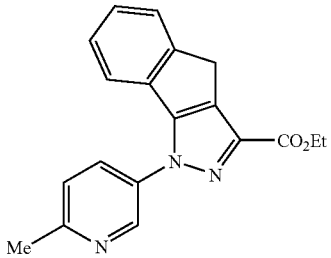

5-tert-Butoxycarbonylamino-2-methylpyridine (625 mg) in concentrated hydrochloric acid (3 mL) was stirred at room temperature for 50 minutes. Under cooling with ice with sodium chloride, sodium nitrite (228 mg) in water (1 mL) was added dropwise to the reaction mixture over a period of 10 minutes, followed by stirring for 10 minutes. Tin(II) chloride dihydrate (2.37 g) in concentrated hydrochloric acid (1.6 mL) was added dropwise to the reaction mixture over a period of 10 minutes, followed by stirring for 3 hours under cooling with ice. 2-Oxo-2-(1-oxoindan-2-yl)acetic acid ethyl ester (696 mg) obtained from Referential Example 62 in ethanol (20 mL) was added to the reaction mixture. The resultant mixture was refluxed under heat for 39 hours. Under cooling with ice, the reaction mixture was alkalinized with an aqueous solution of sodium hydroxide. Subsequently, the resultant mixture was partitioned between ethyl acetate and water. The organic layer was sequentially washed with water and saturated brine, and dried over sodium sulfate anhydrate. The mixture was subjected to filtration, and the solvent was evaporated under reduced pressure. The residue was purified through silica gel column chromatography (chloroform-acetone), to thereby give the title compound as crystals (340 mg, 35%).

$^1$H-NMR (400 MHz, CDCl$_3$) δ: 1.46 (3H, t, J=7.0 Hz), 2.69 (3H, s), 3.85 (2H, s), 4.48 (2H, q, J=7.0 Hz), 7.24-7.35 (2H, m), 7.37 (1H, d, J=8.3 Hz), 7.46 (1H, dd, J=6.8, 1.3 Hz), 7.58 (1H, d, J=7.3 Hz), 8.00 (1H, dd, J=8.3, 2.4 Hz), 8.92 (1H, d, J=2.4 Hz).

MS (ESI) m/z: 320(M+H)$^+$.

Referential Example 64

1,4-Dihydro-1-(6-methyl-3-pyridyl)indeno[1,2-c]pyrazole-3-carboxylic acid

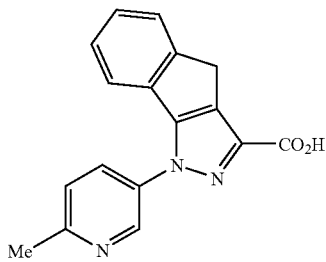

In a manner similar to that described in relation to Referential Example 45, the title compound was produced as a solid substance (287 mg, 95%) by use of 1,4-dihydro-1-(2-methylpyrid-5-yl)indeno[1,2-c]pyrazole-3-carboxylic acid ethyl ester (331 mg) obtained from Referential Example 63.

$^1$H-NMR (400 MHz, DMSO-d$_6$) δ: 2.62 (3H, s), 3.81 (2H, s), 7.31-7.39 (3H, m), 7.56 (1H, d, J=8.1 Hz), 7.60-7.68 (1H, m), 8.10 (1H, dd, J=8.1, 2.4 Hz), 8.85 (1H, d, J=2.4 Hz), 13.02-13.16 (1H, br).

MS (ESI) m/z: 292(M+H)$^+$.

Referential Example 65

5-Nitro-2-vinylpyridine

In an argon atmosphere, tributyl(vinyl)tin (6.658 g) and tetrakis(triphenylphosphine)palladium(0) (1.155 g) were added to 2-chloro-5-nitropyridine (3.171 g) and 2,6-di-tert-butyl-p-cresol (44 mg) in tetrahydrofuran (40 mL), followed by refluxing under heat for 14 hours. The resultant mixture was cooled in air. Subsequently, ethyl acetate and sodium fluoride (2.52 g) in water (60 mL) were added to the reaction mixture at room temperature, followed by stirring for 7 hours. The insoluble matter that was formed in the mixture was filtered. Water was added for partitioning the organic layer. The organic layer was washed with saturated brine, and dried over sodium sulfate anhydrate, followed by filtration. The solvent was evaporated under reduced pressure. The residue was purified through silica gel column chromatography (hexane-ethyl acetate), to thereby give the title compound as crystals (1.519 g, 50%).

$^1$H-NMR (400 MHz, CDCl$_3$) δ: 5.74 (1H, dd, J=10.8, 1.0 Hz), 6.45 (1H, dd, J=17.4, 1.0 Hz), 6.90 (1H, dd, J=17.4, 10.8 Hz), 7.47 (1H, d, J=8.8 Hz), 8.43 (1H, dd, J=8.8, 2.4 Hz), 9.38 (1H, d, J=2.4 Hz).

MS (ESI) m/z: 151(M+H)$^+$.

Referential Example 66

5-Amino-2-ethylpyridine

10% Palladium-carbon (50% wet, 90 mg) was added to 5-nitro-2-vinylpyridine (450 mg) in ethanol (30 mL), followed by stirring in a hydrogen atmosphere at room temperature for 15 hours. The catalyst was removed from the reaction mixture by filtration. Subsequently, the solvent was evaporated under reduced pressure, to thereby give the title compound as an oily substance (359 mg, 98%).

$^1$H-NMR (400 MHz, CDCl$_3$) δ: 1.25 (3H, t, J=7.5 Hz), 2.71 (2H, q, J=7.5 Hz), 3.32-3.78 (2H, br), 6.91-6.98 (2H, m), 8.02-8.05 (1H, m).

MS (ESI) m/z: 123(M+H)$^+$.

Referential Example 67

1-(6-Ethyl-3-pyridyl)-1,4-dihydroindeno[1,2-c]pyrazole-3-carboxylic acid ethyl ester

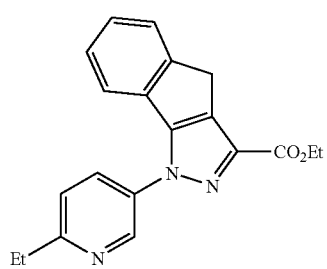

Sodium nitrite (228 mg) in water (1 mL) was added dropwise to 5-amino-2-ethylpyridine (359 mg) in concentrated hydrochloric acid (3 mL) under cooling with ice with sodium chloride over a period of 10 minutes, followed by stirring at a constant temperature for 10 minutes. Tin(II) chloride dihydrate (2.37 g) in concentrated hydrochloric acid (1.6 mL) was added dropwise to the reaction mixture over a period of 10 minutes, followed by stirring with ice cooling for 3 hours. 2-Oxo-2-(1-oxoindan-2-yl)acetic acid ethyl ester (696 mg) obtained from Referential Example 62 in ethanol (20 mL) was added to the reaction mixture. The resultant mixture was refluxed under heat for 39 hours. Under cooling with ice, the reaction mixture was alkalinized by use of an aqueous solution of sodium hydroxide. The resultant mixture was partitioned between ethyl acetate and water. The organic layer was sequentially washed with water and saturated brine, and then dried over sodium sulfate anhydrate. Subsequently, the mixture was subjected to filtration. The solvent was evaporated under reduced pressure. The residue was purified through silica gel column chromatography (chloroform-acetone), to thereby give the title compound as crystals (372 mg, 37%).

$^1$H-NMR (400 MHz, CDCl$_3$) δ: 1.39 (3H, t, J=7.0 Hz), 1.45 (3H, t, J=7.0 Hz), 2.94 (2H, q, J=7.0 Hz), 3.85 (2H, s), 4.48 (2H, q, J=7.0 Hz), 7.25-7.35 (2H, m), 7.38 (1H, d, J=8.3 Hz), 7.46 (1H, dd, J=6.3, 1.7 Hz), 7.58 (1H, d, J=6.8 Hz), 8.02 (1H, dd, J=8.3, 2.4 Hz), 8.94 (1H, d, J=2.4 Hz).

MS (ESI) m/z: 334(M+H)$^+$.

Referential Example 68

1-(6-Ethyl-3-pyridyl)-1,4-dihydroindeno[1,2-c]pyrazole-3-carboxylic acid

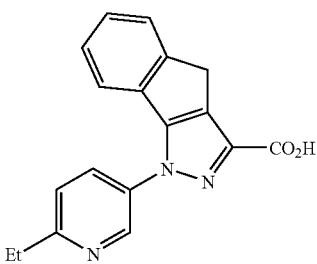

In a manner similar to that described in relation to Referential Example 45, the title compound was produced as crystals (302 mg, 91%) by use of 1-(6-ethyl-3-pyridyl)-1,4-dihydroindeno[1,2-c]pyrazole-3-carboxylic acid ethyl ester (360 mg) obtained from Referential Example 67.

$^1$H-NMR (400 MHz, DMSO-d$_6$) δ: 1.33 (3H, t, J=7.5 Hz), 2.91 (2H, q, J=7.5 Hz), 3.81 (2H, s), 7.32-7.40 (3H, m), 7.57 (1H, d, J=8.3 Hz), 7.62-7.69 (1H, m), 8.13 (1H, dd, J=8.3, 2.4 Hz), 8.89 (1H, d, J=2.4 Hz), 13.05-13.13 (1H, br).

MS (ESI) m/z: 306(M+H)$^+$.

Referential Example 69

1,4-Dihydro-1-(2-methoxypyrid-5-yl)-4-oxoindeno[1,2-c]pyrazole-3-carboxylic acid ethyl ester

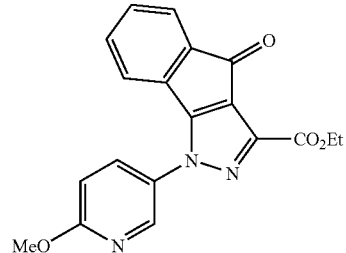

1.1M Lithium bis(trimethylsilyl)amide in hexane (3 mL) was added dropwise to 1,3-indanedione (438 mg) in tetrahydrofuran (15 mL) in an argon atmosphere at −78° C. over a period of 10 minutes, followed by stirring for 45 minutes. Ethyl chloroglyoxylate (450 mg) in tetrahydrofuran (3 mL) was added to the reaction mixture, followed by stirring at 0° C. for 2 hours. Subsequently, the solvent was evaporated under reduced pressure. The residue was dissolved in ethanol (15 mL). 5-Hydrazino-2-methoxypyridine (417 mg) obtained from Referential Example 2 was added to the resultant mixture, followed by refluxing under heat for 14 hours. The mixture was cooled in air. The reaction solvent was evaporated under reduced pressure. The residue was partitioned between water and ethyl acetate. The organic layer was sequentially washed with 5% aqueous solution of citric acid, water, saturated aqueous solution of sodium hydrogencarbonate, water, and saturated brine. Subsequently, the organic layer was dried over sodium sulfate anhydrate, followed by filtration. The solvent was evaporated under reduced pressure. The residue was purified through silica gel column chromatography (hexane-ethyl acetate), to thereby give the title compound as an oily substance (22 mg, 2%).

$^1$H-NMR (400 MHz, CDCl$_3$) δ: 1.47 (3H, t, J=7.0 Hz), 4.04 (3H, s), 4.49 (2H, q, J=7.0 Hz), 6.94 (1H, d, J=8.8 Hz), 7.08-7.15 (1H, m), 7.32-7.40 (2H, m), 7.63-7.71 (1H, m), 7.93 (1H, dd, J=8.8, 2.9 Hz), 8.51 (1H, d, J=2.9 Hz).

MS (ESI) m/z: 350(M+H)$^+$.

Referential Example 70

1,4-Dihydro-1-(6-methoxy-3-pyridyl)-4-oxoindeno[1,2-c]pyrazole-3-carboxylic acid

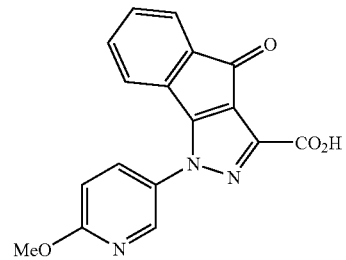

In a manner similar to that described in relation to Referential Example 45, the title compound was produced as a solid substance (16 mg, 80%) by use of 1,4-dihydro-1-(6- methoxy-3-pyridyl)-4-oxoindeno[1,2-c]pyrazole-3-carboxylic acid ethyl ester (22 mg) obtained from Referential Example 69.

¹H-NMR (400 MHz, CDCl₃) δ: 4.05 (3H, s), 6.96 (1H, d, J=8.8 Hz), 7.15-7.20 (1H, m), 7.36-7.43 (2H, m), 7.67-7.73 (1H, m), 7.95 (1H, dd, J=8.8, 2.7 Hz), 8.52 (1H, d, J=2.7 Hz).

MS (ESI) m/z: 322(M+H)⁺.

Referential Example 71

4,5-Dihydro-1-(6-methoxy-3-pyridyl)-1H-benzo[g]indazole-3-carboxylic acid ethyl ester

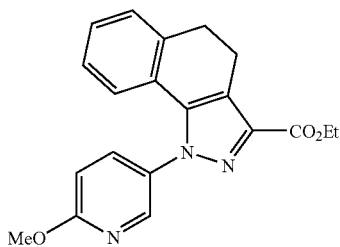

In an argon atmosphere and while cooling at −78° C., 1.1M lithium bis(trimethylsilyl)amide in hexane (5 mL) was added dropwise to α-tetralone (731 mg) in tetrahydrofuran (10 mL) over a period of 10 minutes, and the resultant mixture was stirred for 0.5 hours. Diethyl oxalate (1.461 g) in tetrahydrofuran (5 mL) was added to the reaction mixture, followed by stirring at 0° C. for 2 hours and then at room temperature for 14 hours. The reaction mixture was acidified through addition of aqueous 1M hydrochloric acid (10 mL). The resultant mixture was partitioned between water and ethyl acetate. The organic layer was sequentially washed with water and saturated brine, and then dried over sodium sulfate anhydrate, followed by filtration. The solvent was evaporated under reduced pressure, to thereby give 2-(1,2,3,4-tetrahydro-1-oxonaphthalen-2-yl)-2-oxoacetic acid ethyl ester as an oily product (1.516 g, quantitative amount). The thus-obtained ethyl ester was dissolved in ethanol (20 mL), and to the resultant solution, 5-hydrazino-2-methoxypyridine (696 mg) obtained from Referential Example 2 was added. The mixture was refluxed under heat for 18 hours, and then cooled in air. The solvent was evaporated under reduced pressure, and the residue was partitioned between water and ethyl acetate. The organic layer was sequentially washed with 5% aqueous citric acid, water, and saturated brine, and then dried over sodium sulfate anhydrate, followed by filtration. The solvent was evaporated under reduced pressure, and the residue was purified through silica gel column chromatography (hexane-ethyl acetate), to thereby give the title compound as an oily product (1.093 g, 62%).

¹H-NMR (400 MHz, CDCl₃) δ: 1.42 (3H, t, J=7.1 Hz), 2.96-3.13 (4H, m), 4.01 (3H, s), 4.44 (2H, q, J=7.0 Hz), 6.77 (1H, d-like, J=7.1 Hz), 6.85 (1H, d, J=8.8 Hz), 7.00-7.06 (1H, m), 7.15-7.21 (1H, m), 7.30 (1H, d-like, J=7.6 Hz), 7.70 (1H, dd, J=8.8, 2.7 Hz), 8.33 (1H, d, J=2.7 Hz).

MS (ESI) m/z: 350(M+H)⁺.

Referential Example 72

4,5-Dihydro-1-(6-methoxy-3-pyridyl)-1H-benzo[g]indazole-3-carboxylic acid

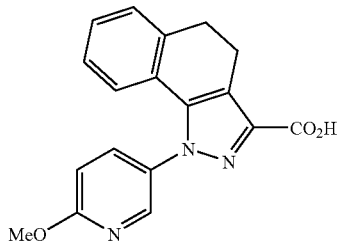

The general procedure of Referential Example 45 was repeated through use of the 4,5-dihydro-1-(6-methoxy-3-pyridyl)-1H-benzo[g]indazole-3-carboxylic acid ethyl ester (1.015 g) prepared in Referential Example 71, to thereby give the title compound in the form of crystals (745 mg, 79%).

¹H-NMR (400 MHz, DMSO-d₆) δ: 2.96 (4H, s), 3.96 (3H, s), 6.68 (1H, d, J=7.6 Hz), 7.03 (1H, d, J=8.8 Hz), 7.08 (1H, dd, J=7.6, 7.6 Hz), 7.21 (1H, dd, J=7.6, 7.6 Hz), 7.36 (1H, d, J=7.6 Hz), 7.90 (1H, dd, J=8.8, 2.7 Hz), 8.36 (1H, d, J=2.7 Hz), 12.92 (1H, s).

MS (ESI) m/z: 322(M+H)⁺.

Referential Example 73

1,4-Dihydro-1-(6-methoxy-3-pyridyl)chromeno[4,3-c]pyrazole-3-carboxylic acid ethyl ester

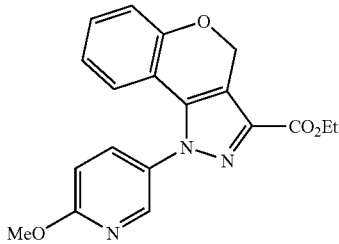

In an argon atmosphere and while cooling at −78° C., 1.1M lithium bis(trimethylsilyl)amide in hexane (3 mL) was added dropwise to 4-chromanone (444 mg) in tetrahydrofuran (10 mL) over a period of 10 minutes, and the resultant mixture was stirred for 0.5 hours. Diethyl oxalate (877 mg) in tetrahydrofuran (3 mL) was added to the reaction mixture, followed by stirring at 0° C. for 2 hours. The reaction mixture was acidified through addition of aqueous 1M hydrochloric acid (6 mL), followed by partitioning between water and ethyl acetate. The organic layer was sequentially washed with water and saturated brine, and then dried over sodium sulfate anhydrate, followed by filtration. The solvent was evaporated under reduced pressure, to thereby give 2-oxo-2-(4-oxochroman-3-yl)acetic acid ethyl ester as a semisolid (855 mg, quantitative amount). The thus-obtained ethyl ester was dissolved in ethanol (30 mL), and to the resultant solution, 5-hydrazino-2-methoxypyridine (417 mg) obtained from Referential Example 2 was added. The mixture was refluxed under heat for 14 hours, and then cooled in air. The reaction solvent was evaporated under reduced pressure, and the residue was partitioned between water and ethyl acetate. The organic layer was sequentially washed with water and saturated brine, and then dried over sodium sulfate anhydrate, followed by filtration. The solvent was evaporated under reduced pressure, and then the residue was purified through silica gel column chromatography (hexane-ethyl acetate). The resultant crystals were recrystallized from ethyl acetate-hexane, to thereby give the title compound in the form of crystals (267 mg). The solvent in the filtrate was evaporated under reduced pressure, and then the residue was purified through silica gel thin-layer chromatography (hexane-ethyl acetate), to thereby give the title compound (28 mg). This compound was combined with the above-obtained crystals, to finally give the title compound (295 mg, 27%).

$^1$H-NMR (400 MHz, CDCl$_3$) δ: 1.42 (3H, t, J=7.1 Hz), 4.03 (3H, s), 4.44 (2H, q, J=7.0 Hz), 5.55 (2H, s), 6.72-6.80 (2H, m), 6.88 (1H, d, J=8.8 Hz), 7.01 (1H, d-like, J=8.8 Hz), 7.16-7.22 (1H, m), 7.70 (1H, dd, J=8.8, 2.7 Hz), 8.34 (1H, d, J=2.7 Hz).

MS (ESI) m/z: 352(M+H)$^+$.

Referential Example 74

1,4-Dihydro-1-(6-methoxy-3-pyridyl)chromeno[4,3-c]pyrazole-3-carboxylic acid

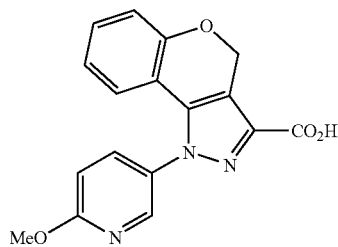

The general procedure of Referential Example 45 was repeated through use of the 1,4-dihydro-1-(2-methoxypyrid-5-yl)chromeno[4,3-c]pyrazole-3-carboxylic acid ethyl ester (265 mg) prepared in Referential Example 73, to thereby give the title compound in the form of crystals (226 mg, 93%).

$^1$H-NMR (400 MHz, DMSO-d$_6$) δ: 3.97 (3H, s), 5.48 (2H, s), 6.67 (1H, dd, J=7.8, 1.3 Hz), 6.84 (1H, dd, J=7.8, 7.8 Hz), 7.02 (1H, d, J=8.3 Hz), 7.06 (1H, d, J=8.8 Hz), 7.22 (1H, dd, J=8.3, 7.6 Hz), 7.97 (1H, dd, J=8.8, 2.7 Hz), 8.43 (1H, d, J=2.7 Hz), 13.26 (1H, br s).

MS (ESI) m/z: 324(M+H)$^+$.

Referential Example 75

[1-(6-Methoxy-3-pyridyl)-5-phenylpyrazol-3-yl]methanol

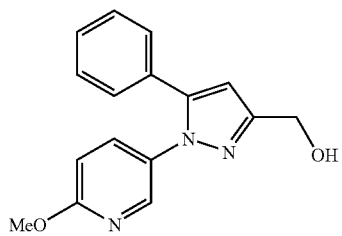

In an argon atmosphere while cooling with ice, 1.08M borane-tetrahydrofuran complex in tetrahydrofuran (9.2 mL) was added dropwise to 1-(6-methoxy-3-pyridyl)-5-phenylpyrazole-3-carboxylic acid (1.181 g) in tetrahydrofuran (20 mL) obtained from Referential Example 41 over a period of 10 minutes, and the resultant mixture was stirred at room temperature for 7 hours. Water and ethyl acetate were added to the reaction mixture, followed by stirring, and precipitated insoluble matter was removed by filtration, and then an organic layer was separated. The organic layer was sequentially washed with water and saturated brine, and then dried over sodium sulfate anhydrate, followed by filtration. The solvent was evaporated under reduced pressure, and the residue was purified through silica gel column chromatography (hexane-ethyl acetate), to thereby give the title compound as an oily product (682 mg, 60%).

$^1$H-NMR (400 MHz, CDCl$_3$) δ: 3.92 (3H, s), 4.79 (2H, s), 6.52 (1H, s), 6.72 (1H, d, J=8.5 Hz), 7.18-7.27 (2H, m), 7.29-7.37 (3H, m), 7.52 (1H, dd, J=8.5, 2.7 Hz), 8.07 (1H, d, J=2.7 Hz).

MS (ESI) m/z: 282(M+H)$^+$.

Referential Example 76

[1-(6-Methoxy-3-pyridyl)-5-phenylpyrazol-3-yl]methyl methanesulfonate

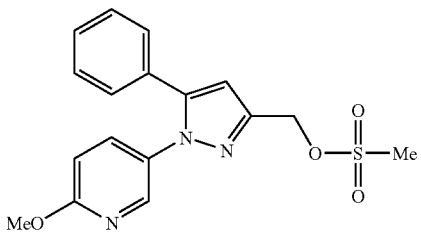

[1-(6-Methoxy-3-pyridyl)-5-phenylpyrazol-3-yl]methanol (112 mg) obtained from Referential Example 75 was dissolved in methylene chloride (4 mL). To the solution, triethylamine (61 μL) and methanesulfonyl chloride (34 μL) were added at room temperature, followed by stirring for 15 minutes. The reaction mixture was partitioned between water and ethyl acetate. The organic layer was sequentially washed with water and saturated brine, and then dried over sodium sulfate anhydrate, followed by filtration. The solvent was evaporated under reduced pressure, to thereby give the title compound as an oily product (13.8 mg, 96%).

MS (ESI) m/z: 360(M+H)$^+$.

Referential Example 77

2-(2-Hydroxyethyl)piperidine-1-carboxylic acid tert-butyl ester

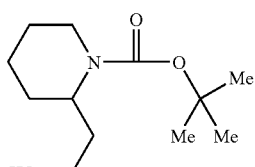

2-Piperidineethanol (1.292 g) and triethylamine (1.393 mL) were dissolved in methylene chloride (40 mL). To the resultant solution, di-tert-butyl dicarbonate (2.182 g) in methylene chloride (40 mL) was added at room temperature, followed by stirring for 1 hour. The residue obtained by removal through evaporation of the reaction solvent under reduced pressure was partitioned between water and ethyl acetate. The organic layer was sequentially washed with 5% aqueous citric acid, water, and saturated brine, and then dried over sodium sulfate anhydrate, followed by filtration. The solvent was evaporated under reduced pressure, to thereby give the title compound as an oily product (2.182 g, 95%).

$^1$H-NMR (400 MHz, CDCl$_3$) δ: 1.33-1.81 (7H, m), 1.49 (9H, s), 1.88-2.00 (1H, br m), 2.63-2.73 (1H, m), 3.25-3.47 (1H, br), 3.56-3.66 (1H, br m), 3.75-4.08 (2H, br), 4.35-4.54 (1H, br).

Referential Example 78

2-(N-tert-Butoxycarbonylpiperidin-2-yl)ethyl methanesulfonate

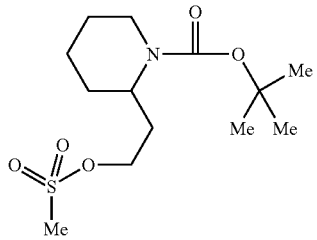

2-(2-Hydroxyethyl)piperidine-1-carboxylic acid tert-butyl ester (229 mg) obtained from Referential Example 77 and triethylamine (209 µL) were dissolved in methylene chloride (5 mL) To the resultant solution, methanesulfonyl chloride (116 µL) was added at room temperature, followed by stirring for 30 minutes. The residue obtained by removal through evaporation of the reaction solvent under reduced pressure was partitioned between water and methylene chloride. The organic layer was sequentially washed with water and saturated brine, and then dried over sodium sulfate anhydrate, followed by filtration. The solvent was evaporated under reduced pressure, to thereby give the title compound in the form of crystals (288 mg, 93%).

$^1$H-NMR (400 MHz, CDCl$_3$) δ: 1.34-1.70 (6H, m), 1.46 (9H, s), 1.75-1.86 (1H, m), 2.16-2.27 (1H, m), 2.71-2.81 (1H, br m), 3.01 (3H, s), 3.92-4.08 (1H, br), 4.20 (2H, t, J=6.8 Hz), 4.34-4.48 (1H, br).

Referential Example 79

2-(2-Azidoethyl)piperidine-1-carboxylic acid tert-butyl ester

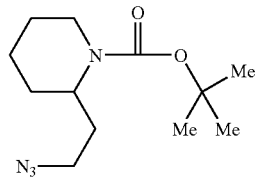

Sodium azide (325 mg) was added to the mesilate (288 mg) obtained from Referential Example 78 in N,N-dimethylformamide (10 mL), and the resultant mixture was stirred at 80° C. for 15 hours. The reaction mixture was partitioned between water and ethyl acetate. The organic layer was sequentially washed with water and saturated brine, and then dried over sodium sulfate anhydrate, followed by filtration. The solvent was evaporated under reduced pressure, to thereby give the title compound as an oily product (217 mg, 91%).

$^1$H-NMR (400 MHz, CDCl$_3$) δ: 1.32-1.70 (7H, m), 1.46 (9H, s), 1.98-2.09 (1H, m), 2.68-2.80 (1H, br m), 3.22-3.31 (2H, m), 3.91-4.09 (1H, br), 4.28-4.39 (1H, br).

Referential Example 80

2-(2-Azidoethyl)piperidine

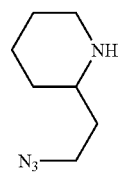

Trifluoroacetic acid (1 mL) was added to the azide compound (215 mg) obtained from Referential Example 79 in methylene chloride (3 mL) at room temperature, and the resultant mixture was stirred for 30 minutes. The residue obtained by removal through evaporation of the reaction solvent under reduced pressure was partitioned by use of saturated aqueous sodium hydrogencarbonate and methylene chloride. The aqueous layer was extracted with methylene chloride, and the organic layers were combined, and then dried over sodium sulfate anhydrate, followed by filtration. The solvent was evaporated under reduced pressure, to thereby give the title compound as an oily product (62 mg). The aqueous layer from the partitioning was saturated with sodium chloride, and the mixture was extracted twice with chloroform. The organic layers were combined, and then dried over sodium sulfate anhydrate, followed by filtration. The solvent was evaporated under reduced pressure, to thereby give the title compound as an oily product (39 mg). The overall yield of the title compound is 101 mg (77%).

$^1$H-NMR (400 MHz, CDCl$_3$) δ: 1.04-1.17 (1H, m), 1.30-1.45 (2H, m), 1.53-1.71 (5H, m), 1.75-1.86 (1H, m), 2.56-2.69 (2H, m), 3.02-3.11 (1H, m), 3.32-3.44 (2H, m).

MS (ESI) m/z: 155(M+H)$^+$.

Referential Example 81

1-[1-(6-Methoxy-3-pyridyl)-5-phenylpyrazole-3-carbonyl]-2-(2-azidoethyl)piperidine

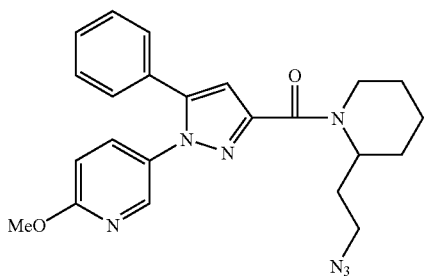

1-(6-Methoxy-3-pyridyl)-5-phenylpyrazole-3-carboxylic acid (191 mg) obtained from Referential Example 41, 2-(2-azidoethyl)piperidine (100 mg) obtained from Referential Example 80, 1-hydroxybenzotriazole (88 mg), and triethylamine (316 μL) were dissolved in methylene chloride (10 mL). To the resultant mixture, 1-(3-dimethylaminopropyl)-3-ethylcarbodiimide hydrochloride (186 mg) was added at room temperature, followed by stirring for 14 hours. The residue obtained by removal through evaporation of the reaction solvent under reduced pressure was partitioned between water and ethyl acetate. The organic layer was sequentially washed with water and saturated brine, and then dried over sodium sulfate anhydrate, followed by filtration. The residue obtained by removal through evaporation of the solvent under reduced pressure was purified through silica gel thin-layer chromatography (hexane-ethyl acetate), to thereby give the title compound as an oily product (227 mg, 81%).

$^1$H-NMR (400 MHz, CDCl$_3$) [as a mixture of two isomers] δ: 1.51-1.87 (7H, m), 2.13-2.28 (1H, br), 2.76-2.89 (0.5H, br m), 3.13-3.27 (0.5H, br m), 3.30-3.49 (2H, m), 3.94 (3H, s), 4.67 and 4.70 (1H, br s), 4.99-5.19 (1H, br m), 6.71 (1H, d, J=8.8 Hz), 6.86 and 6.88 (each 0.5H, each br s), 7.20-7.27 (2H, m), 7.30-7.37 (3H, m), 7.48 (1H, dd, J=8.8, 2, 7 Hz), 8.12 (1H, d, J=2.7 Hz).

MS (ESI) m/z: 432(M+H)$^+$.

Referential Example 82

3-Methylpiperazine-1-carboxylic acid tert-butyl ester

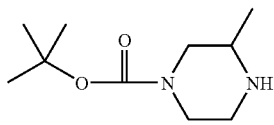

2-Methylpiperazine (3.19 g) was added to 2-(tert-butylcarbonyloxyimino)-2-phenylacetonitrile (7.87 g) in tetrahydrofuran (100 mL) at 0° C., followed by stirring for 2 hours. The residue obtained by removal through evaporation of the reaction solvent under reduced pressure was purified through silica gel column chromatography (chloroform–7N ammonia/methanol mixture), to thereby give the title compound as an oily product (5.70 g, 89%).

$^1$H-NMR (400 MHz, CDCl$_3$) δ: 1.05 (3H, d, J=6.4 Hz), 1.46 (9H, s), 2.40 (1H, br), 2.65-2.84 (3H, m), 2.90-3.00 (1H, br), 3.94 (2H, br).

MS (ESI) m/z: 201(M+H)$^+$.

Referential Example 83

3,4-Dimethylpiperazine-1-carboxylic acid tert-butyl ester

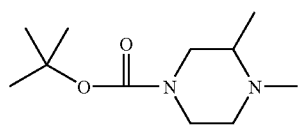

3-Methylpiperazine-1-carboxylic acid tert-butyl ester (5.70 g) obtained from Referential Example 82 was dissolved in methanol (100 mL). To the resultant solution, 10% palladium-carbon (0.59 g), 35% aqueous formalin (9.7 mL), and 1M HCl in ethanol (31.3 mL) were added at room temperature, followed by stirring in a hydrogen atmosphere for 15 hours. After the system was purged with nitrogen, insoluble matter was filtered off, and the solvent of the filtrate was evaporated under reduced pressure. To the residue, chloroform-methanol (9%) was added, and the resultant mixture was alkalinized through addition of aqueous sodium hydroxide, followed by partition. The aqueous layer was extracted with chloroform-methanol (9%). The organic layers were combined and washed with saturated brine, and then dried over sodium sulfate anhydrate, followed by filtration. The solvent was evaporated under reduced pressure, and the residue was purified through silica gel column chromatography (chloroform-methanol), to thereby give the title compound as an oily product (3.10 g, 51%).

$^1$H-NMR (400 MHz, CDCl$_3$) δ: 1.04 (3H, d, J=6.3 Hz), 1.46 (9H, s), 1.95-2.20 (2H, m), 2.28 (3H, s), 2.50-2.78 (2H, br), 2.90-3.05 (1H, br), 3.88 (1H, br).

MS (ESI) m/z: 215(M+H)$^+$.

Referential Example 84

1,2-Dimethylpiperazine trifluoroacetic acid salt

Trifluoroacetic acid (15 mL) was added to 3,4-dimethylpiperazine-1-carboxylic acid tert-butyl ester (3.10 g) obtained from Referential Example 83 in methylene chloride (30 mL) at room temperature, followed by stirring for 1 hour. The residue obtained by removal through evaporation of the reaction solvent under reduced pressure was crystallized from chloroform-ether, and the crystals were recovered by filtration, to thereby give the title compound (2.756 g, 56%).

$^1$H-NMR (400 MHz, DMSO-d$_6$) δ: 1.24 (3H, d, J=6.4 Hz), 2.30-3.70 (10H, br).

MS (ESI) m/z: 115(M+H)$^+$.

Referential Example 85

1-Benzyl-2-methylpiperazine trifluoroacetic acid salt

1) N-Benzyl Compound

3-Methylpiperazine-1-carboxylic acid tert-butyl ester (0.530 g) obtained from Referential Example 82 was dissolved in ethanol (10 mL). To the resultant solution, benzaldehyde (0.405 mL), acetic acid (0.230 mL), and sodium cyanoborohydride (0.164 g) were added at room temperature, followed by stirring for 19 hours. Under cooling at 0° C., the mixture was partitioned by use of saturated aqueous sodium hydrogencarbonate and chloroform. The aqueous layer was extracted with chloroform. The organic layers were combined, and washed with saturated brine, and then dried over sodium sulfate anhydrate, followed by filtration. The solvent was evaporated under reduced pressure, and the residue was purified through silica gel column chromatography (chloroform-acetone), to thereby give an N-benzyl compound as an oily product (0.547 g, 71%).

$^1$H-NMR (400 MHz, CDCl$_3$) δ: 1.12 (3H, d, J=6.1 Hz), 1.44 (9H, s), 2.07 (1H, br), 2.35-2.47 (1H, m), 2.56-2.69 (1H, m), 2.97-3.23 (2H, m), 3.57-3.65 (1H, m), 3.90-4.01 (1H, m), 4.69 (2H, s), 7.15-7.45 (5H, m).

LC-MS m/z: 291 (M+H)$^+$.

2) The Title Compound

Trifluoroacetic acid (1.5 mL) was added to the above-obtained N-benzyl compound (0.547 g) in methylene chloride (10 mL) at room temperature, followed by stirring for 2 hours. The reaction solvent was evaporated under reduced pressure, and toluene was added thereto, followed by azeotropic evaporation under reduced pressure. The residue was crystallized from chloroform-diethyl ether, and the crystals were recovered by filtration, and then dried, to thereby give the title compound (0.610 g, 55%).

$^1$H-NMR (400 MHz, DMSO-$d_6$) δ: 1.35 (3H, d, J=6.3 Hz), 2.5-4.5 (9H, m), 7.30-7.60 (5H, m), 9.00 (1H, br).

MS (ESI) m/z: 191(M+H)$^+$.

Referential Example 86

(4'-Benzyloxy)acetophenone

Potassium carbonate (6.15 g) and benzyl bromide (2.75 mL) were added to 4'-hydroxyacetophenone (3.00 g) in N,N-dimethylformamide (60 mL) at room temperature. The resultant mixture was stirred at 80° C. for 3 hours, and then cooled in air. The mixture was partitioned between water and ethyl acetate. The aqueous layer was extracted with ethyl acetate. The organic layers were combined and washed with saturated brine, and then dried over sodium sulfate anhydrate, followed by filtration. The solvent was evaporated under reduced pressure, to thereby give the title compound as a solid (4.49 g, 90%).

$^1$H-NMR (400 MHz, CDCl$_3$) δ: 2.55 (3H, s), 5.13 (2H, s), 7.00 (2H, d-like, J=9.1 Hz), 7.30-7.50 (5H, m), 7.93 (2H, d-like, J=9.1 Hz).

MS (FAB) m/z: 227(M+H)+

Referential Example 87

3,5-Dimethylpiperazine-1-carboxylic acid tert-butyl ester cis-2,6-Dimethylpiperazine (5.08 g) was added to 2-(tert-butoxycarbonylimino)-2-phenylacetonitrile (11.35 g) in tetrahydrofuran (150 mL) at 0° C., followed by stirring for 2 hours. The reaction solvent was evaporated under reduced pressure. The residue was purified through silica gel column chromatography (chloroform–7N ammonia/methanol mixture), to thereby give the title compound (15.36 g, 72%).

$^1$H-NMR (400 MHz, CDCl$_3$) δ: 1.16 (6H/d, J=6.5 Hz), 1.47 (9H, s), 2.50 (2H, br), 2.90 (2H, br), 4.02 (2H, br).

MS (ESI) m/z: 214(M+H)$^+$.

Referential Example 88

3,4,5-Trimethylpiperazine-1-carboxylic acid tert-butyl ester 3,5-Dimethylpiperazine-1-carboxylic acid tert-butyl ester (3.31 g) obtained from Referential Example 87 was dissolved in methanol (50 mL). To the resultant solution, 10% palladium-carbon (0.504 g), 35% aqueous formalin (1.85 mL), and 1M HCl in ethanol (15.4 mL) were added at room temperature, and the mixture was stirred in a hydrogen atmosphere for 19 hours. 10% Palladium-carbon (0.95 g), 35% aqueous formalin (1.8 mL), and 1M HCl-ethanol (15 mL) were added thereto, followed by stirring in a hydrogen atmosphere for 23 hours. After the system was purged with nitrogen, the resultant mixture was neutralized through addition of the aqueous sodium hydroxide, and insoluble matter was removed by filtration. The filtrate was brought to dryness under reduced pressure. The residue was purified through silica gel column chromatography (chloroform–7N ammonia/methanol), to thereby give the title compound as an oily product (2.28 g, 65%).

$^1$H-NMR (400 MHz, CDCl$_3$) δ: 1.08 (6H, d, J=6.1 Hz), 1.45 (9H, s), 2.00-2.20 (2H, m), 2.25 (3H, s), 2.60 (2H, br), 3.85 (2H, br).

MS (FAB) m/z: 229(M+H)$^+$.

Referential Example 89

1,2,6-Trimethylpiperazine trifluoroacetic acid salt

The general procedure of Referential Example 84 was repeated through use of the 3,4,5-trimethylpiperazine-1-carboxylic acid tert-butyl ester (2.28 g) prepared in Referential Example 88, to thereby give the title compound as a solid (3.579 g, quantitative amount).

$^1$H-NMR (400 MHz, DMSO-$d_6$) δ: 1.28 (6H, d, J=6.6 Hz), 2.71 (3H, br), 2.90-3.60 (6H, br).

MS (ESI) m/z: 128(M+H)$^+$.

Referential Example 90

4-Methyl-3-oxopiperazine-1-carboxylic acid tert-butyl ester 1) 3-Oxopiperazine-1-carboxylic acid tert-butyl ester Triethylamine (3.9 mL) and di-tert-butyl dicarbonate (6.31 g) were added to 2-oxopiperazine (2.61 g) in a mixture of tetrahydrofuran (40 mL) and methanol (50 mL) at room temperature, followed by stirring for 3 hours. The solvent was evaporated under reduced pressure. To the residue, diethyl ether was added, and the precipitated solid was recovered by filtration, to thereby give 3-oxopiperazine-1-carboxylic acid tert-butyl ester (4.54 g, 87%).

$^1$H-NMR (400 MHz, DMSO-$d_6$) δ: 1.40 (9H, s), 3.15 (2H, br), 3.45 (2H, br), 3.81 (2H, br), 8.03 (1H, br).

LC-MS m/z: 201(M+H)$^+$.

2) The Title Compound

To 3-oxopiperazine-1-carboxylic acid tert-butyl ester (0.303 g) in N,N-dimethylformamide (12 mL), sodium hydride (being washed with pentane and dried, 44.3 mg) was added at 0° C., followed by stirring for 10 minutes. To the reaction mixture, methyl iodide (0.141 mL) was added, and the resultant mixture was stirred at room temperature for 20 hours. The reaction mixture was partitioned between water and ethyl acetate. The aqueous layer was extracted with ethyl acetate. The organic layers were combined, and washed with saturated brine, and then dried over sodium sulfate anhydrate, followed by filtration. The solvent was evaporated under reduced pressure, to thereby give the title compound as an oily product (0.308 g, 95%).

$^1$H-NMR (400 MHz, CDCl$_3$) δ: 1.46 (9H, s), 2.99 (3H, s), 3.34 (2H, t-like, J=5.3 Hz), 3.65 (2H, t-like, J=5.3 Hz), 4.07 (2H, s).

MS (FAB) m/z: 215(M+H)$^+$.

Referential Example 91

1-Methylpiperazin-2-one trifluoroacetic acid salt

The general procedure of Referential Example 84 was repeated through use of the 3-oxopiperazine-1-carboxylic acid tert-butyl ester (0.308 g) prepared in Referential Example 90, to thereby give the title compound (0.485 g, quantitative amount).
$^1$H-NMR (400 MHz, CDCl$_3$-CD$_3$OD (15:1)) δ: 2.98 (3H, s), 3.39 (2H, t-like, J=6.1 Hz), 3.54 (2H, t-like, J=6.1 Hz), 3.72 (2H, s).
MS (EI) m/z: 114(M)$^+$.

Referential Example 92

2-(2-Dimethylaminoethyl)piperidine-1-carboxylic acid tert-butyl ester

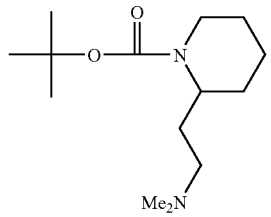

Under cooling with ice, 2M dimethylamine in methanol (5 mL) was added to the methanesulfonate (292 mg) obtained from Referential Example 78 in methanol (5 mL), and the resultant mixture was stirred at room temperature for 87 hours. The solvent was evaporated under reduced pressure, and the residue was partitioned between water and chloroform. The aqueous layer was extracted with chloroform. The organic layers were combined, and dried over sodium sulfate anhydrate, followed by filtration. The solvent was evaporated under reduced pressure, to thereby give the title compound as an oily product (172 mg, 70%).
MS (ESI) m/z: 257(M+H)$^+$.

Referential Example 93

2-(Piperidin-2-yl)acetic acid ethyl ester

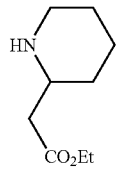

Platinum(IV) oxide (15 mg) was added to a mixture of 2-(2-pyridyl)acetic acid ethyl ester (1.652 g) in water (1.25 mL) and concentrated hydrochloric acid (1.25 mL) in methanol (15 mL), and the resultant mixture was stirred in a hydrogen atmosphere at room temperature for 15 hours. The catalyst was filtered off. The solvent was evaporated under reduced pressure, and ethanol was added to the residue, and then the solvent of the mixture was evaporated again under reduced pressure. To the residue, a small amount of water, diethyl ether (about 100 mL), and an excessive amount of potassium carbonate were added, and the resultant mixture was stirred, followed by filtration. The solvent of the filtrate was evaporated under reduced pressure, to thereby give the title compound as an oily product (1.322 g, 77%).
$^1$H-NMR (400 MHz, CDCl$_3$) δ: 1.08-1.23 (1H, m), 1.25 (3H, t, J=7.0 Hz), 1.29-1.47 (2H, m), 1.53-1.67 (2H, m), 1.73-1.82 (1H, m), 2.30-2.40 (2H, m), 2.60-2.71 (1H, m), 2.84-2.94 (1H, m), 2.98-3.08 (1H, m), 4.13 (3H, t, J=7.0 Hz).
MS (ESI) m/z: 172(M+H)$^+$.

Referential Example 94

1-Isopropylpiperazine-4-carboxylic acid tert-butyl ester

Acetone (1.47 mL) and 10% palladium-carbon (50% wet, 186 mg) were added to piperazine-1-carboxylic acid tert-butyl ester (1.862 g) in methanol (20 mL), and the resultant mixture was stirred in a hydrogen atmosphere at room temperature for 10 hours. Acetone (1.47 mL) was added thereto, and the mixture was stirred in a hydrogen atmosphere at room temperature for 36 hours. The catalyst was filtered off. The solvent was evaporated under reduced pressure, to thereby give the title compound as an oily product (2.253 g, 98%).
$^1$H-NMR (400 MHz, CDCl$_3$) δ: 1.03 (6H, d, J=6.6 Hz), 1.45 (9H, s), 2.45 (4H, t, J=5.1 Hz), 2.68 (1H, septet, J=6.6 Hz), 3.42 (4H, t, J=5.1 Hz).
MS (ESI) m/z: 229(M+H)$^+$.

Referential Example 95

1-Isopropylpiperazine hydrochloride

1M HCl in ethanol (40 mL) was added to 1-isopropylpiperazine-4-carboxylic acid tert-butyl ester (2.253 g) obtained from Referential Example 94, and the resultant mixture was stirred at room temperature for 17 hours, and then refluxed under heat for 1 hour. The solvent was evaporated under reduced pressure. Ethanol was added to the residue, and the insoluble solid was recovered by filtration, to thereby give the title compound (824 mg, 41%).
$^1$H-NMR (400 MHz, DMSO-d$_6$) δ: 1.29 (6H, d, J=6.3 Hz), 3.26-3.63 (9H, br), 9.47-10.02 (2H, br), 11.60-12.00 (1H, br).
MS (ESI) m/z: 129(M+H)$^+$.

Referential Example 96

1-(2-Methoxyethyl)piperazine-4-carboxylic acid tert-butyl ester

2-Bromoethyl methyl ether (0.94 mL) was added dropwise to a suspension of piperazine-4-carboxylic acid tert-butyl ester (1.87 g) and potassium carbonate (1.38 g) in N,N-dimethylformamide (20 mL) at room temperature, and the resultant mixture was stirred at 60° C. for 24 hours. The reaction mixture was partitioned by use of ice-water and ethyl acetate. The organic layer was sequentially washed with water and saturated brine, and then dried over magnesium sulfate anhydrate, followed by filtration. The solvent was evaporated under reduced pressure. The residue was purified through silica gel column chromatography (chloroform-methanol), to thereby give the title compound as an oily product (1.39 g, 57%).
$^1$H-NMR (400 MHz, CDCl$_3$) δ: 1.46 (9H, s), 2.42-2.45 (4H, m), 2.58 (2H, t, J=5.6 Hz), 3.36 (3H, s), 3.44-3.47 (4H, m), 3.51 (2H, t, J=5.6 Hz).
MS (ESI) m/z: 245(M+H)$^+$.

Referential Example 97

1-(2-Methoxyethyl)piperazine hydrochloride 1-(2-Methoxyethyl)piperazine-4-carboxylic acid tert-butyl ester (1.39 g) obtained from Referential Example 96 was dissolved in 4N HCl-dioxane (20 mL). The resultant solution was stirred at room temperature for 3 hours. The solvent of the reaction mixture was evaporated under reduced pressure, and ethanol was added to the residue, and then the solvent of the resultant mixture was evaporated. Ethanol and ether were added to the residue, and the precipitated solid was recovered by filtration, to thereby give the title compound (900 mg, 74%).

$^1$H-NMR (400 MHz, DMSO-$d_6$) δ: 3.36-3.38 (2H, m), 3.45 (8H, br), 3.73-3.76 (2H, m), 10.00 (2H, br).

LC-MSm/z: 145(M+H)$^+$.

Referential Example 98

1-Cyclopropylpiperazine-4-carboxylic acid tert-butyl ester

Piperazine-1-carboxylic acid tert-butyl ester (1.87 g), [(1-ethoxycyclopropyl)oxy]trimethylsilane (8.05 mL), and acetic acid (5.72 mL) were dissolved in methanol (60 mL). To the resultant solution, sodium cyanoborohydride (1.89 g) was added at room temperature, followed by stirring for 5 days. Diethyl ether was added to the residue obtained by removal through evaporation of the reaction solvent under reduced pressure, and insoluble matter was filtered off. The filtrate was partitioned by addition of aqueous 1N sodium hydroxide thereto. The organic layer was washed with saturated brine, and then dried over magnesium sulfate anhydrate, followed by filtration. The solvent was evaporated under reduced pressure. The residue was purified through silica gel column chromatography (hexane-ethyl acetate), to thereby give the title compound as a solid (1.62 g, 71%).

$^1$H-NMR (400 MHz, CDCl$_3$) δ: 0.41-0.48 (4H, m), 1.46 (9H, s), 2.54-2.56 (4H, m), 3.37-3.44 (4H, m).

MS (ESI) m/z: 268(M+MeCN)$^+$.

Referential Example 99

1-Cyclopropylpiperazine hydrochloride

The general procedure of Referential Example 97 was repeated through use of the 1-cyclopropylpiperazine-4-carboxylic acid tert-butyl ester (1.61 g, 7.11 mmol) prepared in Referential Example 98, to thereby give the title compound as a solid (1.30 g, 93%).

$^1$H-NMR (400 MHz, DMSO-$d_6$) δ: 0.79-0.81 (2H, m), 1.14 (2H, br s), 3.52 (8H, br s), 9.94 (2H, br).

LC-MSm/z: 127(M+H)$^+$.

Referential Example 100

1-Benzhydrylazetidin-3-one

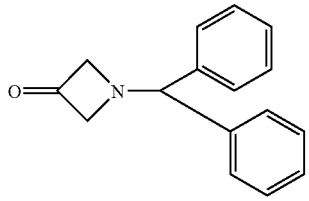

Under cooling with ice, pyridinesulfonic acid (19.7 g) in dimethyl sulfoxide (84 mL) was added dropwise to 1-benzhydrylazetidin-3-ol (4.79 g) in triethylamine (27.9 mL), and the resultant mixture was stirred at 50° C. for 40 minutes. The reaction mixture was partitioned between ice-water and ethyl acetate. The organic layer was washed with saturated brine, and then dried over magnesium sulfate anhydrate, followed by filtration. The solvent was evaporated under reduced pressure. The residue was purified through silica gel column chromatography (hexane-ethyl acetate), to thereby give the title compound as a solid (2.85 g, 60%).

$^1$H-NMR (400 MHz, CDCl$_3$) δ: 4.00 (4H, s), 4.59 (1H, s), 7.19-7.49 (10H, m).

Referential Example 101

(1-Benzhydrylazetidin-3-yl)dimethylamine

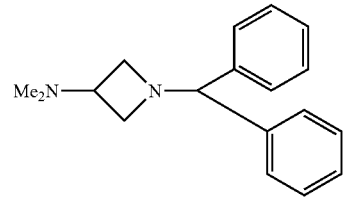

5% Palladium-carbon (1.5 g) was added to 1-benzhydrylazetidin-3-one (1.50 g) obtained from Referential Example 100 and 40% aqueous dimethylamine (4 mL) in methanol (30 mL). The resultant mixture was subjected to catalytic reduction in a hydrogen atmosphere overnight. The catalyst was filtered off, and then the solvent of the filtrate was evaporated under reduced pressure. The residue was purified through silica gel column chromatography (chloroform-methanol), to thereby give the title compound as a solid (1.55 g, 92%).

$^1$H-NMR (400 MHz, CDCl$_3$) δ: 2.08 (6H, s), 2.80-2.87 (3H, m), 3.36-3.42 (2H, m), 4.37 (1H, s), 7.15-7.41 (10H, m).

MS (ESI) m/z: 267(M+H)$^+$.

Referential Example 102

Azetidin-3-yldimethylamine hydrochloride

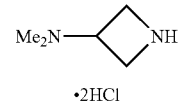

20% Palladium hydroxide-carbon (533 mg) was added to (1-benzhydrylazetidin-3-yl)dimethylamine (533 mg) obtained from Referential Example 101 in ethanol (15 mL), and the resultant mixture was subjected to catalytic reduction in a hydrogen reduction for 18 hours. The catalyst was filtered off, and then 1N HCl-ethanol (4 mL) was added to the filtrate. The solvent was evaporated under reduced pressure. Ether was added to the residue, and the precipitated solid was recovered by filtration, to thereby give the title compound (300 mg, 87%).

$^1$H-NMR (400 MHz, DMSO-$d_6$) δ: 2.70 (6H, m), 4.05-4.10 (2H, m), 4.25-4.31 (1H, m), 4.38-4.43 (2H, m).

LC-MSm/z: 101(M+H)$^+$.

Referential Example 103

(1-Benzhydrylazetidin-3-yl) methanesulfonate

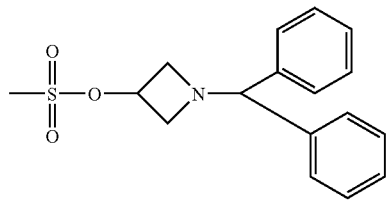

Under cooling with ice, methanesulfonyl chloride (0.68 mL) was added dropwise to 1-benzhydrylazetidin-3-ol (1.50 g) in pyridine (12 mL), followed by stirring at room temperature overnight. Ice-water was added to the reaction mixture, and the precipitated material was recovered by filtration, to thereby give the title compound (890 mg, 45%).

LC-MSm/z: 318(M+H)$^+$.

Referential Example 104

3-Azido-1-benzhydrylazetidine

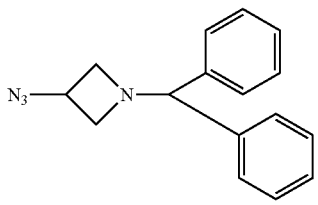

Methanesulfonate (890 mg) obtained from Referential Example 103 was dissolved in a mixture of N,N-dimethylformamide (17.8 mL) and water (1.8 mL). To the resultant solution, sodium azide (237 mg) was added, followed by stirring at 70° C. for 3 hours. The reaction mixture was partitioned between water and ethyl acetate. The organic layer was sequentially washed with water and saturated brine, and then dried over magnesium sulfate anhydrate, followed by filtration. The solvent was evaporated under reduced pressure. The residue was purified through silica gel column chromatography (hexane-ethyl acetate), to thereby give the title compound as an oily product (635 mg, 86%).

$^1$H-NMR (400 MHz, CDCl$_3$) δ: 3.01-3.05 (2H, m), 3.47-3.51 (2H, m), 3.96-4.01 (1H, m), 4.34 (1H, s), 7.17-7.40 (10H, m).

LC-MSm/z: 265(M+H)$^+$.

Referential Example 105

3-Amino-1-benzhydrylazetidine

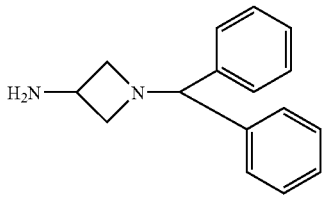

5% Palladium-carbon (200 mg) was added to 3-azido-1-benzhydrylazetidine (630 mg) obtained from Referential Example 104 in ethyl acetate (12 mL). The resultant mixture was subjected to catalytic reduction in a hydrogen atmosphere for 15 hours. The catalyst was filtered off. The solvent was evaporated under reduced pressure. The residue was purified through silica gel column chromatography (chloroform-methanol), to thereby give the title compound as a solid (410 mg, 65%).

$^1$H-NMR (400 MHz, CDCl$_3$) δ: 1.45 (2H, br), 2.62-2.67 (2H, m), 3.51-3.54 (2H, m), 3.59-3.66 (1H, m), 4.28 (1H, s), 7.16-7.40 (10H, m).

LC-MSm/z: 239(M+H)$^+$.

Referential Example 106

1-Benzhydryl-3-methoxyazetidine

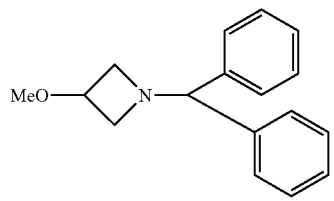

Under cooling with ice, 1-benzhydrylazetidin-3-ol (718 mg) in tetrahydrofuran (8 mL) was added dropwise to a suspension of 60% sodium hydride (144 mg) in N,N-dimethylformamide (8 mL), and the resultant mixture was stirred for 20 minutes. Methyl iodide (0.23 mL) was added to the reaction mixture, followed by stirring at room temperature overnight. The reaction mixture was partitioned between cold saturated aqueous ammonium chloride and ethyl acetate. The organic layer was washed with saturated brine, and then dried over magnesium sulfate anhydrate, followed by filtration. The solvent was evaporated under reduced pressure. The residue was purified through silica gel column chromatography (hexane-ethyl acetate), to thereby give the title compound as an oily product (680 mg, 90%).

$^1$H-NMR (400 MHz, CDCl$_3$) δ: 2.89-2.93 (2H, m), 3.23 (3H, s), 3.47-3.51 (2H, m), 4.04-4.07 (1H, m), 4.35 (1H, s), 7.16-7.41 (10H, m).

LC-MSm/z: 254(M+H)$^+$.

Referential Example 107

3-Methoxyazetidine hydrochloride

The general procedure of Referential Example 102 was repeated through use of the 1-benzhydryl-3-methoxyazetidine (680 mg) prepared in Referential Example 106, to thereby give the title compound as a solid (287 mg, 87%).

$^1$H-NMR (400 MHz, DMSO-d$_6$) δ: 2.17 (3H, s), 3.75-3.79 (2H, m), 4.06-4.11 (2H, m), 4.21-4.27 (1H, m), 9.28 (2H, br).

Referential Example 108

3-Hydroxyazetidine hydrochloride

The general procedure of Referential Example 102 was repeated through use of 1-benzhydrylazetidin-3-ol (500 mg), to thereby give the title compound as a solid (190 mg, 83%).

$^1$H-NMR (400 MHz, DMSO-d$_6$) δ: 3.73 (2H, br), 3.93-4.03 (2H, m), 4.47-4.55 (1H, m), 6.21 (1H, d, J=6.3 Hz), 9.12 (2H, br).

Referential Example 109

1-Cyclobutylpiperazine-4-carboxylic acid tert-butyl ester

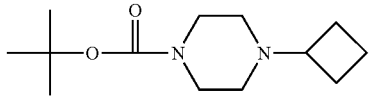

Piperazine-4-carboxylic acid tert-butyl ester (3.74 g), cyclobutanone (3.00 mL), and acetic acid (1.15 mL) were dissolved in methanol (100 mL). To the resultant solution, sodium cyanoborohydride (1.89 g) was added at room temperature, followed by stirring for 3 hours. The solvent was evaporated under reduced pressure, and the residue was partitioned by use of ethyl acetate and saturated aqueous sodium hydrogencarbonate. The organic layer was washed with saturated brine, and then dried over magnesium sulfate anhydrate, followed by filtration. The solvent was evaporated under reduced pressure. The residue was purified through silica gel column chromatography (chloroform-methanol), to thereby give the title compound as an oily product (4.43 g, 92%).

$^1$H-NMR (400 MHz, CDCl$_3$) δ: 1.46 (9H, s), 1.61-1.73 (2H, m), 1.82-1.85 (2H, m), 1.87-1.94 (2H, m), 2.25-2.27 (4H, m), 2.62-2.73 (1H, m), 3.42-3.44 (4H, m).

Referential Example 110

4-Cyclobutylpiperazine hydrochloride

The general procedure of Referential Example 97 was repeated through use of the 1-cyclobutylpiperazine-4-carboxylic acid tert-butyl ester (4.40 g) prepared in Referential Example 109, to thereby give the title compound as a solid (3.24 g, 83%).

$^1$H-NMR (400 MHz, DMSO-d$_6$) δ: 1.65-1.80 (2H, m), 2.13-2.19 (2H, m), 2.33-2.42 (2H, m), 3.49 (8H, br s), 3.70-3.73 (1H, m), 9.83 (2H, br), 12.38 (1H, br).

LC-MSm/z: 141(M+H)$^+$.

Referential Example 111

(1-Benzhydrylazetidin-3-yl)-N,N-dimethylmethylamine

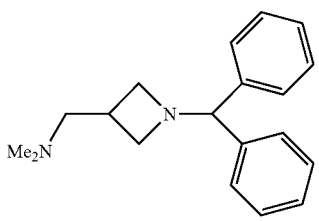

1-Benzhydrylazetidine-3-carbonitrile (880 mg) in tetrahydrofuran (10 mL) was added dropwise to a suspension of lithium aluminum hydride (134 mg) in tetrahydrofuran (20 mL) at 0° C., and the resultant mixture was refluxed under heat for 40 minutes. Under cooling at 0° C., to the reaction mixture, water (134 μL) and 15% aqueous sodium hydroxide (134 μL) were added dropwise, and then water (387 μL) was added thereto, followed by stirring for 20 minutes. The reaction mixture was filtered, and the filtrate was partitioned between water and ethyl acetate. The aqueous layer was extracted with ethyl acetate. The organic layers were combined, and washed twice with saturated brine, and then dried over sodium sulfate anhydrate, followed by filtration. The solvent was evaporated under reduced pressure. Methanol (20 mL) was added to the residue. To the mixture, sodium cyanoborohydride (1.11 g) and 37% aqueous formaldehyde (1.48 mL) were added at room temperature, followed by stirring for 24 hours. The solvent was evaporated under reduced pressure, and the residue was partitioned between water and chloroform. The aqueous layer was extracted with chloroform. The organic layers were combined, and sequentially washed with saturated aqueous sodium hydrogencarbonate and saturated brine, and then dried over sodium sulfate anhydrate, followed by filtration. The solvent was evaporated under reduced pressure, and the residue was purified through silica gel column chromatography (chloroform-methanol), to thereby give the title compound as an oily product (161 mg, 16%).

$^1$H-NMR (400 MHz, CDCl$_3$) δ: 2.16 (6H, s), 2.45 (2H, d, J=6.8 Hz), 2.67 (1H, m), 2.74 (2H, t, J=7.6 Hz), 3.39 (2H, t, J=7.6 Hz), 4.32 (1H, s), 7.14-7.18 (2H, m), 7.23-7.27 (4H, m), 7.38 (4H, dd, J=1.5, 8.3 Hz).

LC-MSm/z: 281(M+H)$^+$.

Referential Example 112

3-Dimethylaminomethylazetidine hydrochloride

The general procedure of Referential Example 102 was repeated through use of the (1-benzhydrylazetidin-3-yl)-N,N-dimethylmethylamine (160 mg) prepared in Referential Example 111, to thereby give the title compound as a solid (47 mg, 44%).

$^1$H-NMR (400 MHz, DMSO-d$_6$) δ: 2.67 (6H, s), 3.28-3.40 (3H, m), 3.85-3.89 (2H, m), 4.01-4.06 (2H, m).

Referential Example 113

4-Chloropyridine-2-carbonitrile

The general procedure of Referential Example 15 was repeated through use of 4-chloropyridine-N-oxide (6.00 g) and trimethylsilyl cyanide (17.5 mL), to thereby give the title compound as a solid (5.89 g, 92%).

$^1$H-NMR (400 MHz, CDCl$_3$) δ: 7.54-7.56 (1H, m), 7.72 (1H, m), 8.63-8.87 (1H, m).

MS (EI) m/z: 138(M$^+$).

Referential Example 114

4-Methylthiopyridine-2-carbonitrile

Sodium thiomethoxide (1.01 g) was added to 4-chloropyridine-2-carbonitrile (2.00 g) obtained from Referential Example 113 in N,N-dimethylformamide (20 mL) at 0° C., followed by stirring for 2 hours. The reaction mixture was partitioned between water and ethyl acetate. The organic layer was dried over sodium sulfate anhydrate, followed by filtration. The solvent was evaporated under reduced pressure. The residue was purified through silica gel column chromatography (hexane-ethyl acetate), to thereby give the title compound as a solid (1.96 g, 90%).

$^1$H-NMR (400 MHz, CDCl$_3$) δ: 2.53 (3H, s), 7.26-7.27 (1H, m), 7.45-7.46 (1H, m), 8.45-8.46 (1H, m).

MS (EI) m/z: 150(M$^+$).

Referential Example 115

1-(4-Methylthio-2-pyridyl)ethanone

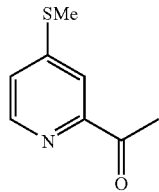

The general procedure of Referential Example 16 was repeated through use of the 4-methylthiopyridine-2-carbonitrile (1.94 g) prepared in Referential Example 114, to thereby give the title compound as a solid (1.77 g, 82%).

$^1$H-NMR (400 MHz, CDCl$_3$) δ: 2.53 (3H, s), 2.71 (3H, s), 7.25-7.27 (1H, m), 7.83-7.84 (1H, m), 8.44-8.45 (1H, m).

MS (EI) m/z: 167(M$^+$).

Referential Example 116

4-(4-Methylthio-2-pyridyl)-2,4-dioxobutanoic acid ethyl ester

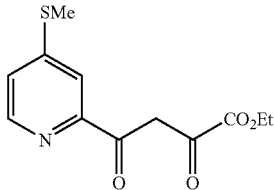

The general procedure of Referential Example 17 was repeated through use of 1-(4-methylthio-2-pyridyl)ethanone (1.76 g) and diethyl oxalate (2.86 mL), to thereby give the title compound as a solid (1.64 g, 58%).

$^1$H-NMR (400 MHz, CDCl$_3$) δ: 1.39-1.43 (3H, m), 2.56 (3H, s), 4.37-4.42 (2H, m), 7.30 (1H, d, J=5.2, 2.0 Hz), 7.51 (1H, br), 7.97 (1H, d, J=2.0 Hz), 8.46 (1H, d, J=5.2 Hz).

MS (EI) m/z: 267(M$^+$).

Referential Example 117

1-(6-Methoxy-3-pyridyl)-5-(4-methylthio-2-pyridyl)pyrazole-3-carboxylic acid ethyl ester

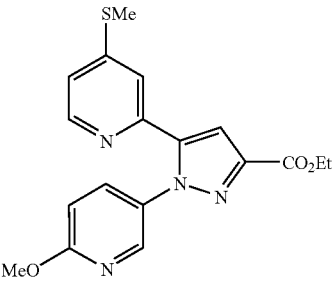

The general procedure of Referential Example 3-2) was repeated through use of 4-(4-methylthio-2-pyridyl)-2,4-dioxobutanoic acid ethyl ester (1.62 g) and the 5-hydrazino-2-methoxypyridine (0.843 g) prepared in Referential Example 2, to thereby give the title compound as a solid (0.366 g, 16%).

$^1$H-NMR (400 MHz, CDCl$_3$) δ: 1.43 (3H, t, J=7.2 Hz), 2.42 (3H, s), 3.95 (3H, s), 4.46 (2H, q, J=7.2 Hz), 6.77 (1H, d, J=8.8 Hz), 7.01-7.03 (1H, m), 7.16 (1H, d, J=1.6 Hz), 7.26 (1H, s), 7.68 (1H, dd, J=8.8, 2.8 Hz), 8.11 (1H, d, J=2.8 Hz), 8.28 (1H, d, J=5.6 Hz).

MS (FAB) m/z: 371(M+H)$^+$.

Referential Example 118

1-(6-Methoxy-3-pyridyl)-5-(4-methylthio-2-pyridyl)pyrazole-3-carboxylic acid

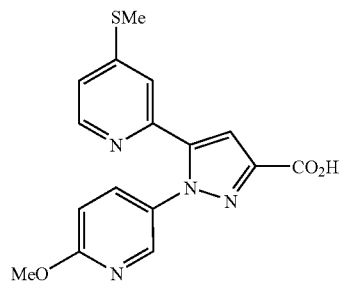

The general procedure of Referential Example 19 was repeated through use of 1-(6-methoxy-3-pyridyl)-5-(4-methylthio-2-pyridyl)pyrazole-3-carboxylic acid ethyl ester (0.326 g), to thereby give the title compound as a solid (0.312 g, quantitative amount).

$^1$H-NMR (400 MHz, CDCl$_3$) δ: 2.43 (3H, s), 3.95 (3H, s), 6.78 (1H, d, J=8.8 Hz), 7.05-7.07 (1H, m), 7.17 (1H, d, J=1.6 Hz), 7.31 (1H, s), 7.69 (1H, d, J=8.8, 2.8 Hz), 8.13 (1H, d, J=2.8 Hz), 8.33 (1H, d, J=5.2 Hz).

MS (FAB) m/z: 343(M+H)$^+$.

Referential Example 119

1-Benzylhexahydro-1H-1,4-diazepin-5-one

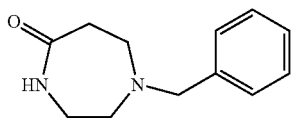

Concentrated sulfuric acid (25 mL) was added to 1-benzyl-4-piperidone (10.14 g) in acetic acid (50 mL) at room temperature, and sodium azide (3.880 g) was added thereto at 0° C. over a period of 2 hours, followed by stirring at 5° C. for 25 hours. The reaction mixture was alkalinized through addition of aqueous sodium hydroxide, followed by partitioning by use of chloroform. The aqueous layer was extracted with chloroform. The organic layers were combined, and washed with saturated brine, and then dried over sodium sulfate anhydrate, followed by filtration. The solvent was evaporated under reduced pressure, and then the residue was purified through silica gel column chromatography (chloroform-methanol), to thereby give the title compound as a solid (5.081 g, 47%).

$^1$H-NMR (400 MHz, CDCl$_3$) δ: 2.50-2.70 (6H, m), 3.20-3.35 (2H, m), 3.60 (2H, s), 6.07 (1H, br), 7.20-7.40 (5H, m).
MS (ESI) m/z: 205(M+H)$^+$.

Referential Example 120

Hexahydro-1H-1,4-diazepin-5-one hydrochloride

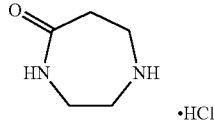

1M HCl in ethanol (7.2 mL) and 10% palladium-carbon (0.34 g) were added to 1-benzylhexahydro-1H-1,4-diazepin-5-one (1.490 g) in methanol (10 mL) at room temperature, and the resultant mixture was stirred in a hydrogen atmosphere for 4 hours. After the reaction atmosphere was purged with nitrogen, insoluble matter was removed by filtration. The solvent of the filtrate was evaporated under reduced pressure, and diethyl ether was added to the residue, and then the precipitated solid was recovered by filtration, to thereby give the title compound (1.045 g, 96%).
$^1$H-NMR (400 MHz, CD$_3$OD) δ: 2.75-2.85 (2H, m), 3.25-3.40 (6H, m), 3.48-3.56 (2H, m).
MS (ESI) m/z: 115(M+H)$^+$.

Referential Example 121

(2,2-Dimethylazetidin-3-yl)dimethylamine hydrochloride

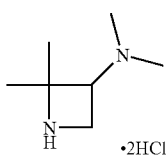

1) 3-Bromo-3-methylbutan-2-one

Under irradiation with a 250 W incandescent lamp, to potassium chloride (2.1 g) and 3-methylbutan-2-one (30 mL) in water (20 mL), 3 drops of bromine were added at 60° C. After the color of the mixture disappeared, under irradiation with a 100 W incandescent lamp, bromine (7.6 mL) was added dropwise to the mixture at 40 to 45° C. over a period of 1 hour. The resultant mixture was stirred at 40° C. for 2 hours, and then cooled in air. The reaction mixture was partitioned between water and ethyl acetate. The organic layer was sequentially washed by water, saturated aqueous sodium bicarbonate, and saturated brine, and then dried over calcium chloride anhydrate, followed by filtration. The solvent was evaporated under reduced pressure, and the residue was distilled (boiling point: 120-130° C.), to thereby give 3-bromo-3-methylbutan-2-one as an oily product (5.88 g, 13%).
$^1$H-NMR (400 MHz, CDCl$_3$) δ: 1.86 (6H, s), 2.44 (3H, s).

2) 3-(Benzhydrylamino)-3-methylbutan-2-one

To the above-obtained 3-bromo-3-methylbutan-2-one (5.88 g) in methanol (30 mL), benzhydrylamine (5.0 mL) and triethylamine (7.5 mL) were added. The resultant mixture was stirred at 70° C. for 24 hours, and then cooled in air. The reaction mixture was partitioned between water and ethyl acetate. The organic layer was sequentially washed with saturated aqueous sodium hydrogencarbonate and saturated brine, and then dried over magnesium sulfate anhydrate, followed by filtration. The solvent was evaporated under reduced pressure, and to the solid, diethyl ether was added, and then insoluble matter was removed by filtration. The mother liquid was brought to the dryness under reduced pressure. The residue was purified through silica gel column chromatography (hexane-ethyl acetate), to thereby give 3-(benzhydrylamino)-3-methylbutan-2-one as an oily product (3.3 g, 34%).
$^1$H-NMR (400 MHz, CDCl$_3$) δ: 1.18 (6H, s), 2.09 (3H, s), 4.76 (1H, s), 7.17 (2H, m), 7.25-7.29 (4H, m), 7.37-7.39 (4H, m).
LC-MSm/z: 268(M+H)$^+$.

3) 1-Benzhydryl-2,2-dimethylazetidin-3-one

Into 3-(benzhydrylamino)-3-methylbutan-2-one (6.5 g) in acetic acid (20 mL), HCl gas was blown up to saturation, and bromine (1.25 mL) was added dropwise thereto, followed by stirring for 3 hours. 20% Aqueous sodium hydroxide was added to the reaction mixture, and thereby pH of the mixture was adjusted at 14 or higher, followed by partitioning by use of carbon tetrachloride. The organic layer was washed with water. The solvent was evaporated under reduced pressure, and to the residue, N,N-dimethylformamide (30 mL) and saturated aqueous sodium hydrogencarbonate (7 mL) were added, followed by stirring for 3 minutes. The reaction mixture was partitioned between water and carbon tetrachloride. The organic layer was washed twice with saturated brine, and then dried over magnesium sulfate anhydrate, followed by filtration. The solvent was evaporated under reduced pressure, and the residue was purified through silica gel column chromatography, to thereby give 1-benzhydryl-2,2-dimethylazetidin-3-one as a solid (754 mg, 12%).
$^1$H-NMR (400 MHz, CDCl$_3$) δ: 1.20 (6H, s), 3.95 (2H, s), 4.85 (1H, s), 7.18 (2H, m), 7.26-7.31 (4H, m), 7.52-7.54 (4H, m).

4) The Title Compound

To a suspension of 1-benzhydryl-2,2-dimethylazetidin-3-one (265 mg) in methanol (4 mL), 2M dimethylamine in tetrahydrofuran (3 mL) and 10% palladium-carbon (50% wet, 250 mg) were added, and the resultant mixture was stirred in a hydrogen atmosphere at room temperature for 20 hours. The reaction mixture was filtered. The solvent was evaporated under reduced pressure, and ethanol (4 mL) was added to the residue, and 20% palladium hydroxide (50% wet, 265 mg) was added thereto, followed by stirring in a hydrogen atmosphere at room temperature for 22 hours. The reaction mixture was filtered, and 1N HCl in ethanol (2.2 mL) was added to the filtrate, followed by stirring for 10 minutes. The solvent of the reaction mixture was evaporated under reduced pressure, and the residue was solidified from diethyl ether-ethyl acetate, and the thus-obtained solid was recovered by filtration, to thereby give the title compound (60 mg, 30%).
$^1$H-NMR (400 MHz, DMSO-d$_6$) δ: 1.62 (3H, s), 1.81 (3H, s), 2.57 (6H, m), 3.89 (2H, m), 4.06 (1H, m).
LC-MSm/z: 129(M+H)$^+$.

Referential Example 122

4,7-Diazaspiro[2.5]octane hydrochloride

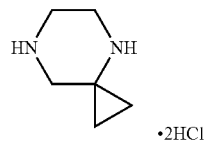

1.04M Borane-tetrahydrofuran complex in tetrahydrofuran (24.7 mL) was added dropwise to 4,7-diazaspiro[2.5]octane-5,8-dione (1.2 g) in tetrahydrofuran (30 mL) at 0° C. over a period of 30 minutes, and the resultant mixture was refluxed under heat for 13 hours. To the reaction mixture, methanol (4 mL) and 4N HCl-dioxane (8 mL) were added at 0° C., and the mixture was refluxed under heat for 1 hour, and then cooled in air. The precipitated solid was recovered by filtration, and washed with tetrahydrofuran, to thereby give a product mixture containing the title compound (1.86 g).

Triethylamine (3.16 mL) was added to the thus-obtained product mixture (1.4 g) in water (25 mL), and to the reaction mixture, N-carbobenzoxysuccinimide (4.7 g) in acetonitrile (15 mL) was added, followed by stirring at room temperature for 24 hours. The reaction mixture was partitioned between water and ethyl acetate. The aqueous layer was extracted with ethyl acetate. The organic layers were combined, and sequentially washed with saturated aqueous sodium hydrogencarbonate and saturated brine, and then dried over magnesium sulfate anhydrate, followed by filtration. The solvent was evaporated under reduced pressure, and the residue was purified through silica gel column chromatography (hexane-ethyl acetate), to thereby give an N-benzyloxycarbonyl compound as an oily product (1.4 g).

10% Palladium-carbon (50% wet, 100 mg) was added to the thus-obtained oily product (1.4 g) in ethanol (10 mL), and the resultant mixture was stirred in a hydrogen atmosphere at room temperature for 1.5 hours. The reaction mixture was filtered, and 1N HCl in ethanol (5.78 mL) was added to the filtrate at 0° C., followed by stirring for 1 hour. The solvent of the reaction mixture was evaporated under reduced pressure, and the residue was solidified from ethanol and ethyl acetate, and the thus-obtained solid was recovered by filtration, to thereby give the title compound (315 mg, 26%).

$^1$H-NMR (400 MHz, DMSO-$d_6$) δ: 0.96-1.03 (2H, m), 1.18-1.21 (2H, m), 3.30 (2H, s), 8.36 (4H, m).

LC-MS m/z: 113(M+H)$^+$.

Referential Example 123

1-(6-Chloro-3-pyridyl)-5-phenylpyrazole-3-carboxylic acid

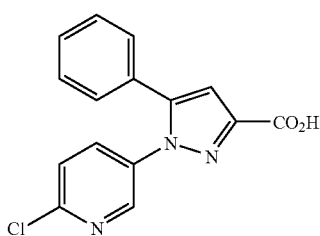

1) 4-Phenyl-2,4-dioxobutanoic acid ethyl ester

60% Sodium hydride (1.50 g) was washed hexane, and suspended in tetrahydrofuran (60 mL). While stirring at room temperature, acetophenone (4.20 g) was added to the reaction mixture, and then to the mixture, diethyl oxalate (5.0 mL) was added. N,N-Dimethylformamide (50 mL) was added thereto, and the resultant mixture was stirred in an atmosphere of 60° C. for 3 hours, and then cooled in air. The reaction mixture was acidified with aqueous 1N hydrochloric acid, followed by partitioning between water and ethyl acetate. The organic layer was sequentially washed with water and saturated brine, and then dried over magnesium sulfate anhydrate, followed by filtration. The solvent was evaporated under reduced pressure, to thereby give 4-phenyl-2,4-dioxobutanoic acid ethyl ester as an oily product.

2) 5-(2-Chloropyridyl)hydrazine

Under cooling with ice, concentrated hydrochloric acid (40 mL) was added to 5-amino-2-chloropyridine (5.22 g), followed by stirring. The mixture was stirred keeping the temperature below 5° C., and sodium nitrite (3.20 g) in water (20 mL) was added dropwise thereto. The resultant mixture was stirred under cooling with ice for 1 hour to yield a diazo compound mixture.

Tin(II) chloride dihydrate (40 g) was dissolved in concentrated hydrochloric acid (25 mL), and the resultant solution was stirred under cooling with ice. The mixture was stirred keeping the temperature below 10° C., the above-obtained diazo compound mixture was added dropwise to the resultant solution held at 10° C. or lower, followed by stirring under cooling with ice for 1 hour. The precipitated product was recovered by filtration, and washed with ether, to thereby give a crude tin salt of 5-(2-chloropyridyl)hydrazine.

3) 1-(6-Chloro-3-pyridyl)-5-phenylpyrazole-3-carboxylic acid ethyl ester

The above-obtained crude 4-phenyl-2,4-dioxobutanoic acid ethyl ester and the crude 5-(2-chloropyridyl)hydrazine (tin salt) in ethanol (150 mL) was refluxed under heat for 2 hours. The solvent was evaporated under reduced pressure, and the residue was dissolved in ethyl acetate. The resultant solution was sequentially washed with 30% aqueous potassium hydroxide solution, water (twice), and saturated brine, and then dried over magnesium sulfate anhydrate, followed by filtration. The solvent was evaporated under reduced pressure, and the residue was purified through silica gel column chromatography (hexane-ethyl acetate), to thereby give 1-(6-chloro-3-pyridyl)-5-phenylpyrazole-3-carboxylic acid ethyl ester in the form of crystals (6.01 g, 52%).

$^1$H-NMR (400 MHz, CDCl$_3$) δ: 1.43 (3H, t, J=7 Hz), 4.46 (2H, q, J=7 Hz), 7.05 (1H, s), 7.21-7.23 (2H, m), 7.35-7.42 (4H, m), 7.70 (1H, dd, J=9, 3 Hz), 8.34 (1H, d, J=3 Hz).

Elementary analysis: as $C_{17}H_{14}ClN_3O_2$

Calculated: C, 62.30%; H, 4.31%; N, 12.81%.

Found: C, 62.20%; H, 4.25%; N112.60%.

4) The Title Compound

To 1-(6-chloro-3-pyridyl)-5-phenylpyrazole-3-carboxylic acid ethyl ester (3.01 g), methanol (50 mL), tetrahydrofuran (40 mL), and aqueous 1N sodium hydroxide (20 mL) were added, and the resultant mixture was stirred for 6 hours. To the residue obtained by removal by evaporation of the reaction solvent under reduced pressure, water (50 mL) and aqueous 1N sodium hydroxide (30 mL) were added. The mixture was washed twice with ether, and acidified through addition of aqueous 1N hydrochloric acid. The precipitated crystals were recovered by filtration, and washed with water. The crystals were dissolved in ethyl acetate, and the resultant solution was washed with saturated brine, and then dried over magnesium sulfate anhydrate, followed by filtration. The solvent was evaporated under reduced pressure, to thereby give the title compound in the form of crystals (2.66 g, 97%).

$^1$H-NMR (400 MHz, CDCl$_3$) δ: 7.13 (1H, s), 7.21-7.25 (2H, m), 7.35-7.42 (4H, m), 7.74 (1H, dd, J=9, 3 Hz), 8.38 (1H, d, J=3 Hz).

Elementary analysis: as $C_{15}H_{10}ClN_3O_2$
Calculated: C, 60.11%; H, 3.36%; N, 14.02%.
Found: C, 60.06%; H, 3.30%; N, 13.84%.

Referential Example 124

[1-(6-Chloro-3-pyridyl)-5-phenylpyrazole-3-carbo-nyl]-1-succinimide

Chloroform (50 mL) and triethylamine (6.5 mL) were added to 1-(6-chloro-3-pyridyl)-5-phenylpyrazole-3-carboxylic acid (2.56 g). The resultant mixture was stirred under cooling with ice, and di(N-succinimidyl) carbonate (4.70 g) was added thereto, followed by stirring overnight. The reaction mixture was partitioned between water and chloroform. The organic layer was sequentially washed with saturated aqueous sodium hydrogencarbonate, water, and aqueous 1N hydrochloric acid, and then dried over magnesium sulfate anhydrate, followed by filtration. The solvent was evaporated under reduced pressure, and ether-hexane was added to the residue, and the precipitated powders were recovered by filtration, to thereby give the title compound (3.33 g).

$^1$H-NMR (400 MHz, CDCl$_3$) δ: 2.93 (4H, s), 7.20-7.25 (3H, m), 7.35-7.44 (4H, m), 7.71 (1H, dd, J=9 Hz, 3 Hz), 8.35 (1H, d, J=3 Hz).

Referential Example 125

1-(6-Ethoxy-3-pyridyl)-5-phenylpyrazole-3-carboxylic acid

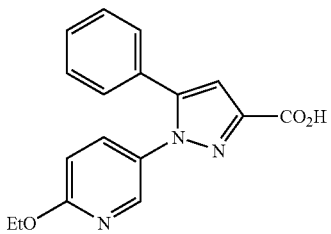

1-(6-Chloro-3-pyridyl)-5-phenylpyrazole-3-carboxylic acid ethyl ester (207 mg) obtained from Referential Example 123-3) and sodium ethoxide (500 mg) were dissolved in ethanol (15 mL). The resultant solution sealed in a tube was heated at 90° C. overnight. The residue obtained by evaporation of the reaction solvent under reduced pressure was partitioned by use of 1N sodium hydroxide (50 mL) and diethyl ether. The aqueous layer was acidified through addition of 1N HCl, and extracted with ethyl acetate. The organic layer was sequentially washed with water and saturated brine, and then dried over magnesium sulfate anhydrate, followed by filtration. The solvent was evaporated under reduced pressure, and the residual solid was recrystallized from ether-hexane, to thereby give the title compound (120 mg, 71%).

$^1$H-NMR (400 MHz, CDCl$_3$) δ: 1.39 (3H, t, J=7 Hz), 4.36 (2H, q, J=7 Hz), 6.72 (1H, d, J=9 Hz), 7.10 (1H, s), 7.22-7.25 (2H, m), 7.32-7.36 (3H, m), 7.56 (1H, dd, J=9, 3 Hz), 8.11 (1H, d, J=3 Hz).

Elementary analysis: as $C_{17}H_{15}N_3O_3$
Calculated: C, 66.01%; H, 4.89%; N, 13.58%.
Found: C, 65.65%; H, 4.85%; N, 13.44%.

Referential Example 126

[1-(6-Ethoxy-3-pyridyl)-5-phenylpyrazole-3-carbo-nyl]-1-succinimide

Under cooling with ice, triethylamine (0.30 mL) and di(N-succinimidyl) carbonate (200 mg) were added to 1-(6-ethoxy-3-pyridyl)-5-phenylpyrazole-3-carboxylic acid (110 mg) obtained from Referential Example 125 in chloroform (5 mL). The resulting mixture was stirred overnight, and di(N-succinimidyl) carbonate (500 mg) was added thereto, followed by stirring for 7 hours. The reaction mixture was partitioned between water and chloroform. The organic layer was sequentially washed with 10% aqueous citric acid, water, 5% aqueous potassium carbonate, and water, and then dried over magnesium sulfate anhydrate, followed by filtration. The solvent was evaporated under reduced pressure, and the residue was purified through silica gel column chromatography (hexane-ethyl acetate), to thereby give the title compound as an oily product (232 mg, quantitative amount).

$^1$H-NMR (400 MHz, CDCl$_3$) δ: 1.38 (3H, t, J=7 Hz), 2.83 (4H, s), 4.38 (2H, q, J=7 Hz), 6.71 (1H, d, J=9 Hz), 7.17 (1H, s), 7.21-7.26 (2H, m), 7.33-7.36 (3H, m), 7.54 (1H, dd, J=9, 3 Hz), 8.10 (1H, d, J=3 Hz).

Referential Example 127

1-(6-Isopropoxy-3-pyridyl)-5-phenylpyrazole-3-carboxylic acid

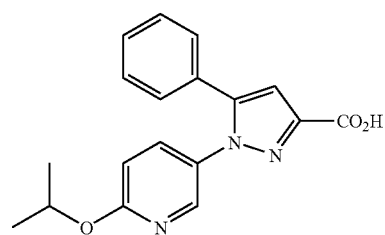

The general procedure of Referential Example 125 was repeated through use of the 1-(6-chloro-3-pyridyl)-5-phe-nylpyrazole-3-carboxylic acid ethyl ester (1.05 g) prepared in Referential Example 123-3) and isopropanol, to thereby give the title compound as a powder (840 mg, 81%).

$^1$H-NMR (400 MHz, CDCl$_3$) δ: 1.34 (6H, d, J=6 Hz), 5.28 (1H, sep, J=6 Hz), 6.66 (1H, d, J=9 Hz), 7.10 (1H, s), 7.23-7.27 (2H, m), 7.33-7.38 (3H, m), 7.53 (1H, dd, J=9, 3 Hz), 8.11 (1H, d, J=3 Hz).

Elementary analysis: as $C_{18}H_{17}N_3O_3$
Calculated: C, 66.86%; H, 5.30%; N, 13.00%.
Found: C, 66.62%; H, 5.25%; N, 13.03%.

Referential Example 128

[1-(6-Isopropoxy-3-pyridyl)-5-phenylpyrazole-3-carbonyl]-1-succinimide

The general procedure of Referential Example 126 was repeated through use of the 1-(6-isopropoxy-3-pyridyl)-5-phenylpyrazole-3-carboxylic acid (0.80 g) prepared in Referential Example 127 and di(N-succinimidyl) carbonate (1.9 g), to thereby give the title compound as a foamy product (1.11 g, quantitative amount).

$^1$H-NMR (400 MHz, CDCl$_3$) δ: 1.33 (6H, d, J=6 Hz), 2.91 (4H, s), 5.27 (1H, sep, J=6 Hz), 6.66 (1H, d, J=9 Hz), 7.17 (1H, s), 7.22-7.26 (2H, m), 7.33-7.38 (3H, m), 7.52 (1H, dd, J=9, 3 Hz), 8.11 (1H, d, J=3 Hz).

Referential Example 129

[1-(6-Methoxy-3-pyridyl)-5-phenylpyrazole-3-carbonyl]-1-succinimide

The general procedure of Referential Example 126 was repeated through use of the 1-(6-methoxy-3-pyridyl)-5-phenylpyrazole-3-carboxylic acid (1.00 g) prepared in Referential Example 41 and di(N-succinimidyl) carbonate (1.88 g), to thereby give the title compound (1.22 g, 92%).

$^1$H-NMR (400 MHz, CDCl$_3$) δ: 2.93 (4H, s), 3.94 (3H, s), 6.75 (1H, d, J=9 Hz), 7.18-7.26 (3H, m), 7.34-7.39 (3H, m), 7.57 (1H, dd, J=9, 3 Hz), 8.12 (1H, d, J=3 Hz).

Referential Example 130

1,3,3-Trimethylpiperazine-2,5-dione

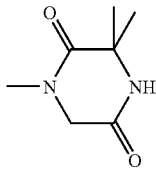

1) N-[(α,α-Dimethyl-(9H-fluoren-9-ylmethoxy)carbamino]acetylsarcosine ethyl ester To N-[(9H-fluoren-9-ylmethoxy)carbonyl]-α-aminoisobutyric acid (976 mg) in N,N-dimethylformamide (15 mL), diisopropylethylamine (1.25 mL) and O-(7-azabenzotriazol-1-yl)-N,N,N',N'-tetramethyluroniumhexafluorophosphate (1.25 g) were added. The resultant mixture was stirred at room temperature for 10 minutes, and then sarcosine ethyl ester hydrochloride (553 mg) was added thereto, followed by stirring at room temperature for 14 hours. The solvent was evaporated under reduced pressure, and the residue was partitioned between chloroform and water. The aqueous layer was extracted with chloroform. The organic layers were combined, and washed with saturated brine, and then dried over sodium sulfate anhydrate, followed by filtration. The solvent was evaporated under reduced pressure, and the residue was purified through silica gel column chromatography (hexane-ethyl acetate), to thereby give N-[α,α-dimethyl-(9H-fluoren-9-ylmethoxy)carbamino] acetylsarcosine ethyl ester as a solid (824 mg, 67%).

$^1$H-NMR (400 MHz, CDCl$_3$) δ: 1.26 (3H, t, J=7.08 Hz), 1.59 (6H, s), 3.10 (3H, s), 4.05 (2H, br s), 4.17-4.21 (4H, m), 4.47 (2H, m), 5.56 (1H, br s), 7.31 (2H, t, J=7.57 Hz), 7.40 (2H, t, J=7.57 Hz), 7.60 (2H, d, J=7.57 Hz), 7.76 (2H, d, J=7.57 Hz).

2) The Title Compound

Piperidine (867 mL) was added to N-[(α,α-dimethyl-(9H-fluoren-9-ylmethoxy)carbamino] acetylsarcosine ethyl ester (743 mg) in N,N-dimethylformamide (20 mL), followed by stirring at room temperature for 1 hour. N,N-Dimethylformamide (60 mL) was added thereto. The resultant mixture was stirred at 80° C. for 14 hours, and cooled in air. The reaction solvent was evaporated under reduced pressure, and the residue was dissolved in ethyl acetate, and then to the resultant solution, hexane was added. The precipitated crystals were recovered by filtration, to thereby give the title compound (162 mg, 59%).

$^1$H-NMR (400 MHz, DMSO-d$_6$) δ: 1.30 (6H, s), 2.82 (3H, s), 3.95 (2H, s), 8.32 (1H, br s).

Referential Example 131

Piperidine-2-carboxamide

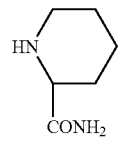

N-benzyloxypiperidine-2-carboxylic acid (2.0 g), 1-hydroxybenzotriazole (1.6 g), and 1-(3-dimethylaminopropyl)-3-ethylcarbodiimide hydrochloride (2.3 g) were dissolved in methylene chloride (20 mL). Concentrated aqueous ammonia (3 mL) and triethylamine (2 mL) were added to the resultant solution at room temperature, followed by stirring for 3 days. The reaction mixture was partitioned between water and methylene chloride. The organic layer was dried over magnesium sulfate anhydrate, followed by filtration. The solvent was evaporated under reduced pressure. 10% Palladium-carbon (1 g, 50% wet) was added to the residue in methanol (30 mL), and the resultant mixture was stirred in a hydrogen atmosphere for 20 hours. The catalyst was removed by filtration. The solvent was evaporated under reduced pressure, and the thus-obtained oily product was dried, to thereby give the title compound as a solid (970 mg, quantitative amount).

MS (ESI) m/z: 128(M$^+$).

Referential Example 132

Piperidine-2-carboxylic acid methyl amide

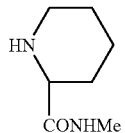

The general procedure of Referential Example 131 was repeated through use of N-benzyloxypiperidine-2-carboxylic acid (2.0 g) and 1.0 M methylamine in tetrahydrofuran (4 mL), to thereby give the title compound as an oily product (970 mg, quantitative amount).

MS (ESI) m/z: 142(M$^+$).

Referential Example 133

Piperidine-2-carboxylic acid dimethylamide

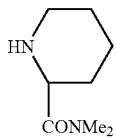

The general procedure of Referential Example 131 was repeated through use of N-benzyloxypiperidine-2-carboxylic acid (6.4 g) and dimethylamine hydrochloride (2 g), to thereby give the title compound as an oily product (3.8 g, quantitative amount).

MS (ESI) m/z: 156(M$^+$).

Referential Example 134

4-(4-Fluorophenyl)-2,4-dioxobutanoic acid ethyl ester

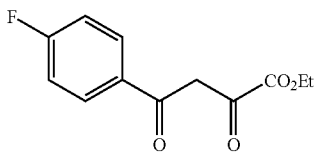

The general procedure of Referential Example 3-1) was repeated through use of 4'-fluoroacetophenone (3.0 g) and diethyl oxalate (5.9 mL), to thereby give the title compound as a solid (3.12 g, 60%).

$^1$H-NMR (400 MHz, CDCl$_3$) δ: 1.41 (3H, t, J=7.1 Hz), 4.40 (2H, q, J=7.1 Hz), 7.02 (1H, s), 7.17 (2H, t, J=8.8 Hz), 8.02 (2H, dd, J=8.8, 5.4 Hz).

MS (ESI) m/z: 239(M+1)$^+$.

Referential Example 135

5-(4-Fluorophenyl)-1-(6-methoxy-3-pyridyl)pyrazole-3-carboxylic acid ethyl ester

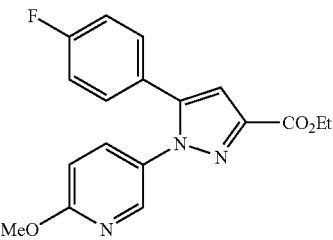

The general procedure of Referential. Example 3-2) was repeated through use of the 5-hydrazino-2-methoxypyridine (1.0 g) prepared in Referential Example 2 and the 4-(4-fluorophenyl)-2,4-dioxobutanoic acid ethyl ester (1.88 g) prepared in Referential Example 134, to thereby give the title compound as an oily product (2.12 g, 86%).

$^1$H-NMR (400 MHz, CDCl$_3$) δ: 1.43 (3H, t, J=7.1 Hz), 3.94 (3H, s), 4.46 (2H, q, J=7.1 Hz), 6.75 (1H, d, J=8.8 Hz), 7.02 (1H, s), 7.02 (2H, t, J=8.5 Hz), 7.21 (2H, dd, J=8.5, 5.1 Hz), 7.57 (1H, dd, J=8.8, 2.7 Hz), 8.09 (1H, d, J=2.7 Hz).

MS (EI) m/z: 341(M$^+$).

Referential Example 136

5-(4-Fluorophenyl)-1-(6-methoxy-3-pyridyl)pyrazole-3-carboxylic acid

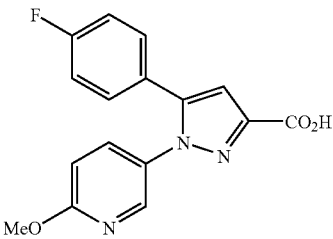

Aqueous 1N sodium hydroxide (1.2 L) was added to 5-(4-fluorophenyl)-1-(6-methoxy-3-pyridyl)pyrazole-3-carboxylic acid ethyl ester (164 g) in methanol (1.6 L), and the resultant mixture was stirred at room temperature for 5 hours. The reaction solvent was removed under reduced pressure, and the residue was partitioned between water and diethyl ether. The aqueous layer was adjusted at pH 2 through addition of aqueous 1N hydrochloric acid (1.5 L), and the precipitated crystals were dissolved in chloroform. The resultant solution was partitioned by use of saturated brine, and the organic layer was dried over sodium sulfate anhydrate, followed by filtration. The solvent was evaporated under reduced pressure, and the precipitated crystals from diethyl ether were recovered by filtration, to thereby give the title compound (132.0 g, 88%).

$^1$H-NMR (400 MHz, CDCl$_3$) δ: 3.95 (3H, s), 6.76 (1H, d, J=8.8 Hz), 7.02-7.09 (3H, m), 7.18-7.26 (2H, m), 7.56 (1H, dd, J=8.8, 2.7 Hz), 8.09 (1H, d, J=2.7 Hz).

Referential Example 137

1-(5-Methoxy-2-pyridyl)-5-phenylpyrazole-3-carboxylic acid

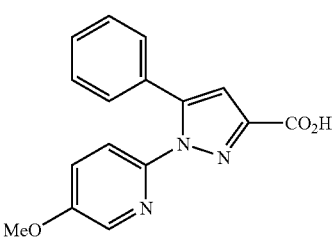

1) 5-Amino-2-chloropyridine

Concentrated hydrochloric acid (1 mL) was added to 2-chloro-5-nitropyridine (20 g) in a mixture of ethanol (160 mL) and water (40 mL). Reduced iron (70.5 g) was added little by little to the resultant mixture at room temperature, and the mixture was stirred at 90° C. for 1 hour, and then cooled in air. The reaction mixture was filtered through Celite, and the solvent of the mother liquid was removed under reduced pressure. The residue was purified through silica gel chromatography (ethyl acetate-hexane), to thereby give an amine compound as a solid (15.2 g, 94%).

$^1$H-NMR (400 MHz, CDCl$_3$) δ: 3.71 (2H, br s), 6.96 (1H, dd, J=8.3, 2.9 Hz), 7.08 (1H, d, J=8.3 Hz), 7.85 (1H, d, J=2.9 Hz).

LC-MSm/z: 129(M+H)$^+$.

2) 5-Acetoxy-2-chloropyridine

48% Aqueous tetrafluoroboric acid (40.5 mL) was added to the above-obtained 5-amino-2-chloropyridine (18 g) in ethanol (360 mL), and under cooling at −5° C., tert-butyl nitrite (23.5 mL) was added dropwise to the resultant mixture, followed by stirring for 20 minutes. Diethyl ether was added to the reaction mixture, and the precipitated product was recovered by filtration, followed by drying, to thereby give 6-chloropyridine-3-diazonium tetrafluoroborate (32 g, quantitative amount). The thus-obtained diazonium salt (32 g) in acetic anhydride (160 mL) was heated gradually to 90° C., and the mixture was stirred for 45 minutes, and then cooled in air. The reaction solvent was removed under reduced pressure, and the residue was partitioned between ethyl acetate and water. The organic layer was sequentially washed with water and saturated brine, and then dried over magnesium sulfate anhydrate, followed by filtration. The solvent was removed under reduced pressure, and the residue was purified through silica gel chromatography (hexane-ethyl acetate), to thereby give 5-acetoxy-2-chloropyridine as a solid (10 g, 42%).

$^1$H-NMR (400 MHz, CDCl$_3$) δ: 2.33 (3H, s), 7.34 (1H, d, J=8.8 Hz), 7.47 (1H, dd, J=8.8, 2.9 Hz), 8.21 (1H, d, J=2.9 Hz).

LC-MSm/z: 172(M+H)$^+$.

3) 2-Chloro-5-hydroxypyridine

Potassium carbonate (400 mg) was added to the above-obtained 5-acetoxy-2-chloropyridine (10 g) in methanol (200 mL), followed by stirring at room temperature for 20 hours. The reaction solvent was removed under reduced pressure, and the residue was purified through silica gel chromatography (ethyl acetate), to thereby give 2-chloro-5-hydroxypyridine as a solid (6.86 g, 91%).

$^1$H-NMR (400 MHz, DMSO-d$_6$) δ: 7.24 (1H, dd, J=8.8, 2.9 Hz), 7.29 (1H, d, J=8.8 Hz), 7.91 (1H, d, J=2.9 Hz), 10.22 (1H, br).

LC-MSm/z: 130(M+H)$^+$.

4) 2-Chloro-5-methoxypyridine

28% Sodium methoxide-methanol (2.0 mL) was added dropwise to the above-obtained 2-chloro-5-hydroxypyridine (1.30 g) and methyl iodide (1.25 mL) in N,N-dimethylformamide (26 mL), followed by stirring at room temperature for 1.5 hours. The reaction mixture was partitioned by use of saturated aqueous ammonium chloride and ethyl acetate. The organic layer was washed with saturated brine, and then dried over magnesium sulfate anhydrate, followed by filtration. The solvent was removed under reduced pressure, and the residue was purified through silica gel chromatography (hexane-ethyl acetate), to thereby give 2-chloro-5-methoxypyridine as a solid (1.40 g, 98%).

$^1$H-NMR (400 MHz, CDCl$_3$) δ: 3.85 (3H, s), 7.17-7.25 (2H, m), 8.05 (1H, d, J=2.9 Hz).

LC-MSm/z: 144(M+H)$^+$.

5) 2-Hydrazino-5-methoxypyridine

The above-obtained 2-chloro-5-methoxypyridine (4.0 g) in hydrazine monohydrate (30 mL) was stirred at 100° C. for 24 hours, and then cooled in air. The reaction solvent was removed under reduced pressure, and the residue was partitioned by use of chloroform and aqueous 1N sodium hydroxide. The organic layer was dried over magnesium sulfate anhydrate, followed by filtration. The solvent was removed under reduced pressure, to thereby give 2-hydrazino-5-methoxypyridine as an oily product (705 mg, 18%).

LC-MSm/z: 140(M+H)$^+$.

6) 1-(5-Methoxy-2-pyridyl)-5-phenylpyrazole-3-carboxylic acid ethyl ester

The above-obtained 2-hydrazino-5-methoxypyridine (705 mg) and the 2,4-dioxo-4-phenylbutyric acid ethyl ester (1.12 g) prepared in Referential Example 123-1) in ethanol (25 mL) was refluxed under heat for 19 hours, and then cooled in air. The reaction solvent was removed under reduced pressure, and the residue was partitioned by use of ethyl acetate and saturated aqueous sodium hydrogencarbonate. The organic layer was washed with saturated brine, and then dried over magnesium sulfate anhydrate, followed by filtration. The solvent was removed under reduced pressure, and the residue was purified through silica gel chromatography (hexane-ethyl acetate), to thereby give 1-(5-methoxy-2-pyridyl)-5-phenylpyrazole-3-carboxylic acid ethyl ester as an amorphous product (705 mg, 43%).

$^1$H-NMR (400 MHz, CDCl$_3$) δ: 1.42 (3H, t, J=7.1 Hz), 3.88 (3H, s), 4.45 (2H, q, J=7.1 Hz), 7.03 (1H, s), 7.22-7.32 (6H, m), 7.45 (1H, d, J=6.8 Hz), 8.05 (1H, d, J=3.1 Hz).

LC-MSm/z: 324(M+H)$^+$.

7) The Title Compound

Aqueous 1N sodium hydroxide (3.5 mL) was added to the above-obtained 1-(5-methoxy-2-pyridyl)-5-phenylpyrazole-3-carboxylic acid ethyl ester (700 mg) in a mixture of methanol (7 mL) and tetrahydrofuran (7 mL), followed by stirring at room temperature for 2 hours. To the reaction mixture, under cooling with ice, aqueous 1N hydrochloric acid (3.6 mL) was added. The mixture was partitioned between water and ethyl acetate. The organic layer was washed with saturated brine, and then dried over magnesium sulfate anhydrate, followed by filtration. The solvent was removed under reduced pressure, to thereby give the title compound as a solid (602 mg, 94%).

$^1$H-NMR (400 MHz, CDCl$_3$) δ: 3.89 (3H, s), 7.09 (1H, s), 7.23-7.35 (6H, m), 7.46 (1H, d, J=6.9 Hz), 8.08 (1H, d, J=3.1 Hz).

LC-MSm/z: 296(M+H)$^+$.

Referential Example 138

1-(5-Methoxy-2-pyridyl)-5-(2-pyridyl)pyrazole-3-carboxylic acid

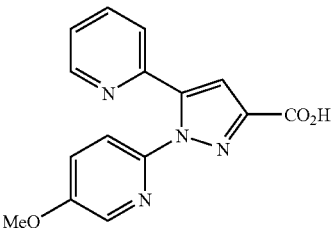

1) 5-Bromo-2-hydrazinopyridine

Hydrazine monohydrate (10 mL) was added to 2,5-dibromopyridine (10.0 g) in pyridine (100 mL) at room temperature, and the resultant mixture was refluxed under heat for 13 hours, and then cooled in air. The reaction solvent was removed under reduced pressure, and the residue was partitioned by use of aqueous 0.5N sodium hydroxide and chloroform. The organic layer was dried over sodium sulfate anhydrate, followed by filtration. The solvent was removed under reduced pressure, to thereby give 5-bromo-2-hydrazinopyridine as a solid (7.61 g, 96%).
$^1$H-NMR (400 MHz, DMSO-$d_6$) δ: 6.67 (1H, d, J=9.0 Hz), 7.55 (1H, dd, J=9.0, 2.4 Hz), 7.64 (1H, s), 8.00 (1H, d, J=2.4 Hz).
EI-MSm/z: 188(M$^+$).

2) 1-(5-Bromo-2-pyridyl)-5-(2-pyridyl)pyrazole-3-carboxylic acid ethyl ester The above-obtained 5-bromo-2-hydrazinopyridine (7.12 g) and 4-(2-pyridyl)-2,4-dioxobutanoic acid ethyl ester (8.38 g) obtained from Referential Example 31 were suspended in ethanol (126 mL). To the suspension, acetic acid (8.67 mL) was added at room temperature, and the mixture was refluxed under heat for 12 hours, and then cooled in air. The reaction mixture was partitioned by use of saturated aqueous sodium hydrogencarbonate and ethyl acetate. The organic layer was dried over sodium sulfate anhydrate, followed by filtration. The solvent was removed under reduced pressure, and the residue was purified through silica gel column chromatography (hexane-ethyl acetate), to thereby give a dihydropyrazole compound. Concentrated hydrochloric acid (4.9 mL) was added to the thus-obtained dihydropyrazole compound in ethanol (146 mL) at room temperature, and the resultant mixture was refluxed under heat for 3 hours, and then cooled in air. The reaction mixture was partitioned by use of saturated aqueous sodium hydrogencarbonate and ethyl acetate. The organic layer was dried over sodium sulfate anhydrate, followed by filtration. The solvent was removed under reduced pressure, and the residue was purified through silica gel column chromatography (hexane-ethyl acetate), to thereby give 1-(5-bromo-2-pyridyl)-5-(2-pyridyl)pyrazole-3-carboxylic acid ethyl ester as a solid (11.6 g, 82%).
$^1$H-NMR (400 MHz, CDCl$_3$) δ: 1.42 (3H, t, J=7.2 Hz), 4.45 (2H, q, J=7.2 Hz), 7.20 (1H, s), 7.23-7.25 (1H, m), 7.49 (1H, dd, J=7.8, 0.7 Hz), 7.72-7.75 (2H, m), 7.95-7.97 (1H, m), 8.26 (1H, d, J=2.2 Hz), 8.45-8.46 (1H, m).
EI-MSm/z: 373(M$^+$).

3) The Title Compound

In an argon atmosphere at room temperature, sodium methoxide (1.74 g) and copper(I) bromide (0.231 g) were added to the above-obtained 1-(5-bromo-2-pyridyl)-5-(2-pyridyl)pyrazole-3-carboxylic acid ethyl ester (3.00 g) in a mixture of methanol (30 mL) and toluene (30 mL). The resultant mixture was refluxed under heat for 47 hours, and then cooled in air. Water (50 mL) was added to the reaction mixture, followed by stirring at room temperature for 1.5 hours. The reaction mixture was partitioned by use of water, acetic acid (10 mL), and methanol-chloroform (1:10) solvent mixture. The organic layer was dried over sodium sulfate anhydrate, followed by filtration. The solvent was removed under reduced pressure, to thereby give the title compound as a solid (1.68 g, 71%).
$^1$H-NMR (400 MHz, DMSO-$d_6$) δ: 4.17 (3H, s), 7.56-8.71 (8H, m), 13.35 (1H, s).
FAB-MSm/z: 297(M+H)$^+$.

Referential Example 139

1-(6-Methoxy-3-pyridazinyl)-5-(2-pyridyl)pyrazole-3-carboxylic acid

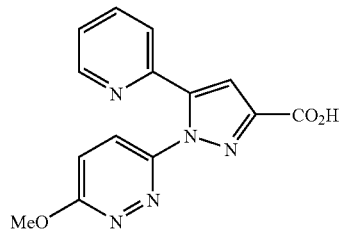

Method A)

1) 1-(6-Chloro-3-pyridazinyl)-5-(2-pyridyl)pyrazole-3-carboxylic acid ethyl ester 3-Chloro-6-hydrazinopyridazine (1.59 g) and the 4-(2-pyridyl)-2,4-dioxobutanoic acid ethyl ester (2.45 g) obtained from Referential Example 31 in ethanol (60 mL) was refluxed under heat for 6 hours. To the reaction mixture, concentrated hydrochloric acid (1 mL) was added, and the mixture was refluxed under heat for 1 hour, and then cooled in air. The reaction solvent was removed under reduced pressure, and the residue was partitioned by use of ethyl acetate and saturated aqueous sodium hydrogencarbonate. The organic layer was washed with saturated brine, and then dried over magnesium sulfate anhydrate, followed by filtration. The solvent was removed under reduced pressure, and the residue was purified through silica gel chromatography (ethyl acetate-hexane), to thereby give 1-(6-chloro-3-pyridazinyl)-5-(2-pyridyl)pyrazole-3-carboxylic acid ethyl ester as a solid (1.50 g, 41%).
$^1$H-NMR (400 MHz, CDCl$_3$) δ: 1.44 (3H, t, J=7.0 Hz), 4.46 (2H, q, J=7.0 Hz), 7.23 (1H, s), 7.24-7.27 (1H, m), 7.62-7.65 (1H, m), 7.69 (1H, d, J=9.0 Hz), 7.76-7.81 (1H, m), 8.10 (1H, d, J=9.0 Hz), 8.40 (1H, d, J=4.6 Hz).
LC-MSm/z: 330(M+H)$^+$.

2) 1-(6-Methoxy-3-pyridazinyl)-5-(2-pyridyl)pyrazole-3-carboxylic acid methyl ester 28% Sodium methoxide-methanol (3 mL) was added to the above-obtained 1-(6-chloro-3-pyridazinyl)-5-(2-pyridyl)

pyrazole-3-carboxylic acid ethyl ester (1.50 g) in methanol (45 mL), and the resultant mixture was refluxed under heat for 2 hours, and then cooled in air. The reaction solvent was removed under reduced pressure, and the residue was partitioned by use of ethyl acetate and saturated aqueous sodium hydrogencarbonate. The organic layer was dried over magnesium sulfate anhydrate, followed by filtration. The solvent was removed under reduced pressure, and the residue was purified through silica gel chromatography (ethyl acetate-hexane), to thereby give 1-(6-methoxy-3-pyridazinyl)-5-(2-pyridyl)pyrazole-3-carboxylic acid methyl ester as a solid (480 mg, 34%).

$^1$H-NMR (400 MHz, CDCl$_3$) δ: 3.99 (3H, s), 4.10 (3H, s), 7.15 (1H, d, J=9.3 Hz), 7.21-7.23 (1H, m), 7.24 (1H, s), 7.58-7.61 (1H, m), 7.73-7.78 (1H, m), 7.93 (1H, d, J=9.3 Hz), 8.40-8.41 (1H, m).

LC-MSm/z: 312(M+H)$^+$.

3) The Title Compound

Aqueous 1N sodium hydroxide (3 mL) was added to the above-obtained 1-(6-methoxy-3-pyridazinyl)-5-(2-pyridyl)pyrazole-3-carboxylic acid methyl ester (475 mg) in a mixture of ethanol (10 mL) and tetrahydrofuran (10 mL), followed by stirring at room temperature for 20 hours. Under cooling with ice, the reaction mixture was neutralized through addition of aqueous 1N hydrochloric acid (3 mL), and then the reaction mixture was partitioned by use of chloroform-methanol (10:1) solvent mixture. The organic layer was dried over magnesium sulfate anhydrate, followed by filtration. The solvent was removed under reduced pressure, to thereby give the title compound as a solid (300 mg, 66%).

$^1$H-NMR (400 MHz, DMSO-d$_6$) δ: 4.04 (3H, s), 7.32-7.35 (1H, m), 7.41 (1H, s), 7.49 (1H, d, J=9.3 Hz), 7.80-7.82 (1H, m), 7.87-7.91 (1H, m), 7.99 (1H, d, J=9.3 Hz), 8.35-8.36 (1H, m).

LC-MSm/z: 298(M+H)$^+$.

Method B)

1) 4-(2-Pyridyl)-2,4-dioxobutanoic acid methyl ester

In an argon atmosphere at room temperature, 2-acetylpyridine (2.56 g) in methanol (26 mL) was added to dimethyl oxalate (5.00 g) and sodium methoxide (2.29 g) in methanol (26 mL), followed by stirring for 15 minutes. The mixture was stirred at 60° C. for 45 minutes, and then cooled in air. Water was added to the reaction mixture, and the resultant mixture was washed with diethyl ether. The aqueous layer was partitioned by use of saturated aqueous ammonium chloride and chloroform. The organic layer was dried over sodium sulfate anhydrate, followed by filtration. The solvent was removed under reduced pressure, to thereby give 4-(2-pyridyl)-2,4-dioxobutanoic acid methyl ester as a solid (3.44 g, 79%).

$^1$H-NMR (400 MHz, CDCl$_3$) δ: 3.94 (3H, s), 7.54-7.50 (1H, m), 7.64 (1H, s), 7.93-7.89 (1H, m), 8.19-8.16 (1H, m), 8.74-8.72 (1H, m).

EI-MSm/z: 207(M$^+$).

2) 1-(6-Chloro-3-pyridazinyl)-5-(2-pyridyl)pyrazole-3-carboxylic acid methyl ester The above-obtained 4-(2-pyridyl)-2,4-dioxobutanoic acid methyl ester (4.143 g) and 3-chloro-6-hydrazinopyridine (2.891 g) in methanol (100 mL) was refluxed under heat for 109 hours. Concentrated hydrochloric acid (2 mL) was added to the reaction mixture, and the mixture was refluxed under heat for 6 hours, and then cooled in air. The reaction mixture was partitioned by use of saturated aqueous sodium hydrogencarbonate and ethyl acetate. The organic layer was sequentially washed with water and saturated brine, and then dried over sodium sulfate anhydrate, followed by filtration. The solvent was removed under reduced pressure, to thereby give 1-(6-chloro-3-pyridazinyl)-5-(2-pyridyl)pyrazole-3-carboxylic acid methyl ester as a solid (3.169 g, 50%).

$^1$H-NMR (400 MHz, CDCl$_3$) δ: 4.00 (3H, s), 7.24-7.28 (1H, m), 7.24 (1H, s), 7.64 (1H, dt, J=7.8, 1.2 Hz), 7.70 (1H, d, J=9.0 Hz), 7.79 (1H, td, J=7.8, 1.7 Hz), 8.09 (1H, d, J=9.0 Hz), 8.38-8.41 (1H, m).

ESI-MSm/z: 316(M+H)$^+$.

3) 1-(6-Methoxy-3-pyridazinyl)-5-(2-pyridyl)pyrazole-3-carboxylic acid methyl ester Sodium methoxide (1.530 g) was added to the above-obtained 1-(6-chloro-3-pyridazinyl)-5-(2-pyridyl)pyrazole-3-carboxylic acid methyl ester (2.981 g) in methanol (190 mL) at room temperature, followed by stirring for 19 hours. Aqueous 1N hydrochloric acid (19 mL) was added to the reaction mixture. Water was added to the residue obtained by evaporation of methanol under reduced pressure. The insoluble product was recovered by filtration, and dried, to thereby give 1-(6-methoxy-3-pyridazinyl)-5-(2-pyridyl)pyrazole-3-carboxylic acid methyl ester as a solid (2.571 g, 87%).

Referential Example 140

1-(6-Methoxy-3-pyridazinyl)-5-(4-dimethylaminophenyl)pyrazole-3-carboxylic acid

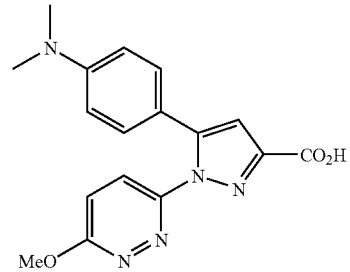

1) 4-(4-Dimethylaminophenyl)-2,4-dioxobutanoic acid methyl ester

The general procedure of Method B step 1) of Referential Example 139 was repeated through use of 4'-dimethylaminoacetophenone (1.224 g), dimethyl oxalate (1.771 g), and sodium methoxide (180 mg), to thereby give 4-(4-dimethylaminophenyl)-2,4-dioxobutanoic acid methyl ester as a solid (742 mg, 39%).

$^1$H-NMR (400 MHz, CDCl$_3$) δ: 3.10 (6H, s), 3.93 (3H, s), 6.69 (2H, d, J=9.0 Hz), 7.01 (1H, s), 7.92 (2H, d, J=9.0 Hz).

ESI-MSm/z: 250(M+H)$^+$.

2) 1-(6-Chloro-3-pyridazinyl)-5-(4-dimethylaminophenyl)pyrazole-3-carboxylic acid methyl ester The above-obtained 4-(4-dimethylaminophenyl)-2,4-dioxobutanoic acid methyl ester (742 mg) and 3-chloro-6-hydrazinopyridazine (473 mg) in methanol (30 mL) was refluxed under heat for 18 hours, and then cooled in air. The reaction solvent was removed under reduced pressure, and the residue was partitioned by use of saturated aqueous sodium hydrogencarbonate and chloroform. The organic layer was dried over sodium sulfate anhydrate, followed by filtration. The solvent was removed under reduced pressure, and the residue was purified through silica gel column chromatography (chloroform-methanol), to thereby give 1-(6-chloro-3-pyridazinyl)-5-(4-dimethylaminophenyl)pyrazole-3-carboxylic acid methyl ester as a solid (679 mg, 63%).

$^1$H-NMR (400 MHz, CDCl$_3$) δ: 2.98 (6H, s), 3.98 (3H, s), 6.65 (2H, d, J=8.8 Hz), 6.97 (1H, s), 7.16 (2H, d, J=8.8 Hz), 7.62 (1H, d, J=9.0 Hz), 7.90 (1H, d, J=9.0 Hz).

ESI-MSm/z: 358(M+H)$^+$.

3) The Title Compound

The general procedure of Referential Example 137-7) was repeated through use of the above-obtained 1-(6-chloro-3-pyridazinyl)-5-(4-dimethylaminophenyl)pyrazole-3-carboxylic acid methyl ester (679 mg), to thereby give the title compound as a solid (592 mg, 91%).

$^1$H-NMR (400 MHz, CDCl$_3$) δ: 2.97 (6H, s), 4.16 (3H, s), 6.64 (2H, d, J=8.8 Hz), 7.01 (1H, s), 7.07 (1H, d, J=9.0 Hz), 7.15 (2H, d, J=8.8 Hz), 7.60 (1H, d, J=9.0 Hz).

ESI-MSm/z: 340(M+H)$^+$.

Referential Example 141

5-(5-Chloro-2-pyridyl)-1-(6-methoxy-3-pyridazinyl)pyrazole-3-carboxylic acid

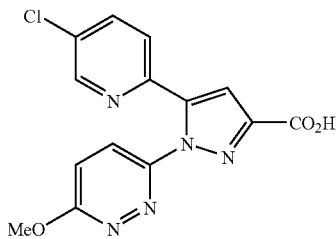

1) 2-Bromo-5-chloropyridine

Bromine (12 mL) was added to 2-amino-5-chloropyridine (5 g) in 47% hydrobromic acid (50 mL) at 0° C., and sodium nitrite (15 g) in water (20 mL) was added dropwise to the reaction mixture, followed by stirring for 1 hour. The reaction mixture was partitioned by use of sodium hydroxide (32 g) in water (80 mL) and ethyl acetate. The organic layer was dried over sodium sulfate anhydrate, followed by filtration. The solvent was removed under reduced pressure, to thereby give 2-bromo-5-chloropyridine as a solid (6.8 g, 91%).

$^1$H-NMR (400 MHz, CDCl$_3$) δ: 7.44 (1H, d, J=8.42 Hz), 7.54 (1H, m), 8.36 (1H, s).

2) 1-(5-Chloro-2-pyridyl)ethanone

Under cooling at −78° C., 1.56M n-butyllithium in hexane (27 mL) was added dropwise to 2-bromo-5-chloropyridine (6.8 g) in diethyl ether (45 mL), and then N,N-dimethylacetamide (5 mL) was added dropwise thereto, followed by stirring for 30 minutes. The reaction mixture was partitioned by use of saturated aqueous ammonium chloride and ethyl acetate. The organic layer was dried over sodium sulfate anhydrate, followed by filtration. The solvent was removed under reduced pressure, and the residue was purified through silica gel column chromatography (hexane-ethyl acetate), to thereby give 1-(5-chloro-2-pyridyl)ethanone as a solid (3.26 g, 59%).

$^1$H-NMR (400 MHz, CDCl$_3$) δ: 2.70 (3H, s), 7.80 (1H, dd, J=8.42, 2.32 Hz), 8.00 (1H, d, J=8.42 Hz), 8.62 (1H, d, J=2.32 Hz).

3) 4-(5-Chloro-2-pyridyl)-2,4-dioxobutanoic acid ethyl ester

Dimethyl oxalate (5 g) was added to sodium methoxide (2.26 g) in ethanol (100 mL), and the mixture was stirred for 5 minutes. 1-(5-Chloro-2-pyridyl)ethanone (3.26 g) was added to the mixture, followed by stirring at room temperature for 45 minutes. Water was added to the reaction mixture, and the resultant mixture was washed with diethyl ether. The aqueous layer was acidified with aqueous 1N hydrochloric acid, and chloroform was added thereto to partition the mixture. The organic layer was dried over sodium sulfate anhydrate, followed by filtration. The solvent was removed under reduced pressure, to thereby give 4-(5-chloro-2-pyridyl)-2,4-dioxobutanoic acid ethyl ester as a solid (4.12 g, 77%).

$^1$H-NMR (400 MHz, CDCl$_3$) δ: 1.42 (3H, t, J=7.08 Hz), 4.41 (2H, q, J=7.08 Hz), 7.64 (1H, s), 7.87 (1H, dd, J=8.42, 2.44 Hz), 8.11 (1H, d, J=8.42 Hz), 8.67 (1H, d, J=2.44 Hz).

EI-MSm/z: 256(M+H)$^+$.

4) 1-(6-Chloro-3-pyridazinyl)-5-(5-chloro-2-pyridyl)pyrazole-3-carboxylic acid ethyl ester The general procedure of Method A step 1) of Referential Example 139 was repeated through use of the above-obtained 4-(5-chloro-2-pyridyl)-2,4-dioxobutanoic acid ethyl ester (1 g) and 3-chloro-6-hydrazinopyridazine (735 mg), to thereby give 1-(6-chloro-3-pyridazinyl)-5-(5-chloro-2-pyridyl)pyrazole-3-carboxylic acid ethyl ester as a solid (500 mg, 35%).

$^1$H-NMR (400 MHz, CDCl$_3$) δ: 1.42 (3H, t, J=3.52 Hz), 4.47 (2H, q, J=3.52 Hz), 7.28 (1H, s), 7.58 (1H, d, J=8.30 Hz), 7.76 (1H, d, J=8.30 Hz), 7.93 (1H, d, J=9.28 Hz), 8.11 (1H, d, J=9.28 Hz), 8.34 (1H, s).

5) The Title Compound

Sodium methoxide (150 mg) was added to the above-obtained 1-(6-chloro-3-pyridazinyl)-5-(5-chloro-2-pyridyl)pyrazole-3-carboxylic acid ethyl ester (500 mg) in methanol (10 mL), followed by stirring at room temperature for 15 hours. The reaction mixture was partitioned by use of aqueous 1N hydrochloric acid and chloroform. The organic layer was dried over sodium sulfate anhydrate, followed by filtration. The solvent was removed under reduced pressure, to thereby give the title compound as an amorphous product (483 mg, >100%).

$^1$H-NMR (400 MHz, CDCl$_3$) δ: 4.12 (3H, s), 7.15 (1H, d, J=9.28 Hz), 7.19 (1H, s), 7.57 (1H, dd, J=8.42, 2.81 Hz), 7.75 (1H, dt, J=8.42, 2.81 Hz), 7.97 (1H, d, J=9.28 Hz), 8.40 (1H, s).

EI-MSm/z: 332(M+H)$^+$.

Referential Example 142

1-(5-Methoxy-2-pyrazinyl)-5-(2-pyridyl)pyrazole-3-carboxylic acid

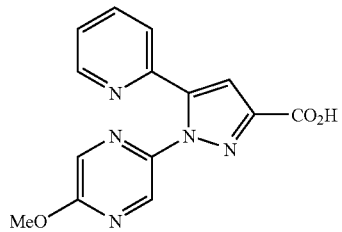

1) 5-Chloro-2-hydrazinopyrazine

5-Chloro-2-hydroxypyrazine (1.84 g), synthesized from aminopyrazine according to the method of Palamidessi et al. (J. Org. Chem., vol. 29, p.p. 2491-2492, 1964), was dissolved in phosphorus oxychloride (28 mL). The solution sealed in a tube was stirred in an atmosphere of 130° C. for 6 hours, and then cooled in air. The reaction mixture was partitioned between ice-water and methylene chloride. The organic layer was dried over sodium sulfate anhydrate, followed by filtration. The solvent was removed under reduced pressure. Hydrazine monohydrate (1.39 mL) was added to the residue in ethanol (14 mL), and the resultant mixture was stirred at room temperature for 150 minutes, and at 80° C. for 15 minutes, and then cooled in air. The solvent of the reaction mixture was removed under reduced pressure, and the residue was partitioned by use of water and chloroform-methanol (1:10) solvent mixture. The organic layer was dried over sodium sulfate anhydrate, followed by filtration. The solvent was removed under reduced pressure, to thereby give 5-chloro-2-hydrazinopyrazine as a solid (0.325 g, 16%).

$^1$H-NMR (400 MHz, DMSO-$d_6$) δ: 4.32 (2H, br s), 7.92 (1H, s), 7.99 (1H, s), 8.13 (1H, s).

EI-MSm/z: 144(M$^+$).

2) 1-(5-Chloro-2-pyrazinyl)-5-(2-pyridyl)pyrazole-3-carboxylic acid methyl ester The general procedure of Method B step 2) of Referential Example 139 was repeated through use of the 4-(2-pyridyl)-2,4-dioxobutanoic acid methyl ester (0.414 g) prepared in Method B step 1) of Referential Example 139 and the above-obtained 5-chloro-2-hydrazinopyrazine (0.289 g), to thereby give 1-(5-chloro-2-pyrazinyl)-5-(2-pyridyl)pyrazole-3-carboxylic acid methyl ester as a solid (0.260 g, 41%).

$^1$H-NMR (400 MHz, CDCl$_3$) δ: 4.00 (3H, s), 7.25-7.28 (2H, m), 7.59-7.61 (1H, m), 7.77-7.81 (1H, m), 8.25-8.25 (1H, m), 8.39-8.41 (1H, m), 8.85-8.84 (1H, m).

FAB-MSm/z: 316(M+H)$^+$.

3) The Title Compound

The general procedure of Referential Example 137-7) was repeated through use of the above-obtained 1-(5-chloro-2-pyrazinyl)-5-(2-pyridyl)pyrazole-3-carboxylic acid methyl ester (0.254 g), to thereby give the title compound as a solid (0.237 g, 99%).

$^1$H-NMR (400 MHz, DMSO-$d_6$) δ: 3.98 (3H, s), 7.29-7.32 (1H, m), 7.37 (1H, s), 7.74-7.87 (2H, m), 8.11 (1H, s), 8.33-8.34 (1H, m), 8.52 (1H, s), 13.15 (1H, br s).

FAB-MSm/z: 298(M+H)$^+$.

Referential Example 143

1-(6-Methyl-3-pyridyl)-5-(2-pyridyl)pyrazole-3-carboxylic acid ethyl ester

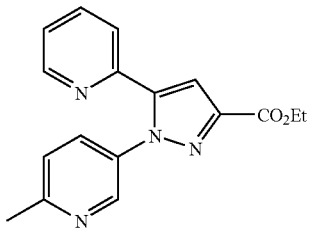

The general procedure of Referential Example 3-2) was repeated through use of the 5-hydrazino-2-methylpyridine (1.20 g) prepared in Referential Example 63 and the 4-(2-pyridyl)-2,4-dioxobutanoic acid ethyl ester (3.48 g) prepared in Referential Example 31, to thereby give the title compound as an oily product (0.459 g, 15%).

$^1$H-NMR (400 MHz, CDCl$_3$) δ: 1.43 (3H, t like, J=7.3 Hz), 2.60 (3H, s), 4.46 (2H, q, J=7.3 Hz), 7.20-7.50 (4H, m), 7.67-7.80 (2H, m), 8.39 (1H, br), 8.51 (1H, br).

FAB-MSm/z: 309(M+H)$^+$.

Referential Example 144

1-(6-Methoxy-3-pyridyl)-5-(3-pyridazinyl)pyrazole-3-carboxylic acid lithium salt

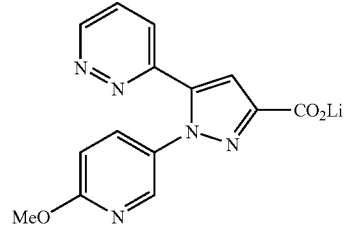

1) 4-(3-Pyridazinyl)-2,4-dioxobutanoic acid methyl ester

In an argon atmosphere and while cooling at –78° C., 1.0M lithium bis(trimethylsilyl)amide in tetrahydrofuran (19 mL) was added dropwise to 3-acetylpyridazine (2.097 g) in tetrahydrofuran (50 mL), followed by stirring for 1 hour. To the reaction mixture, dimethyl oxalate (4.055 g) in tetrahydrofuran (35 mL) was added dropwise, and the resultant mixture was stirred at 0° C. for 2 hours. The reaction solvent was removed under reduced pressure. Water was added to the residue, and the mixture was washed with diethyl ether. The aqueous layer was slightly acidified with aqueous 1N hydrochloric acid, and extracted with ethyl acetate. The organic layer was dried over sodium sulfate anhydrate, followed by filtration. The solvent was removed under reduced pressure, to thereby give 4-(3-pyridazinyl)-2,4-dioxobutanoic acid methyl ester as a solid (2.63 g, 73%).

¹H-NMR (400 MHz, CDCl₃) δ: 3.97 (3H, s), 7.73 (1H, dd, J=8.5, 5.1 Hz), 7.96 (1H, s), 8.28 (1H, dd, J=8.5, 1.8 Hz), 9.38 (1H, dd, J=5.1, 1.8 Hz).
ESI-MSm/z: 209(M+H)⁺.

2) 1-(6-Methoxy-3-pyridyl)-5-(3-pyridazinyl)pyrazole-3-carboxylic acid methyl ester The general procedure of Referential Example 140-2) was repeated through use of the above-obtained 4-(3-pyridazinyl)-2,4-dioxobutanoic acid methyl ester (1.086 g) and the 5-hydrazino-2-methoxypyridine (726 mg) prepared in Referential Example 2, to thereby give 1-(6-methoxy-3-pyridyl)-5-(3-pyridazinyl)pyrazole-3-carboxylic acid methyl ester as a solid (309 mg, 19%).
¹H-NMR (400 MHz, CDCl₃) δ: 3.95 (3H, s), 4.00 (3H, s), 6.80 (1H, d, J=8.8 Hz), 7.43 (1H, s), 7.51 (2H, d, J=3.4 Hz), 7.70 (1H, dd, J=8.8, 2.7 Hz), 8.11 (1H, d, J=2.7 Hz), 9.15 (1H, t, J=3.4 Hz).
ESI-MSm/z: 312(M+H)⁺.

3) The Title Compound

Lithium hydroxide monohydrate (42 mg) was added to the above-obtained 1-(6-methoxy-3-pyridyl)-5-(3-pyridazinyl)pyrazole-3-carboxylic acid methyl ester (309 mg) in methanol (20 mL), and the resultant mixture was refluxed under heat for 18 hours, and then cooled in air. The reaction solvent was removed under reduced pressure, to thereby give the title compound as an amorphous product (322 mg, >100%).
ESI-MSm/z: 298(M+H)⁺.

Referential Example 145

1-(6-Methoxy-3-pyridyl)-5-(4-methyl-2-pyridyl)pyrazole-3-carboxylic acid

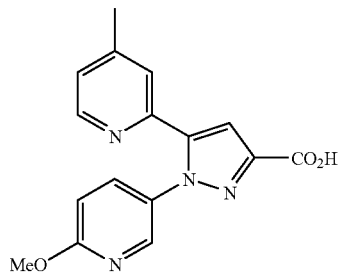

1) 4-Methylpyridine-2-carbonitrile

The general procedure of Referential Example 15 was repeated through use of 4-methylpyridine-N-oxide (6.00 g), to thereby give 4-methylpyridine-2-carbonitrile as a solid (4.65 g, 72%).
¹H-NMR (400 MHz, CDCl₃) δ: 2.44 (3H, s), 7.33-7.35 (1H, m), 7.53 (1H, s), 8.57 (1H, d, J=4.8 Hz).
EI-MSm/z: 118(M⁺).

2) 1-(4-Methyl-2-pyridyl)ethanone

The general procedure of Referential Example 16 was repeated through use of the above-obtained 4-methylpyridine-2-carbonitrile (4.46 g), to thereby give 1-(4-methyl-2-pyridyl)ethanone as an oily product (4.38 g, 86%).
¹H-NMR (400 MHz, CDCl₃) δ: 2.43 (3H, s), 2.72 (3H, s), 7.28-7.29 (1H, m), 7.87 (1H, m), 8.54 (1H, d, J=5.2 Hz).
EI-MSm/z: 135(M⁺).

3) 4-(4-Methyl-2-pyridyl)-2,4-dioxobutanoic acid ethyl ester

Diethyl oxalate (4.42 mL) was added to sodium ethoxide (2.22 g) in ethanol (22 mL), and the mixture was stirred for 10 minutes. The above-obtained 1-(4-methyl-2-pyridyl)ethanone (2.20 g) in ethanol (22 mL) was added to the mixture, followed by stirring at room temperature for 20 minutes. Water was added to the reaction mixture, and the resultant mixture was washed with diethyl ether, and then the aqueous layer was partitioned by use of saturated aqueous ammonium chloride and chloroform. The organic layer was dried over sodium sulfate anhydrate, followed by filtration. The solvent was removed under reduced pressure, to thereby give 4-(4-methyl-2-pyridyl)-2,4-dioxobutanoic acid ethyl ester as an oily product (2.84 g, 74%).
¹H-NMR (400 MHz, CDCl₃) δ: 1.41 (3H, t, J=7.2 Hz), 2.47 (3H, s), 4.40 (2H, q, J=7.2 Hz), 7.34-7.35 (1H, m), 7.52 (1H, br), 8.01 (1H, s), 8.57 (1H, d, J=5.2 Hz).
EI-MSm/z: 235(M⁺).

4) 1-(6-Methoxy-3-pyridyl)-5-(4-methyl-2-pyridyl)pyrazole-3-carboxylic acid ethyl ester The general procedure of Referential Example 138-2) was repeated through use of the above-obtained 4-(4-methyl-2-pyridyl)-2,4-dioxobutanoic acid ethyl ester (2.83 g) and the 5-hydrazino-2-methoxypyridine (1.67 g) prepared in Referential Example 2, to thereby give 1-(6-methoxy-3-pyridyl)-5-(4-methyl-2-pyridyl)pyrazole-3-carboxylic acid ethyl ester as a solid (1.66 g, 41%).
¹H-NMR (400 MHz, CDCl₃) δ: 1.43 (3H, t, J=7.2 Hz), 2.34 (3H, s), 3.94 (3H, s), 4.46 (2H, q, J=7.2 Hz), 6.76 (1H, d, J=8.8 Hz), 7.05-7.06 (1H, m), 7.23-7.24 (2H, m), 7.66-7.69 (1H, m), 8.10 (1H, d, J=2.8 Hz), 8.36 (1H, d, J=4.8 Hz).
EI-MSm/z: 338 (M⁺).

5) The Title Compound

The general procedure of Referential Example 137-7) was repeated through use of the above-obtained 1-(6-methoxy-3-pyridyl)-5-(4-methyl-2-pyridyl)pyrazole-3-carboxylic acid ethyl ester (1.04 g), to thereby give the title compound as a solid (0.944 g, 99%).
¹H-NMR (400 MHz, DMSO-d₆) δ: 2.43 (3H, s), 3.89 (3H, s), 6.87 (1H, d, J=8.8 Hz), 7.17-7.19 (1H, m), 7.30 (1H, s), 7.59 (1H, s), 7.68-7.71 (1H, m), 8.13 (1H, d, J=2.8 Hz), 8.27-8.30 (1H, m), 13.04 (1H, br).
EI-MSm/z: 310(M⁺).

Referential Example 146

1-(6-Methoxy-3-pyridyl)-5-(5-methyl-2-pyridyl)pyrazole-3-carboxylic acid

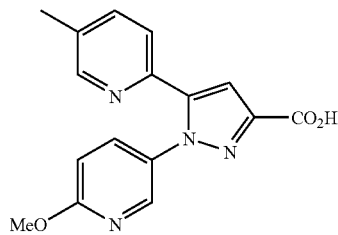

1) 1-(5-Methyl-2-pyridyl)ethanone

The general procedure of Referential Example 141-2) was repeated through use of 2-bromo-5-methylpyridine (10.0 g), to thereby give 1-(5-methyl-2-pyridyl)ethanone as an oily product (6.71 g, 85%).

$^1$H-NMR (400 MHz, CDCl$_3$) δ: 2.42 (3H, s), 2.71 (3H, s), 7.61-7.64 (1H, m), 7.95 (1H, d, J=8.0 Hz), 8.50 (1H, m).
EI-MSm/z: 135(M$^+$).

2) 4-(5-Methyl-2-pyridyl)-2,4-dioxobutanoic acid ethyl ester

The general procedure of Referential Example 146-3) was repeated through use of the above-obtained 1-(5-methyl-2-pyridyl)ethanone (6.7 g) and diethyl oxalate (13.5 mL), to thereby give 4-(5-methyl-2-pyridyl)-2,4-dioxobutanoic acid ethyl ester as a solid (8.99 g, 77%).

$^1$H-NMR (400 MHz, CDCl$_3$) δ: 1.41 (3H, t, J=7.2 Hz), 2.45 (3H, s), 4.40 (2H, q, J=7.2 Hz), 7.56 (1H, br), 7.69-7.71 (1H, m), 8.08 (1H, d, J=8.0 Hz), 8.54 (1H, m). EI-MSm/z: 235 (M$^+$).

3) 1-(6-Methoxy-3-pyridyl)-5-(5-methyl-2-pyridyl)pyrazole-3-carboxylic acid ethyl ester The general procedure of Referential Example 138-2) was repeated through use of the above-obtained 4-(5-methyl-2-pyridyl)-2,4-dioxobutanoic acid ethyl ester (8.98 g) and the 5-hydrazino-2-methoxypyridine (5.31 g) prepared in Referential Example 2, to thereby give 1-(6-methoxy-3-pyridyl)-5-(5-methyl-2-pyridyl)pyrazole-3-carboxylic acid ethyl ester as a solid (7.31 g, 57%).

$^1$H-NMR (400 MHz, CDCl$_3$) δ: 1.42 (3H, t, J=7.2 Hz), 2.34 (3H, s), 3.95 (3H, s), 4.45 (2H, q, J=7.2 Hz), 6.76 (1H, d, J=8.8 Hz), 7.23-7.30 (2H, m), 7.47-7.50 (1H, m), 7.66-7.69 (1H, m), 8.10 (1H, d, J=2.4 Hz), 8.36 (1H, m).
FAB-MSm/z: 339(M+H)$^+$.

4) The Title Compound

The general procedure of Referential Example 137-7) was repeated through use of the above-obtained 1-(6-methoxy-3-pyridyl)-5-(5-methyl-2-pyridyl)pyrazole-3-carboxylic acid ethyl ester (1.00 g), to thereby give the title compound as a solid (0.789 g, 86%).

$^1$H-NMR (400 MHz, DMSO-d$_6$) δ: 2.29 (3H, s), 3.89 (3H, s), 6.87-6.90 (1H, m), 7.26 (1H, s), 7.55-7.57 (1H, m), 7.67-7.72 (2H, m), 8.13 (1H, d, J=2.8 Hz), 8.30 (1H, m), 13.04 (1H, br).
FAB-MSm/z: 311(M+H)$^+$.

Referential Example 147

1-tert-Butoxycarbonylpiperazine-3-carboxylic acid ethyl ester

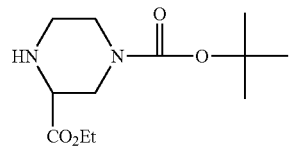

1) 1,4-Di-tert-butoxycarbonylpiperazine-3-carboxylic acid ethyl ester

Piperazine-2-carboxylic acid hydrochloride (5.0 g) and di-tert-butoxycarbonate (11.8 g) were dissolved in tetrahydrofuran (50 mL). Triethylamine (10.7 mL) and 6N aqueous sodium hydroxide (1 mL) were added to the resultant solution, followed by stirring at room temperature for 6 hours. The reaction mixture was partitioned by use of methylene chloride. The organic layer was dried over magnesium sulfate anhydrate, followed by filtration. The solvent was removed under reduced pressure, and the residue was purified through silica gel column chromatography (methylene chloride-methanol), to thereby give 1,4-di-tert-butoxycarbonylpiperazine-3-carboxylic acid (5.45 g, 67%). The general procedure of Referential Example 81 was repeated through use of the thus-obtained 1,4-di-tert-butoxycarbonylpiperazine-3-carboxylic acid and ethanol (2 mL), to thereby give 1,4-di-tert-butoxycarbonylpiperazine-3-carboxylic acid ethyl ester (5.5 g, 62%).

EI-MSm/z: 358(M$^+$).

2) The Title Compound

Concentrated hydrochloric acid (5 mL) was added to the above-obtained 1,4-di-tert-butoxycarbonylpiperazine-3-carboxylic acid ethyl ester (5.5 g) in ethanol (50 mL), followed by stirring at room temperature for 3 days. The solvent of the reaction mixture was removed under reduced pressure, to thereby give piperazine-2-carboxylic acid ethyl ester hydrochloride (3.4 g, 95.7%). Under cooling with ice, triethylamine (5 mL) and 2-(tert-butoxycarbonyloxyimino)-2-phenylacetonitrile (4.0 g) were added to the thus-obtained piperazine-2-carboxylic acid ethyl ester hydrochloride (3.4 g) in tetrahydrofuran (30 mL), followed by stirring at room temperature for 16 hours. The reaction mixture was partitioned by use of methylene chloride. The organic layer was dried over magnesium sulfate anhydrate, followed by filtration. The solvent was removed under reduced pressure, and the residue was purified through silica gel column chromatography (methylene chloride-methanol), to thereby give the title compound as an oily product (3.14 g, 49%).

$^1$H-NMR (400 MHz, CDCl$_3$) δ: 1.28 (3H, t, J=7.3 Hz), 1.47 (9H, s), 2.70-2.80 (1H, m), 3.00-3.15 (3H, m), 3.40-3.45 (1H, m), 3.68-3.75 (1H, m), 4.20 (2H, q, J=7.3 Hz).
EI-MSm/z: 258(M$^+$).

Referential Example 148

(3S)-Morpholine-3-carboxylic acid methyl ester

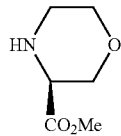

1) (2S)-2-(N-Benzyloxycarbonyl)amino-3-(2-chloro-ethoxy)propanoic acid methyl ester To (S)-(−)-1,2-azetidinedicarboxylic acid 1-benzyl 2-methyl ester (1 g) in chloroform (10 mL), 2-chloroethanol (3 mL) and a catalytic amount of boron trifluoride-diethyl ether complex (3 drops) were added dropwise, followed by stirring at room temperature for 4 hours. The reaction mixture was partitioned between water and chloroform. The organic layer was dried over sodium sulfate anhydrate, followed by filtration. The solvent was removed under reduced pressure, and the residue was purified through silica gel column chromatography (hexane-ethyl acetate), to thereby give (2S)-2-(N-benzyloxycarbonyl)amino-3-(2-chloroethoxy)propanoic acid methyl ester as an oily product (1.09 g, 81%).

$^1$H-NMR (400 MHz, CDCl$_3$) δ: 3.56 (2H, t, J=5.74 Hz), 3.69 (2H, m), 3.77 (3H, s), 3.85 (1H, m), 3.95 (1H, dd, J=9.40, 3.17 Hz), 4.51 (1H, dt, J=8.67, 3.17 Hz), 5.13 (2H, s), 5.67 (1H, br), 7.36 (5H, m).

EI-MS m/z: 316(M+H)$^+$.

2) (2S)-2-Amino-3-(2-chloroethoxy)propanoic acid methyl ester

5% Palladium-carbon (170 mg) was added to the above-obtained (2S)-2-(N-benzyloxycarbonyl)amino-3-(2-chloroethoxy)propanoic acid methyl ester (1.09 g) in methanol (15 mL), and the resultant mixture was stirred in a hydrogen atmosphere at room temperature for 16.5 hours. The reaction mixture was filtered through Celite, and the solvent of the filtrate was removed under reduced pressure, to thereby give (2S)-2-amino-3-(2-chloroethoxy)propanoic acid methyl ester as an oily product (608 mg, 97%).

$^1$H-NMR (400 MHz, CD$_3$OD) δ: 3.62 (2H, m), 3.70 (5H, m), 3.74 (3H, s), 3.84 (1H, m), 3.90 (1H, m).

EI-MS m/z: 182(M+H)$^+$.

3) The Title Compound

Triethylamine (1.2 mL) was added to the above-obtained (2S)-2-amino-3-(2-chloroethoxy)propanoic acid methyl ester (726 mg) in methanol (10 mL), and the resultant mixture was refluxed under heat for 3 hours, and then cooled in air. The reaction solvent was removed under reduced pressure. Ethyl acetate was added to the residue, and insoluble matter was removed by filtration. The solvent of the filtrate was removed under reduced pressure, to thereby give the title compound as an oily product (467 mg, 80%).

$^1$H-NMR (400 MHz, D$_2$O) δ: 2.70 (1H, m), 2.88 (1H, m), 3.50-3.70 (4H, m), 3.65 (3H, s), 3.87 (1H, dd, J=11.60, 3.05 Hz).

Referential Example 149

1,4-Oxazepane hydrochloride

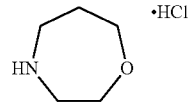

1) 1,4-Oxazepan-5-one

Under cooling with ice, sodium azide (17.8 g) was added to tetrahydro-4H-pyran-4-one (9.80 g) in concentrated hydrochloric acid (50 mL) over a period of 40 minutes, followed by stirring for 30 minutes and then at room temperature for 16 hours. Under cooling with ice, to the reaction mixture, sodium carbonate was added to adjust pH at 8 to 9, followed by partitioning of the mixture by addition of chloroform. The organic layer was washed with saturated brine, and then dried over magnesium sulfate anhydrate, followed by filtration. The solvent was removed under reduced pressure, to thereby give 1,4-oxazepan-5-one as a solid (5.34 g, 47.4%).

$^1$H-NMR (300 MHz, CDCl$_3$) δ: 2.70-2.74 (2H, m), 3.32-3.37 (2H, m), 3.75-3.83 (4H, m), 6.31 (1H, br s).

FAB-MS m/z: 116(M+H)$^+$.

2) 1,4-Oxazepane-4-carboxylic acid tert-butyl ester

In a nitrogen stream and while cooling with ice, the above-obtained 1,4-oxazepan-5-one (3.041 g) was added to 1.0 M borane-tetrahydrofuran complex in tetrahydrofuran (40 mL) over a period of 30 minutes, followed by stirring at room temperature for 30 minutes. The resultant mixture was refluxed under heat for 2.5 hours, and then cooled in air. 4N HCl-dioxane (25 mL) and methanol (12 mL) were added to the reaction mixture, and the mixture was refluxed under heat for 1 hour, and then cooled in air. Aqueous 1N sodium hydroxide (80 mL) was added to the reaction mixture, and di-tert-butoxycarbonate (8.849 g) in tetrahydrofuran (25 mL) and methanol (20 mL) were added thereto at room temperature, followed by stirring for 17 hours. The reaction mixture was partitioned between water and chloroform. The organic layer was washed with saturated brine, and dried over sodium sulfate anhydrate, followed by filtration. The solvent was removed under reduced pressure, and the residue was purified through silica gel column chromatography (hexane-ethyl acetate), to thereby give 1,4-oxazepane-4-carboxylic acid tert-butyl ester as an oily product (2.68 g, 50%).

$^1$H-NMR (400 MHz, CDCl$_3$) δ: 1.46 (9H, s), 1.82-1.95 (2H, m), 3.45-3.58 (4H, m), 3.66-3.77 (4H, m).

3) The Title Compound

4N Dioxane-HCl (4.6 mL) was added to the above-obtained 1,4-oxazepane-4-carboxylic acid tert-butyl ester (0.468 g) in methylene chloride (9.2 mL) at 0° C., followed by stirring at room temperature for 0.5 hours. The reaction solvent was removed under reduced pressure, to thereby give the title compound as a solid (0.263 g, 82%).

¹H-NMR (400 MHz, CDCl₃) δ: 2.22-2.33 (2H, m), 3.27-3.43 (4H, m), 3.82-3.90 (2H, m), 3.92-4.01 (2H, m), 9.89 (1H, br).
ESI-MS m/z: 102(M+H)⁺.

Referential Example 150

1-Methylhexahydropyridazine

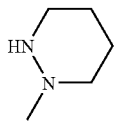

1) Benzyl ethyl hydrazine-1,2-dicarboxylate

Triethylamine (100 mL) and benzyl chloroformate (103 mL) were added to ethyl carbazate (50.0 g) in methylene chloride (400 mL) at 0° C., followed by stirring at room temperature for 18 hours. The reaction mixture was partitioned by use of saturated aqueous sodium hydrogencarbonate and chloroform. The organic layer was washed with brine, and then dried over magnesium sulfate anhydrate, followed by filtration. The solvent was removed under reduced pressure, and the residue was purified through silica gel column chromatography (hexane-ethyl acetate), to thereby give benzyl ethyl hydrazine-1,2-dicarboxylate as an oily product (31.7 g, 27.7%).
¹H-NMR (300 MHz, CDCl₃) δ: 1.25 (3H, t, J=7.16 Hz), 4.12 (2H, q, J=7.16 Hz), 5.16 (2H, s), 7.28-7.36 (5H, m).

2) Benzyl ethyl azo-1,2-dicarboxylate tert-Butyl hypochlorite (19.1 mL) was added to the above-obtained benzyl ethyl hydrazine-1,2-dicarboxylate (31.0 g) in ethyl acetate (150 mL) at room temperature, followed by stirring for 3 hours. The reaction mixture was partitioned by use of saturated aqueous sodium carbonate and water. The organic layer was dried over magnesium sulfate anhydrate, followed by filtration. The solvent was removed under reduced pressure, to thereby give benzyl ethyl azo-1,2-dicarboxylate as an oily product (28.7 g, 93.4%).
¹H-NMR (300 MHz, CDCl₃) δ: 1.39 (3H, t, J=7.16 Hz), 4.46 (2H, q, J=7.16 Hz), 5.41 (2H, s), 7.30-7.53 (5H, m).

3) 1,2,3,6-Tetrahydropyridazine-1,2-dicarboxylic acid 1-benzyl ester 2-ethyl ester 1,3-Butadiene (64.0 g) was blown into the above-obtained benzyl ethyl azo-1,2-dicarboxylate (28.0 g) in benzene (100 mL) at −10° C., followed by stirring at room temperature for 18 hours. The reaction solvent was removed under reduced pressure, to thereby give 1,2,3,6-tetrahydropyridazine-1,2-dicarboxylic acid 1-benzyl ester 2-ethyl ester having impurities as an oily product (32 g).
FAB-MS m/z: 291(M+H)⁺.

4) Hexahydropyridazine-1-carboxylic acid ethyl ester

In a hydrogen atmosphere, 10% palladium-carbon (3.2 g) was added to the above-obtained 1,2,3,6-tetrahydropyridazine-1,2-dicarboxylic acid 1-benzyl ester 2-ethyl ester (32 g) in ethanol (100 mL), and the resultant mixture was stirred at 40° C. for 24 hours, and then cooled in air. The reaction mixture was filtered, and the solvent of the filtrate was removed under reduced pressure, and the residue was purified by distillation (boiling point 81° C./1 mmHg), to thereby give hexahydropyridazine-1-carboxylic acid ethyl ester as an oily product (5.96 g, yield from the 2 processes: 31.1%).
¹H-NMR (300 MHz, CDCl₃) δ: 1.29 (3H, t, J=7.16 Hz), 1.65 (4H, Brs), 2.92 (2H, t, J=5.69 Hz), 3.57 (2H, t, J=5.69 Hz), 4.19 (2H, q, J=7.16 Hz).

5) The Title Compound

To a suspension of lithium aluminum hydride (2.64 g) in diethyl ether (50 mL), the above-obtained hexahydropyridazine-1-carboxylic acid ethyl ester (5.5 g) in diethyl ether (20 mL) was added dropwise over a period of 1 hour at room temperature. The resultant mixture was refluxed under heat for 4 hours. Under cooling at −10° C., 40% aqueous potassium hydroxide solution (100 mL) was added dropwise to the reaction mixture, and then diethyl ether was added thereto, whereby the mixture was partitioned. The organic layer was washed with brine, and then dried over magnesium sulfate anhydrate, followed by filtration. The solvent was removed under reduced pressure, to thereby give the title compound as an oily product (1.75 g, 50.3%).
¹H-NMR (300 MHz, CDCl₃) δ: 1.42 (2H, br s), 1.73-1.81 (2H, m), 2.38 (3H, s), 2.48 (2H, br s), 3.02 (2H, t, J=5.51 Hz).

Referential Example 151

4-Methoxypiperidine trifluoroacetic acid salt

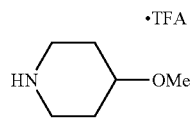

1) 4-Methoxypiperidine-1-carboxylic acid tert-butyl ester

The general procedure of Referential Example 106 was repeated through use of 4-hydroxy-1-piperazinecarboxylic acid tert-butyl ester (2.0 g), to thereby give 4-methoxypiperidine-1-carboxylic acid tert-butyl ester as an oily product (1.43 g, 67%).
¹H-NMR (400 MHz, CDCl₃) δ: 1.39-1.54 (2H, m), 1.46 (9H, s), 1.81-1.84 (2H, m), 3.05-3.12 (2H, m), 3.31-3.39 (1H, m), 3.35 (3H, s), 3.74-3.77 (2H, m).

2) The Title Compound

The general procedure of Referential Example 85-2) was repeated through use of the above-obtained 4-methoxypiperidine-1-carboxylic acid tert-butyl ester (1.42 g), to thereby give the title compound as an oily product (2.65 g, quantitative amount).

¹H-NMR (400 MHz, CDCl₃) δ: 1.98-2.02 (4H, m), 3.19-3.23 (2H, m), 3.30-3.42 (2H, m), 3.37 (3H, s), 3.54-3.60 (1H, m).

Referential Example 152

4,4-Difluoropiperidine hydrochloride

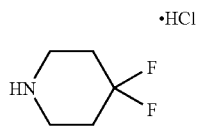

1) N-Benzyl-4,4-difluoropiperidine

In an argon atmosphere, diethylaminosulfur trifluoride (8.38 mL) was added dropwise to 1-benzyl-4-piperidone (5.00 g) in benzene (200 mL) at 0° C., and the resultant mixture was stirred for 30 minutes, and then refluxed under heat for 18 hours. Under cooling at 0° C., The resultant mixture was partitioned by use of saturated aqueous sodium hydrogencarbonate and ethyl acetate. The organic layer was dried over sodium sulfate anhydrate, followed by filtration. The solvent was removed under reduced pressure, and the residue was purified through silica gel column chromatography (hexane-ethyl acetate), to thereby give N-benzyl-4,4-difluoropiperidine as an oily product (4.67 g, 84%).

¹H-NMR (400 MHz, CDCl₃) δ: 1.93-2.04 (4H, m), 2.53-2.55 (4H, m), 3.54 (2H, s), 7.24-7.34 (5H, m).

EI-MSm/z: 211 (M⁺).

2) The Title Compound

In an argon atmosphere, 1-chloroethyl chloroformate (2.62 mL) was added dropwise to the above-obtained N-benzyl-4,4-difluoropiperidine (4.66 g) in methylene chloride (93 mL) at 0° C., and the resultant mixture was stirred at 55° C. for 2 hours, and then cooled in air. The reaction solvent was removed under reduced pressure, and the residue in methanol (93 mL) was refluxed under heat for 4 hours, and then cooled in air. The reaction solvent was removed under reduced pressure, to thereby give the title compound as a solid (3.03 g, 87%).

FAB-MSm/z: 122(M+H)⁺.

Referential Example 153

3,3-Difluoropiperidine hydrochloride

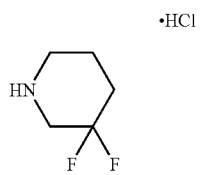

1) N-Benzyl-3,3-difluoropiperidine

The general procedure of Referential Example 152-1) was repeated through use of 1-benzyl-3-piperidone hydrochloride (4.00 g), to thereby give N-benzyl-3,3-difluoropiperidine as an oily product (1.09 g, 31%).

¹H-NMR (400 MHz, CDCl₃) δ: 1.73-1.92 (4H, m), 2.45 (2H, t, J=5.4 Hz), 2.63 (2H, t, J=11.4 Hz), 3.60 (2H, s), 7.24-7.37 (5H, m).

FAB-MSm/z: 212(M+H)⁺.

2) The Title Compound

The general procedure of Referential Example 152-2) was repeated through use of the above-obtained N-benzyl-3,3-difluoropiperidine (1.08 g), to thereby give the title compound as a solid (0.764 g, 95%).

¹H-NMR (400 MHz, D₂O) δ: 1.85-1.91 (2H, m), 2.01-2.11 (2H, m), 3.12 (2H, t, J=5.2 Hz), 3.40 (2H, t, J=11.5 Hz).

FAB-MSm/z: 122(M+H)⁺.

Referential Example 154

4-Fluoropiperidine hydrochloride

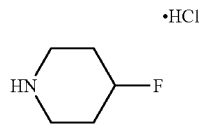

1) 4-Fluoropiperidine-N-carboxylic acid tert-butyl ester

In an argon atmosphere and while cooling at −78° C., [bis(2-methoxyethyl)amino]sulfur trifluoride (7.33 mL) was added dropwise to 4-hydroxy-1-piperidinecarboxylic acid tert-butyl ester (4.00 g) in methylene chloride (80 mL), followed by stirring for 30 minutes. The resultant mixture was stirred at 0° C. for 30 minutes and then at room temperature for 2 hours. The reaction mixture was partitioned by use of saturated aqueous sodium hydrogencarbonate and chloroform. The organic layer was dried over sodium sulfate anhydrate, followed by filtration. The solvent was removed under reduced pressure, and the residue was purified through silica gel column chromatography (chloroform-ethyl acetate) to thereby give 4-fluoropiperidine-N-carboxylic acid tert-butyl ester as an oily product (1.77 g, 44%).

¹H-NMR (400 MHz, CDCl₃) δ: 1.45 (9H, s), 1.86-1.76 (4H, m), 3.41-3.54 (4H, m), 4.70-4.87 (1H, m).

EI-MSm/z: 203(M⁺).

2) The Title Compound

The general procedure of Referential Example 85-2) was repeated through use of the above-obtained 4-fluoropiperidine-N-carboxylic acid tert-butyl ester (1.74 g), to thereby give the title compound as a solid (0.870 g, 73%).

¹H-NMR (400 MHz, DMSO-d₆) δ: 2.13-1.92 (4H, m), 3.01-3.12 (4H, m), 4.83-4.97 (1H, m).

FAB-MSm/z: 104(M+H)⁺.

Referential Example 155

(3R)-3-Methoxypyrrolidine-1-carboxylic acid tert-butyl ester

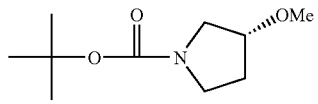

The general procedure of Referential Example 106 was repeated through use of (3R)-3-hydroxypyrrolidine-1-carboxylic acid tert-butyl ester (0.955 g) and methyl iodide (0.47 mL), to thereby give the title compound as an oily product (0.899 g, 89%).

$^1$H-NMR (400 MHz, CDCl$_3$) δ: 1.46 (9H, s), 1.88-2.03 (2H, m), 3.33-3.50 (4H, m), 3.33 (3H, s), 3.92 (1H, br s).
ESI-MSm/z: 146(M-Bu+H)$^+$.

Referential Example 156

Hexahydropyridazine

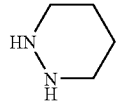

1) 1,2,3,6-Tetrahydropyridazine-1,2-dicarboxylic acid dibenzyl ester

The general procedure of Referential Example 151-3) was repeated through use of 1,2-azodicarboxylic acid dibenzyl ester (10.28 g), to thereby give 1,2,3,6-tetrahydropyridazine-1,2-dicarboxylic acid dibenzyl ester as an oily product (2.57 g, 21%).

$^1$H-NMR (400 MHz, CDCl$_3$) δ: 3.70-3.85 (2H, br), 4.35-4.52 (2H, br), 5.05-5.25 (4H, br), 5.78 (2H, br), 7.03-7.40 (10H, m).
FAB-MSm/z: 353(M+H)$^+$.

2) The Title Compound

The general procedure of Referential Example 151-4) was repeated through use of the above-obtained 1,2,3,6-tetrahydropyridazine-1,2-dicarboxylic acid dibenzyl ester (2.57 g), to thereby give the title compound as an oily product (0.629 g, quantitative amount).

$^1$H-NMR (400 MHz, DMSO-d$_6$) δ: 1.67-1.75 (2H, m), 1.96-2.05 (2H, m), 2.60-3.10 (4H, m).
ESI-MSm/z: 87(M+H)$^+$.

Referential Example 157

1-Methylpiperazin-2-one hydrochloride

4N HCl-dioxane (20 mL) was added to 3-oxopiperazine-1-carboxylic acid tert-butyl ester (2.06 g) obtained from Referential Example 90, followed by stirring at room temperature for 1 hour. The reaction solvent was removed under reduced pressure, to thereby give the title compound as an oily product (1.44 g, 99%).

$^1$H-NMR (400 MHz, DMSO-d$_6$) δ: 2.86 (3H, s), 3.34 (2H, br m), 3.50 (2H, m), 3.64 (2H, m).
ESI-MSm/z: 115(M+H)$^+$.

Referential Example 158

1-(6-Methoxy-3-pyridazinyl)-5-(4-methoxy-2-pyridyl)pyrazole-3-carboxylic acid

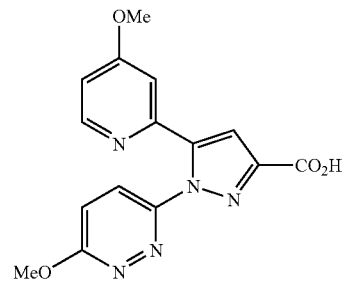

1) 1-(6-Chloro-3-pyridazinyl)-5-(4-methoxy-2-pyridyl)pyrazole-3-carboxylic acid ethyl ester The general procedure of Method A step 1) of Referential Example 139 was repeated through use of the 4-(4-methoxy-2-pyridyl)-2,4-dioxobutanoic acid ethyl ester (4.94 g) prepared in Referential Example 17 and 3-chloro-6-hydrazinopyridazine (2.84 g), to thereby give 1-(6-chloro-3-pyridazinyl)-5-(4-methoxy-2-pyridyl)pyrazole-3-carboxylic acid ethyl ester as a solid (2.02 g, 29%).

$^1$H-NMR (400 MHz, CDCl$_3$) δ: 1.41-1.44 (3H, m), 3.88 (3H, s), 4.43-4.49 (2H, m), 6.75 (1H, dd, J=5.9, 2.4 Hz), 7.15 (1H, d, J=2.4 Hz), 7.19 (1H, s), 7.66-7.68 (1H, m), 8.07 (1H, d, J=9.0 Hz), 8.19 (1H, d, J=5.9 Hz).
EI-MSm/z: 359(M$^+$).

2) The Title Compound

Aqueous 1N sodium hydroxide (14 mL) was added to the above-obtained 1-(6-chloro-3-pyridazinyl)-5-(4-methoxy-2-pyridyl)pyrazole-3-carboxylic acid ethyl ester (2.01 g) in a mixture of methanol (40 mL) and tetrahydrofuran (40 mL) at room temperature, followed by stirring for 1 hour. The reaction solvent was removed under reduced pressure, and water was added to the residue, and the mixture was washed with chloroform. The aqueous layer was partitioned between acetic acid (20 mL) and a methanol-chloroform (1:5) solvent mixture. The organic layer was dried over sodium sulfate anhydrate, followed by filtration. The solvent was removed under reduced pressure, and the residue was dissolved in methanol (14 mL). In an argon atmosphere, sodium methoxide (0.332 g) was added to the resultant solution at room temperature, followed by stirring for 3 hours. The mixture was refluxed under heat for 2 hours, and then cooled in air. The reaction mixture was partitioned by use of acetic acid (10 mL), water, and methanol-chloroform (1:10) solvent mixture. The organic layer was dried over sodium sulfate anhydrate, followed by filtration. The solvent was removed under reduced pressure, to thereby give the title compound as a solid (0.626 g, 34%).

$^1$H-NMR (400 MHz, DMSO-$d_6$) δ: 3.87 (3H, s), 4.03 (3H, s), 6.87-6.89 (1H, m), 7.40-7.45 (3H, m), 7.92 (1H, d, J=9.3 Hz), 8.12 (1H, d, J=5.9 Hz), 13.09 (1H, br s).
EI-MSm/z: 327 (M$^+$).

Referential Example 159

1-(6-Methoxy-3-pyridyl)-5-(pyrrol-2-yl)pyrazole-3-carboxylic acid

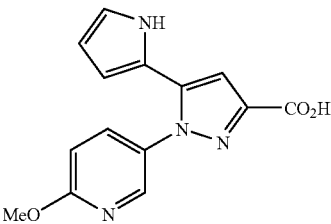

Under cooling with ice, diethyl oxalate (3.10 mL) and 1-[1-(phenylsulfonyl)pyrrol-2-yl]-1-ethanone (2.49 g) were added to sodium ethoxide (1.63 g) in ethanol (20 mL), followed by stirring at room temperature for 5 hours. To the reaction mixture, 5-hydrazino-2-methoxypyridine hydrochloride (2.52 g) obtained from Referential Example 1 and ethanol (20 mL) were added, and the resultant mixture was refluxed under heat for 14.5 hours, and then cooled in air. The reaction solvent was removed under reduced pressure, and the residue was partitioned by use of ethyl acetate and saturated aqueous sodium hydrogencarbonate. The aqueous layer was extracted again with ethyl acetate. The organic layers were combined, and then dried over sodium sulfate anhydrate, followed by filtration. The solvent was removed under reduced pressure, the residue was purified through silica gel column chromatography (ethyl acetate-hexane), to thereby give 1-(6-methoxy-3-pyridyl)-5-[1-(phenylsulfonyl)pyrrol-2-yl] pyrazole-3-carboxylic acid ethyl ester as an oily product (3.28 g, 72%). To the thus-obtained ethyl ester (3.28 g) in ethanol (22 mL), aqueous 1N sodium hydroxide (22 mL) was added, followed by stirring at room temperature for 2 days. Aqueous 1N hydrochloric acid was added to the reaction mixture, and the precipitated solid was recovered by filtration, to thereby give the title compound as a solid (1.40 g, 68%).

$^1$H-NMR (400 MHz, DMSO-$d_6$) δ: 3.94 (3H, s), 5.49-5.51 (1H, m), 5.98-6.00 (1H, m), 6.87-6.89 (1H, m), 6.98 (1H, dd, J=8.8, 0.5 Hz), 7.08 (1H, s), 7.80 (1H, dd, J=8.8, 2.7 Hz), 8.25 (1H, dd, J=2.7, 0.5 Hz), 11.39 (1H, br s).
ESI-MSm/z: 285(M+H)$^+$.

Referential Example 160

1-(6-Methoxy-3-pyridazinyl)-5-(2-pyridyl)pyrazole-3-carboxylic acid 1-(6-Methoxy-3-pyridazinyl)-5-(2-pyridyl)pyrazole-3-carboxylic acid methyl ester (2.20 g) obtained in Method B step 3) of Referential Example 139 was dissolved in a solvent mixture of methanol (30 mL) and tetrahydrofuran (30 mL), and 1N aqueous sodium hydroxide (15 mL) was added to the solution at room temperature, followed by stirring for 2.5 hours. Under cooling with ice, 1N aqueous hydrochloric acid (15 mL) and a solvent mixture of chloroform-methanol (10:1) were added to the reaction mixture for partitioning the mixture. The organic layer was dried over sodium sulfate anhydrate, followed by filtration. The solvent was removed under reduced pressure, and isopropyl ether was added to the residue, and then the precipitated solid was recovered by filtration, to thereby give the title compound (1.42 g, 47.6%).

$^1$H-NMR (400 MHz, DMSO-$d_6$) δ: 4.04 (3H, s), 7.32-7.35 (1H, m), 7.41 (1H, s), 7.49 (1H, d, J=9.3 Hz), 7.80-7.82 (1H, m), 7.87-7.91 (1H, m), 7.99 (1H, d, J=9.3 Hz), 8.35-8.36 (1H, m).
LC-MSm/z: 298(M+H)$^+$.

Referential Example 161

1-(6-Methoxy-3-pyridyl)-5-(1-methylpyrrol-2-yl)pyrazole-3-carboxylic acid

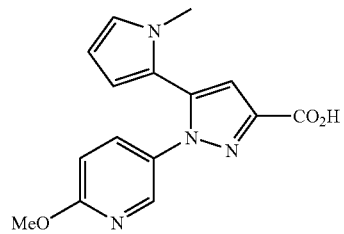

Under cooling at −78° C., 1.0 M lithium bis(trimethylsilyl)amide in tetrahydrofuran (10.4 mL) was added to 1-(1-methylpyrrol-2-yl)-1-ethanone (1.19 mL) in tetrahydrofuran (10 mL), followed by stirring for 35 minutes. Diethyl oxalate (2.05 mL) was added to the reaction mixture, and the resultant mixture was gradually returned to room temperature, followed by stirring at room temperature for 2.5 hours. To the reaction mixture, triethylamine (1.64 mL), 5-hydrazino-2-methoxypyridine hydrochloride (2.52 g) obtained from Referential Example 1, and ethanol (50 mL) were added. The mixture was refluxed under heat for 2.5 days. Acetic acid (5 mL) was added thereto, and the reaction mixture was refluxed under heat for 3 days, and then cooled in air. The reaction solvent was removed under reduced pressure. The residue was partitioned by use of ethyl acetate and saturated aqueous sodium hydrogencarbonat, and the aqueous layer was extracted with ethyl acetate. The organic layers were combined, and then dried over sodium sulfate anhydrate, followed by filtration. The solvent was removed under reduced pressure, and the residue was purified through silica gel column chromatography (ethyl acetate-hexane), to thereby give 1-(6-methoxy-3-pyridyl)-5-(1-methylpyrrol-2-yl)pyrazole-3-carboxylic acid ethyl ester as an oily product (2.70 g, 82%). Aqueous 1N sodium hydroxide (21 mL) was added to the thus-obtained ethyl ester (2.70 g) in ethanol (20 mL), followed by stirring at room temperature for 26 hours. The reaction mixture was partitioned by use of aqueous 1N hydrochloric acid and ethyl acetate, and the aqueous layer was extracted again with ethyl acetate. The organic layers were combined, and then dried over magnesium sulfate anhydrate, followed by filtration. The solvent was removed under reduced pressure, to thereby give the title compound as an amorphous solid (2.57 g, quantitative amount). Without further purification, the compound was subjected to the following reaction.

Example 1

1-[5-(4-Chlorophenyl)-1-(6-methoxy-3-pyridyl)pyrazole-3-carbonyl]-4-methylpiperazine

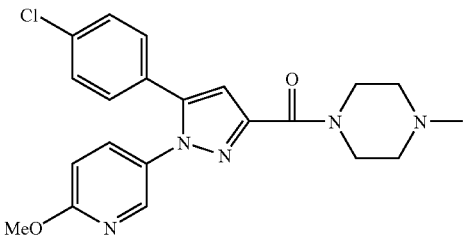

1) The Title Compound

To a solution of 5-(4-chlorophenyl)-1-(6-methoxy-3-pyridyl)pyrazole-3-carboxylic acid (0.237 g) obtained in Referential Example 4 in N,N-dimethylformamide (5.0 mL), 1-hydroxybenzotriazole (0.110 g), 1-(3-dimethylaminopropyl)-3-ethylcarbodiimide hydrochloride (0.303 g), triethylamine (0.255 mL), and N-methylpiperazine (0.240 mL) were added at room temperature. The resultant mixture was stirred for 21 hours and partitioned between water and ethyl acetate. Subsequently, the aqueous layer was extracted with ethyl acetate. The organic layers were combined, and the resultant organic layer was washed with saturated brine and dried over sodium sulfate anhydrate. After filtration, the solvent was removed under reduced pressure. The residue was purified through silica gel column chromatography (chloroform-methanol), to thereby give the title compound (0.261 g, 88%).

$^1$H-NMR (400 MHz, CDCl$_3$) δ: 2.33 (3H, s), 2.40-2.60 (4H, m), 3.84 (2H, br), 3.94 (3H, s), 4.11 (2H, br), 6.74 (1H, d-like, J=8.7 Hz), 6.91 (1H, s), 7.17 (2H, d-like, J=8.8 Hz), 7.31 (2H, d-like, J=8.8 Hz), 7.49 (1H, dd, J=8.7, 2.7 Hz), 8.09 (1H, d-like, J=2.7 Hz).

MS (ESI) m/z: 412(M+H)$^+$.

2) Hydrochloric Acid Salt of the Title Compound

To a solution of the title compound (0.261 g) in chloroform (1.0 mL), 1M HCl in ethanol (0.635 mL) was added, followed by stirring of the mixture. Diethyl ether and pentane were added to the reaction mixture for precipitation. The thus-precipitated solid was collected through filtration and washed with diethyl ether, followed by drying, to thereby give a hydrochloric acid salt of the title compound (0.223 g, 75%).

$^1$H-NMR (400 MHz, DMSO-d$_6$) δ: 2.79 (3H, s), 3.00-3.70 (6H, m), 3.88 (3H, s), 4.60 (1H, br), 4.95 (1H, br), 6.92 (1H, d, J=8.8 Hz), 7.05 (1H, s), 7.32 (2H, d, J=8.5 Hz), 7.47 (2H, d, J=8.5 Hz), 7.71 (1H, dd, J=8.8, 2.9 Hz), 8.21 (1H, d, J=2.9 Hz), 10.60 (1H, br).

MS (ESI) m/z: 412(M+H)$^+$.

Example 2

1-[5-(4-Ethylphenyl)-1-(6-methoxy-3-pyridyl)pyrazole-3-carbonyl]-4-methylpiperazine

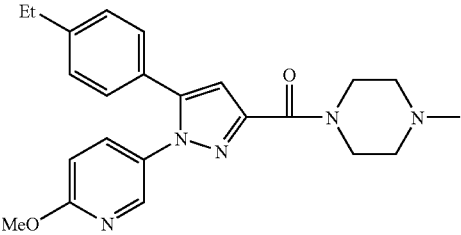

1) The Title Compound

In a manner similar to that employed in step 1) of Example 1, the title compound was obtained as an oily product (0.294 g, 87%) through use of 5-(4-ethylphenyl)-1-(6-methoxy-3-pyridyl)pyrazole-3-carboxylic acid (0.269 g) obtained in Referential Example 6 and N-methylpiperazine (0.275 mL).

$^1$H-NMR (400 MHz, CDCl$_3$) δ: 1.23 (3H, t, J=7.8 Hz), 2.32 (3H, s), 2.40-2.60 (4H, m), 2.64 (2H, q, J=7.8 Hz), 3.84 (2H, br), 3.93 (3H, s), 4.12 (2H, br), 6.72 (1H, d, J=8.7 Hz), 6.88 (1H, s), 7.10-7.20 (4H, m), 7.49 (1H, dd, J=8.7, 2.4 Hz), 8.13 (1H, d, J=2.4 Hz).

MS (ESI) m/z: 406(M+H)$^+$.

2) Hydrochloric Acid Salt of the Title Compound

In a manner similar to that employed in step 2) of Example 1, a hydrochloric acid salt of the title compound was obtained as a solid (0.276 g, 81%) through use of the above-obtained title compound (0.294 g).

$^1$H-NMR (400 MHz, DMSO-d$_6$) δ: 1.17 (3H, t, J=7.6 Hz), 2.60 (2H, q, J=7.6 Hz), 2.79 (3H, s), 3.00-3.75 (6H, m), 3.88 (3H, s), 4.65 (1H, br), 5.00 (1H, br), 6.91 (1H, d, J=9.1 Hz), 6.97 (1H, s), 7.17-7.28 (4H, m), 7.70 (1H, dd, J=9.1, 2.7 Hz), 8.21 (1H, d, J=2.7 Hz).

LC-MSm/z: 406(M+H)$^+$.

Elementary analysis: as C$_{23}$H$_{27}$N$_5$O$_2$.1.0HCl.1.5H$_2$O
Calculated: C, 58.90; H, 6.66; Cl, 7.56; N, 14.93.
Found: C, 58.65; H, 6.51; Cl, 7.63; N, 14.84.

Example 3

1-[1-(6-Methoxy-3-pyridyl)-5-(3-methylphenyl)pyrazole-3-carbonyl]-4-methylpiperazine

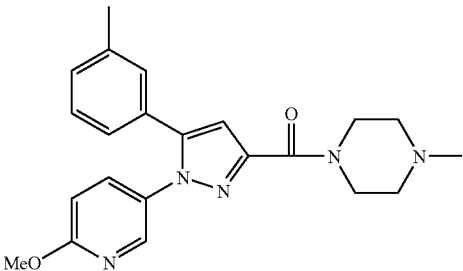

1) The Title Compound

In a manner similar to that employed in step 1) of Example 1, the title compound was obtained as an oily product (0.471 g, quantitative amount) through use of 1-(6-methoxy-3-pyridyl)-5-(3-methylphenyl)pyrazole-3-carboxylic acid (0.353 g) obtained in Referential Example 8 and N-methylpiperazine (0.380 mL).

$^1$H-NMR (400 MHz, CDCl$_3$) δ: 2.31 (3H, s), 2.33 (3H, s), 2.40-2.60 (4H, m), 3.84 (2H, br), 3.94 (3H, s), 4.12 (2H, br), 6.71 (1H, d, J=8.8 Hz), 6.88 (1H, s), 6.97 (1H, d-like, J=7.3 Hz), 7.08-7.25 (3H, m), 7.48 (1H, dd, J=8.8, 2.6 Hz), 8.12 (1H, d, J=2.6 Hz).

MS (ESI) m/z: 392(M+H)$^+$.

2) Hydrochloric Acid Salt of the Title Compound

In a manner similar to that employed in step 2) of Example 1, a hydrochloric acid salt of the title compound was obtained as a solid (0.356 g, 70%) through use of the above-obtained title compound (0.471 g).

$^1$H-NMR (400 MHz, DMSO-d$_6$) δ: 2.28 (3H, s), 2.79 (3H, s), 2.95-3.70 (6H, m), 3.7 (3H, s), 4.60 (1H, br), 4.99 (1H, br), 6.90 (1H, d, J=8.7 Hz), 6.95-7.03 (2H, m), 7.17-7.30 (3H, m), 7.68 (1H, dd, J=8.7, 2.0 Hz), 8.19 (1H, d, J=2.0 Hz), 10.79 (1H, br).

LC-MS m/z: 392(M+H)$^+$.

Example 4

1-[1-(6-Methoxy-3-pyridyl)-5-(2-methylphenyl)pyrazole-3-carbonyl]-4-methylpiperazine

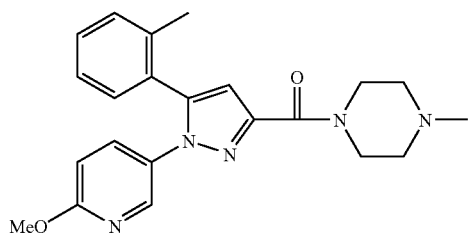

1) The Title Compound

In a manner similar to that employed in step 1) of Example 1, the title compound was obtained as an oily product (0.335 g, 86%) through use of 1-(6-methoxy-3-pyridyl)-5-(2-methylphenyl)pyrazole-3-carboxylic acid (0.307 g) obtained in Referential Example 10 and N-methylpiperazine (0.330 mL).

$^1$H-NMR (400 MHz, CDCl$_3$) δ: 2.04 (3H, s), 2.34 (3H, s), 2.50 (4H, m), 3.85 (2H, br), 3.89 (3H, s), 4.17 (2H, br), 6.64 (1H, d, J=9.1 Hz), 6.83 (1H, s), 7.15-7.35 (5H, m), 7.42 (1H, dd, J=9.1, 2.7 Hz), 8.03 (1H, d, J=2.7 Hz).

MS (ESI) m/z: 392(M+H)$^+$.

2) Hydrochloric Acid Salt of the Title Compound

In a manner similar to that employed in step 2) of Example 1, a hydrochloric acid salt of the title compound was obtained as a solid (0.30 g, 81%) through use of the above-obtained title compound (0.335 g).

$^1$H-NMR (400 MHz, DMSO-d$_6$) δ: 2.04 (3H, s), 2.80 (3H, s), 3.00-3.80 (6H, m), 3.82 (3H, s), 4.60 (1H, br), 5.02 (1H, br), 6.83 (1H, d, J=9.0 Hz), 6.90 (1H, s), 7.18-7.40 (4H, m), 7.62 (1H, dd, J=9.0, 2.7 Hz), 8.07 (1H, d, J=2.7 Hz).

MS (ESI) m/z: 392(M+H)$^+$.

Example 5

1-[5-(3-Fluorophenyl)-1-(6-methoxy-3-pyridyl)pyrazole-3-carbonyl]-4-methylpiperazine

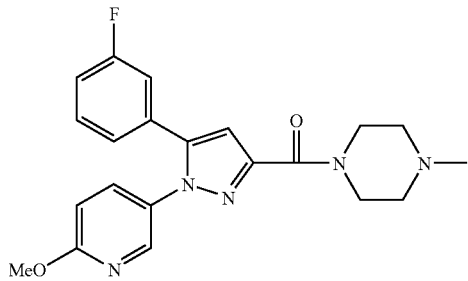

1) The Title Compound

In a manner similar to that employed in step 1) of Example 1, the title compound was obtained as an oily product (0.314 g, 83%) through use of 5-(3-fluorophenyl)-1-(6-methoxy-3-pyridyl)pyrazole-3-carboxylic acid (0.302 g) obtained in Referential Example 12 and N-methylpiperazine (0.320 mL).

$^1$H-NMR (400 MHz, CDCl$_3$) δ: 2.31 (3H, s), 2.40-2.60 (4H, m), 3.82 (2H, br), 3.93 (3H, s), 4.09 (2H, br), 6.72 (1H, d, J=8.8 Hz), 6.90 (1H, s), 6.90-7.10 (3H, m), 7.25-7.35 (1H, m), 7.47 (1H, dd, J=8.8, 2.7 Hz), 8.08 (1H, d, J=2.7 Hz).

MS (ESI) m/z: 396(M+H)$^+$.

2) Hydrochloric Acid Salt of the Title Compound

In a manner similar to that employed in step 2) of Example 1, a hydrochloric acid salt of the title compound was obtained as a solid (0.282 g, 79%) through use of the above-obtained title compound (0.314 g).

$^1$H-NMR (400 MHz, DMSO-d$_5$) δ: 2.79 (3H, s), 3.00-3.75 (6H, m), 3.88 (3H, s), 4.60 (1H, br), 4.95 (1H, br), 6.92 (1H, d, J=8.8 Hz), 7.05-7.13 (1H, m), 7.09 (1H, s), 7.18-7.30 (2H, m), 7.39-7.50 (1H, m), 7.72 (1H, dd, J=8.8, 2.7 Hz), 8.22 (1H, d, J=2.7 Hz), 10.50 (1H, br).

LC-MS m/z: 396(M+H)$^+$.

Elementary analysis: as $C_{21}H_{22}FN_5O_2 \cdot 1.0HCl \cdot 1.0H_2O$
Calculated: C, 56.06; H, 5.60; Cl, 7.88; F, 4.22; N, 15.57.
Found: C, 55.97; H, 5.60; Cl, 8.01; F, 4.20; N, 15.36.

Example 6

4-[1-(6-Methoxy-3-pyridyl)-5-phenylpyrazole-3-carbonyl]morpholine

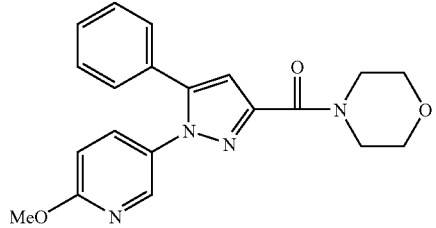

In a manner similar to that employed in step 1) of Example 1, the title compound was obtained as a solid (0.126 g, 66%) through use of 1-(6-methoxy-3-pyridyl)-5-phenylpyrazole-3-carboxylic acid (0.155 g) obtained in Referential Example 41 and morpholine (0.137 mL).

¹H-NMR (400 MHz, CDCl₃) δ: 3.65-4.05 (6H, m), 3.94 (3H, s), 4.10-4.30 (2H, m), 6.72 (1H, d, J=8.8 Hz), 6.95 (1H, s), 7.15-7.40 (5H, m), 7.47 (1H, dd, J=8.8, 2.7 Hz), 8.12 (1H, d, J=2.7 Hz).

MS (FAB) m/z: 365(M+H)⁺.

Example 7

1-[1-(6-Methoxy-3-pyridyl)-5-phenylpyrazole-3-carbonyl]-3,4-dimethylpiperazine

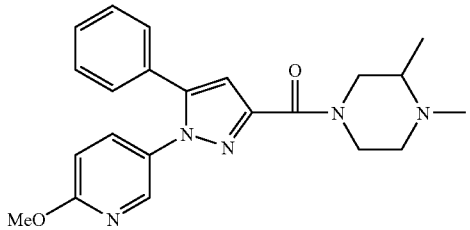

1) The Title Compound

In a manner similar to that employed in step 1) of Example 1, the title compound was obtained as an oily product (0.268 g, 84%) through use of 1-(6-methoxy-3-pyridyl)-5-phenylpyrazole-3-carboxylic acid (0.241 g) obtained in Referential Example 41 and 1,2-dimethylpiperazine trifluoroacetic acid salt (0.838 g) obtained in Referential Example 84.

¹H-NMR (400 MHz, CDCl₃) δ: 1.09 and 1.15 (3H, each d, each J=6.1 Hz), 2.10-2.40 (1.5H, m), 2.33 (3H, s), 2.70-2.95 (2H, m), 3.08-3.20 (1H, m), 3.45-3.60 (0.5H, m), 3.93 (3H, s), 4.45-4.85 (2H, m), 6.71 (1H, d, J=8.8 Hz), 6.91 (1H, s), 7.20-7.60 (6H, m), 8.12 (1H, s).

LC-MS m/z: 392(M+H)⁺.

2) Hydrochloric Acid Salt of the Title Compound

In a manner similar to that employed in step 2) of Example 1, a hydrochloric acid salt of the title compound was obtained as a solid (0.173 g, 54%) through use of the above-obtained title compound (0.268 g).

¹H-NMR (400 MHz, DMSO-d₆) δ: 1.15-1.45 (3H, m), 2.0-4.0 (5H, m), 2.79 (3H, s), 3.86 (3H, s), 4.60 (1H, br), 4.95 (1H, br), 6.89 (1H, d, J=8.7 Hz), 7.00 (1H, s), 7.20-7.45 (5H, m), 7.68 (1H, dd, J=8.7, 2.5 Hz), 8.18 (1H, d, J=2.5 Hz).

LC-MS m/z: 392(M+H)⁺.

Example 8

1-[4-Methyl-5-phenyl-1-(3-pyridyl)pyrazole-3-carbonyl]-4-methylpiperazine

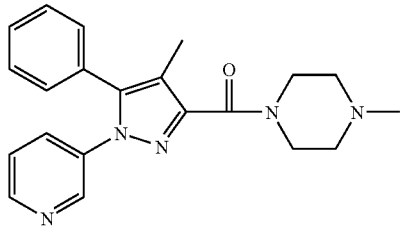

1) The Title Compound

In a manner similar to that employed in step 1) of Example 1, the title compound was obtained as an oily product (0.596 g, 61%) through use of 4-methyl-5-phenyl-1-(3-pyridyl)pyrazole-3-carboxylic acid (0.752 g) obtained in Referential Example 54 and N-methylpiperazine (0.90 mL).

¹H-NMR (400 MHz, CDCl₃) δ: 2.18 (3H, s), 2.34 (3H, s), 2.45-2.59 (4H, m), 3.87 (4H, br), 7.15-7.30 (3H, m), 7.35-7.43 (3H, m), 7.51-7.57 (1H, m), 8.47 (1H, dd, J=4.7 Hz, J=1.5 Hz), 8.49 (1H, d, J=2.2 Hz).

MS (ESI) m/z: 362(M+H)⁺.

2) Hydrochloric Acid Salt of the Title Compound

In a manner similar to that employed in step 2) of Example 1, a hydrochloric acid salt of the title compound was obtained as a solid (0.565 g, 84%) through use of the above-obtained title compound (0.596 g).

¹H-NMR (400 MHz, DMSO-d₆) δ: 2.11 (3H, s), 2.82 (3H, s), 3.00-3.65 (6H, m), 4.55-4.80 (2H, m), 7.21-7.32 (2H, m), 7.40-7.50 (3H, m), 7.63-7.70 (1H, m), 8.48 (1H, d, J=2.4 Hz), 8.52 (1H, d-like, J 4.8 Hz), 10.45 (1H, br).

MS (ESI) m/z: 362(M+H)⁺.

Example 9

1-[4-Methyl-1,5-diphenylpyrazole-3-carbonyl]-4-methylpiperazine

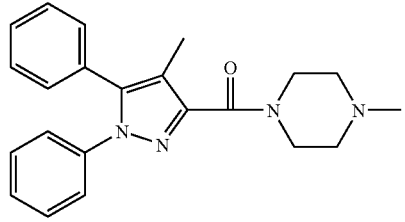

1) The Title Compound

In a manner similar to that employed in step 1) of Example 1, the title compound was obtained as an oily product (0.818 g, 90%) through use of 4-methyl-1,5-diphenylpyrazole-3-carboxylic acid (0.70 g) obtained in Referential Example 56 and N-methylpiperazine (0.840 mL).

¹H-NMR (400 MHz, CDCl₃) δ: 2.18 (3H, s), 2.34 (3H, s), 2.45-2.60 (4H, m), 3.80-3.96 (4H, m), 7.10-7.50 (10H, m).

MS (ESI) m/z: 361(M+H)⁺.

2) Hydrochloric Acid Salt of the Title Compound

In a manner similar to that employed in step 2) of Example 1, a hydrochloric acid salt of the title compound was obtained as a solid (0.685 g, 56%) through use of the above-obtained title compound (0.818 g).

¹H-NMR (400 MHz, DMSO-d₆) δ: 2.10 (3H, s), 2.81 (3H, s-like), 3.00-3.65 (6H, m), 4.55-4.80 (2H, m), 7.16-7.30 (4H, m), 7.30-7.50 (6H, m), 10.57 (1H, br).

MS (ESI) m/z: 361(M+H)⁺.

Elementary analysis: as $C_{22}H_{24}N_4O \cdot 1.1HCl \cdot 1.0H_2O$

Calculated: C, 63.13; H, 6.53; Cl, 9.32; N, 13.38.

Found: C, 63.32; H, 6.42; Cl, 9.11; N, 13.45.

Example 10

1-[4-Fluoro-1,5-diphenylpyrazole-3-carbonyl]-4-methylpiperazine

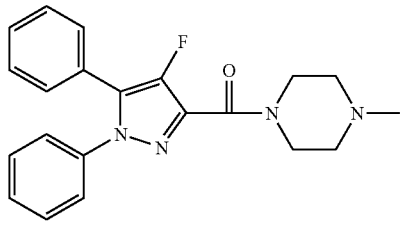

1) The Title Compound

In a manner similar to that employed in step 1) of Example 1, the title compound was obtained as an oily product (0.124 g, 49%) through use of 4-fluoro-1,5-diphenylpyrazole-3-carboxylic acid (0.169 g) obtained in Referential Example 59 and N-methylpiperazine (0.20 mL).

$^1$H-NMR (400 MHz, CDCl$_3$) δ: 2.08-2.18 (2H, m), 2.24 (3H, s), 2.32-2.43 (2H, m), 3.30-3.45 (2H, m), 3.68-3.82 (2H, m), 7.32-7.68 (8H, m), 7.93 (2H, d-like, J=7.8 Hz).

MS (ESI) m/z: 365(M+H)$^+$.

2) Hydrochloric Acid Salt of the Title Compound

In a manner similar to that employed in step 2) of Example 1, the title compound was obtained as a solid (0.108 g, 79%) through use of the above-obtained title compound (0.124 g).

$^1$H-NMR (400 MHz, DMSO-d$_6$) δ: 2.80 (3H, s), 2.80-3.65 (6H, m), 4.08-4.22 (1H, m), 4.40-4.55 (1H, m), 7.35-7.60 (8H, m), 7.86 (2H, d, J=7.4 Hz), 11.09 (1H, br).

MS (ESI) m/z: 365(M+H)$^+$.

Example 11

4-[1-(6-Methoxy-3-pyridyl)-5-phenylpyrazole-3-carbonyl]-1,1-dioxothiomorpholine

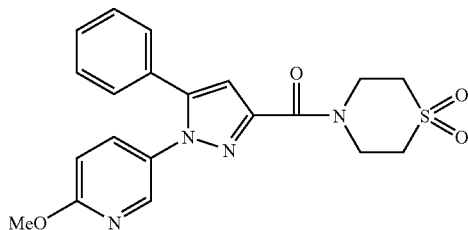

In a manner similar to that employed in step 1) of Example 1, the title compound was obtained as a solid (0.185 g, 51%) through use of 1-(6-methoxy-3-pyridyl)-5-phenylpyrazole-3-carboxylic acid (0.250 g) obtained in Referential Example 41 and thiomorpholine-1,1-dioxide (0.126 g).

$^1$H-NMR (400 MHz, CDCl$_3$) δ: 3.17-3.21 (4H, m), 3.96 (3H, s), 4.29 (2H, m), 4.66 (2H, m), 6.74 (1H, d, J=8.8 Hz), 7.02 (1H, s), 7.22-7.39 (5H, m), 7.42-7.45 (1H, m), 8.12 (1H, d, J=2.8 Hz).

MS (EI) m/z: 412(M$^+$).

Example 12

1-[5-(4-Fluorophenyl)-1-(6-methoxy-3-pyridyl)pyrazole-3-carbonyl]-4-methylpiperazine

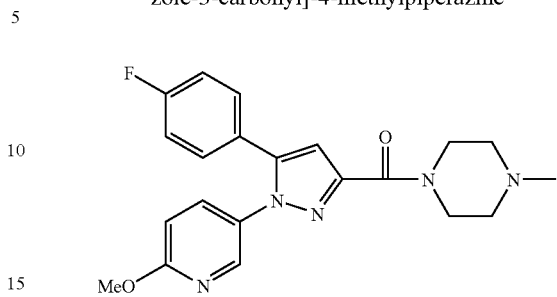

1) The Title Compound

To a solution of 5-(4-fluorophenyl)-1-(6-methoxy-3-pyridyl)pyrazole-3-carboxylic acid ethyl ester (2.1 g) obtained in Referential Example 135 in methanol (20 mL), 1M aqueous sodium hydroxide (15.4 mL) was added at 0° C. The resultant mixture was stirred at room temperature for 4.5 hours, and then cooled to 0° C. Concentrated hydrochloric acid was slowly added thereto, to thereby adjust the pH to 3. Subsequently, chloroform was added thereto, and the formed solid was dissolved. The solvent was removed under reduced pressure, and the residue was partitioned between water and a chloroform-methanol solvent mixture (9:1). The organic layer was washed with saturated brine and dried over sodium sulfate anhydrate. After filtration, the solvent was removed under reduced pressure. The residue was dissolved in a solvent mixture of N,N-dimethylformamide (50 mL) and methylene chloride (30 mL). To the resultant mixture were added N-methylpiperazine (1.37 mL), triethylamine (3.4 mL), 1-hydroxybenzotriazole (1.66 g), and 1-(3-dimethylaminopropyl)-3-ethylcarbodiimide hydrochloride (2.36 g) at room temperature. The mixture was stirred at room temperature for 62 hours and partitioned between saturated aqueous sodium hydrogencarbonate and chloroform. The organic layer was washed with saturated brine and dried over sodium sulfate anhydrate. The resultant mixture was subjected to filtration, and the solvent was removed under reduced pressure. The residue was purified through silica gel column chromatography (chloroform-methanol), to thereby give the title compound (2.421 g, 99.5%).

$^1$H-NMR (400 MHz, CDCl$_3$) δ: 2.33 (3H, s), 2.49 (4H, dt, J=14.0, 4.9 Hz), 3.84 (2H, br s), 3.94 (3H, s), 4.12 (2H, br s), 6.74 (1H, d, J=8.8 Hz), 6.89 (1H, s), 7.04 (2H, t, J=8.8 Hz), 7.22 (2H, dd, J=8.8, 5.1 Hz), 7.48 (1H, dd, J=8.8, 2.9 Hz), 8.10 (1H, d, J=2.9 Hz).

MS (EI) m/z: 395(M$^+$).

2) Hydrochloric Acid Salt of the Title Compound

1-[5-(4-Fluorophenyl)-1-(6-methoxy-3-pyridyl)pyrazole-3-carbonyl]-4-methylpiperazine (1.12 g) was dissolved in diethyl ether (10 mL). Under flow of argon, 1M HCl in ethanol (8.5 mL) was added to the solution at room temperature. The resultant mixture was stirred at a constant temperature for 4 hours. Ethanol was added to the mixture, and then the solvent was removed under reduced pressure. Ether and hexane were added to the residue, and the precipitated solid was washed, followed by filtration. The filtrated solid was recrystallized from ethanol, to thereby give the title compound as a solid (715 mg, 57%).

MS (EI) m/z: 395(M+).

Elementary analysis: as $C_{21}H_{22}FN_5O_2 \cdot 1.0HCl \cdot 0.5H_2O$
Calculated: C, 57.21; H, 5.49; N, 15.88; F, 4.31; Cl, 8.04.
Found: C, 57.28; H, 5.37; N, 16.22; F, 4.19; Cl, 8.06.

Example 13

4-[5-(4-Fluorophenyl)-1-(6-methoxy-3-pyridyl)pyrazole-3-carbonyl]morpholine

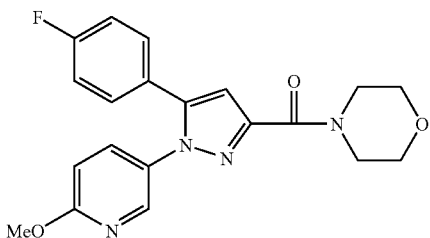

In a manner similar to that employed in step 1) of Example 1, the title compound was obtained as a solid (0.386 g, 86%) through use of 5-(4-fluorophenyl)-1-(6-methoxy-3-pyridyl)pyrazole-3-carboxylic acid (0.368 g) obtained in Referential Example 136 and morpholine (0.310 mL).

$^1$H-NMR (400 MHz, CDCl$_3$) δ: 3.70-3.90 (6H, m), 3.93 (3H, s), 4.18 (2H, br), 6.74 (1H, d, J=8.8 Hz), 6.94 (1H, s), 7.04 (2H, t-like, J=8.6 Hz), 7.18-7.29 (2H, m), 7.49 (1H, dd, J=8.6, 2.2 Hz), 8.10 (1H, d, J=2.2 Hz).

Example 14

1-[1-(6-Methoxy-3-pyridyl)-5-phenylpyrazole-3-carbonyl]-4-benzyl-3-methylpiperazine

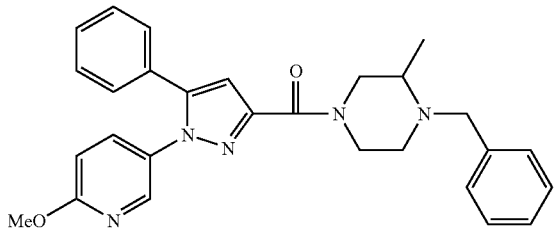

In a manner similar to that employed in step 1) of Example 1, the title compound was obtained as an oily product (0.462 g, quantitative amount) through use of 1-(6-methoxy-3-pyridyl)-5-phenylpyrazole-3-carboxylic acid (0.290 g) obtained in Referential Example 41 and 1-benzyl-2-methylpiperazine trifluoroacetic acid salt (0.609 g) obtained in step 2) of Referential Example 85.

$^1$H-NMR (400 MHz, CDCl$_3$) δ: 1.16 and 1.22 (3H, each d, each J=6.1 Hz), 2.00-4.60 (9H, m), 3.89 and 3.91 (3H, each s), 6.65-6.74 (1H, m), 6.92 and 6.93 (1H, each s), 7.15-7.55 (11H, m), 8.08 and 8.14 (1H, each d, each J=2.5 Hz).

MS (FAB) m/z: 468(M+H)+.

Example 15

1-[1-(6-Methoxy-3-pyridyl)-5-phenylpyrazole-3-carbonyl]-3-methylpiperazine

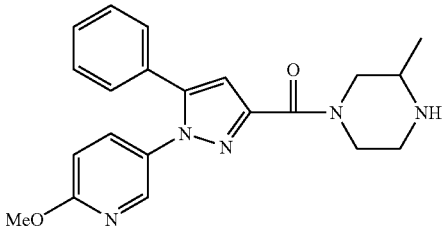

1) The Title Compound

To a solution of 1-[1-(6-methoxy-3-pyridyl)-5-phenylpyrazole-3-carbonyl]-4-benzyl-3-methylpiperazine (0.459 g) obtained in Example 14 in ethanol (10 mL), 1M HCl-ethanol (0.980 mL) and 10% palladium-carbon (123 mg) were added at room temperature. The resultant mixture was stirred in a hydrogen atmosphere for 5.5 hours. After the atmosphere was changed to nitrogen, the mixture was neutralized to pH 8 with 1M aqueous sodium hydroxide, followed by removal of insoluble matter through filtration. Solvent of the filtrate was removed under reduced pressure, and then the residue was partitioned between water and chloroform. The aqueous layer was extracted with chloroform. The organic layers were combined and washed with saturated brine, followed by drying over sodium sulfate anhydrate. The resultant mixture was subjected to filtration, and the solvent was removed under reduced pressure. The residue was purified through silica gel column chromatography (chloroform-methanol), to thereby give the title compound as an oily product (0.250 g, 67%).

$^1$H-NMR (400 MHz, CDCl$_3$) δ: 2.51 (0.5; H, t-like, J=11.0 Hz), 2.80-3.30 (4.5H, m), 3.93 (3H, s), 4.59-4.87 (2H, m), 6.71 (1H, d, J=8.7 Hz), 6.90 (1H, s), 7.20-7.60 (6H, m), 8.12 (1H, s-like).

MS (ESI) m/z: 378(M+H)+.

2) Hydrochloric Acid Salt of the Title Compound

In a manner similar to that employed in step 2) of Example 1, a hydrochloric acid salt of the title compound was obtained as a solid (0.201 g, 68%) through use of the above-obtained compound (0.250 g).

$^1$H-NMR (400 MHz, CDCl$_3$) δ: 1.20-1.34 (3H, br), 3.00-3.75 (5H, m), 4.40-4.53 (1H, m), 4.70-4.90 (1H, m), 6.91 (1H, d, J=8.8 Hz), 7.01 (1H, s), 7.25-7.45 (5H, m), 7.70 (1H, dd, J=8.8, 3.0 Hz), 8.18 (1H, d, J=2.7 Hz), 9.10-9.50 (2H, br).

MS (ESI) m/z: 378(M+H)+.

Elementary analysis: as $C_{21}H_{23}N_5O_2 \cdot 1.2H_2O \cdot 1.5HCl$
Calculated: C, 56.27; H, 6.12; Cl, 9.49; N, 15.62.
Found: C, 56.12; H, 6.00; Cl, 9.84; N, 15.45.

Example 16

1-[1-(6-Methoxy-3-pyridyl)-5-phenylpyrazole-3-carbonyl]piperazine

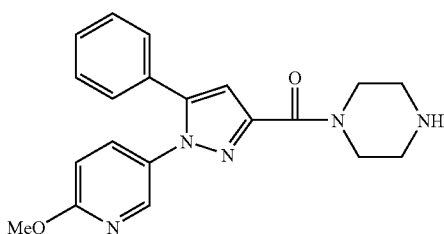

1) 1-[1-(6-Methoxy-3-pyridyl)-5-phenylpyrazole-3-carbonyl]piperazine-4-carboxylic acid tert-butyl ester In a manner similar to that employed in step 1) of Example 1, 1-[1-(6-methoxy-3-pyridyl)-5-phenylpyrazole-3-carbonyl]piperazine-4-carboxylic acid tert-butyl ester was obtained as an oily product (0.772 g, quantitative amount) through use of 1-(6-methoxy-3-pyridyl)-5-phenylpyrazole-3-carboxylic acid (0.407 g) obtained in Referential Example 41 and piperazine-1-carboxylic acid tert-butyl ester.

$^1$H-NMR (400 MHz, CDCl$_3$) δ: 1.48 (9H, s), 3.53 (4H, br), 3.79 (2H, br), 3.94 (3H, s), 4.10 (2H, br), 6.72 (1H, d, J=8.8 Hz), 6.94 (1H, s), 7.20-7.40 (5H, m), 7.47 (1H, dd, J=8.8, 2.7 Hz), 8.12 (1H, d, J=2.7 Hz).

MS (ESI) m/z: 464(M+H)$^+$.

2) The Title Compound

At room temperature, trifluoroacetic acid (2.4 mL) was added to a solution of the above-mentioned 1-[1-(6-methoxy-3-pyridyl)-5-phenylpyrazole-3-carbonyl]piperazine-4-carboxylic acid tert-butyl ester (0.639 g) in methylene chloride (15 mL), followed by stirring of the mixture for 0.7 hours. The reaction solvent was removed under reduced pressure, and the residue was partitioned between chloroform and saturated aqueous sodium hydrogencarbonate. The aqueous layer was extracted with chloroform. The organic layers were combined and washed with saturated brine, followed by drying over sodium sulfate anhydrate. After filtration, the solvent was removed under reduced pressure. The residue was purified through silica gel column chromatography (chloroform-methanol), to thereby give the title compound as an oily product (0.446 g, 89%).

$^1$H-NMR (400 MHz, CDCl$_3$) δ: 2.90-3.02 (4H, m), 3.80 (2H, br), 3.94 (3H, s), 4.07 (2H, br), 6.72 (1H, d-like, J=8.7 Hz), 6.90 (1H, s), 7.20-7.38 (5H, m), 7.48 (1H, dd, J=8.7, 2.2 Hz), 8.12 (1H, d-like, J=2.2 Hz).

MS (FAB) m/z: 364(M+H)$^+$.

Example 17

1-[1-(6-Methoxy-3-pyridyl)-5-phenylpyrazole-3-carbonyl]-4-isopropylpiperazine

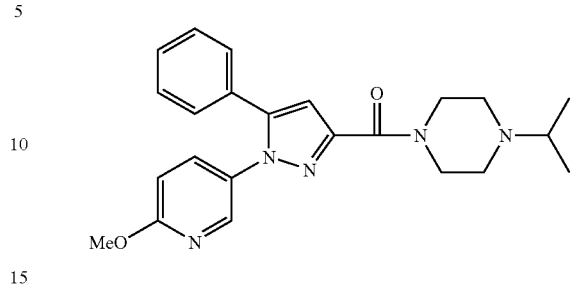

1) The Title Compound

To a solution of 1-[1-(6-methoxy-3-pyridyl)-5-phenylpyrazole-3-carbonyl]piperazine (0.446 g) obtained in Example 16 in N,N-dimethylformamide (7.5 mL), potassium carbonate (0.505 g) and isopropyl bromide (0.30 mL) were added at room temperature, and the mixture was stirred at 60° C. for 16 hours, and then cooled in air. The reaction mixture was partitioned between water and ethyl acetate. Subsequently, the aqueous layer was extracted with ethyl acetate. The organic layers were combined and washed with saturated brine, followed by drying over sodium sulfate anhydrate. After filtration, the solvent was removed under reduced pressure. The residue was purified through silica gel column chromatography (chloroform-methanol), to thereby give the title compound as an oily product (0.283 g, 57%).

$^1$H-NMR (400 MHz, CDCl$_3$) δ: 1.06 (6H, d, J=6.5 Hz), 2.50-2.81 (5H, m), 3.83 (2H, br), 3.93 (3H, s), 4.10 (2H, br), 6.71 (1H, d, J=8.8 Hz), 6.90 (1H, s), 7.19-7.38 (5H, m), 7.47 (1H, dd, J=8.8, 2.7 Hz), 8.11 (1H, d, J=2.7 Hz).

MS (ESI) m/z: 406(M+H)$^+$.

2) Hydrochloric Acid Salt of the Title Compound

In a manner similar to that employed in step 2) of Example 1, the title compound was obtained as a solid (0.226 g, 73%) through use of the above-obtained title compound (0.283 g).

$^1$H-NMR (400 MHz, DMSO-d$_6$) δ: 1.26 (6H, d, J=6.4 Hz), 2.95-3.60 (6H, m), 3.67 (1H, br), 3.86 (3H, s), 4.63 (1H, br), 5.03 (1H, br), 6.89 (1H, d, J=8.8 Hz), 7.00 (1H, s), 7.25-7.43 (5H, m), 7.68 (1H, dd, J=8.8, 2.7 Hz), 8.17 (1H, d, J=2.7 Hz), 10.49 (1H, br).

MS (ESI) m/z: 406(M+H)$^+$.

Example 18

1-[5-(4-Benzyloxyphenyl)-1-(6-methoxy-3-pyridyl)pyrazole-3-carbonyl]-4-methylpiperazine

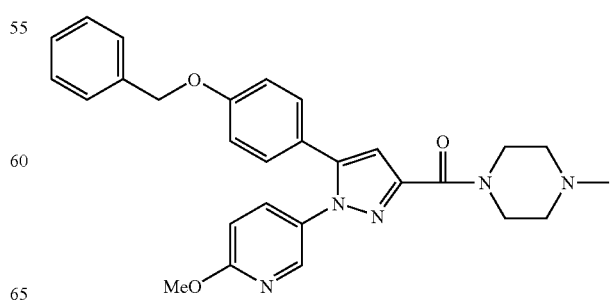

In a manner similar to that employed in step 1) of Example 1, the title compound was obtained as an oily product (0.802 g, 72%) through use of 5-(4-benzyloxyphenyl)-1-(6-methoxy-3-pyridyl)pyrazole-3-carboxylic acid (0.926 g) obtained in Referential Example 14 and N-methylpiperazine (0.765 mL).

$^1$H-NMR (400 MHz, CDCl$_3$) δ: 2.33 (3H, s), 2.42-2.60 (4H, m), 3.84 (2H, br), 3.94 (3H, s), 4.12 (2H, br), 6.72 (1H, d, J=9.0 Hz), 6.84 (1H, s), 6.93 (2H, d-like, J=8.7 Hz), 7.15 (2H, d-like, J=8.7 Hz), 7.30-7.45 (5H, m), 7.48 (1H, dd, J=9.0, 2.7 Hz), 8.13 (1H, d, J=2.7 Hz).

MS (FAB) m/z: 484(M+H)$^+$.

Example 19

1-[5-(4-Hydroxyphenyl)-1-(6-methoxy-5-pyridyl)pyrazole-3-carbonyl]-4-methylpiperazine

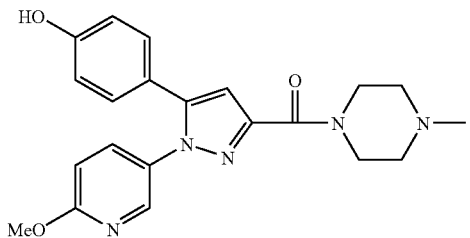

1) The Title Compound

To a solution of 1-[5-(4-benzyloxyphenyl)-1-(6-methoxy-3-pyridyl)pyrazole-3-carbonyl]-4-methylpiperazine (0.802 g) obtained in Example 18 in ethanol (15 mL), 10% palladium-carbon (0.466 g) and 1M HCl-ethanol (1.65 mL) were added, and the mixture was stirred at room temperature in a hydrogen atmosphere for 24 hours. After completion of the reaction, the atmosphere was changed to nitrogen, and the mixture was neutralized with aqueous sodium hydroxide. Insoluble matter was separated, and the residue was washed with methanol the filtrate was removed under reduced pressure, and the residue was partitioned between water and chloroform. Subsequently, the aqueous layer was extracted with chloroform. The organic layers were combined and washed with saturated brine, followed by drying over sodium sulfate anhydrate. After filtration, the solvent was removed under reduced pressure. The residue was purified through silica gel column chromatography (chloroform-methanol), to thereby give the title compound as a foamy substance (0.493 g, 69%).

$^1$H-NMR (400 MHz, CDCl$_3$) δ: 2.34 (3H, s), 2.45-2.60 (4H, m), 3.85 (2H, br), 3.94 (3H, s), 4.13 (2H, br), 6.71 (1H, d, J=8.8 Hz), 6.77 (2H, d, J=8.8 Hz), 6.80 (1H, s), 7.05 (2H, d, J=8.8 Hz), 7.47 (2H, dd, J=8.8, 2.2 Hz), 8.12 (1H, d, J=2.2 Hz).

MS (ESI) m/z: 394(M+H)$^+$.

2) Hydrochloric Acid Salt of the Title Compound

In a manner similar to that employed in step 2) of Example 1, a hydrochloric acid salt of the title compound was obtained as a solid (0.436 g, 72%) through use of the above-obtained title compound (0.493 g).

$^1$H-NMR (400 MHz, DMSO-d$_6$) δ: 2.77 (3H, s-like), 3.00-3.70 (6H, m), 3.86 (3H, s), 4.60 (1H, br), 4.97 (1H, br), 6.75 (2H, d-like, J=6.6 Hz), 6.86 (1H, s), 6.89 (1H, d, J=8.8 Hz), 7.66 (1H, dd, J=8.8, 2.7 Hz), 8.16 (1H, d, J=2.7 Hz), 9.85 (1H, br), 10.85 (1H, br).

MS (ESI) m/z: 394(M+H)$^+$.

Example 20

1-[1-(6-Methoxy-3-pyridyl)-5-phenylpyrazole-3-carbonyl]-4-methyl-3-oxopiperazine

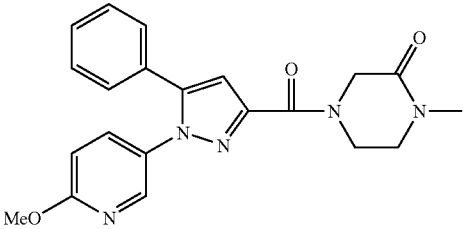

At room temperature, 1-hydroxybenzotriazole (0.341 g), 1-(3-dimethylaminopropyl)-3-ethylcarbodiimide hydrochloride (0.971 g), triethylamine (1.61 mL), and N-methylpiperazin-2-one trifluoroacetic acid salt (1.06 g) obtained in Referential Example 91 were added to a solution of 1-(6-methoxy-3-pyridyl)-5-phenylpyrazole-3-carboxylic acid (0.695 g) obtained in Referential Example 41 in methylene chloride (15 mL), followed by stirring of the mixture for 26 hours. The reaction mixture was acidified to pH 4 with 1M aqueous hydrochloric acid. The mixture was partitioned between water and chloroform. Subsequently, the aqueous layer was extracted with chloroform, and the organic layers were combined, followed by washing with saturated brine and drying over sodium sulfate anhydrate. After filtration, the solvent was removed under reduced pressure. The residue was purified through silica gel column chromatography (chloroform-acetone), to thereby give the title compound as a solid (0.707 g, 79%).

$^1$H-NMR (400 MHz, CDCl$_3$) δ: 3.40-3.60 (2H, m), 3.94 (3H, s), 4.04 (1H, br), 4.25-4.50 (2H, m), 4.83 (1H, s), 6.73 (1H, d, J=8.7 Hz), 7.18-7.40 (5H, m).

MS (ESI) m/z: 392(M+H)$^+$.

Example 21

4-[1-(6-Methoxy-3-pyridyl)-5-phenylpyrazole-3-carbonyl]-1,2,6-trimethylpiperazine

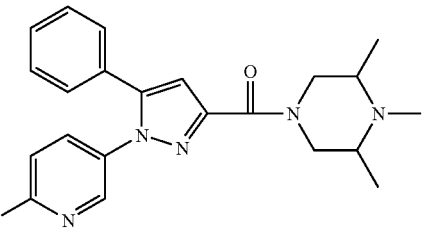

1) The Title Compound

In a manner similar to that employed in step 1) of Example 1, the title compound was obtained as an oily product (0.351 g, 76%) through use of 1-(6-methoxy-3-pyridyl)-5-phenylpyrazole-3-carboxylic acid (0.337 g) obtained in Referential Example 41 and 1,2,6-trimethylpiperazine trifluoroacetic acid salt (1.178 g) obtained in Referential Example 89.

¹H-NMR (400 MHz, CDCl₃) δ: 1.09 (3H, d, J=6.1 Hz), 1.16 (3H, d, J=6.1 Hz), 2.20-2.30 (2H, m), 2.28 (3H, s), 2.65 (1H, t-like, J=13.2 Hz), 3.03 (1H, t-like, J=13.2 Hz), 3.92 (3H, s), 4.51-4.61 (1H, m), 4.68-4.79 (1H, m), 6.69 (1H, d, J=8.8 Hz), 6.88 (1H, s), 7.17-7.36 (5H, m), 7.43 (1H, dd, J=8.8, 2.7 Hz), 8.10 (1H, d, J=2.7 Hz).

MS (ESI) m/z: 406(M+H)⁺.

2) Hydrochloric Acid Salt of the Title Compound

In a manner similar to that employed in step 2) of Example 1, a hydrochloric acid salt of the title compound was obtained as a solid (0.277 g, 71%) through use of the above-obtained title compound (0.335 g).

¹H-NMR (400 MHz, DMSO-d₆) δ: 1.30-1.45 (6H, br), 3.86 (3H, s), 4.62 (1H, br), 4.97 (1H, br), 6.90 (1H, d, J=8.8 Hz), 7.00 (1H, s), 7.25-7.50 (5H, m), 7.69 (1H, dd, J=8.8, 2.7 Hz), 8.18 (1H, d, J=2.7 Hz), 10.61 (1H, br).

MS (ESI) m/z: 406(M+H)⁺.

Example 22

4-[1-(6-Methoxy-3-pyridyl)-5-phenylpyrazole-3-carbonyl]-2,6-dimethylpiperazine

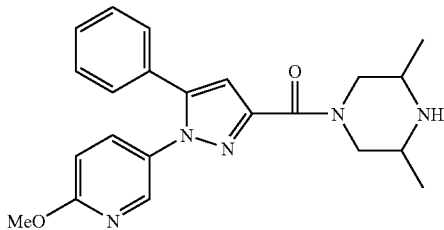

In a manner similar to that employed in Example 20, the title compound was obtained as a solid (0.312 g, 94%) through use of 1-(6-methoxy-3-pyridyl)-5-phenylpyrazole-3-carboxylic acid (0.278 g) obtained in Referential Example 41 and 2,6-dimethylpiperazine (0.214 g).

¹H-NMR (400 MHz, CDCl₃) δ: 1.08 (3H, d, J=6.4 Hz), 1.14 (3H, d, J=6.4 Hz), 2.40 (1H, t-like, J=9.0 Hz), 2.76 (1H, t-like, J=10.7 Hz), 2.85-3.02 (2H, m), 3.93 (3H, s), 4.67 (1H, d-like, J=12.6 Hz), 4.76 (1H, d-like, J=12.6 Hz), 6.71 (1H, d, J=8.7 Hz), 6.89 (1H, s), 7.20-7.37 (5H, m), 7.46 (1H, dd, J=8.7, 2.5 Hz), 8.12 (1H, d, J=2.5 Hz).

LC-MS m/z: 392(M+H)⁺.

Example 23

1-[1-(6-Methoxy-3-pyridyl)-5 (2-pyridyl)pyrazole-3-carbonyl]-4-methyl-3-oxopiperazine

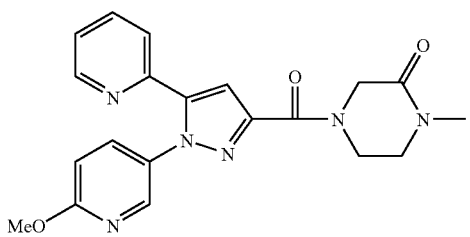

In a manner similar to that employed in Example 20, the title compound was obtained as a foamy substance (0.213 g, 94%) through use of 1-(6-methoxy-3-pyridyl)-5-(2-pyridyl)pyrazole-3-carboxylic acid (0.171 g) obtained in Referential Example 33 and N-methylpiperazin-2-one trifluoroacetic acid (0.251 g) obtained in Referential Example 91.

¹H-NMR (400 MHz, CDCl₃) δ: 3.02 (3H, s), 3.47 (2H, br), 3.95 (3H, s), 4.04 (1H, br), 4.42 (2H, s-like), 4.84 (1H, s-like), 6.76 (1H, d, J=8.8 Hz), 7.15-7.28 (2H, m), 7.37-7.48 (1H, m), 7.55-7.75 (2H, m), 8.05-8.17 (1H, m), 8.51 (1H, d, J=4.1 Hz).

MS (FAB) m/z: 393(M+H)⁺.

Elementary analysis: as $C_{20}H_{20}N_6O_3 \cdot 1.5H_2O$

Calculated: C, 57.27; H, 5.53; N, 20.04.

Found: C, 57.03; H, 5.06; N, 19.66.

Example 24

4-[1-(6-Methoxy-3-pyridyl)-5-(2-pyridyl)pyrazole-3-carbonyl]-1,2,6-trimethylpiperazine

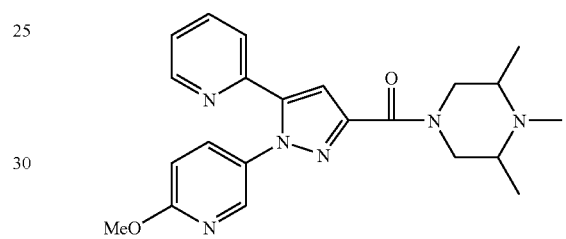

1) The Title Compound

In a manner similar to that employed in Example 20, the title compound was obtained as a foamy substance (0.272 g, quantitative amount) through use of 1-(6-methoxy-3-pyridyl)-5-(2-pyridyl)pyrazole-3-carboxylic acid (0.197 g) obtained in Referential Example 33 and 1,2,6-trimethylpiperazine trifluoroacetic acid (0.477 g) obtained in Referential Example 89.

¹H-NMR (400 MHz, CDCl₃) δ: 1.10 (3H, d, J=6.1 Hz), 1.18 (3H, d, J=6.1 Hz), 2.15-2.30 (2H, m), 2.29 (3H, s), 2.69 (1H, dd, J=13.0, 11.2 Hz), 3.06 (1H, dd, J=13.0, 11.2 Hz), 3.95 (3H, s), 4.55-4.74 (2H, m), 6.75 (1H, d, J=8.8 Hz), 7.11 (1H, s), 7.21-7.27 (1H, m), 7.43 (1H, d, J=7.8 Hz), 7.57 (1H, dd, J=8.8, 2.7 Hz), 7.63-7.75 (1H, m), 8.12 (1H, d, J=2.7 Hz), 8.51 (1H, br d, J=4.4 Hz).

MS (SEI) m/z: 407(M+H)⁺.

2) Hydrochloric Acid Salt of the Title Compound

In a manner similar to that employed in step 2) of Example 1, a hydrochloric acid salt of the title compound was obtained as a solid (0.222 g, 67%) through use of the above-obtained title compound (0.272 g).

¹H-NMR (400 MHz, DMSO-d₆) δ: 1.33 (3H, br), 1.39 (3H, br), 2.80 (3H, d, J=4.4 Hz), 2.80-3.80 (4H, m), 3.87 (3H, s), 4.64 (1H, br), 4.94 (1H, br), 6.88 (1H, d, J=8.8 Hz), 7.26 (1H, s), 7.33-7.40 (1H, m), 7.67-7.75 (2H, m), 7.88 (1H, dt, J=7.8, 1.9 Hz), 8.20 (1H, d, J=2.7 Hz), 8.44 (1H, d-like, J=4.9 Hz), 10.23 (1H, br).

MS (ESI) m/z: 407(M+H)⁺.

Example 25

1-[1-(6-Methoxy-3-pyridyl)-5-phenylpyrazole-3-carbonyl]-4-phenylpiperazine

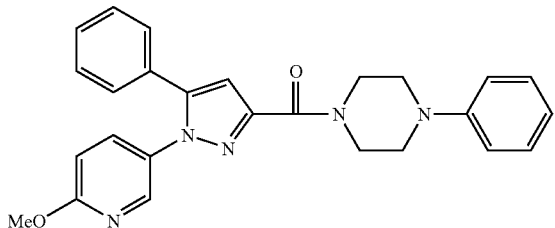

In a manner similar to that employed in Example 20, the title compound was obtained as a foamy substance (0.372 g, 85%) through use of 1-(6-methoxy-3-pyridyl)-5-phenylpyrazole-3-carboxylic acid (0.296 g) obtained in Referential Example 41 and N-phenylpiperazine (0.305 mL).

$^1$H-NMR (400 MHz, CDCl$_3$) δ: 3.20-3.35 (4H, m), 3.94 (3H, s), 3.99 (2H, br), 4.30 (2H, br), 6.72 (1H, d, J=8.8 Hz), 6.82-7.00 (4H, m), 7.20-7.37 (7H, m), 7.48 (1H, dd, J=8.8, 2.7 Hz), 8.13 (1H, d, J=2.7 Hz).

MS (FAB) m/z: 440(M+H)$^+$.

Example 26

1-[1-(6-Methoxy-3-pyridyl)-5-phenylpyrazole-3-carbonyl]-4-(2-pyridyl)piperazine

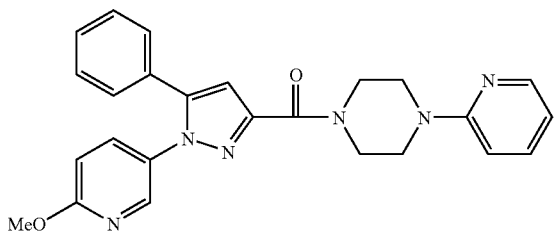

In a manner similar to that employed in Example 20, the title compound was obtained as an amorphous product (0.393 g, 90%) through use of 1-(6-methoxy-3-pyridyl)-5-phenylpyrazole-3-carboxylic acid (0.299 g) obtained in Referential Example 41 and N-(pyridin-2-yl)piperazine (0.275 mL).

$^1$H-NMR (400 MHz, CDCl$_3$) δ: 3.60-3.70 (4H, m), 3.90-3.95 (2H, m), 3.93 (3H, s), 4.24 (2H, br), 6.62-6.73 (3H, m), 6.94 (1H, s), 7.20-7.37 (5H, m), 7.43-7.52 (2H, m), 8.11 (1H, dd, J=2.7, 0.8 Hz), 8.16-8.23 (1H, m).

MS (FAB) m/z: 441 (M+H)$^+$.

Example 27

1-[1-(6-Methoxy-3-pyridyl)-5-(4-methoxy-2-pyridyl)pyrazole-3-carbonyl]-4-methylpiperazine

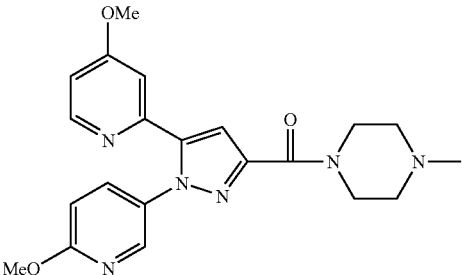

In a manner similar to that employed in step 1) of Example 1, the title compound was obtained as a solid (0.140 g, 65%) through use of 1-(6-methoxy-3-pyridyl)-5-(4-methoxy-2-pyridyl)pyrazole-3-carboxylic acid (0.171 g) obtained in Referential Example 19 and N-methylpiperazine (0.0639 mL).

$^1$H-NMR (400 MHz, CDCl$_3$) δ: 2.33 (3H, s), 2.44-2.52 (4H, m), 3.83 (3H, s), 3.85 (2H, m), 3.95 (3H, s), 4.09 (2H, m), 6.74-6.77 (2H, m), 6.95 (1H, d, J=2.8 Hz), 7.09 (1H, s), 7.59 (1H, dd, J=8.8, 2.8 Hz), 8.12 (1H, d, J=2.8 Hz), 8.32 (1H, d, J=6.0 Hz).

MS (EI) m/z: 408(M$^+$).

Example 28

4-[1-(6-Methoxy-3-pyridyl)-5-(4-methoxy-2-pyridyl)pyrazole-3-carbonyl]morpholine

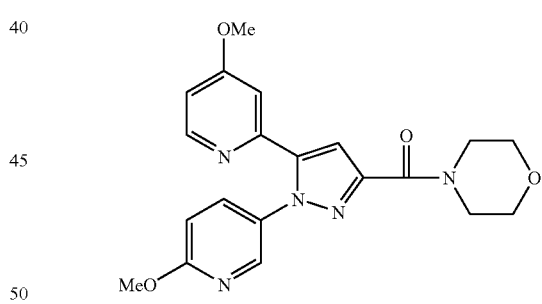

In a manner similar to that employed in step 1) of Example 1, the title compound was obtained as a solid (0.132 g, 62%) through use of 1-(6-methoxy-3-pyridyl)-5-(4-methoxy-2-pyridyl)pyrazole-3-carboxylic acid (0.171 g) obtained in Referential Example 19 and morpholine (0.0502 mL).

$^1$H-NMR (400 MHz, CDCl$_3$) δ: 3.73-3.75 (2H, m), 3.81-3.84 (4H, m), 3.84 (3H, s), 3.95 (3H, s), 4.14 (2H, m), 6.74-6.78 (2H, m), 6.96 (1H, d, J=2.4 Hz), 7.13 (1H, s), 7.57-7.60 (1H, m), 8.12 (1H, d, J=2.8 Hz), 8.32 (1H, d, J=6.0 Hz).

MS (FAB) m/z: 396(M+H)$^+$.

Elementary analysis: as C$_{20}$H$_{21}$N$_5$O$_4$·0.5H$_2$O

Calculated: C, 59.40%; H, 5.48%; N, 17.32%.

Found: C, 59.64%; H, 5.31%; N, 17.19%.

Example 29

1-[1-(6-Methoxy-3-pyridyl)-5-(2-pyridyl)pyrazole-3-carbonyl]-4-ethylpiperazine

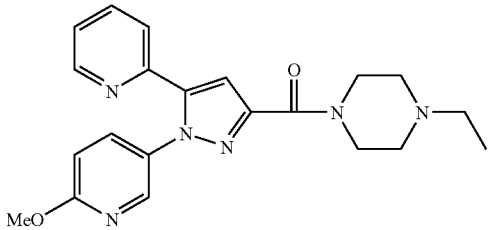

1) The Title Compound

In a manner similar to that employed in step 1) of Example 1, the title compound was obtained as an oily product (0.265 g, quantitative amount) through use of 1-(6-methoxy-3-pyridyl)-5-(2-pyridyl)pyrazole-3-carboxylic acid (0.20 g) obtained in Referential Example 33 and N-ethylpiperazine (0.0942 mL).

$^1$H-NMR (400 MHz, CDCl$_3$) δ: 1.09-1.13 (3H, m), 2.43-2.55 (6H, m), 3.86 (2H, m), 3.95 (3H, s), 4.10 (2H, m), 6.75 (1H, d, J=8.8 Hz), 7.12 (1H, s), 7.22-7.25 (1H, m), 7.41 (1H, d, J=7.6 Hz), 7.57-7.60 (1H, m), 7.68-7.73 (1H, m), 8.11 (1H, d, J=2.8 Hz), 8.51 (1H, d, J=4.8 Hz).

MS (EI) m/z: 392(M$^+$).

2) Hydrochloric Acid Salt of the Title Compound

At 0° C., 1N HCl-ethanol (1.27 mL) was added dropwise to a solution of the above-obtained title compound (0.249 g) in diethyl ether (10 mL), followed by stirring of the mixture for 10 minutes. The precipitated crystals were collected through filtration, followed by washing with diethyl ether and drying, to thereby give a hydrochloric acid salt of the title compound as a solid (0.257 g, 81%).

$^1$H-NMR (400 MHz, DMSO-d$_6$) δ: (1.04-1.11 (¾H, m, for 0.25 EtOH)), 1.26-1.29 (3H, m), 3.06-3.72 (8H, m, (²⁄₄H, m, for 0.25 EtOH)), 3.89 (3H, s), 4.60 (1H, m), 4.99 (1H, m), 6.89 (1H, d, J=8.8 Hz), 7.27 (1H, s), 7.37-7.40 (1H, m), 7.69-7.73 (2H, m), 7.88-7.92 (1H, m), 8.21 (1H, d, J=2.8 Hz), 8.48 (1H, d, J=4.8 Hz).

MS (EI) m/z: 392(M$^+$).

Example 30

1-[1-(6-Methoxy-3-pyridyl)-5-(2-pyridyl)pyrazole-3-carbonyl]-3,4-dimethylpiperazine

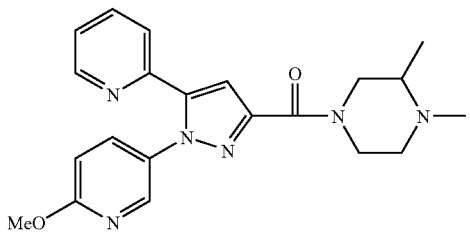

1) The Title Compound

In a manner similar to that employed in step 1) of Example 1, the title compound was obtained as an oily product (0.234 g, 88%) through use of 1-(6-methoxy-3-pyridyl)-5-(2-pyridyl)pyrazole-3-carboxylic acid (0.20 g) obtained in Referential Example 33 and 1,2-dimethylpiperazine trifluoroacetic acid salt (0.254 g) obtained in Referential Example 84.

$^1$H-NMR (400 MHz, CDCl$_3$) δ: 1.07-1.17 (3H, m), 2.20 (2H, m), 2.33 (3H, s), 2.71-3.52 (3H, m), 3.95 (3H, s), 4.50-4.76 (2H, m), 6.76 (1H, d, J=8.8 Hz), 7.12 (1H, m), 7.23-7.27 (1H, m), 7.40-7.44 (1H, m), 7.56-7.61 (1H, m), 7.69-7.73 (1H, m), 8.12 (1H, m), 8.52 (1H, d, J=4.8 Hz).

MS (EI) m/z: 392(M$^+$).

2) Hydrochloric Acid Salt of the Title Compound

In a manner similar to that employed in step 2) of Example 29, a hydrochloric acid salt of the title compound was obtained as a solid (0.192 g, 67%) through use of the above-obtained title compound (0.223 g).

$^1$H-NMR (400 MHz, DMSO-d$_6$) δ: 1.04-1.11 ((3/2H, m, for 0.5 EtOH)), 1.23-1.39 (3H, m), 2.73-3.89 (5H, m, (2/2H, for 0.5 EtOH)), 3.89 (3H, s), 4.58-4.62 (1H, m), 4.90-5.00 (1H, m), 6.89 (1H, d, J=8.8 Hz), 7.27 (1H, s), 7.37-7.40 (1H, m), 7.69-7.74 (2H, m), 7.88-7.92 (1H, m), 8.21 (1H, d, J=2.8 Hz), 8.48 (1H, d, J=4.8 Hz).

MS (EI) m/z: 392(M$^+$).

Example 31

1-[1-(6-Methoxy-3-pyridyl)-5-(6-methoxy-2-pyridyl)pyrazole-3-carbonyl]-4-methylpiperazine

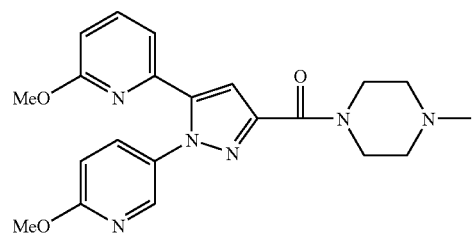

1) The Title Compound

In a manner similar to that employed in step 1) of Example 1, the title compound was obtained as an oily product (0.217 g, 96%) through use of 1-(6-methoxy-3-pyridyl)-5-(6-methoxy-2-pyridyl)pyrazole-3-carboxylic acid (0.180 g) obtained in Referential Example 25 and N-methylpiperazine (0.0673 mL).

$^1$H-NMR (400 MHz, CDCl$_3$) δ: 2.33 (3H, s), 2.46-2.52 (4H, m), 3.43 (3H, s), 3.85 (2H, m), 3.95 (3H, s), 4.12 (2H, m), 6.63-6.66 (1H, m), 6.76-6.78 (1H, m), 7.10-7.12 (1H, m), 7.14 (1H, s), 7.56-7.59 (2H, m), 8.16-8.17 (1H, m).

MS (EI) m/z: 408(M$^+$).

2) Hydrochloric Acid Salt of the Title Compound

In a manner similar to that employed in step 2) of Example 29, a hydrochloric acid salt of the title compound was obtained as a solid (0.185 g, 78%) through use of the above-obtained title compound (0.209 g).

$^1$H-NMR (400 MHz, CD$_3$OD) δ: 2.95 (3H, s), 3.30-3.60 (8H, m), 3.38 (3H, s), 3.95 (3H, s), 6.71 (1H, d, J=8.4 Hz), 6.88 (1H, d, J=8.8 Hz), 7.25 (1H, s), 7.29-7.30 (1H, m), 7.68-7.72 (2H, m), 8.16 (1H, d, J=2.8 Hz).

MS (EI) m/z: 408(M+).

Elementary analysis: as C$_{21}$H$_{24}$N$_6$O$_3$·HCl·H$_2$O
Calculated: C, 54.49%; H, 5.88%; N, 18.15%; Cl, 7.66%.
Found: C, 54.46%; H, 5.94%; N, 18.01%; Cl, 7.75%.

Example 32

4-[1-(6-Methoxy-3-pyridyl)-5-(6-methoxy-2-pyridyl)pyrazole-3-carbonyl]morpholine

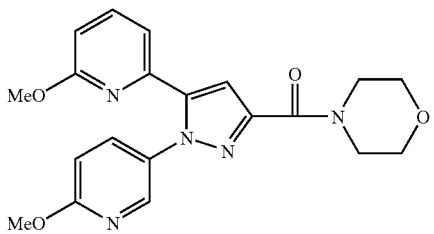

In a manner similar to that employed in step 1) of Example 1, the title compound was obtained as a solid (0.176 g, 80%) through use of 1-(6-methoxy-3-pyridyl)-5-(6-methoxy-2-pyridyl)pyrazole-3-carboxylic acid (0.180 g) obtained in Referential Example 25 and morpholine (0.0529 mL).

$^1$H-NMR (400 MHz, CDCl$_3$) δ: 3.43 (3H, s), 3.73-3.82 (6H, m), 3.95 (3H, s), 4.17 (2H, m), 6.64-6.66 (1H, m), 6.76-6.78 (1H, m), 7.10-7.13 (1H, m), 7.17 (1H, s), 7.55-7.60 (2H, m), 8.16-8.17 (1H, m).

MS (EI) m/z: 395(M+).

Example 33

1-[1-(6-Methoxy-3-pyridyl)-5-(6-methyl-2-pyridyl)pyrazole-3-carbonyl]-4-methylpiperazine

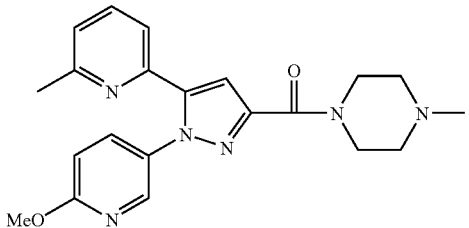

In a manner similar to that employed in step 1) of Example 1, the title compound was obtained as a solid (0.148 g, 72%) through use of 1-(6-methoxy-3-pyridyl)-5-(6-methyl-2-pyridyl)pyrazole-3-carboxylic acid (0.162 g) obtained in Referential Example 30 and N-methylpiperazine (0.0637 mL).

$^1$H-NMR (400 MHz, CDCl$_3$) δ: 2.33 (3H, s), 2.41 (3H, s), 2.43-2.52 (4H, m), 3.85 (2H, m), 3.95 (3H, s), 4.08 (2H, m), 6.75 (1H, d, J=8.8 Hz), 7.09 (1H, d, J=8.0 Hz), 7.11 (1H, s), 7.19 (1H, d, J=8.0 Hz), 7.56-7.62 (2H, m), 8.12 (1H, d, J=2.8 Hz).

MS (EI) m/z: 392(M+).

Example 34

4-[1-(6-Methoxy-3-pyridyl)-5-(6-methyl-2-pyridyl)pyrazole-3-carbonyl]morpholine

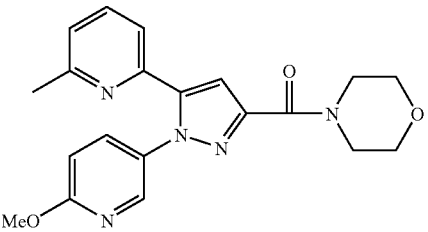

In a manner similar to that employed in step 1) of Example 1, the title compound was obtained as a solid (0.156 g, 78%) through use of 1-(6-methoxy-3-pyridyl)-5-(6-methyl-2-pyridyl)pyrazole-3-carboxylic acid (0.162 g) obtained in Referential Example 30 and morpholine (0.050 mL).

$^1$H-NMR (400 MHz, CDCl$_3$) δ: 2.40 (3H, s), 3.72-3.82 (6H, m), 3.95 (3H, s), 4.14 (2H, m), 6.74-6.77 (1H, m), 7.09 (1H, d, J=7.6 Hz), 7.14 (1H, s), 7.19 (1H, d, J=8.0 Hz), 7.56-7.61 (2H, m), 8.11-8.12 (1H, m).

MS (EI) m/z: 379(M+).

Elementary analysis: as C$_{20}$H$_{21}$N$_5$O$_3$·0.25H$_2$O
Calculated: C, 62.57%; H, 5.64%; N, 18.24%.
Found: C, 62.61%; H, 5.53%; N, 17.98%.

Example 35

1-[1-(6-Methoxy-3-pyridyl)-5-(2-pyridyl)pyrazole-3-carbonyl]-4-methylpiperazine

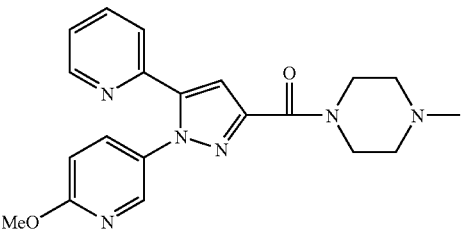

1) The Title Compound

In a manner similar to that employed in step 1) of Example 1, the title compound was obtained as an amorphous product (0.132 g, 63%) through use of 1-(6-methoxy-3-pyridyl)-5-(2-pyridyl)pyrazole-3-carboxylic acid (0.164 g) obtained in Referential Example 33 and N-methylpiperazine (0.0675 mL).

$^1$H-NMR (400 MHz, CDCl$_3$) δ: 2.33 (3H, s), 2.45-2.53 (4H, m), 3.85 (2H, m), 3.95 (3H, s), 4.09 (2H, m), 6.76 (1H, d, J=8.8 Hz), 7.12 (1H, s), 7.22-7.27 (1H, m), 7.42 (1H, d, J=7.6 Hz), 7.59 (1H, dd, J=8.8, 2.8 Hz), 7.69-7.73 (1H, m), 8.12 (1H, d, J=2.8 Hz), 8.52 (1H, d, J=4.4 Hz).

MS (EI) m/z: 378(M+).

2) Hydrochloric Acid Salt of the Title Compound

In a manner similar to that employed in step 2) of Example 29, the title compound was obtained as a solid (0.135 g, 45%) through use of the above-obtained title compound (0.241 g).

$^1$H-NMR (400 MHz, DMSO-d$_6$) δ: (1.06-1.11 (¾H, m, for 0.25 EtOH)), 2.79-2.80 (3H, m), 3.06-3.66 (6H, m, (⅔H, m, for 0.25 EtOH)), 3.89 (3H, s), 4.60-4.63 (1H, m), 4.96-5.00 (1H, m), 6.89 (1H, d, J=8.8 Hz), 7.2.7 (1H, s), 7.36-7.40 (1H, m), 7.69-7.74 (2H, m), 7.88-7.92 (1H, m), 8.21 (1H, d, J=2.8 Hz), 8.47 (1H, d, J=4.4 Hz).

MS (EI) m/z: 378(M$^+$).

Example 36

4-[1-(6-Methoxy-3-pyridyl)-5-(2-pyridyl)pyrazole-3-carbonyl]morpholine

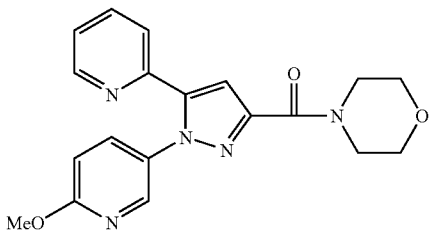

In a manner similar to that employed in step 1) of Example 1, the title compound was obtained as a solid (0.171 g, 83%) through use of 1-(6-methoxy-3-pyridyl)-5-(2-pyridyl)pyrazole-3-carboxylic acid (0.164 g) obtained in Referential Example 33 and morpholine (0.053 mL).

$^1$H-NMR (400 MHz, CDCl$_3$) δ: 3.74-3.83 (6H, m), 3.95 (3H, s), 4.15 (2H, m), 6.75-6.77 (1H, m), 7.16 (1H, s), 7.22-7.27 (1H, m), 7.41-7.43 (1H, m), 7.57-7.60 (1H, m), 7.69-7.73 (1H, m), 8.11-8.12 (1H, m), 8.51-8.53 (1H, m).

MS (EI) m/z: 365(M$^+$).

Example 37

1-[1-(6-Methoxy-3-pyridyl)-5-(4-methylphenyl)pyrazole-3-carbonyl]-4-methylpiperazine

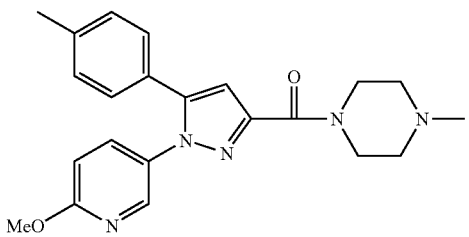

1) The Title Compound

In a manner similar to that employed in step 1) of Example 1, the title compound was obtained as an amorphous product (0.912 g, quantitative amount) through use of 1-(6-methoxy-3-pyridyl)-5-(4-methylphenyl)pyrazole-3-carboxylic acid (0.70 g) obtained in Referential Example 36 and N-methylpiperazine (0.276 mL).

$^1$H-NMR (400 MHz, CDCl$_3$) δ: 2.33 (3H, s), 2.35 (3H, s), 2.46-2.52 (4H, m), 3.85 (2H, m), 3.95 (3H, s), 4.13 (2H, m), 6.71-6.74 (1H, m), 6.88 (1H, s), 7.11-7.16 (4H, m), 7.48-7.50 (1H, m), 8.13 (1H, d, J=2.8 Hz).

MS (EI) m/z: 391(M$^+$).

2) Hydrochloric Acid Salt of the Title Compound

In a manner similar to that employed in step 2) of Example 29, a hydrochloric acid salt of the title compound was obtained as a solid (0.425 g, 75%) through use of the above-obtained title compound (0.493 g).

$^1$H-NMR (400 MHz, CD$_3$OD) δ: 2.35 (3H, s), 2.95 (3H, s), 3.39 (8H, m), 3.93 (3H, s), 6.81-6.84 (1H, m), 6.95 (1H, s), 7.15-7.25 (4H, m), 7.61-7.64 (1H, m), 8.08-8.09 (1H, m).

MS (EI) m/z: 391(M$^+$).

Example 38

1-[5-(2-Fluorophenyl)-1-(6-methoxy-3-pyridyl)pyrazole-3-carbonyl]-4-methylpiperazine

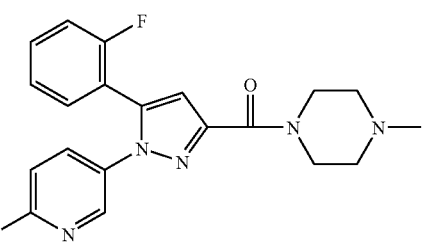

1) The Title Compound

In a manner similar to that employed in step 1) of Example 1, the title compound was obtained as an oily product (0.238 g, 97%) through use of 5-(2-fluorophenyl)-1-(6-methoxy-3-pyridyl)pyrazole-3-carboxylic acid (0.195 g) obtained in Referential Example 39 and N-methylpiperazine (0.076 mL).

$^1$H-NMR (400 MHz, CDCl$_3$) δ: 2.34 (3H, s), 2.47-2.52 (4H, m), 3.85 (2H, m), 3.92 (3H, s), 4.13 (2H, m), 6.70-6.73 (1H, m), 6.95 (1H, s), 7.03-7.41 (4H, m), 7.51-7.54 (1H, m), 8.06 (1H, m).

MS (EI) m/z: 395(M$^+$).

2) Hydrochloric Acid Salt of the Title Compound

In a manner similar to that employed in step 2) of Example 29, a hydrochloric acid salt of the title compound was obtained as a solid (0.125 g, 51%) through use of the above-obtained title compound (0.224 g).

$^1$H-NMR (400 MHz, CD$_3$OD) δ: 2.96 (3H, s), 3.41 (8H, m), 3.91 (3H, s), 6.80-6.82 (1H, m), 7.03 (1H, s), 7.12-7.51 (4H, m), 7.63-7.65 (1H, m), 8.06 (1H, m).

MS (EI) m/z: 395(M$^+$).

Example 39

1-[1-(6-Methoxy-3-pyridyl)-5-phenylpyrazole-3-carbonyl]-2-(2-aminoethyl)piperidine hydrochloride

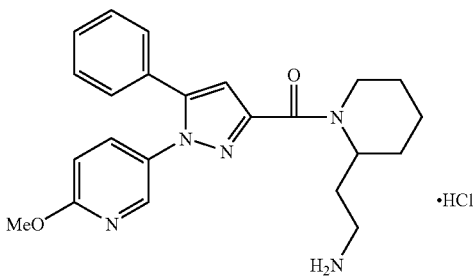

To a solution of 1-[1-(6-methoxy-3-pyridyl)-5-phenylpyrazole-3-carbonyl]-2-(2-azidoethyl)piperidine (179 mg) obtained in Referential Example 81 in methanol (5 mL), 1M aqueous hydrochloric acid (415 μL) and 10% palladium-carbon (50% wet, 36 mg) were added. The resultant mixture was stirred at room temperature for 10 hours in a hydrogen atmosphere. After removal of the catalyst through filtration, the solvent of the filtrate was removed under reduced pressure, and the residue was dissolved in water, followed by lyophilization, to thereby give the title compound as a solid (172 mg, 89%).

$^1$H-NMR (400 MHz, DMSO-$d_6$) [as a mixture of two isomers] δ: 1.31-1.85 (7H, br m), 2.14-2.32 (1H, br m), 2.64-2.92 (2.5H, br m), 3.10-3.24 (0.5H, br m), 3.91 (3H, s), 4.41-4.53 (1H, br m), 4.75-4.85 (1H, br m), 6.85-6.93 (2H, m), 7.25-7.32 (2H, m), 7.35-7.42 (3H, m), 7.64-7.74 (1H, br m), 7.80-8.00 (3H, br), 8.12 and 8.18 (1H, br s).

MS (ESI) m/z: 406(M+H)$^+$.

Example 40

1-[1-(6-Methoxy-3-pyridyl)-5-phenylpyrazole-3-carbonyl]-2-(2-dimethylaminoethyl)piperidine

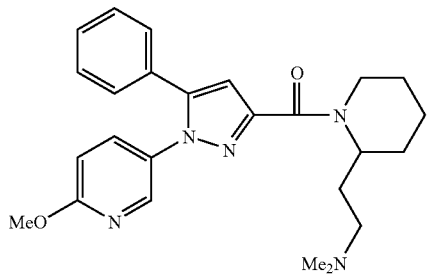

1) The Title Compound

To a solution of 2-(2-dimethylaminoethyl)piperidine-1-carboxylic acid tert-butyl ester (172 mg) obtained in Referential Example 92 in methylene chloride (3 mL), trifluoroacetic acid (1 mL) was added. The resultant mixture was stirred at room temperature for 30 minutes. The solvent was removed under reduced pressure, and the residue was dissolved in methylene chloride (10 mL). 1-(6-Methoxy-3-pyridyl)-5-phenylpyrazole-3-carboxylic acid (198 mg) obtained in Referential Example 41, 1-hydroxybenzotriazole (90 mg), triethylamine (467 μL), and 1-(3-dimethylaminopropyl)-3-ethylcarbodiimide hydrochloride (192 mg) were added thereto, followed by stirring at room temperature for 15 hours. The solvent was removed under reduced pressure, and the residue was partitioned between water and ethyl acetate. The organic layer was washed with water and saturated brine, followed by drying over sodium sulfate anhydrate. The resultant mixture was subjected to filtration, and the solvent was removed under reduced pressure. The residue was purified through silica gel thin-layer chromatography (chloroform-methanol), to thereby give the title compound as an oily product (100 mg, 34%).

$^1$H-NMR (400 MHz, CDCl$_3$) [as a mixture of two isomers] δ: 1.50-1.85 (6H, m), 1.95-2.43 (10H, m), 2.79-2.92 (0.5H, m), 3.15-3.28 (0.5H, m), 3.93 (3H, s), 4.53-4.74 (1H, br), 4.81-5.04 (1H, br), 6.71 (1H, d, J=8.8 Hz), 6.84 (1H, s), 7.15-7.39 (5H, m), 7.49 (1H, dd, J=8.8, 2.7 Hz), 8.11 (1H, d, J=2.7 Hz).

MS (ESI) m/z: 434(M+H)$^+$.

2) Hydrochloric Acid Salt of the Title Compound

In a manner similar to that employed in step 2) of Example 29, a hydrochloric acid salt of the title compound was obtained as a solid (109 mg, 93%) through use of the above-obtained title compound (100 mg).

$^1$H-NMR (400 MHz, DMSO-$d_6$) δ: [as a mixture of two isomers] 1.32-1.80 (6H, m), 1.86-2.01 (1H, br), 2.22-2.40 (1H, br m), 2.63-2.81 (0.5H, br m), 2.67 and 2.70 (6H, br s), 2.86-3.01 (1H, br m), 3.03-3.16 (1H, br m), 3.18-3.29 (0.5H, br), 3.87 (3H, s), 4.40-4.57 (1H, br m), 4.73-4.82 (1H, br), 6.85-6.94 (2H, m), 7.25-7.33 (2H, m), 7.35-7.42 (3H, br), 7.62-7.78 (1H, br m), 10.08-10.47 (1H, br).

MS (ESI) m/z: 434(M+H)$^+$.

Example 41

1-[1,4-Dihydro-1-(6-methoxy-3-pyridyl)indeno[1,2-c]pyrazole-3-carbonyl]-4-methylpiperazine

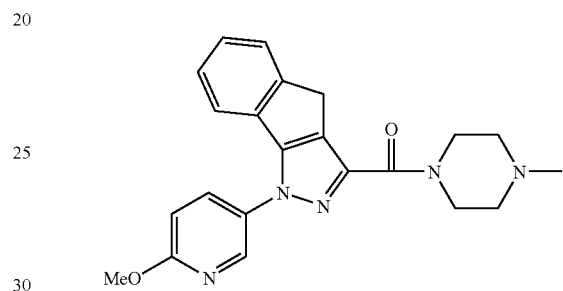

In a manner similar to that employed in Example 20, the title compound was obtained as an amorphous product (281 mg, 72%) through use of 1,4-dihydro-1-(6-methoxy-3-pyridyl)indeno[1,2-c]pyrazole-3-carboxylic acid (307 mg) obtained in Referential Example 61 and N-methylpiperazine (166 μL).

$^1$H-NMR (400 MHz, CDCl$_3$) δ: 2.33 (3H, s), 2.44-2.56 (4H, br m), 3.82 (2H, s), 3.80-3.90 (2H, br), 4.03 (3H, s), 4.19-4.29 (2H, br), 6.93 (1H, d, J=8.8 Hz), 7.24-7.32 (2H, m), 7.37-7.42 (1H, m), 7.53-7.58 (1H, m), 7.91 (1H, dd, J=8.8, 2.7 Hz), 8.53 (1H, d, J=2.7 Hz).

MS (ESI) m/z: 390(M+H)$^+$.

Example 42

1-[4,5-Dihydro-1-(6-methoxy-3-pyridyl)benzo[g]indazole-3-carbonyl]-4-methylpiperazine

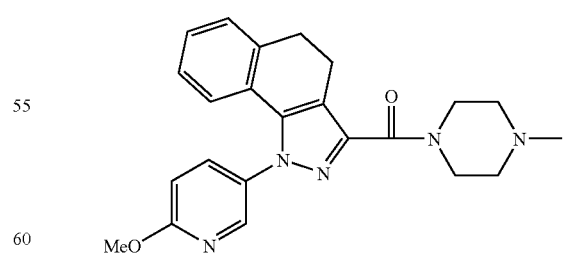

1) The Title Compound

In a manner similar to that employed in Example 20, the title compound was obtained as a solid (281 mg, 93%) through use of 4,5-dihydro-1-(6-methoxy-3-pyridyl)benzo

[g]indazole-3-carboxylic acid (241 mg) obtained in Referential Example 72 and N-methylpiperazine (125 μL).

2) Hydrochloric Acid Salt of the Title Compound

In a manner similar to that employed in step 2) of Example 29, a hydrochloric acid salt of the title compound was obtained as crystals (259 mg, 83%) through use of the above-obtained title compound (278 mg).

$^1$H-NMR (400 MHz, DMSO-$d_6$) δ: 2.79 (3H, s), 2.81-2.90 (2H, m), 2.92-3.00 (2H, m), 3.00-3.68 (6H, br m), 3.96 (3H, s), 4.53-4.68 (1H, br), 4.77-4.91 (1H, br), 6.74 (1H, d, J=7.8 Hz), 7.04 (1H, d, J=8.8 Hz), 7.10 (1H, dd, J=7.8, 7.6 Hz), 7.23 (1H, dd, J=7.6, 7.3 Hz), 7.38 (1H, d, J=7.3 Hz), 7.92 (1H, dd, J=8.8, 2.7 Hz), 8.41 (1H, d, J=2.7 Hz), 10.81-11.01 (1H, br).

MS (ESI) m/z: 404(M+H)$^+$.
Elementary analysis: as $C_{23}H_{25}N_5O_2 \cdot HCl \cdot 0.5H_2O$
Calculated: C, 61.53; H, 6.06; N, 15.60; Cl, 7.90.
Found: C, 61.70; H, 6.06; N, 15.57; Cl, 8.06.

Example 43

1-[1,4-Dihydro-1-(6-methoxy-3-pyridyl)chromeno[4,3-c]pyrazole-3-carbonyl]-4-methylpiperazine

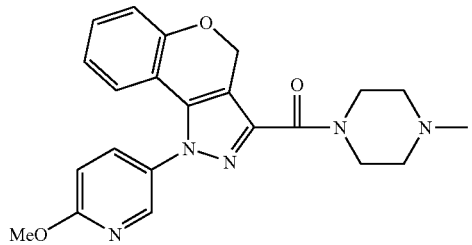

In a manner similar to that employed in Example 20, the title compound was obtained as crystals (187 mg, 76%) through use of 1,4-dihydro-1-(6-methoxy-3-pyridyl)chromeno[4,3-c]pyrazole-3-carboxylic acid (194 mg) obtained in Referential Example 74 and N-methylpiperazine (100 μL).

$^1$H-NMR (400 MHz, CDCl$_3$) δ: 2.32 (3H, s), 3.42-3.54 (4H, m), 3.76-3.85 (2H, br), 4.03 (3H, s), 4.19-4.29 (2H, br), 5.51 (2H, s), 6.72-6.80 (2H, m), 6.89 (1H, d, J=8.8 Hz), 7.00 (1H, d-like, J=7.8 Hz), 7.12-7.20 (1H, m), 7.68 (1H, dd, J=8.8, 2.7 Hz), 8.33 (1H, d, J=2.7 Hz).
MS (ESI) m/z: 406(M+H)$^+$.
Elementary analysis: as $C_{22}H_{23}N_5O_3$
Calculated: C, 65.17; H, 5.72; N, 17.27.
Found: C, 65.02; H, 5.64; N, 17.19.

Example 44

1-[1,4-Dihydro-1-(6-methoxy-3-pyridyl)-4-oxoindeno[1,2-c]pyrazole-3-carbonyl]-4-methylpiperazine

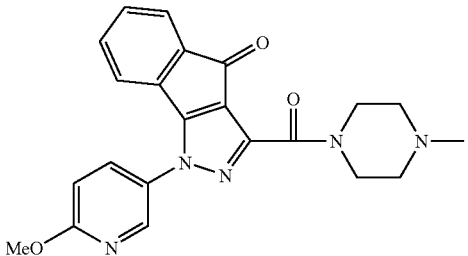

In a manner similar to that employed in Example 20, the title compound was obtained as an oily product (12 mg, 60%) through use of 1,4-dihydro-1-(6-methoxy-3-pyridyl)-4-oxoindeno[1,2-c]pyrazole-3-carboxylic acid (16 mg) obtained in Referential Example 70 and N-methylpiperazine (11 μL).

$^1$H-NMR (400 MHz, CDCl$_3$) δ: 2.34 (3H, s), 2.41-2.60 (4H, br m), 3.69-3.93 (4H, br m), 4.04 (3H, s), 6.94 (1H, d, J=8.8 Hz), 7.11-7.20 (1H, m), 7.31-7.40 (2H, m), 7.60-7.68 (1H, m), 7.92 (1H, dd, J=8.8, 2.4 Hz), 8.50 (1H, d, J=2.4 Hz).
MS (ESI) m/z: 404(M+H)$^+$.

Example 45

1-[1,4-Dihydro-1-(6-methyl-3-pyridyl)indeno[1,2-c]pyrazole-3-carbonyl]-4-methylpiperazine

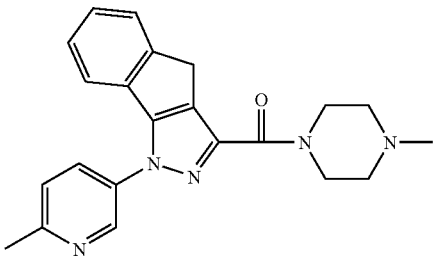

In a manner similar to that employed in Example 20, the title compound was obtained as crystals (108 mg, 57%) through 1,4-dihydrol-(6-methyl-3-pyridyl)indeno[1,2-c]pyrazole-3-carboxylic acid (145 mg) obtained in Referential Example 64 and N-methylpiperazine (66 μL).

$^1$H-NMR (400 MHz, CDCl$_3$) δ: 2.34 (3H, s), 2.43-2.60 (4H, m), 2.69 (3H, s), 3.83 (2H, s), 3.78-3.93 (2H, br), 4.18-4.30 (2H, br), 7.23-7.34 (2H, m), 7.37 (1H, d, J=8.0 Hz), 7.46 (1H, dd, J=6.3, 1.7 Hz), 7.57 (1H, d, J=6.3 Hz), 7.94 (1H, dd, J=8.0, 2.4 Hz), 8.91 (1H, d, J=2.4 Hz).
MS (ESI) m/z: 374(M+H)$^+$.
Elementary analysis: as $C_{22}H_{23}N_5O \cdot 0.25H_2O$
Calculated: C, 69.91; H, 6.27; N, 18.53.
Found: C, 69.79; H, 6.10; N, 18.24.

Example 46

1-[1,4-Dihydro-1-(6-ethyl-3-pyridyl)indeno[1,2-c]pyrazole-3-carbonyl]-4-methylpiperazine

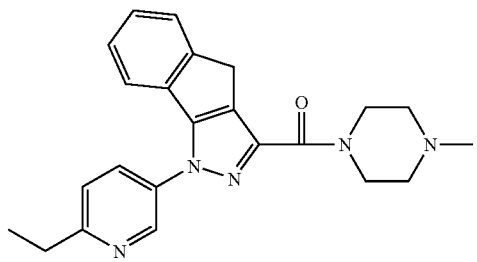

In a manner similar to that employed in Example 20, the title compound was obtained as crystals (163 mg, 84%) through use of 1,4-dihydro1-(6-ethyl-3-pyridyl)indeno[1,2-c]pyrazole-3-carboxylic acid (152 mg) obtained in Referential Example 68 and N-methylpiperazine (66 µL).

$^1$H-NMR (400 MHz, CDCl$_3$) δ: 1.40 (3H, t, J=7.5 Hz), 2.34 (3H, s), 2.42-2.58 (4H, m), 2.96 (2H, q, J=7.0 Hz), 3.84 (2H, s), 3.78-3.93 (2H, br), 4.17-4.30 (2H, br), 7.25-7.35 (2H, m), 7.38 (1H, d, J=8.3 Hz), 7.47 (1H, dd, J=6.3, 1.9 Hz), 7.57 (1H, d, J=6.3 Hz), 7.96 (1H, dd, J=8.3, 2.4 Hz), 8.94 (1H, d, J=2.4 Hz).

MS (ESI) m/z: 388(M+H)$^+$.

Elementary analysis: as C$_{23}$H$_{25}$N$_5$O

Calculated: C, 71.29; H, 6.50; N, 18.07.

Found: C, 71.06; H, 6.49; N, 17.73.

Example 47

4-[1-(6-Methoxy-3-pyridyl)-5-(4-methylthio-2-pyridyl)pyrazole-3-carbonyl]piperazine-1-carboxylic acid tert-butyl ester

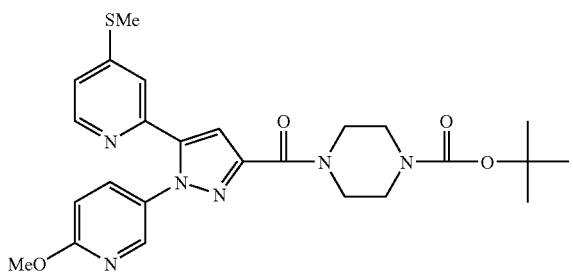

In a manner similar to that employed in step 1) of Example 1, the title compound was obtained as a solid (0.379 g, 84%) through use of 1-(6-methoxy-3-pyridyl)-5-(4-methylthio-2-pyridyl)pyrazole-3-carboxylic acid (0.305 g) obtained in Referential Example 118 and piperidine-1-carboxylic acid tert-butyl ester (0.180 g).

$^1$H-NMR (400 MHz, CDCl$_3$) δ: 1.48 (9H, s), 2.44 (3H, s), 3.51-3.52 (4H, m), 3.79 (2H, m), 3.95 (3H, s), 4.08 (2H, m), 6.76 (1H, d, J=8.8 Hz), 7.02-7.04 (1H, m), 7.13 (1H, s), 7.22 (1H, d, J=1.6 Hz), 7.59 (1H, dd, J=8.8, 2.8 Hz), 8.12 (1H, d, J=2.4 Hz), 8.27 (1H, d, J=5.2 Hz).

MS (EI) m/z: 510(M$^+$).

Example 48

4-[1-(6-Methoxy-3-pyridyl)-5-(4-methylsulfonyl-2-pyridyl)pyrazole-3-carbonyl]piperazine-1-carboxylic acid tert-butyl ester

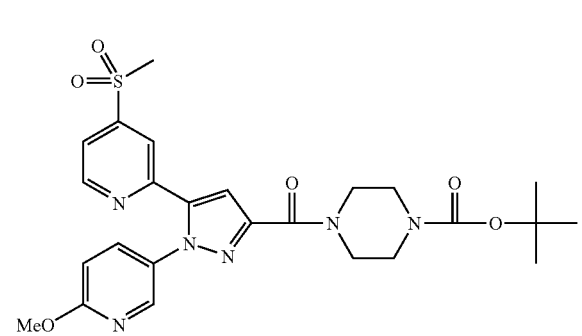

At 0° C., 3-chloroperbenzoic acid (0.260 g) was added to a solution of 4-[1-(6-methoxy-3-pyridyl)-5-(4-methylthio-2-pyridyl)pyrazole-3-carbonyl]piperazine-1-carboxylic acid tert-butyl ester (0.366 g) obtained in Example 47 in methylene chloride (7.3 mL), and the mixture was stirred for 20 minutes. Subsequently, the mixture was stirred at room temperature for a further 2 hours. At 0° C., 3-chloroperbenzoic acid (0.124 g) was added thereto, and the resultant mixture was stirred for 2 hours. Saturated aqueous sodium thiosulfate (10 mL) and saturated aqueous sodium hydrogencarbonate (10 mL) were added to the reaction mixture, followed by stirring. The reaction mixture was partitioned between water and chloroform. The organic layer was dried over sodium sulfate anhydrate. After filtration, the solvent was removed under reduced pressure. The residue was purified through silica gel column chromatography (chloroform-methanol), to thereby give the title compound as an amorphous product (0.387 g, 99%).

$^1$H-NMR (400 MHz, CDCl$_3$) δ: 1.48 (9H, s), 3.08 (3H, s), 3.53-3.54 (4H, m), 3.80 (2H, m), 3.97 (3H, s), 4.09 (2H, m), 6.80 (1H, d, J=8.8 Hz), 7.31 (1H, s), 7.60-7.63 (1H, m), 7.70-7.72 (1H, m), 7.94 (1H, d, J=0.8 Hz), 8.10 (1H, d, J=2.4 Hz), 8.75-8.77 (1H, m).

MS (EI) m/z: 542(M$^+$).

Example 49

1-[5-(4-Ethoxy-2-pyridyl)-1-(6-methoxy-3-pyridyl)pyrazole-3-carbonyl]-4-methylpiperazine

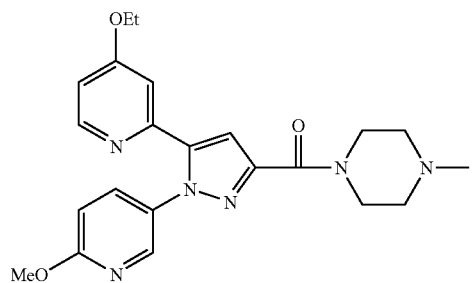

1) 4-[5-(4-Ethoxy-2-pyridyl)-1-(6-methoxy-3-pyridyl)pyrazole-3-carbonyl]piperazine-1-carboxylic acid tert-butyl ester In an argon atmosphere, sodium ethoxide (28.4 mg) was added to a solution of 4-[1-(6-methoxy-3-pyridyl)-5-(4-methylsulfonyl-2-pyridyl)pyrazole-3-carbonyl]piperazine-1-carboxylic acid tert-butyl ester (0.189 g) obtained in Example 48 in tetrahydrofuran (3.8 mL) at room temperature. The resultant mixture was stirred for 1 hour, and then stirred for 90 minutes at 80° C. Subsequently, sodium ethoxide (85.2 mg) was added thereto. The mixture was stirred at 80° C. for 2 hours and 20 minutes, and then cooled in air. The resultant mixture was partitioned between water and ethyl acetate. The organic layer was dried over sodium sulfate anhydrate. After filtration, the solvent was removed under reduced pressure. The residue was purified through silica gel column chromatography (ethyl acetate-chloroform), to thereby give 4-[5-(4-ethoxy-2-pyridyl)-1-(6-methoxy-3-pyridyl)pyrazole-3-carbonyl]piperazine-1-carboxylic acid tert-butyl ester (0.139 g, 79%) as a solid.

$^1$H-NMR (400 MHz, CDCl$_3$) δ: 1.41-1.44 (3H, m), 1.48 (9H, s), 3.51-3.53 (4H, m), 3.79 (2H, m), 3.95 (3H, s), 4.03-4.13 (4H, m), 6.73-6.77 (2H, m), 6.94 (1H, d, J=2.0 Hz), 7.10 (1H, s), 7.26-7.27 (1H, m), 7.58 (1H, dd, J=8.8, 2.8 Hz), 8.12 (1H, d, J=2.8 Hz), 8.30 (1H, d, J=5.6 Hz).

MS (EI) m/z: 508(M$^+$).

2) The Title Compound

At room temperature, trifluoroacetic acid (1.4 mL) was added to a solution of the above-obtained 4-[5-(4-ethoxy-2-pyridyl)-1-(6-methoxy-3-pyridyl)pyrazole-3-carbonyl]piperazine-1-carboxylic acid tert-butyl ester (0.135 g) in methylene chloride (2.7 mL), and the mixture was stirred for 30 minutes. The solvent was removed under reduced pressure, and the residue was dissolved in ethanol (2.7 mL). To the mixture were added 35% aqueous formalin solution (0.114 g), acetic acid (0.076 mL) and sodium cyanoborohydride (50.0 mg). The resultant mixture was stirred for 100 minutes at room temperature. Sodium cyanoborohydride (33.3 mg) was further added thereto, and the mixture was stirred for 50 minutes. The reaction mixture was partitioned between saturated aqueous sodium hydrogencarbonate and chloroform. The organic layer was dried over sodium sulfate anhydrate. After filtration, the solvent was removed under reduced pressure. The residue was purified through silica gel column chromatography (chloroform-methanol). Subsequently, the residue was purified through silica gel thin-layer chromatography (chloroform-methanol), to thereby give the title compound as an oily product (86.9 mg, 78%).

$^1$H-NMR (400 MHz, CDCl$_3$) δ: 1.41-1.44 (3H, m), 2.33 (3H, s), 2.44-2.52 (4H, m), 3.85 (2H, m), 3.95 (3H, s), 4.03-4.08 (4H, m), 6.72-6.76 (2H, m), 6.94 (1H, d, J=2.4 Hz), 7.07 (1H, s), 7.57-7.61 (1H, m), 8.12-8.13 (1H, m), 8.30 (1H, d, J=6.0 Hz).

MS (EI) m/z: 422(M$^+$).

Example 50

4-[1-(6-Methoxy-3-pyridyl)-5-[4-(pyrrolidin-1-yl)-2-pyridyl]pyrazole-3-carbonyl]piperazine-1-carboxylic acid tert-butyl ester

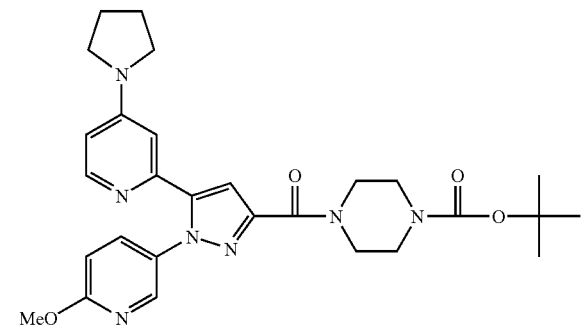

A solution of 4-[1-(6-methoxy-3-pyridyl)-5-(4-methylsulfonyl-2-pyridyl)pyrazole-3-carbonyl]piperazine-1-carboxylic acid tert-butyl ester (0.186 g) obtained in Example 48 in pyrrolidine (3.7 mL) was stirred at 100° C. for 17 hours, and then the mixture was cooled in air. The reaction mixture was partitioned between water and ethyl acetate. The organic layer was dried over sodium sulfate anhydrate. After filtration, the solvent was removed under reduced pressure. The residue was purified through silica gel column chromatography (chloroform-methanol), to thereby give the title compound as a solid (0.176 g, 96%).

$^1$H-NMR (400 MHz, CDCl$_3$) δ: 1.48 (9H, s), 1.84-2.07 (4H, m), 2.05 (3H, s), 3.25-3.51 (8H, m), 3.79 (2H, m), 3.94 (3H, s), 4.07 (2H, m), 6.31-6.33 (1H, m), 6.53 (1H, d, J=2.0 Hz), 6.73 (1H, d, J=8.8 Hz), 7.05 (1H, s), 7.60 (1H, dd, J=8.8, 2.8 Hz), 8.09 (1H, d, J=6.0 Hz), 8.16 (1H, d, J=2.8 Hz).

MS (EI) m/z: 533(M$^+$).

Example 51

1-[1-(6-Methoxy-3-pyridyl)-5-[4-(pyrrolidin-1-yl)-2-pyridyl]pyrazole-3-carbonyl]-4-methylpiperazine

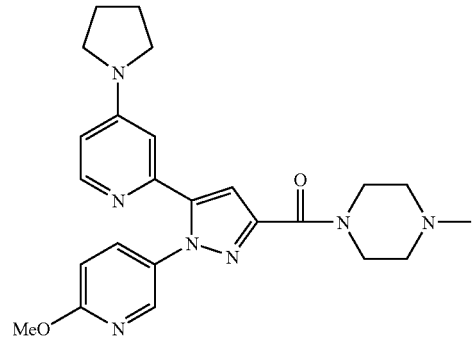

In a manner similar to that employed in step 2) of Example 49, the title compound was obtained as a solid (70.1 mg, 50%) through use of 1-[1-(6-methoxy-3-pyridyl)-5-[4-(pyrrolidin-1-yl)-2-pyridyl]pyrazole-3-carbonyl]piperazine-4-carboxylic acid tert-butyl ester (0.167 g) obtained in Referential Example 50.

¹H-NMR (400 MHz, CDCl₃) δ: 1.19-2.05 (4H, m), 2.33 (3H, s), 2.45-2.50 (4H, m), 3.25-3.28 (4H, m), 3.84 (2H, m), 3.93 (3H, s), 4.08 (2H, m), 6.31 (1H, dd, J=6.0, 2.8 Hz), 6.53 (1H, d, J=2.4 Hz), 6.72 (1H, d, J=8.8 Hz), 7.02 (1H, s), 7.59-7.62 (1H, m), 8.09 (1H, d, J=6.0 Hz), 8.16 (1H, d, J=2.8 Hz).

MS (EI) m/z: 447(M⁺).
Elementary analysis: as $C_{24}H_{29}N_7O_2 \cdot 0.25H_2O$
Calculated: C, 63.77%; H, 6.58%; N, 21.69%.
Found: C, 63.93%; H, 6.67%; N, 21.31%.

Example 52

1-[1-(6-Methoxy-3-pyridyl)-5-phenylpyrazole-3-carbonyl]piperidin-2-ylacetic acid ethyl ester

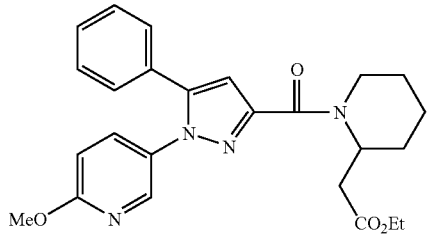

In a manner similar to that employed in Example 20, the title compound was obtained as an oily product (331 mg, 98%) through use of 1-(6-methoxy-3-pyridyl)-5-phenylpyrazole-3-carboxylic acid (221 mg) obtained in Referential Example 41 and piperidin-2-ylacetic acid ethyl ester (154 mg) obtained in Referential Example 93.

¹H-NMR (400 MHz, CDCl₃) [as a mixture of two isomers] δ: 1.19 and 1.26 (each 0.5×3H, each t, each J=7.0 Hz), 1.48-1.85 (6H, br m), 2.64-2.95 (2.5H, m), 3.15-3.29 (0.5H, m), 3.93 (3H, s), 4.01-4.19 (2H, br), 4.62-4.75 (1H, br), 5.32-5.41 (1H, br), 6.70 (1H, d, J=8.8 Hz), 6.84 and 6.87 (each 0.5×1H, each br s), 7.18-7.28 (2H, m), 7.30-7.37 (3H, m), 7.45-7.57 (1H, br m), 8.11 (1H, d, J=2.7 Hz).

MS (ESI) m/z: 449(M+H)⁺.

Example 53

1-[1-(6-Methoxy-3-pyridyl)-5-phenylpyrazole-3-carbonyl]piperidin-2-ylacetic acid

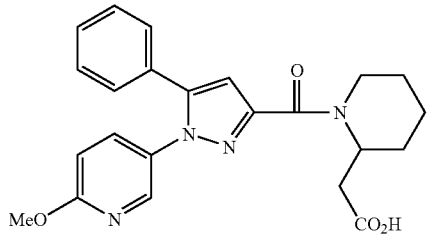

To a solution of 1-[1-(6-methoxy-3-pyridyl)-5-phenylpyrazole-3-carbonyl]piperidin-2-ylacetic acid ethyl ester (330 mg) obtained in Example 52 in methanol (4 mL), 1M aqueous sodium hydroxide (1.84 mL) was added, and the mixture was stirred for 2 hours at room temperature. The solvent was removed under reduced pressure, and the residue was partitioned between water and ethyl acetate. The aqueous layer was acidified with 1M aqueous hydrochloric acid (2 mL), followed by extraction with ethyl acetate. The thus-obtained organic layer was washed with water and saturated brine and dried over sodium sulfate anhydrate. The resultant mixture was subjected to filtration, and the solvent was removed under reduced pressure, to thereby give the title compound as an amorphous product (311 mg, 98%).

¹H-NMR (400 MHz, CDCl₃) δ: 1.48-1.90 (6H, br m), 2.67-3.00 (2.5H, br m), 3.12-3.28 (0.5H, br), 3.92 (3H, s), 4.65-4.82 (1H, br), 5.23-5.43 (1H, br), 6.70 (1H, d, J=8.8 Hz), 6.90 (1H, br s), 7.19-7.28 (2H, m), 7.30-7.38 (3H, m), 7.48 (1H, dd, J=8.8, 2.7 Hz), 8.13 (1H, br s).

MS (ESI) m/z: 421(M+H)⁺.
Elementary analysis: as $C_{23}H_{24}N_4O_4 \cdot 0.5H_2O$
Calculated: C, 64.32; H, 5.87; N, 13.05.
Found: C, 64.11; H, 5.90; N, 12.75.

Example 54

1-[1-(6-Methoxy-3-pyridyl)-5-(2-pyridyl)pyrazole-3-carbonyl]-4-isopropylpiperazine

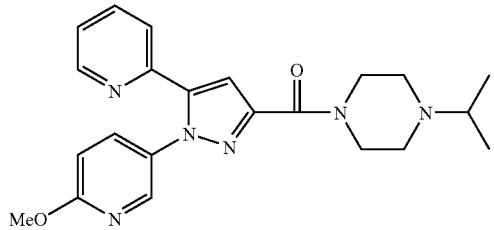

1) The Title Compound

In a manner similar to that employed in Example 20, the title compound was obtained as an amorphous product (251 mg, 82%) through use of 1-(6-methoxy-3-pyridyl)-5-(2-pyridyl)pyrazole-3-carboxylic acid (222 mg) obtained in Referential Example 33 and 1-isopropylpiperazine hydrochloride (181 mg) obtained in Referential Example 95.

¹H-NMR (400 MHz, CDCl₃) δ: 1.06 (6H, d, J=6.6 Hz), 2.56 (2H, t, J=4.9 Hz), 2.61 (2H, t, J=4.9 Hz), 2.73 (1H, septet, J=6.6 Hz), 3.83 (2H, t, J=4.9 Hz), 3.95 (3H, s), 4.07 (2H, t, J=4.9 Hz), 6.71 (1H, dd, J=8.8, 0.7 Hz), 7.11 (1H, s), 7.23 (1H, ddd, J=7.8, 4.9, 1.2 Hz), 7.41 (1H, ddd, J=7.8, 1.2, 1.0 Hz), 7.59 (1H, dd, J=8.8, 2.7 Hz), 7.70 (1H, ddd, J=7.8, 7.8, 1.2 Hz), 8.12 (1H, dd, J=2.7, 0.7 Hz), 8.51 (1H, ddd, J=4.9, 1.7, 1.0 Hz).

MS (ESI) m/z: 407(M+H)⁺.

2) Hydrochloric Acid Salt of the Title Compound

In a manner similar to that employed in step 2) of Example 29, a hydrochloric acid salt of the title compound was obtained as crystals (235 mg, 73%) through use of the above-obtained title compound (251 mg).

¹H-NMR (400 MHz, DMSO-d₆) δ: 1.30 (6H, d, J=6.6 Hz), 3.01-3.20 (2H, br), 3.33-3.56 (4H, br m), 3.69-3.74 (1H, br m), 3.89 (3H, s), 4.60-4.73 (1H, br m), 5.03-5.17 (1H, br m), 6.88 (1H, d, J=8.8 Hz), 7.27 (1H, s), 7.35-7.41 (1H, m), 7.64-7.74 (2H, m), 7.85-7.94 (1H, m), 8.20 (1H, d, J=2.7 Hz), 8.47 (1H, dd, J=4.9, 0.7 Hz), 10.84-11.04 (1H, br).

MS (ESI) m/z: 407(M+H)⁺.
Elementary analysis: as $C_{22}H_{26}N_6O_2 \cdot 2HCl \cdot 2H_2O$
Calculated: C, 51.27; H, 6.26; N, 16.30; Cl, 13.76.
Found: C, 51.30; H, 6.18; N, 15.97; Cl, 13.36.

Example 55

1-[1-(6-Methoxy-3-pyridyl)-5-(2-pyridyl)pyrazole-3-carbonyl]-4-cyclopropylpiperazine

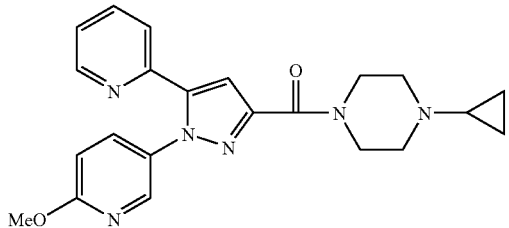

In a manner similar to that employed in Example 20, the title compound was obtained as crystals (253 mg, 83%) through use of 1-(6-methoxy-3-pyridyl)-5-(2-pyridyl)pyrazole-3-carboxylic acid (222 mg) obtained in Referential Example 33 and 1-cyclopropylpiperazine hydrochloride (179 mg) obtained in Referential Example 99.

$^1$H-NMR (400 MHz, CDCl$_3$) δ: 0.41-0.51 (4H, m), 1.60-1.69 (1H, m), 2.66 (2H, t, J=4.9 Hz), 2.71 (2H, t, J=4.9 Hz), 3.79 (2H, br t, J=4.9 Hz), 3.95 (3H, s), 4.02 (2H, br t, J=4.9 Hz), 6.75 (1H, d, J=8.8 Hz), 7.11 (1H, s), 7.23 (1H, ddd, J=7.8, 4.9, 1.2 Hz), 7.41 (1H, d, J=7.8 Hz), 7.59 (1H, dd, J=8.8, 2.7 Hz), 7.71 (1H, ddd, J=7.8, 7.8, 1.7 Hz), 8.12 (1H, d, J=2.7 Hz), 8.52 (1H, ddd, J=4.9, 1.7, 1.0 Hz).

MS (ESI) m/z: 404(M+H)$^+$.
Elementary analysis: as C$_{22}$H$_{24}$N$_6$O$_2$
Calculated: C, 65.33; H, 5.98; N, 20.78.
Found: C, 64.97; H, 5.92; N, 20.53.

Example 56

1-[1-(6-Methoxy-3-pyridyl)-5-phenylpyrazole-3-carbonyl]-2-(2-hydroxyethyl)piperidine

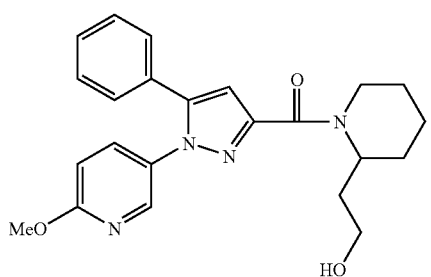

In a manner similar to that employed in Example 20, the title compound was obtained as an amorphous product (82 mg, 39%) through use of 1-(6-methoxy-3-pyridyl)-5-phenylpyrazole-3-carboxylic acid (148 mg) obtained in Referential Example 41 and 2-(piperidin-2-yl)ethanol (78 mg).

$^1$H-NMR (400 MHz, CDCl$_3$) [as a mixture of two isomers] δ: 1.53-1.80 (5H, m), 1.84-1.95 (0.5H, br), 2.04-2.13 (0.5H, m), 2.25-2.36 (0.5H, m), 2.74-2.85 (0.5H, m), 2.98-3.08 (0.5H, m), 3.43-3.53 (0.5H, m), 3.57-3.79 (2H, m), 3.92 and 3.94 (each 3H, each s), 4.00-4.09 (0.5H, m), 4.62-4.78 (1H, m), 4.88-5.04 (1H, m), 5.10-5.17 (0.5H, m), 6.71 and 6.75 (each 0.5×1H, each d, each J=8.8 Hz), 6.88 and 6.96 (each 0.5×1H, each s), 7.18-7.27 (2H, m), 7.29-7.38 (3H, m), 7.47 and 7.51 (each 0.5×1H, each dd, each J=8.8, 2.7 Hz), 8.04 and 8.13 (each 0.5×1H, each d, each J=2.7 Hz).

MS (ESI) m/z: 407(M+H)$^+$.
Elementary analysis: as C$_{23}$H$_{26}$N$_4$O$_3$·0.5H$_2$O
Calculated: C, 66.49; H, 6.55; N, 13.48.
Found: C, 66.68; H, 6.53; N, 13.31.

Example 57

1-[1-(6-Methoxy-3-pyridyl)-5-phenylpyrazole-3-carbonyl]piperidine

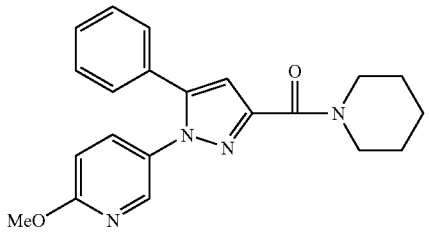

In a manner similar to that employed in Example 20, the title compound was obtained as crystals (137 mg, 75%) through use of 1-(6-methoxy-3-pyridyl)-5-phenylpyrazole-3-carboxylic acid (148 mg) obtained in Referential Example 41 and piperidine (59 µL).

$^1$H-NMR (400 MHz, CDCl$_3$) δ: 1.56-1.75 (6H, br m), 3.71-3.78 (2H, br), 3.89-3.97 (2H, br), 3.93 (3H, s), 6.71 (1H, d, J=8.8 Hz), 6.84 (1H, s), 7.21-7.27 (2H, m), 7.30-7.37 (3H, m), 7.48 (1H, dd, J=8.8, 2.7 Hz), 8.11 (1H, d, J=2.7 Hz).

MS (ESI) m/z: 363(M+H)$^+$.
Elementary analysis: as C$_{21}$H$_{22}$N$_4$O$_2$
Calculated: C, 69.59; H, 6.12; N, 15.46.
Found: C, 69.43; H, 6.09; N, 15.20.

Example 58

1-[5-(4-Methoxyphenyl)-1-(6-methoxy-3-pyridyl)pyrazole-3-carbonyl]-4-methylpiperazine

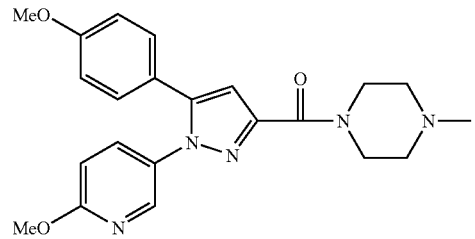

In a manner similar to that employed in Example 20, the title compound was obtained as crystals (237 mg, 77%) through use of 5-(4-methoxyphenyl)-1-(6-methoxy-3-pyridyl)pyrazole-3-carboxylic acid (244 mg) obtained in Referential Example 45 and N-methylpiperazine (125 µL).

$^1$H-NMR (400 MHz, CDCl$_3$) δ: 2.33 (3H, s), 2.42-2.54 (4H, m), 3.78-3.88 (2H, br), 3.81 (3H, s), 3.94 (3H, s), 4.07-4.17 (2H, br), 6.71 (1H, d, J=8.8 Hz), 6.84 (1H, s), 6.85 (2H, d-like, J=8.8 Hz), 7.15 (2H, d-like, J=8.8 Hz), 7.48 (1H, dd, J=8.8, 2.7 Hz), 8.12 (1H, d, J=2.7 Hz).

MS (ESI) m/z: 408(M+H)$^+$.
Elementary analysis: as C$_{22}$H$_{25}$N$_5$O$_3$

Example 59

1-[5-(3-Methoxyphenyl)-1-(6-methoxy-3-pyridyl)pyrazole-3-carbonyl]-4-methylpiperazine

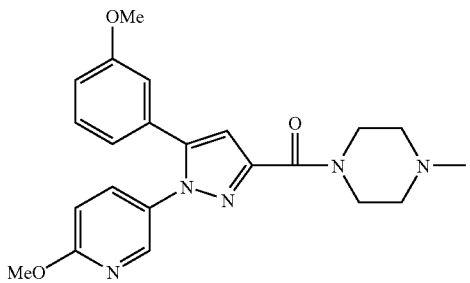

1) The Title Compound

In a manner similar to that employed in Example 20, the title compound was obtained as an oily product (243 mg, 79%) through use of 5-(3-methoxyphenyl)-1-(6-methoxy-3-pyridyl)pyrazole-3-carboxylic acid (244 mg) obtained in Referential Example 47 and N-methylpiperazine (125 μL).

2) Hydrochloric Acid Salt of the Title Compound

In a manner similar to that employed in step 2) of Example 29, a hydrochloric acid salt of the title compound was obtained as crystals (253 mg, 92%) through use of the above-obtained title compound.

$^1$H-NMR (400 MHz, DMSO-$d_6$) δ: 2.79 (3H, s), 2.98-3.73 (6H, br m), 3.70 (3H, s), 3.88 (3H, s), 4.53-4.70 (1H, br), 4.92-5.08 (1H, br), 6.80 (1H, d, J=7.5 Hz), 6.85-6.98 (3H, m), 7.02 (1H, s), 7.23-7.32 (1H, m), 7.70 (1H, dd, J=8.8, 2.7 Hz), 8.19 (1H, d, J=2.7 Hz), 10.78-10.94 (1H, br).

MS (ESI) m/z: 408(M+H)$^+$.

Elementary analysis: as $C_{22}H_{25}N_5O_3$·HCl·$H_2O$

Calculated: C, 57.20; H, 6.11; N, 15.16; Cl, 7.67.

Found: C, 57.12; H, 6.09; N, 15.08; Cl, 7.74

Example 60

1-[5-(2-Methoxyphenyl)-1-(6-methoxy-3-pyridyl)pyrazole-3-carbonyl]-4-methylpiperazine

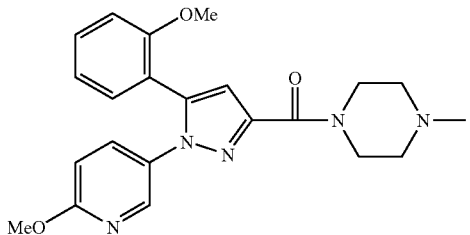

In a manner similar to that employed in Example 20, the title compound was obtained as crystals (263 mg, 84%) through use of 5-(2-methoxyphenyl)-1-(6-methoxy-3-pyridyl)pyrazole-3-carbonyl (244 mg) obtained in Referential Example 49 and N-methylpiperazine (125 μL).

$^1$H-NMR (400 MHz, CDCl$_3$) δ: 2.33 (3H, s), 2.43-2.56 (4H, br), 3.48 (3H, s), 3.78-3.92 (2H, br), 3.90 (3H, s), 4.11-4.22 (2H, br), 6.67 (1H, d, J=8.8 Hz), 6.82 (1H, d, J=8.3 Hz), 6.86 (1H, s), 6.95-7.03 (1H, m), 7.27-7.32 (1H, m), 7.34-7.40 (1H, m), 7.48 (1H, dd, J=8.8, 2.7 Hz), 8.06 (1H, d, J=2.7 Hz).

MS (ESI) m/z: 408(M+H)$^+$.

Example 61

1-[1-(6-Methoxy-3-pyridyl)-5-(4-trifluoromethylphenyl)pyrazole-3-carbonyl]-4-methylpiperazine

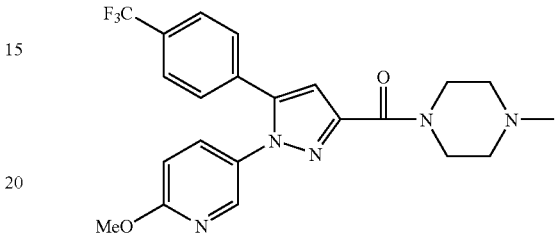

In a manner similar to that employed in Example 20, the title compound was obtained as crystals (272 mg, 81%) through use of 1-(6-methoxy-3-pyridyl)-5-(4-trifluoromethylphenyl)pyrazole-3-carboxylic acid (272 mg) obtained in Referential Example 51 and N-methylpiperazine (125 μL).

$^1$H-NMR (400 MHz, CDCl$_3$) δ: 2.33 (3H, s), 2.42-2.57 (4H, m), 3.79-3.91 (2H, br), 3.95 (3H, s), 4.07-4.18 (2H, br), 6.76 (1H, d, J=8.8 Hz), 6.98 (1H, s), 7.36 (2H, d, J=8.0 Hz), 7.49 (1H, dd, J=8.8, 2.4 Hz), 7.60 (2H, d, J=8.0 Hz), 8.09 (1H, d, J=2.4 Hz).

MS (ESI) m/z: 446(M+H)$^+$.

Elementary analysis: as $C_{22}H_{22}F_3N_5O_2$

Calculated: C, 59.32; H, 4.98; N, 15.72; F, 12.80.

Found: C, 58.95; H, 4.93; N, 15.71; F, 12.57.

Example 62

1-[1-(6-Methoxy-3-pyridyl)-5-phenylpyrazole-3-carbonyl]-4-methylpiperazine

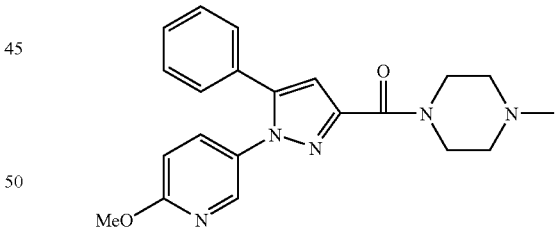

1) The Title Compound

In a manner similar to that employed in Example 20, the title compound was obtained as an oily product (6.23 g, 66%) through use of 1-(6-methoxy-3-pyridyl)-5-phenylpyrazole-3-carboxylic acid (7.38 g) obtained in Referential Example 41 and N-methylpiperazine (3.32 mL).

2) Hydrochloric Acid Salt of the Title Compound

To a solution of the above-obtained title compound (6.23 g) in methanol (200 mL), 1M aqueous hydrochloric acid (17 mL) was added, followed by stirring. The solvent was removed under reduced pressure, and ethanol was added to the residue, and the solvent was further removed under reduced pressure. The residue was crystallized from ethanol-diethyl ether, followed by collection through filtration, to thereby give a hydrochloric acid salt of the title compound as crystals (5.04 g, 72%).

$^1$H-NMR (40.0 MHz, DMSO-$d_6$) δ: 2.80 (3H, s), 3.00-3.73 (6H, br m), 3.88 (3H, s), 4.53-4.72 (1H, br), 4.94-5.10 (1H, br), 6.89 (1H, d, J=8.8 Hz), 7.00 (1H, s), 7.25-7.32 (2H, m), 7.36-7.43 (3H, m), 7.68 (1H, dd, J=8.8, 2.6 Hz), 8.18 (1H, d, J=2.6 Hz), 10.71-10.87 (1H, br).

MS (ESI) m/z: 378(M+H)$^+$.

Elementary analysis: as $C_{21}H_{23}N_5O_2 \cdot HCl \cdot 0.5H_2O$
Calculated: C, 59.64; H, 5.96; N, 16.56; Cl, 8.38.
Found: C, 59.60; H, 6.17; N, 16.43; Cl, 8.56.

Example 63

1-[1-(6-Methoxy-3-pyridyl)-5-phenylpyrazole-3-thiocarbonyl]-4-methylpiperazine

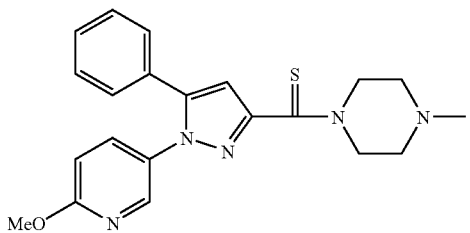

To a solution of 1-[1-(6-methoxy-3-pyridyl)-5-phenylpyrazole-3-carbonyl]-4-methylpiperazine (173 mg) obtained in Example 62 in toluene (10 mL), 2,4-bis(4-methoxyphenyl)-1,3,2,4-dithiadiphosphetane-2,4-disulfide (Lawson reagent, 222 mg) was added. The mixture was refluxed for 14 hours under heat. The reaction mixture was partitioned between water and ethyl acetate. The organic layer was washed with saturated aqueous sodium hydrogencarbonate, water, and saturated brine, followed by drying over sodium sulfate anhydrate. After filtration, the solvent was removed under reduced pressure. The residue was purified through silica gel thin-layer chromatography (chloroform-methanol), to thereby give the title compound as an amorphous product (61 mg, 33%).

$^1$H-NMR (400 MHz, CDCl$_3$) δ: 2.37 (3H, s), 2.50-2.71 (4H, m), 3.93 (3H, s), 4.09-4.20 (2H, br), 4.42-4.55 (2H, br), 6.70 (1H, d, J=8.8 Hz), 6.90 (1H, s), 7.22-7.28 (2H, m), 7.30-7.39 (3H, m), 7.47 (1H, dd, J=8.8, 2.7 Hz), 8.10 (1H, d, J=2.7 Hz).

MS (ESI) m/z: 394(M+H)$^+$.

Example 64

4-[1-(6-Methoxy-3-pyridyl)-5-phenylpyrazole-3-carbonyl]piperazine-1-carboxylic acid tert-butyl ester

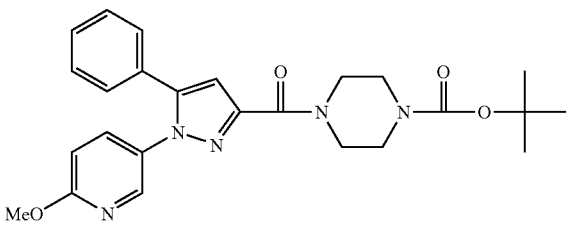

To a solution containing, in methylene chloride (5 mL), 1-(6-methoxy-3-pyridyl)-5-phenylpyrazole-3-carboxylic acid (295 mg) obtained in Referential Example 41, piperazine-1-carboxylic acid tert-butyl ester (186 mg), 1-hydroxybenzotriazole (135 mg), and triethylamine (488 μL), 1-(3-dimethylaminopropyl)-3-ethylcarbodiimide hydrochloride (288 mg) was added. The resultant mixture was stirred at room temperature for 13 hours. The reaction solvent was removed under reduced pressure, and water and ethyl acetate were added to the residue, thereby forming an aqueous layer and an organic layer. The organic layer was washed with water and saturated brine, followed by drying over sodium sulfate anhydrate. After filtration, the solvent was removed under reduced pressure. The thus-obtained solid was recrystallized from ethyl acetate-hexane, to thereby give the title compound as crystals (225 mg). Separately, the solvent of the above-obtained aqueous layer was removed under reduced pressure. The residue was purified through silica gel thin-layer chromatography (hexane-ethyl acetate), to thereby further give the title compound (154 mg). The compound and the above-obtained crystals were combined (379 mg, 81%).

$^1$H-NMR (400 MHz, CDCl$_3$) δ: 1.48 (9H, s), 3.48-3.57 (4H, br), 3.75-3.82 (2H, br), 3.94 (3H, s), 4.06-4.14 (2H, br), 6.72 (1H, d, J=8.8 Hz), 6.93 (1H, s), 7.21-7.27 (2H, m), 7.31-7.38 (3H, m), 7.47 (1H, dd, J=8.8, 2.7 Hz), 8.12 (1H, d, J=2.7 Hz).

MS (ESI) m/z: 464(M+H)$^+$.

Example 65

1-[1-(6-Methoxy-3-pyridyl)-5-phenylpyrazole-3-carbonyl]piperazine hydrochloride

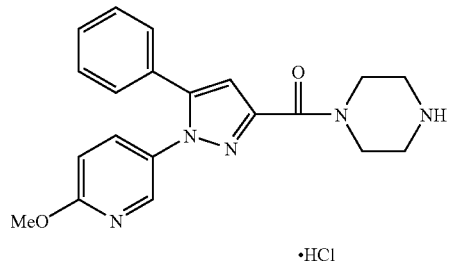

To a solution of 4-[1-(6-methoxy-3-pyridyl)-5-phenylpyrazole-3-carbonyl]piperazine-1-carboxylic acid tert-butyl ester (332 mg) obtained in Example 64 in methylene chloride (2 mL), anisole (0.4 mL) and trifluoroacetic acid (1.6 mL) were added, and the mixture was stirred at room temperature for 30 minutes. The reaction solvent was removed under reduced pressure, and the residue was partitioned between water and diethyl ether. The aqueous layer was alkalinized with saturated aqueous sodium hydrogencarbonate and extracted with ethyl acetate four times. The organic layers were combined, followed by drying over sodium sulfate anhydrate. After filtration, the solvent was removed under reduced pressure. The residue was dissolved in a solvent mixture of diethyl ether and a small amount of methanol. 1M HCl-ethanol (0.78 mL) was added thereto, and the precipitated crystals were collected through filtration. The thus-obtained matter was recrystallized from methanol-diethyl ether, to thereby give the title compound (229 mg, 76%).

$^1$H-NMR (400 MHz, DMSO-$d_6$) δ: 3.12-3.23 (4H, br), 3.83-3.94 (2H, br), 3.87 (3H, s), 4.23-4.33 (2H, br), 6.89 (1H, d, J=8.8 Hz), 6.99 (1H, s), 7.26-7.32 (2H, m), 7.36-7.42 (3H, m), 7.68 (1H, dd, J=8.8, 2.4 Hz), 8.17 (1H, d, J=2.4 Hz), 9.26-9.40 (2H, br).

MS (ESI) m/z: 364(M+H)$^+$.

Elementary analysis: as $C_{20}H_{21}N_5O_2 \cdot HCl \cdot H_2O$
Calculated: C, 57.48; H, 5.79; N, 16.76; Cl, 8.48.
Found: C, 57.11; H, 5.70; N, 16.58; Cl, 8.81.

Example 66

4-[5-(4-Fluorophenyl)-1-(6-methoxy-3-pyridyl)pyrazole-3-carbonyl]piperazine-1-carboxylic acid tert-butyl ester

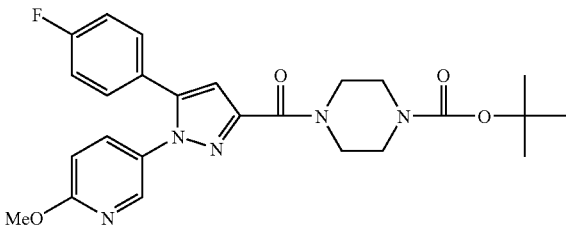

To a solution containing, in methylene chloride (5 mL), 5-(4-fluorophenyl)-1-(6-methoxy-3-pyridyl)pyrazole-3-carboxylic acid (313 mg) obtained in Referential Example 136, piperidine-1-carboxylic acid tert-butyl ester (186 mg), 1-hydroxybenzotriazole (135 mg), and triethylamine (488 μL), 1-(3-dimethylaminopropyl)-3-ethylcarbodiimide hydrochloride (288 mg) was added, and the mixture was stirred at room temperature for 13 hours. The solvent was removed under reduced pressure. Water and ethyl acetate were added to the residue, thereby forming an aqueous layer and an organic layer. The organic layer was washed with water and saturated brine, followed by drying over sodium sulfate anhydrate. After filtration, the solvent was removed under reduced pressure. The thus-obtained solid was recrystallized from ethyl acetate-hexane, to thereby give the title compound (241 mg). Separately, the solvent of the above-obtained layer was removed under reduced pressure. The residue was purified through silica gel thin-layer chromatography (hexane-ethyl acetate), to thereby give the title compound as crystals (170 mg). The former crystals and the latter crystals were combined (411 mg, 85%).

$^1$H-NMR (400 MHz, CDCl$_3$) δ: 1.48 (9H, s), 3.48-3.57 (4H, br), 3.74-3.82 (2H, br), 3.95 (3H, s), 4.07-4.13 (2H, br), 6.74 (1H, d, J=8.8 Hz), 6.92 (1H, s), 7.00-7.08 (2H, m), 7.18-7.25 (2H, m), 7.47 (1H, dd, J=8.8, 2.7 Hz), 8.09 (1H, d, J=2.7 Hz).

MS (ESI) m/z: 482 (M+H)$^+$.

Elementary analysis: as C$_{25}$H$_{28}$FN$_5$O$_4$.0.5H$_2$O
Calculated: C, 61.21; H, 5.96; N, 14.28; F, 3.87.
Found: C, 61.41; H, 5.76; N, 14.18; F, 3.95.

Example 67

1-[5-(4-Fluorophenyl)-1-(6-methoxy-3-pyridyl)pyrazole-3-carbonyl]piperazine hydrochloride

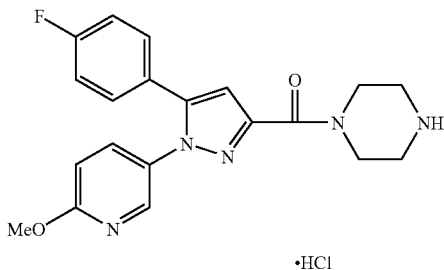

·HCl

In a manner similar to that employed in Example 65, the title compound was obtained as crystals (278 mg, 81%) through use of 4-[5-(4-fluorophenyl)-1-(6-methoxy-3-pyridyl)pyrazole-3-carbonyl]piperazine-1-carboxylic acid tert-butyl ester (363 mg) obtained in Example 66.

$^1$H-NMR (400 MHz, DMSO-d$_6$) δ: 3.10-3.22 (4H, br), 3.82-3.96 (2H, br), 3.88 (3H, s), 4.22-4.3.2 (2H, br), 6.90 (1H, d, J=8.8 Hz), 7.00 (1H, s), 7.20-7.28 (2H, m), 7.31-7.40 (2H, m), 7.69 (1H, dd, J=8.8, 2.7 Hz), 8.19 (1H, d, J=2.4 Hz), 9.30-9.43 (2H, br).

MS (ESI) m/z: 382(M+H)$^+$.

Example 68

1-[1-(6-Methoxy-3-pyridyl)-5-phenylpyrazole-3-carbonyl]-4-methoxyethylpiperazine

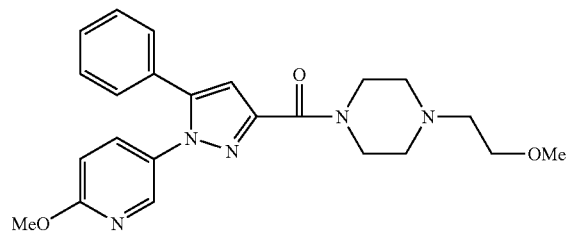

1) The Title Compound

In a manner similar to that employed in step 1) of Example 1, the title compound (285 mg, quantitative amount) was obtained through use of 1-(6-methoxy-3-pyridyl)-5-phenylpyrazole-3-carboxylic acid (200 mg) obtained in Referential Example 41 and 1-(2-methoxyethyl)piperazine hydrochloride (175 mg) obtained in Referential Example 97.

2) Hydrochloric Acid Salt of the Title Compound

In a manner similar to that employed in step 2) of Example 29, a hydrochloric acid salt of the title compound was obtained as a solid (255 mg, 82%) through use of the above-obtained title compound (285 mg).

$^1$H-NMR (400 MHz, DMSO-d$_6$) δ: 3.13 (2H, br), 3.30-3.32 (2H, br), 3.33 (3H, s), 3.56 (3H, br), 3.72-3.73 (3H, m), 4.58 (1H, br), 4.99 (1H, br), 6.90 (1H, d, J=8.8 Hz), 7.00 (1H, s), 7.29-7.31 (2H, m), 7.39-7.41 (3H, m), 7.70 (1H, dd, J=8.8, 2.7 Hz), 8.20 (1H, d, J=2.7 Hz), 10.85 (1H, br).

MS (FAB) m/z: 422(M+H)$^+$.

Elementary analysis: as C$_{23}$H$_{27}$N$_5$O$_3$.HCl
Calculated: C, 60.45; H, 6.18; N, 15.33; Cl, 7.76.
Found: C, 60.15; H, 6.14; N, 15.01; Cl, 7.63.

Example 69

1-[1-(6-Methoxy-3-pyridyl)-5-phenylpyrazole-3-carbonyl]-4-cyclopropylpiperazine

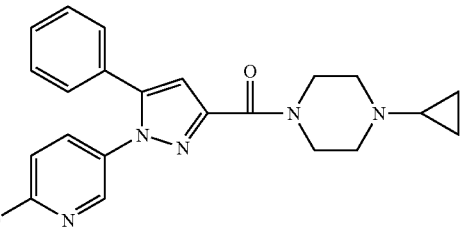

In a manner similar to that employed in step 1) of Example 1, the title compound was obtained as a solid (180 mg, 66%) through use of 1-(6-methoxy-3-pyridyl)-5-phenylpyrazole-3-carboxylic acid (200 mg) obtained in Referential Example 41 and 1-cyclopropylpiperazine hydrochloride (160 mg) obtained in Referential Example 99.

¹H-NMR (400 MHz, DMSO-d₆) δ: 0.34-0.36 (2H, m), 0.41-0.44 (2H, m), 1.64-1.67 (1H, m), 2.58 (4H, br), 3.61 (2H, br), 3.87 (3H, s), 3.89 (2H, br), 6.90 (1H, d, J=8.8 Hz), 6.92 (1H, s), 7.28-7.32 (2H, m), 7.37-7.40 (3H, m), 7.70 (1H, dd, J=8.8, 2.2 Hz), 8.14 (1H, d, J=2.2 Hz).

MS (EI) m/z: 403(M⁺).
Elementary analysis: as $C_{23}H_{25}N_5O_2$
Calculated: C, 68.47; H, 6.25; N, 17.36.
Found: C, 68.45; H, 6.29; N, 17.23.

Example 70

1-[1-(6-Methoxy-3-pyridyl)-5-phenylpyrazole-3-carbonyl]-3-dimethylaminoazetidine

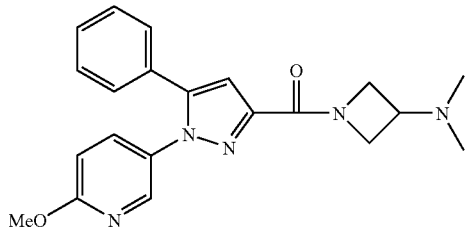

1) The Title Compound

In a manner similar to that employed in step 1) of Example 1, the title compound (185 mg, 95%) was obtained through use of 1-(6-methoxy-3-pyridyl)-5-phenylpyrazole-3-carboxylic acid (150 mg) obtained in Referential Example 41 and azetidin-3-yldimethylamine hydrochloride (106 mg) obtained in Referential Example 102.

2) Hydrochloric Acid Salt of the Title Compound

In a manner similar to that employed in step 2) of Example 29, a hydrochloric acid salt of the title compound was obtained as a solid (155 mg, 74%) through use of the above-obtained title compound (185 mg).

¹H-NMR (400 MHz, DMSO-d₆) δ: 2.75 (6H, s), 3.88 (3H, s), 4.14 (1H, br), 4.24-4.33 (2H, m), 4.70-4.81 (2H, m), 6.90 (1H, d, J=8.8 Hz), 7.04 (1H, s), 7.29-7.32 (2H, m), 7.38-7.41 (3H, m), 7.67 (1H, dd, J=8.8, 2.9 Hz), 8.22 (1H, d, J=2.9 Hz), 11.47 (1H, br).

MS (EI) m/z: 377(M⁺).
Elementary analysis: as $C_{23}H_{27}N_5O_3 \cdot HCl \cdot H_2O$
Calculated: C, 58.40; H, 6.07; N, 16.21; Cl, 8.21.
Found: C, 58.08; H, 6.02; N, 15.97; Cl, 8.23.

Example 71

1-[1-(6-Methoxy-3-pyridyl)-5-phenylpyrazole-3-carbonyl]-3-methoxyazetidine

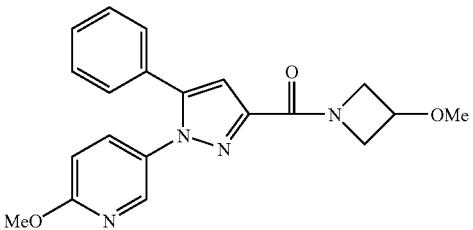

In a manner similar to that employed in step 1) of Example 1, the title compound was obtained as a solid (140 mg, 76%) through use of 1-(6-methoxy-3-pyridyl)-5-phenylpyrazole-3-carboxylic acid (150 mg) obtained in Referential Example 41 and 3-methoxyazetidine hydrochloride (75.6 mg) obtained in Referential Example 107.

¹H-NMR (400 MHz, CDCl₃) δ: 3.37 (3H, s), 3.95 (3H, s), 4.08-4.11 (1H, m), 4.25-4.31 (1H, m), 4.36-4.40 (1H, m), 4.46-4.50 (1H, m), 4.78-4.82 (1H, m), 6.71 (1H, d, J=8.8 Hz), 6.92 (1H, s), 7.22-7.24 (2H, m), 7.32-7.35 (3H, m), 7.46 (1H, dd, J=8.8, 2.9 Hz), 8.15 (1H, d, J=2.9 Hz).

LC-MS m/z: 365(M+H)⁺.
Elementary analysis: as $C_{20}H_{20}N_4O_3 \cdot 0.25 H_2O$
Calculated: C, 65.12; H, 5.60; N, 15.19.
Found: C, 65.12; H, 5.44; N, 15.13.

Example 72

1-[1-(6-Methoxy-3-pyridyl)-5-phenylpyrazole-3-carbonyl]-3-hydroxyazetidine

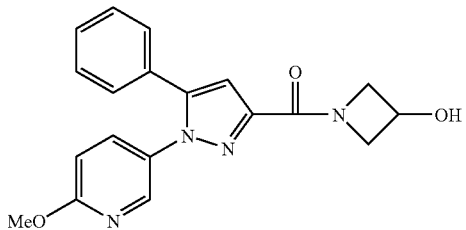

In a manner similar to that employed in step 1) of Example 1, the title compound was obtained as a solid (135 mg, 76%) through use of 1-(6-methoxy-3-pyridyl)-5-phenylpyrazole-3-carboxylic acid (150 mg) obtained in Referential Example 41 and 3-hydroxyazetidine hydrochloride (67.0 mg) obtained Referential Example 108.

¹H-NMR (400 MHz, CDCl₃) δ: 3.94 (3H, s), 4.07-4.12 (1H, m), 4.45-4.50 (2H, m), 4.73 (1H, br), 4.86-4.90 (1H, m), 6.70 (1H, d, J=8.8 Hz), 7.01 (1H, s), 7.20-7.23 (2H, m), 7.30-7.37 (3H, m), 7.46 (1H, dd, J=8.8, 2.8 Hz), 8.12 (1H, d, J=2.8 Hz).

LC-MS m/z: 351(M+H)⁺.
Elementary analysis: as $C_{19}H_{18}N_4O_3 \cdot 0.25 H_2O$
Calculated: C, 64.31; H, 5.25; N, 15.79.
Found: C, 64.19; H, 5.15; N, 15.60.

Example 73

1-[1-(6-Methoxy-3-pyridyl)-5-phenylpyrazole-3-carbonyl]-4-cyclobutylpiperazine

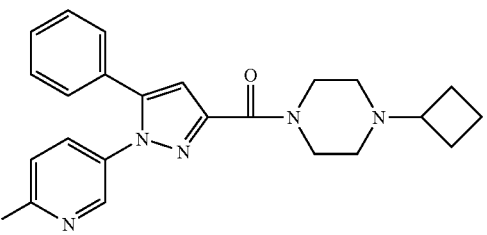

1) The Title Compound

In a manner similar to that employed in step 1) of Example 1, the title compound (283 mg, quantitative amount) was obtained through use of 1-(6-methoxy-3-pyridyl)-5-phenylpyrazole-3-carboxylic acid (200 mg) obtained in Referential Example 41 and 4-cyclobutylpiperazine hydrochloride (173 mg) obtained in Referential Example 110.

2) Hydrochloric Acid Salt of the Title Compound

In a manner similar to that employed in step 2) of Example 29, a hydrochloric acid salt of the title compound was obtained as a solid (254 mg, 83%) through use of the above-obtained title compound (283 mg).

$^1$H-NMR (400 MHz, DMSO-$d_6$) δ: 1.69-1.79 (2H, m), 2.17 (2H, br), 2.37 (2H, br), 2.91 (2H, br), 3.35-3.37 (3H, m), 3.66-3.73 (2H, m), 3.88 (3H, s), 4.62 (1H, br d, J=13.4 Hz), 5.03 (1H, br d, J=13.4 Hz), 6.91 (1H, d, J=8.8 Hz), 7.02 (1H, s), 7.29-7.32 (2H, m), 7.39-7.41 (3H, m), 7.70 (1H, dd, J=8.8, 2.7 Hz), 8.19 (1H, d, J=2.7 Hz), 10.46 (1H, br).

LC-MS m/z: 418 (M+H)$^+$.

Elementary analysis: as $C_{24}H_{27}N_5O_2 \cdot HCl \cdot 0.25H_2O$
Calculated: C, 62.87; H, 6.27; N, 15.28; Cl, 7.73.
Found: C, 63.05; H, 6.25; N, 15.05; Cl, 7.69.

Example 74

1-[1-(6-Methoxy-3-pyridazinyl)-5-phenylpyrazole-3-carbonyl]-4-methylpiperazine

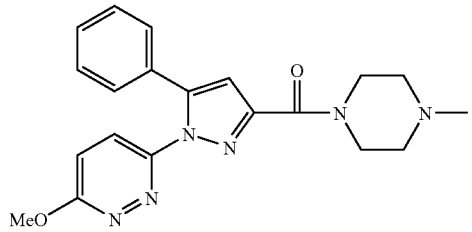

In a manner similar to that employed in step 1) of Example 1, the title compound was obtained as a solid (150 mg, 78%) through use of 1-(6-methoxy-3-pyridazinyl)-5-phenylpyrazole-3-carboxylic acid (150 mg) obtained in Referential Example 43 and N-methylpiperazine (0.068 mL).

$^1$H-NMR (400 MHz, DMSO-$d_6$) δ: 2.21 (3H, s), 2.35-2.38 (4H, m), 3.66 (2H, br s), 3.89 (2H, br s), 4.02 (3H, s), 6.96 (1H, s), 7.29-7.31 (2H, m), 7.37-7.39 (3H, m), 7.48 (1H, d, J=9.3 Hz), 7.99 (1H, d, J=9.3 Hz).

LC-MS m/z: 379(M+H)$^+$.

Elementary analysis: as $C_{20}H_{22}N_6O_2 \cdot 0.25H_2O$
Calculated: C, 62.73; H, 5.92; N, 21.95.
Found: C, 62.69; H, 5.81; N, 21.66.

Example 75

1-[1-(6-Methoxy-3-pyridyl)-5-phenylpyrazole-3-carbonyl]-4-ethylpiperazine hydrochloride

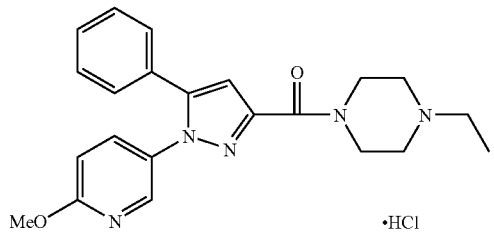

In a manner similar to that employed in step 1) of Example 1, 1-[1-(6-methoxy-3-pyridyl)-5-phenylpyrazole-3-carbo-nyl]-4-ethylpiperazine was produced through use of 1-(6-methoxy-3-pyridyl)-5-phenylpyrazole-3-carboxylic acid (100 mg) obtained in Referential Example 41 and N-ethylpiperazine (52 μL). In a manner similar to that employed in step 2) of Example 29, the title compound was obtained as a solid (111 mg, 76%) by use of the above-obtained product.

$^1$H-NMR (400 MHz, DMSO-$d_6$) δ: 1.27 (3H, t, J=7.1 Hz), 3.05 (2H, br m), 3.13 (2H, br m), 3.33 (3H, s), 3.33 (1H, br m), 3.54 (2H, br m), 3.71 (1H, br m), 3.88 (3H, s), 4.60 (1H, d, J=12.5 Hz), 5.03 (1H, J=13.5 Hz), 6.90 (1H, d, J=8.8 Hz), 7.01 (1H, s), 7.27-7.31 (2H, m), 7.38-7.41 (3H, m), 7.70 (1H, dd, J=8.8, 2.7 Hz), 8.19 (1H, d, J=2.7 Hz), 11.13 (1H, br s).

LC-MS m/z: 392(M+H)$^+$.

Elementary analysis: as $C_{22}H_{25}N_5O_2 \cdot HCl \cdot 0.75H_2O$
Calculated: C, 59.86; H, 6.28; N, 15.87; Cl, 8.03.
Found: C, 59.89; H, 6.20; N, 15.81; Cl, 8.08.

Example 76

1-[5-(4-Fluorophenyl)-1-(6-methoxy-3-pyridyl)pyrazole-3-carbonyl]-4-ethylpiperazine hydrochloride

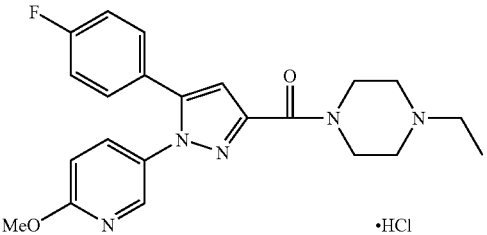

In a manner similar to that employed in step 1) of Example 1, 1-[5-(4-fluorophenyl)-1-(6-methoxy-3-pyridyl)pyrazole-3-carbonyl]-4-ethylpiperazine was produced through use of 5-(4-fluorophenyl)-1-(6-methoxy-3-pyridyl)pyrazole-3-carboxylic acid (150 mg) obtained in Referential Example 136 and N-ethylpiperazine (73 μL). In a manner similar to that employed in step 2) of Example 29, the title compound was obtained as a solid (96 mg, 45%) by use of the above-obtained product.

$^1$H-NMR (400 MHz, DMSO-$d_6$) δ: 1.26 (3H, t, J=7.1 Hz), 3.04 (2H, br m), 3.12 (2H, br m), 3.33 (3H, s), 3.33 (1H, br m), 3.53 (2H, br m), 3.71 (1H, br m), 3.88 (3H, s), 4.60 (1H, br m), 5.00 (1H, br m), 6.91 (1H, d, J=8.8 Hz), 7.02 (1H, s), 7.25 (2H, t, J=8.8 Hz), 7.34-7.37 (2H, m), 7.70 (1H, dd, J=8.8, 2.7 Hz), 8.21 (1H, d, J=2.7 Hz), 11.10 (1H, br s).

LC-MS m/z: 410(M+H)$^+$.

Elementary analysis: as $C_{22}H_{24}FN_5O_2 \cdot HCl \cdot 0.5H_2O$
Calculated: C, 58.08; H, 5.76; N, 15.39; F, 4.18; Cl, 7.79.
Found: C, 57.90; H, 5.82; N, 15.12; F, 4.07; Cl, 7.64.

Example 77

1-[1-(6-Methoxy-3-pyridyl)-5-phenylpyrazole-3-carbonyl]-3-dimethylaminomethylazetidine

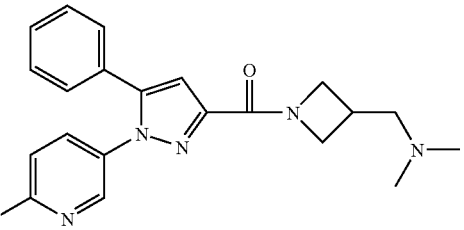

In a manner similar to that employed in step 1) of Example 1, the title compound was obtained as a solid (17 mg, 22%) through use of 1-(6-methoxy-3-pyridyl)-5-phenylpyrazole-3-carboxylic acid (60 mg) obtained in Referential Example 41 and 3-dimethylaminomethylazetidine hydrochloride (40 mg) obtained in Referential Example 112.

$^1$H-NMR (400 MHz, CDCl$_3$) δ: 2.23 (6H, s), 2.52 (1H, dd, J=12.2, 6.8 Hz), 2.60 (1H, dd, J=12.2, 8.3 Hz), 2.86 (1H, m), 3.85 (1H, dd, J=10.3, 5.6 Hz), 3.94 (3H, s), 4.28-4.33 (2H, m), 4.74 (1H, t, J=8.3 Hz), 6.71 (1H, d, J=8.8 Hz), 7.01 (1H, s), 7.21-7.25 (2H, m), 7.32-7.35 (3H, m), 7.46 (1H, dd, J=8.8, 2.7 Hz), 8.12 (1H, d, J=2.7 Hz).

MS (ESI) m/z: 392(M+H)$^+$.

Elementary analysis: as C$_{20}$H$_{22}$N$_6$O$_2$0.5H$_2$O
Calculated: C, 65.98; H, 6.54; N, 17.48.
Found: C, 65.92; H, 6.36; N, 17.37.

Example 78

N-[1-[1-(6-Methoxy-3-pyridyl)-5-phenylpyrazole-3-carbonyl]azetidin-3-yl]-N-methylcarbamic acid tert-butyl ester

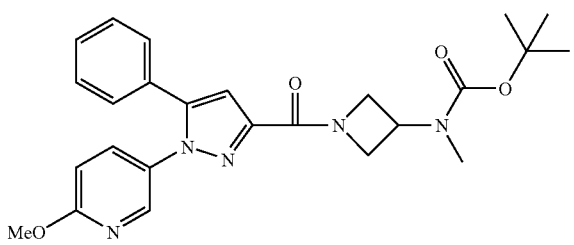

In a manner similar to that employed in step 1) of Example 1, the title compound was obtained as an amorphous product (453 mg, 96%) through use of 1-(6-methoxy-3-pyridyl)-5-phenylpyrazole-3-carboxylic acid (300 mg) obtained in Referential Example 41 and azetidin-3-yl-N-methylcarbamic acid tert-butyl ester (250 mg).

$^1$H-NMR (400 MHz, CDCl$_3$) δ: 1.47 (9H, s), 1.56 (9H, s), 2.95 (3H, s), 3.95 (3H, s), 4.24 (1H, m), 4.41 (1H, m), 4.64 (1H, m), 4.84 (1H, m), 6.72 (1H, d, J=8.8 Hz), 7.03 (1H, s), 7.22-7.24 (2H, m), 7.33-7.35 (3H, m), 7.46 (1H, dd, J=8.8, 2.5 Hz), 8.13 (1H, d, J=2.7 Hz).

MS (ESI) m/z: 464(M+H)$^+$.

Example 79

1-[1-(6-Methoxy-3-pyridyl)-5-phenylpyrazole-3-carbonyl]-3-methylaminoazetidine

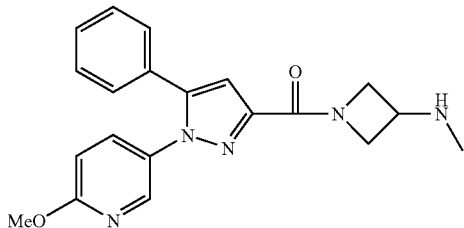

In a manner similar to that employed in step 2) of Example 49, the title compound was obtained as a solid (255 mg, 72%) through use of N-[1-[1-(6-methoxy-3-pyridyl)-5-phenylpyrazole-3-carbonyl]azetidin-3-yl]-N-methylcarbamic acid tert-butyl ester (450 mg) obtained in Example 78.

$^1$H-NMR (400 MHz, CDCl$_3$) δ: 3.51 (3H, s), 3.66 (1H, m), 3.92 (1H, m), 3.95 (3H, s), 4.32 (1H, dd, J=10.6, 4.9 Hz), 4.39 (1H, dd, J=10.6, 7.4 Hz), 4.79 (1H, dd, J=9.5, 7.3 Hz), 6.71 (1H, d, J=8.8 Hz), 7.02 (1H, s), 7.21-7.25 (2H, m), 7.32-7.35 (3H, m), 7.45 (1H, dd, J=8.8, 2.7 Hz), 8.14 (1H, d, J=2.2 Hz).

MS (FAB) m/z: 364(M+H)$^+$.

Example 80

4-[1-(6-Methoxy-3-pyridyl)-5-(2-pyridyl)pyrazole-3-carbonyl]piperazine-1-carboxylic acid tert-butyl ester

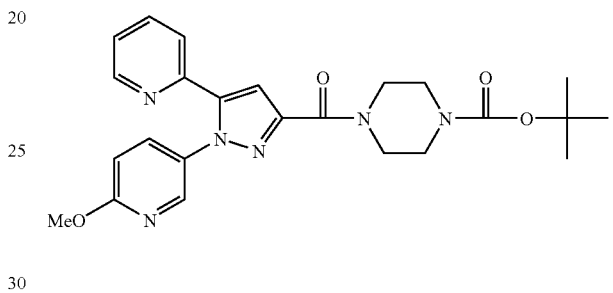

In a manner similar to that employed in Example 20, the title compound was obtained as an amorphous product (0.407 g, quantitative amount) through use of 1-(6-methoxy-3-pyridyl)-5-(2-pyridyl)pyrazole-3-carboxylic acid (0.252 g) obtained in Referential Example 33 and piperazine-1-carboxylic acid tert-butyl ester (0.311 g).

$^1$H-NMR (400 MHz, CDCl$_3$) δ: 1.48 (9H, s), 3.52 (4H, br), 3.79 (2H, br), 3.94 (3H, s), 4.08 (2H, br), 6.75 (1H, d, J=8.7 Hz), 7.15 (1H, s), 7.20-7.30 (1H, m), 7.42 (1H, d, J=7.8 Hz), 7.58 (1H, dd, J=8.7, 2.6 Hz), 7.71 (1H, dt, J=7.8, 1.5 Hz), 8.12 (1H, d, J=2.6 Hz), 8.45-8.55 (1H, m).

MS (FAB) m/z: 465(M+H)$^+$.

Example 81

4-[1-(6-Methoxy-3-pyridyl)-5-(2-pyridyl)pyrazole-3-carbonyl]piperazine

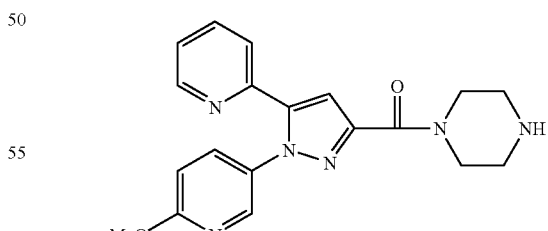

1) The Title Compound

In a manner similar to that employed in step 2) of Example 49, the title compound was obtained as an oily product (0.281 g, 91%) through use of 4-[1-(6-methoxy-3-pyridyl)-5-(2-pyridyl)pyrazole-3-carbonyl]piperazine-1-carboxylic acid tert-butyl ester (0.396 g) obtained in Example 80.

$^1$H-NMR (400 MHz, CDCl$_3$) δ: 2.85-3.02 (4H, m), 3.79 (2H, br), 3.94 (3H, s), 4.03 (2H, br), 6.75 (1H, d, J=8.8 Hz), 7.11 (1H, s), 7.20-7.30 (1H, m), 7.40 (1H, d, J=7.8 Hz), 7.59 (1H, dd, J=7.8, 2.7 Hz), 7.70 (1H, dt, J=7.8, 1.7 Hz), 8.11 (1H, d, J=2.7 Hz), 8.45-8.55 (1H, m).

LC-MS m/z: 365(M+H)$^+$.

2) Hydrochloric Acid Salt of the Title Compound

In a manner similar to that employed in step 2) of Example 1, a hydrochloric acid salt of the title compound was obtained as a solid (0.237 g, 69%) through use of the above-obtained title compound (0.281 g).

$^1$H-NMR (400 MHz, DMSO-d$_6$) δ: 3.18 (4H, br), 3.88 (3H, s), 3.89 (2H, br), 4.25 (2H, br), 6.88 (1H, d, J=9.1 Hz), 7.26 (1H, s), 7.32-7.40 (1H, m), 7.65-7.75 (2H, m), 7.86 (1H, dt, J=7.8, 2.5 Hz), 8.19 (1H, d, J=2.5 Hz), 8.42-8.50 (1H, m), 9.25 (2H, br).

LC-MS m/z: 365(M+H)$^+$.

Example 82

4-[1-(6-Methoxy-3-pyridyl)-5-(2-pyridyl)pyrazole-3-carbonyl]-2-oxopiperazine

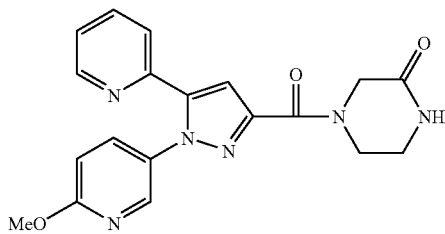

In a manner similar to that employed in Example 20, the title compound was obtained as a solid (0.210 g, 66%) through use of 1-(6-methoxy-3-pyridyl)-5-(2-pyridyl)pyrazole-3-carboxylic acid (0.248 g) obtained in Referential Example 33 and piperazin-2-one (0.129 g).

$^1$H-NMR (400 MHz, CDCl$_3$) δ: 3.45-3.60 (2H, m), 3.96 (3H, s), 4.03 (1H, br), 4.35 (2H, br), 4.88 (1H, br), 6.25-6.40 (1H, br), 6.72-6.80 (1H, br), 7.15-7.30 (2H, m), 7.37-7.75 (3H, m), 8.05-8.16 (1H, br), 8.51 (1H, d, J=4.4 Hz).

MS (ESI) m/z: 379(M+H)$^+$.

Elementary analysis: as C$_{19}$H$_{18}$N$_6$O$_3$·0.3H$_2$O

Calculated: C, 59.46; H, 4.88; N, 21.90.

Found: C, 59.35; H, 4.71; N, 21.57.

Example 83

1-[1-(6-Methoxy-3-pyridyl)-5-(2-pyridyl)pyrazole-3-carbonyl]-3,5-dimethylpiperazine

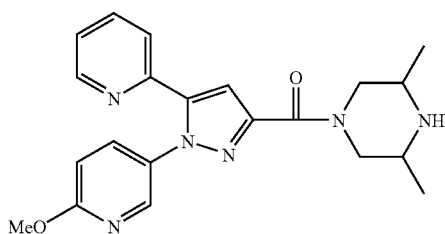

In a manner similar to that employed in Example 20, the title compound was obtained as a solid (0.142 g, 72%) through use of 1-(6-methoxy-3-pyridyl)-5-(2-pyridyl)pyrazole-3-carboxylic acid (0.150 g) obtained in Referential Example 33 and 2,6-dimethylpiperazine (91.4 mg).

$^1$H-NMR (400 MHz, CDCl$_3$) δ: 1.05 (3H, d, J=6.1 Hz), 1.14 (3H, d, J=6.1 Hz), 2.40 (1H, t-like, J=12.7 Hz), 2.76 (1H, t-like, J=12.7 Hz), 2.85-3.00 (2H, m), 3.95 (3H, s), 4.67 (2H, d-like, J=8.8 Hz), 7.09 (1H, s), 7.20-7.30 (1H, m), 7.41 (1H, d, J=8.1 Hz), 7.57 (1H, dd, J=8.8, 2.7 Hz), 7.70 (1H, dt, J=8.1, 2.0 Hz), 8.11 (1H, d, J=2.7 Hz), 8.49-8.55 (1H, m).

MS (ESI) m/z: 393(M+H)$^+$.

Example 84

1-[1-(6-Methoxy-3-pyridyl)-5-(2-pyridyl)pyrazole-3-carbonyl]-3-dimethylaminoazetidine

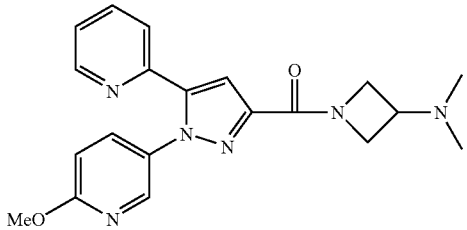

In a manner similar to that employed in Example 20, the title compound was obtained as a solid (0.248 g, 90%) through use of 1-(6-methoxy-3-pyridyl)-5-(2-pyridyl)pyrazole-3-carboxylic acid (0.216 g) obtained in Referential Example 33 and 3-dimethylaminoazetidine hydrochloride (0.252 g) obtained in Referential Example 102.

$^1$H-NMR (400 MHz, CDCl$_3$) δ: 2.21 (6H, s), 3.05-3.25 (1H, m), 3.96 (3H, s), 4.00-4.10 (1H, m), 4.17-4.28 (1H, m), 4.35-4.47 (1H, m), 4.60-4.72 (1H, m), 6.74 (1H, d, J=8.9 Hz), 7.17-7.30 (2H, m), 7.44 (1H, d, J=7.3 Hz), 7.50-7.60 (1H, m), 7.67-7.78 (1H, m), 8.15 (1H, d, J=2.5 Hz), 8.50 (1H, br d, J=3.5 Hz).

MS (ESI) m/z: 379(M+H)$^+$.

Elementary analysis: as C$_{20}$H$_{22}$N$_6$O$_2$:

Calculated: C, 63.48; H, 5.86; N, 22.21.

Found: C, 63.34; H, 5.84; N, 22.31.

Example 85

1-[5-(4-Fluorophenyl)-1-(6-methoxy-3-pyridyl)pyrazole-3-carbonyl]piperidine-4-carboxylic acid ethyl ester

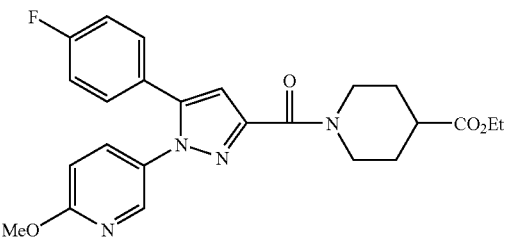

In a manner similar to that employed in Example 20, the title compound was obtained as an oily product (262 mg, 90%) through use of 5-(4-fluorophenyl)-1-(6-methoxy-3-pyridyl)pyrazole-3-carboxylic acid (0.2 g) obtained in Referential Example 136 and isonipecotic acid ethyl ester (0.1 g).

$^1$H-NMR (400 MHz, CDCl$_3$) δ: 1.27 (3H, t, J=7.3 Hz), 1.75-1.90 (2H, m), 1.90-2.10 (2H, m), 2.58-2.66 (1H, m), 2.98-3.10 (1H, m), 3.32-3.43 (1H, m), 3.95 (3H, s), 4.16 (2H, q, J=7.3 Hz), 4.52-4.60 (1H, m), 4.70-4.80 (1H, m), 6.73 (1H, d, J=8.8 Hz), 6.87 (1H, s), 7.02-7.26 (2H, m), 7.48 (1H, dd, J=8.8, 2.7 Hz), 8.09 (1H, d, J=2.7 Hz).

MS (EI) m/z: 452(M$^+$).

Example 86

1-[5-(4-Fluorophenyl)-1-(6-methoxy-3-pyridyl)pyrazole-3-carbonyl]piperidine-4-carboxylic acid

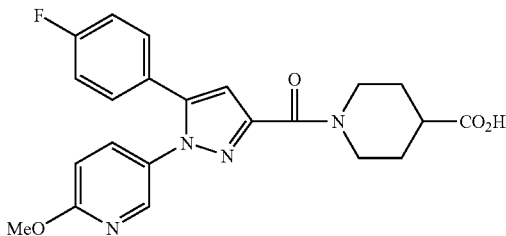

In a manner similar to that employed in Referential Example 4, the title compound was obtained as an amorphous product (170 mg, 69%) through use of 1-[5-(4-fluorophenyl)-1-(6-methoxy-3-pyridyl)pyrazole-3-carbonyl]piperidine-4-carboxylic acid ethyl ester (262 mg) obtained in Example 85.

$^1$H-NMR (400 MHz, CDCl$_3$) δ: 1.77-1.94 (2H, m), 2.00-2.16 (2H, m), 2.65-2.75 (1H, m), 3.05-3.15 (1H, m), 3.35-3.45 (1H, m), 3.95 (3H, s), 4.55-4.60 (1H, m), 4.72-4.76 (1H, m), 6.74 (1H, d, J=8.8 Hz), 6.88 (1H, s), 7.02-7.07 (2H, m), 7.19-7.24 (2H, m), 7.48 (1H, dd, J=8.8, 2.4 Hz), 8.11 (1H, d, J=2.4 Hz).

MS (EI) m/z: 424(M$^+$).
Elementary analysis: as C$_{22}$H$_{21}$FN$_4$O$_4$·0.75H$_2$O
Calculated: C, 60.36; H, 5.18; N, 12.80.
Found: C, 60.24; H, 5.01; N, 12.47.

Example 87

1-[5-(4-Fluorophenyl)-1-(6-methoxy-3-pyridyl)pyrazole-3-carbonyl]piperidine-3-carboxylic acid ethyl ester

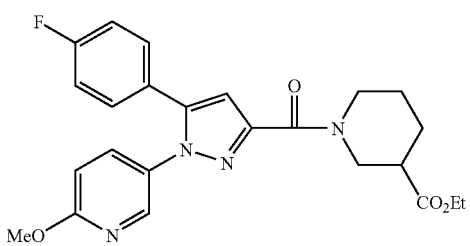

In a manner similar to that employed in Example 20, the title compound was obtained as an oily product (280 mg, 97%) through use of 5-(4-fluorophenyl)-1-(6-methoxy-3-pyridyl)pyrazole-3-carboxylic acid (0.2 g) obtained in Referential Example 136 and nipecotic acid ethyl ester (0.1 g).

$^1$H-NMR (400 MHz, CDCl$_3$) δ: 1.21-1.30 (3H, m), 2.13-2.20 (1H, m), 2.56-2.75 (1H, m), 2.94-3.10 (1H, m), 3.21-3.30 (0.5×1H, m), 3.42-3.50 (0.5×1H, m), 3.94 (3H, s), 4.10-4.20 (2H, m), 4.47-4.55 (0.5×1H, m), 4.67-4.75 (0.5×1H, m), 4.80-4.93 (1H, m), 6.73 (1H, d, J=8.8 Hz), 6.87 (1H, s), 7.05 (2H, t, J=8.8 Hz), 7.20-7.27 (2H, m), 7.47-7.55 (1H, m), 8.10 (1H, d, J=2.7 Hz).

MS (EI) m/z: 452(M$^+$).

Example 88

1-[5-(4-Fluorophenyl)-1-(6-methoxy-3-pyridyl)pyrazole-3-carbonyl]piperidine-3-carboxylic acid

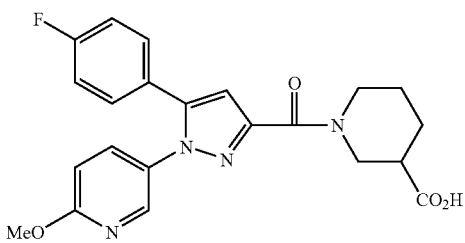

In a manner similar to that employed in Referential Example 4, the title compound was obtained as an amorphous product (150 mg, 57%) through use of 1-[5-(4-fluorophenyl)-1-(6-methoxy-3-pyridyl)pyrazole-3-carbonyl]piperidine-3-carboxylic acid ethyl ester (280 mg) obtained in Example 87.

$^1$H-NMR (400 MHz, CDCl$_3$) δ: 3.94 (3H, s), 6.73 (1H, d, J=8.8 Hz), 6.88 (1H, s), 7.01-7.07 (2H, m), 7.20-7.26 (2H, m), 7.48 (1H, dd, J=8.8, 2.9 Hz), 8.11 (1H, d, J=2.9 Hz).

MS (EI) m/z: 424(M$^+$).
Elementary analysis: as C$_{22}$H$_{21}$FN$_4$O$_4$·0.75H$_2$O
Calculated: C, 60.36; H, 5.18; N, 12.80.
Found: C, 60.49; H, 5.04; N, 12.47.

Example 89

1-[5-(4-Fluorophenyl)-1-(6-methoxy-3-pyridyl)pyrazole-3-carbonyl]piperidine-2-carboxylic acid ethyl ester

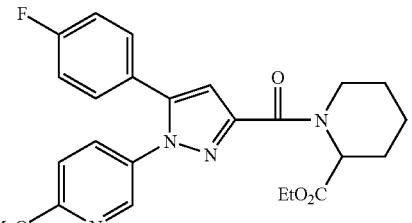

In a manner similar to that employed in Example 20, the title compound was obtained as an oily product (270 mg, 93%) through use of 5-(4-fluorophenyl)-1-(6-methoxy-3-pyridyl)pyrazole-3-carboxylic acid (0.2 g) obtained in Referential Example 136 and nipecotic acid ethyl ester (0.1 g).

$^1$H-NMR (400 MHz, CDCl$_3$) δ: 1.24 (0.5×3H, t, J=7.1 Hz), 1.30 (0.5×3H, t, J=7.1 Hz), 2.26-2.40 (1H, m), 2.95-3.05 (0.5×1H, m), 3.32-3.40 (0.5×1H, m), 3.94 (0.5×3H, s), 3.95 (0.5×3H, s), 4.19-4.28 (2H, m), 4.67-4.73 (0.5×1H, m), 4.80-4.85 (0.5×1H, m), 5.51 (0.5×1H, d, J=4.6 Hz), 5.81 (0.5×1H, d, J=4.6 Hz), 6.71 (0.5×1H, d, J=7.1 Hz), 6.72 (0.5×1H, d, J=7.1 Hz), 6.89 (0.5×1H, s), 6.92 (0.5×1H, s), 7.00-7.07 (2H, m), 7.17-7.21 (2H, m), 7.44 (0.5×1H, dd, J=8.8, 2.7 Hz), 7.50 (0.5×1H, dd, J=8.8, 2.7 Hz), 8.05 (0.5×1H, d, J=2.7 Hz), 8.10 (0.5×1H, d, J=2.7 Hz).

MS (EI) m/z: 452(M+).

Example 90

1-[5-(4-Fluorophenyl)-1-(6-methoxy-3-pyridyl)pyrazole-3-carbonyl]piperidine-2-carboxylic acid

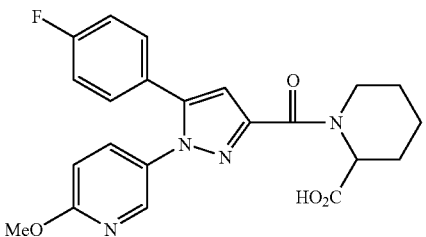

In a manner similar to that employed in Referential Example 4, the title compound was obtained as an amorphous product (130 mg, 51%) through use of 1-[5-(4-fluorophenyl)-1-(6-methoxy-3-pyridyl)pyrazole-3-carbonyl]piperidine-2-carboxylic acid ethyl ester (270 mg) obtained in Example 89.

$^1$H-NMR (400 MHz, CDCl$_3$) δ: 3.95 (3H, s), 4.67-4.92 (1H, m), 5.47-5.65 (1H, m), 6.73-6.75 (1H, m), 6.91-7.24 (5H, m), 7.42-7.53 (1H, m), 8.08-8.11 (1H, m).

MS (EI) m/z: 424(M+).

Elementary analysis: as C$_{22}$H$_{21}$FN$_4$O$_4$·H$_2$O

Calculated: C, 59.74; H, 5.24; N, 12.67.

Found: C, 59.85; H, 5.00; N, 12.26.

Example 91

1-[1-(6-Methoxy-3-pyridyl)-5-phenylpyrazole-3-carbonyl]-2-hydroxymethylpiperidine

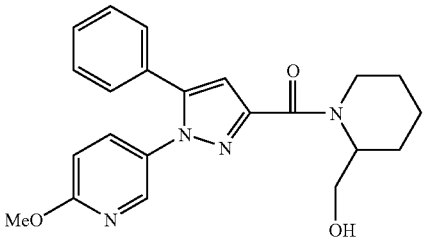

In a manner similar to that employed in Example 20, the title compound was obtained as an amorphous product (220 mg, 48%) through use of 1-(6-methoxy-3-pyridyl)-5-phenylpyrazole-3-carboxylic acid (300 mg) obtained in Referential Example 41 and 2-hydroxymethylpiperidine (234 mg).

$^1$H-NMR (400 MHz, CDCl$_3$) δ: 1.55-1.90 (6H, m), 3.93 (0.5×3H, s, and 0.5×3H, s), 6.72 (1H, d, J=8.8 Hz), 6.92 (1H, br s), 7.31-7.36 (3H, m), 7.46 (1H, dd, J=8.8, 2.4 Hz), 8.09 (1H, br s).

MS (FAB) m/z: 393(M+H)+.

Example 92

1-[1-(6-Methoxy-3-pyridyl)-5-(2-pyridyl)pyrazole-3-carbonyl]-2-hydroxymethylpiperidine

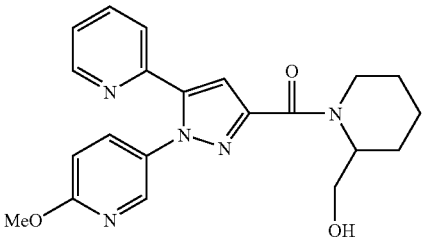

In a manner similar to that employed in Example 20, the title compound was obtained as an amorphous product (250 mg, 55%) through use of 1-(6-methoxy-3-pyridyl)-5-(2-pyridyl)pyrazole-3-carbonyl (300 mg) obtained in Referential Example 33 and 2-hydroxymethylpiperidine (234 mg).

$^1$H-NMR (400 MHz, CDCl$_3$) δ: 1.52-1.88 (6H, m), 3.95 (3H, s), 6.75 (1H, dd, J=8.8, 0.7 Hz), 7.12 (1H, br s), 7.22-7.26 (1H, m), 7.42 (1H, d, J=8.1 Hz), 7.57 (1H, dd, J=8.8, 2.7 Hz), 7.69-7.73 (1H, m), 8.09 (1H, br s), 8.51-8.53 (1H, m).

MS (FAB) m/z: 394 (M+H)+.

Example 93

1-[1-(6-Methoxy-3-pyridyl)-5-phenylpyrazole-3-carbonyl]piperidine-2-carboxamide

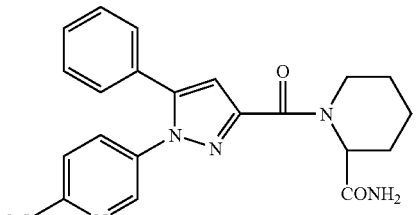

In a manner similar to that employed in Example 20, the title compound was obtained as an amorphous product (270 mg, 58%) through use of 1-(6-methoxy-3-pyridyl)-5-phenylpyrazole-3-carboxylic acid (300 mg) obtained in Referential Example 41 and piperidine-2-carboxamide (131 mg) obtained in Referential Example 131.

$^1$H-NMR (400 MHz, CDCl$_3$) δ: 1.50-1.95 (6H, m), 2.30-2.47 (1H, m), 2.80-2.91 (0.5×1H, m), 3.15-3.28 (0.5×1H, m), 3.94 (3H, s), 4.68-4.88 (2H, m), 5.30-5.65 (2H, m), 6.40 (0.5×1H, br s), 6.70-6.74 (1H, m), 6.93 (1H, d, J=14 Hz), 8.09 (0.5×1H, br s), 8.13 (0.5×1H, br s).

MS (EI) m/z: 405(M+).

Example 94

1-[1-(6-Methoxy-3-pyridyl)-5-phenylpyrazole-3-carbonyl]piperidine-2-carboxylic acid methylamide

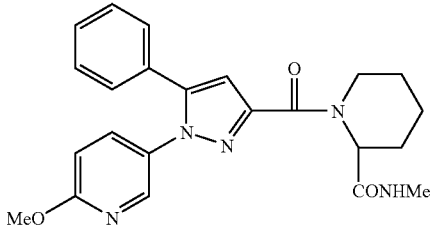

In a manner similar to that employed in Example 20, the title compound was obtained as an amorphous product (150 mg, 32%) through use of 1-(6-methoxy-3-pyridyl)-5-phenylpyrazole-3-carboxylic acid (300 mg) obtained in Referential Example 41 and piperidine-2-carboxylic acid methylamide (145 mg) obtained in Referential Example 132.

$^1$H-NMR (400 MHz, CDCl$_3$) δ: 1.50-1.95 (6H, m), 2.33-2.48 (1H, m), 2.83 (0.5×3H, s), 2.84 (0.5×3H, s), 3.10-3.20 (0.5×1H, m), 3.94 (3H, s), 4.60-4.82 (1H, m), 5.30-5.40 (1H, m), 6.42 (0.5×1H, br s), 6.72 (1H, d, J=8.8 Hz), 6.92 (1H, d, J=9.0 Hz), 8.06 (0.5×1H, br s), 8.14 (0.5×1H, br s).

MS (EI) m/z: 419(M$^+$).

Elementary analysis: as C$_{23}$H$_{25}$N$_5$O$_3$.0.3CHCl$_3$
Calculated: C, 61.46; H, 5.60; N, 15.38.
Found: C, 61.06; H, 5.68; N, 15.08.

Example 95

1-[1-(6-Methoxy-3-pyridyl)-5-phenylpyrazole-3-carbonyl]piperidine-2-carboxylic acid dimethylamide

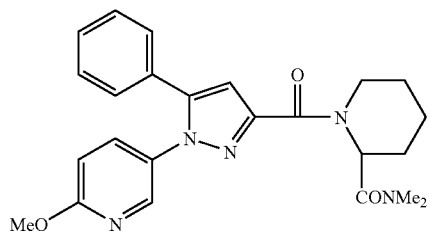

In a manner similar to that employed in Example 20, the title compound was obtained as an amorphous product (194 mg, 42%) through use of 1-(6-methoxy-3-pyridyl)-5-phenylpyrazole-3-carboxylic acid (300 mg) obtained in Referential Example 41 and piperidine-2-carboxylic acid dimethylamide (159 mg) obtained in Referential Example 133.

$^1$H-NMR (400 MHz, CDCl$_3$) δ: 1.52-2.15 (7H, m), 2.98 (3H, s), 3.12 (3H, s), 3.55-3.70 (1H, m), 3.94 (3H, s), 4.70-4.85 (1H, m), 6.72 (1H, d, J=8.8 Hz), 6.88 (1H, s), 7.20-7.40 (4H, m), 7.49 (1H, dd, J=8.8, 2.7 Hz), 8.10-8.13 (1H, m).

MS (EI) m/z: 433(M$^+$).

Elementary analysis: as C$_{24}$H$_{27}$N$_5$O$_3$.0.75H$_2$O
Calculated: C, 64.48; H, 6.43; N, 15.67.
Found: C, 64.11; H, 6.09; N, 15.58.

Example 96

1-[1-(6-Methoxy-3-pyridyl)-5-(4-methylthio-2-pyridyl)pyrazole-3-carbonyl]piperidine

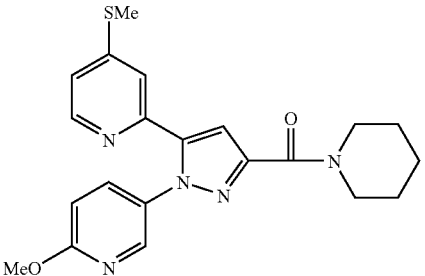

In a manner similar to that employed in step 1) of Example 1, the title compound was obtained as a solid (0.870 g, 91%) through use of 1-(6-methoxy-3-pyridyl)-5-(4-methylthio-2-pyridyl)pyrazole-3-carboxylic acid (0.80 g) obtained in Referential Example 118 and piperidine (0.254 mL).

$^1$H-NMR (400 MHz, CDCl$_3$) δ: 1.64-1.69 (6H, m), 2.44 (3H, s), 3.75-3.76 (2H, m), 3.89-3.92 (2H, m), 3.95 (3H, s), 6.75 (1H, d, J=8.8 Hz), 7.02-7.04 (1H, m), 7.05 (1H, s), 7.22 (1H, d, J=1.6 Hz), 7.59-7.62 (1H, m), 8.12 (1H, d, J=2.4 Hz), 8.27 (1H, d, J=5.6 Hz).

MS (EI) m/z: 409(M$^+$).

Example 97

1-[5-(4-Methanesulfonyl-2-pyridyl)-1-(6-methoxy-3-pyridyl)pyrazole-3-carbonyl]piperidine

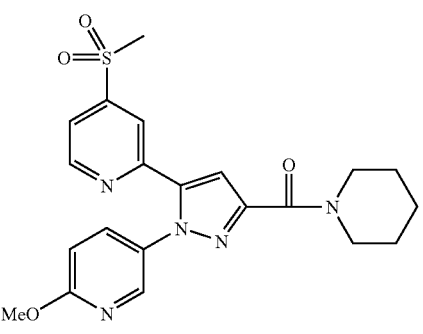

In a manner similar to that employed in Example 48, the title compound was obtained as a solid (0.935 g, quantitative amount) through use of 1-[1-(6-methoxy-3-pyridyl)-5-(4-methylthio-2-pyridyl)pyrazole-3-carbonyl]piperidine (0.869 g) obtained in Example 96 and 3-chloroperbenzoic acid (1.10 g).

$^1$H-NMR (400 MHz, CDCl$_3$) δ: 1.64-1.70 (6H, m), 3.08 (3H, s), 3.76 (2H, m), 3.92 (2H, m), 3.96 (3H, s), 6.80 (1H, d J=8.8 Hz), 7.22 (1H, s), 7.63 (1H, dd, J=8.8, 2.8 Hz), 7.69-7.71 (1H, m), 7.92-7.93 (1H, m), 8.10 (1H, d, J=2.8 Hz), 8.76 (1H, d, J=5.2 Hz).

MS (EI) M/z: 441(M$^+$).

Elementary analysis: as C$_{21}$H$_{23}$N$_5$O$_4$S.0.25H$_2$O
Calculated: C, 56.55%; H, 5.31%; N, 15.70%; S: 7.19%.
Found: C, 56.73%; H, 5.05%; N, 15.68%; S: 7.30%.

Example 98

1-[5-(4-Cyano-2-pyridyl)-1-(6-methoxy-3-pyridyl)pyrazole-3-carbonyl]piperidine

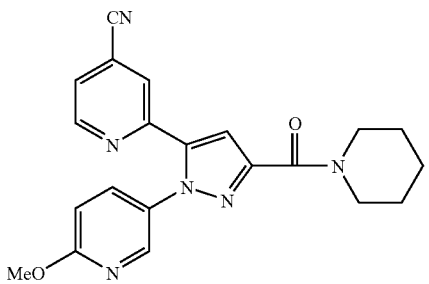

To a solution of 1-[5-(4-methanesulfonyl-2-pyridyl)-1-(6-methoxy-3-pyridyl)pyrazole-3-carbonyl]piperidine (0.60 g) obtained in Example 97 in N,N-dimethylformamide (12 mL), potassium cyanide (97.3 mg) was added at room temperature. The mixture was stirred at 120° C. for 37 hours, and then potassium cyanide (97.3 mg) was further added thereto. The mixture was further stirred at 120° C. for 4 hours, and then cooled in air. The reaction mixture was partitioned between saturated brine and ethyl acetate. The organic layer was dried over sodium sulfate anhydrate. After filtration, the solvent was removed under reduced pressure, and the residue was purified through silica gel column chromatography (chloroform-ethyl acetate), to thereby give the title compound as a solid (0.441 g, 84%).

$^1$H-NMR (400 MHz, CDCl$_3$) δ: 1.63-1.70 (6H, m), 3.75 (2H, m), 3.91 (2H, m), 3.97 (3H, s), 6.79 (1H, d, J=8.8 Hz), 7.17 (1H, s), 7.43-7.45 (1H, m), 7.58-7.61 (1H, m), 7.65 (1H, m), 8.10 (1H, d, J=2.4 Hz), 8.66-8.68 (1H, m).

MS (EI) m/z: 388(M$^+$).

Example 99

2-[1-(6-Methoxy-3-pyridyl)-3-(piperidine-1-carbonyl)pyrazol-5-yl]isonicotinic acid

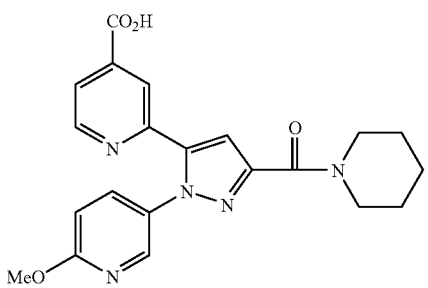

To a solution of 1-[5-(4-cyano-2-pyridyl)-1-(6-methoxy-3-pyridyl)pyrazole-3-carbonyl]piperidine (0.418 g) obtained in Example 98 in a mixture of methanol (8.4 mL) and tetrahydrofuran (8.4 mL), 1N aqueous sodium hydroxide (5.38 mL) was added at room temperature. The resultant mixture was stirred at 80° C. for 7 hours, and then cooled in air. The reaction mixture was partitioned between water and chloroform. The aqueous layer was neutralized to pH 6 with 1N aqueous hydrochloric acid. Chloroform was added for partitioning to the aqueous layer. The aqueous layer was further extracted with chloroform. The organic layers were combined and dried over sodium sulfate anhydrate. After filtration, the solvent was removed under reduced pressure, to thereby give the title compound as a solid (0.239 g, 52%).

$^1$H-NMR (400 MHz, CDCl$_3$) δ: 1.73 (6H, m), 3.84 (2H, m), 3.95 (3H, s), 4.04-4.06 (2H, m), 6.75 (1H, d, J=8.8 Hz), 7.39 (1H, s), 7.58-7.61 (1H, m), 7.80-7.82 (1H, m), 8.14 (1H, d, J=2.4 Hz), 8.26 (1H, m), 8.58 (1H, d, J=4.8 Hz).

MS (EI) m/z: 407(M$^+$).

Example 100

2-[1-(6-Methoxy-3-pyridyl)-3-(piperidine-1-carbonyl)pyrazol-5-yl]isonicotinamide

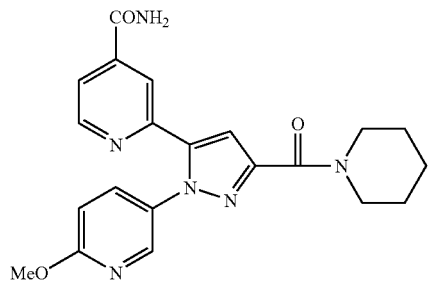

In a manner similar to that employed in step 1) of Example 1, the title compound was obtained as a solid (52.0 mg, 42%) through 2-[1-(6-methoxy-3-pyridyl)-3-(piperidine-1-carbonyl)pyrazol-5-yl]isonicotinic acid (0.120 g) obtained in Example 99 and 28% aqueous ammonia (53.7 mg).

$^1$H-NMR (400 MHz, DMSO-d$_6$) δ: 1.57-1.66 (6H, m), 3.63 (2H, m), 3.86 (2H, m), 3.89 (3H, s), 6.87 (1H, d, J=8.8 Hz), 7.25 (1H, s), 7.69-7.72 (2H, m), 7.78 (1H, s), 8.15-8.17 (2H, m), 8.29-8.30 (1H, m), 8.56 (1H, d, J=4.8 Hz).

MS (EI) m/z: 406(M$^+$).

Example 101

N-[1-(6-Methoxy-3-pyridyl)-5-phenylpyrazol-3-yl]methyl-2-oxopyrrolidine

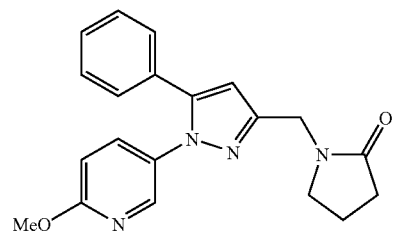

At room temperature, 60% sodium hydride (26 mg) was added to a solution of 2-pyrrolidinone (55 mg) in tetrahydrofuran (5 mL), and the mixture was stirred for 30 minutes. N,N-Dimethylformamide (2 mL) was added to the reaction mixture, and the mixture was stirred for 30 minutes. A solution of [1-(6-methoxy-3-pyridyl)-5-phenylpyrazol-3-yl]methyl methanesulfonate (195 mg) obtained in Referential Example 76 in tetrahydrofuran (3 mL) was added to the mixture, followed by stirring at room temperature for 16 hours. The solvent was removed under reduced pressure, and the residue was partitioned between water and ethyl acetate. The organic layer was washed with water and saturated brine, and then dried over sodium sulfate anhydrate. After filtration, the solvent was removed under reduced pressure. The residue was purified through silica gel thin-layer chromatography (chloroform-methanol), to thereby give the title compound as an oily product (140 mg, 74%).

$^1$H-NMR (400 MHz, CDCl$_3$) δ: 2.04 (2H, tt, J=7.8, 7.1 Hz), 2.45 (2H, t, J=7.8 Hz), 3.48 (2H, t, J=7.1 Hz), 3.93 (3H, s), 4.56 (2H, s), 6.44 (1H, s), 6.72 (1H, d, J=8.8 Hz), 7.17-7.23 (2H, m), 7.28-7.34 (3H, m), 7.51 (1H, dd, J=8.8, 2.7 Hz), 8.07 (1H, d, J=2.7 Hz).

MS (ESI) m/z: 349(M+H)$^+$.

Example 102

3-Methyl-1-[1-(6-methoxy-3-pyridyl)-5-phenylpyrazol-3-yl]methyl-2-oxoimidazolidine

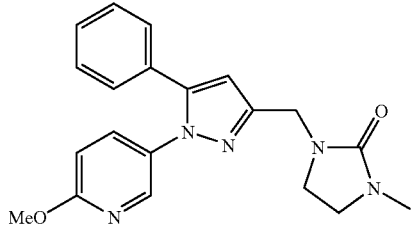

In a manner similar to that employed in Example 101, the title compound was obtained as crystals (167 mg, 77%) through use of 1-methylimidazolidin-2-one (71 mg) and [1-(6-methoxy-3-pyridyl)-5-phenylpyrazol-3-yl]methyl methanesulfonate (214 mg) obtained in Referential Example 76.

$^1$H-NMR (400 MHz, CDCl$_3$) δ: 2.83 (3H, s), 3.26-3.41 (4H, m), 3.92 (3H, s), 4.47 (2H, s), 6.48 (1H, s), 6.71 (1H, d, J=8.8 Hz), 7.17-7.23 (2H, m), 7.27-7.33 (3H, m), 7.51 (1H, dd, J=8.8, 2.7 Hz), 8.06 (1H, d, J=2.7 Hz).

MS (ESI) m/z: 364(M+H)$^+$.

Elementary analysis: as C$_{20}$H$_{21}$N$_5$O$_2$
Calculated: C, 66.10; H, 5.82; N, 19.27.
Found: C, 65.76; H, 5.80; N, 18.97.

Example 103

1-[1-(6-Methoxy-3-pyridyl)-5-phenylpyrazol-3-yl]methyl-2,5-dioxopyrrolidine

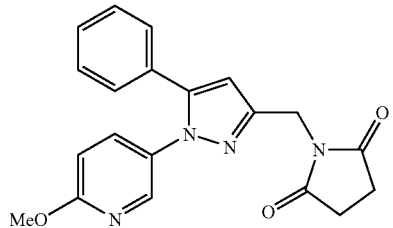

At room temperature, potassium carbonate (373 mg) was added to a solution of [1-(6-methoxy-3-pyridyl)-5-phenylpyrazol-3-yl]methyl methanesulfonate (194 mg) obtained in Referential Example 76 and succinimide (53 mg) in N,N-dimethylformamide (5 mL). The mixture was stirred at 60° C. for 16 hours, and then cooled in air. The reaction mixture was partitioned between water and ethyl acetate. The organic layer was washed with water and saturated brine, and then dried over sodium sulfate anhydrate. After filtration, the solvent was removed under reduced pressure. The residue was purified through silica gel thin-layer chromatography (chloroform-methanol), to thereby give the title compound as crystals (151 mg, 75%).

$^1$H-NMR (400 MHz, CDCl$_3$) δ: 2.77 (4H, s), 3.91 (3H, s), 4.81 (2H, s), 6.44 (1H, s), 6.69 (1H, d, J=8.8 Hz), 7.14-7.22 (2H, m), 7.27-7.33 (3H, m), 7.50 (1H, dd, J=8.8, 2.7 HZ), 8.03 (1H, d, J=2.7 Hz).

MS (ESI) m/z: 363(M+H)$^+$.

Elementary analysis: as C$_{20}$H$_{18}$N$_4$O$_3$.0.5H$_2$O
Calculated: C, 64.68; H, 5.16; N, 15.09.
Found: C, 64.74; H, 4.96; N, 14.85.

Example 104

1-[1-(6-Methoxy-3-pyridyl)-5-phenylpyrazole-3-carbonyl]-2,2-dimethyl-3-dimethylaminoazetidine

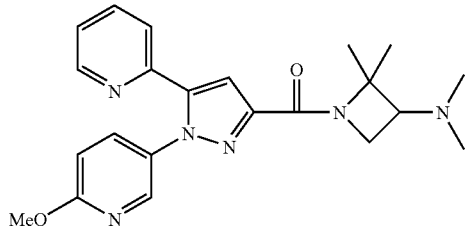

In a manner similar to that employed in step 1) of Example 1, the title compound was obtained as a solid (48 mg, 47%) through use of 1-(6-methoxy-3-pyridyl)-5-phenylpyrazole-3-carboxylic acid (74 mg) obtained in Referential Example 41 and (2,2-dimethylazetidin-3-yl)dimethylamine hydrochloride (50 mg) obtained in Referential Example 121.

$^1$H-NMR (400 MHz, CDCl$_3$) δ: 1.67 (3H, s), 1.70 (3H, s), 2.14 (6H, s), 2.69 (1H, dd, J=7.9, 15.4 Hz), 3.94 (3H, s), 4.21 (1H, dd, J=7.6, 10.0 Hz), 4.60 (1H, dd, J=7.8, 10.0 Hz), 6.71 (1H, d, J=8.8 Hz), 7.00 (1H, s), 7.20-7.23 (2H, m), 7.31-7.34 (3H, m), 7.42 (1H, dd, J=2.7, 8.8 Hz), 8.17 (1H, d, J=2.7 Hz).

MS (ESI) m/z: 406(M+H)$^+$.

Elementary analysis: as C$_{23}$H$_{27}$N$_5$O$_2$.0.25H$_2$O
Calculated: C, 67.38; H, 6.76; N, 17.08.
Found: C, 67.27; H, 6.67; N, 17.03.

Example 105

7-[1-(6-Methoxy-3-pyridyl)-5-phenylpyrazole-3-carbonyl]-4,7-diazaspiro[2.5]octane

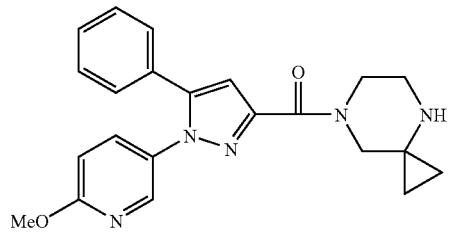

In a manner similar to that employed in step 1) of Example 1, the title compound was obtained as a solid (224 mg, 71%) through use of 1-(6-methoxy-3-pyridyl)-5-phenylpyrazole-3-carboxylic acid (240 mg) obtained in Referential Example 41 and 4,7-diazaspiro[2.5]octane hydrochloride (150 mg) obtained in Referential Example 122.

$^1$H-NMR (400 MHz, DMSO-$d_6$) δ: 0.48 (2H, m), 0.53 (2H, m), 2.82 (2H, t, J=5.1 Hz), 3.12 (2H, s), 3.42-3.55 (2H, m), 3.94 (3H, s), 6.87 (2H, m), 7.29-7.32 (2H, m), 7.38-7.40 (3H, m), 7.65 (1H, m), 8.12 (1H, br s).

MS (ESI) m/z: 390(M+H)$^+$.

Elementary analysis: as $C_{22}H_{23}N_5O_2$

Calculated: C, 67.85; H, 5.95; N, 17.98.

Found: C, 67.62; H, 5.96; N, 17.94.

Example 106

4-Methyl-7-[1-(6-methoxy-3-pyridyl)-5-phenylpyrazole-3-carbonyl]-4,7-diazaspiro[2.5]octane hydrochloride

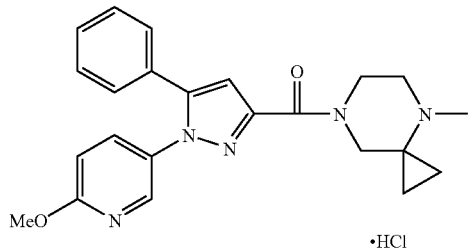

At room temperature, sodium cyanoborohydride (78 mg) and 37% aqueous formaldehyde solution (26 μL) were added to a solution of 7-[1-(6-methoxy-3-pyridyl)-5-phenylpyrazole-3-carbonyl]-4,7-diazaspiro[2.5]octane (120 mg) obtained in Example 105 in methanol (4 mL), and the mixture was stirred for 41.5 hours. Subsequently, sodium cyanoborohydride (78 mg) and 37% aqueous formaldehyde solution (26 μL) were added to the reaction mixture, and the mixture was stirred for 4 hours. The solvent was removed under reduced pressure, and the residue was partitioned between ethyl acetate and water. The organic layer was sequentially washed with saturated aqueous sodium hydrogencarbonate and saturated brine, and then dried over magnesium sulfate anhydrate. After filtration, the solvent was removed under reduced pressure. The residue was purified through silica gel column chromatography (chloroform-methanol), to thereby give 4-methyl-7-[1-(6-methoxy-3-pyridyl)-5-phenylpyrazole-3-carbonyl]-4,7-diazaspiro[2.5]octane. The thus-obtained product was dissolved in diethyl ether (4 mL). At 0° C., 1N HCl in ethanol (372 μL) was added to the solution, followed by stirring for 10 minutes. The solvent was removed under reduced pressure, and the residue was crystallized from diethyl ether-hexane, to thereby give the title compound as a solid (101 mg, 74%).

$^1$H-NMR (400 MHz, DMSO-$d_6$) δ: 0.94 (2H, m), 1.24 (2H, m), 2.85 (3H, br s), 3.25-3.40 (4H, m), 3.88 (3H, s), 4.06 (2H, m), 6.88 (1H, d, J=8.8 Hz), 6.96 (1H, s), 7.29 (2H, m), 7.38 (3H, m), 7.67 (1H, dd, J=9.0, 2.5 Hz), 8.14 (1H, s).

MS (ESI) m/z: 404(M+H)$^+$.

Elementary analysis: as $C_{23}H_{25}N_5O_2 \cdot HCl \cdot 0.25H_2O$

Calculated: C, 62.16; H, 6.01; N, 15.76; Cl, 7.98.

Found: C, 62.17; H, 5.90; N, 15.79; Cl, 7.98.

Example 107

1-[1-(6-Methoxy-3-pyridyl)-5-(2-pyridyl)pyrazole-3-carbonyl]-4-acetylpiperazine

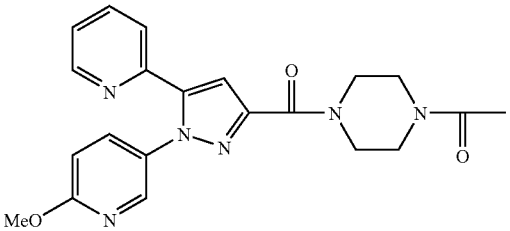

At 0° C., triethylamine (0.205 mL) and acetyl chloride (0.0447 mL) were added to a solution of 4-[1-(6-methoxy-3-pyridyl)-5-(2-pyridyl)pyrazole-3-carbonyl]piperazine hydrochloride (0.185 g) obtained in Example 81 in methylene chloride (5.0 mL). The mixture was stirred at room temperature for 1 hour. The reaction mixture was partitioned between water and chloroform. The aqueous layer was further extracted with chloroform, and the organic layers were combined, followed by washing with saturated brine and drying over sodium sulfate anhydrate. After filtration, the solvent was removed under reduced pressure. The residue was purified through silica gel column chromatography (chloroform-methanol), to thereby give the title compound as an amorphous product (0.147 g, 87%).

$^1$H-NMR (400 MHz, CDCl$_3$) δ: 2.13 (3H, br), 3.56 (2H, br), 3.65-3.90 (2H, br), 3.95 (3H, s), 4.06-4.25 (2H, m), 6.76 (1H, d, J=8.6 Hz), 7.13-7.20 (2H, m), 7.42 (1H, br), 7.58 (1H, br), 7.71 (1H, t-like, J=7.8 Hz), 8.10 (1H, br), 8.51 (1H, d, J=4.1 Hz).

LC-MS m/z: 407(M+H)$^+$.

Example 108

1-[1-(6-Methoxy-3-pyridyl)-5-(2-pyridyl)pyrazole-3-carbonyl]-5-oxo-1,4-diazepane

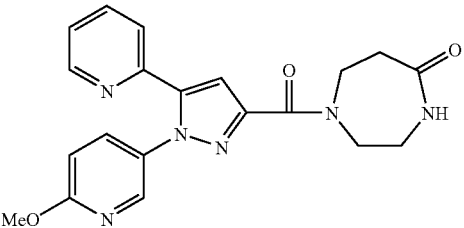

In a manner similar to that employed in Example 20, the title compound was obtained as a solid (0.223 g, 76%) through use of 1-(6-methoxy-3-pyridyl)-5-(2-pyridyl)pyrazole-3-carboxylic acid (0.223 g) obtained in Referential Example 33 and hexahydro-1H-1,4-diazepin-5-one hydrochloride (0.227 g) obtained in Referential Example 120.

$^1$H-NMR (400 MHz, CDCl$_3$) δ: 2.70-2.85 (2H, m), 3.39-3.49 (2H, m), 3.87-4.02 (2H, m), 3.94 (3H, s), 4.16-4.25 (2H, m), 6.76 (1H, d, J=8.8 Hz), 7.17 (1H, s), 7.44 (1H, d, J=7.8 Hz), 7.48 (1H, br), 7.58 (1H, br), 7.65-7.76 (1H, m), 8.11 (1H, d, J=2.5 Hz), 8.51 (1H, br d, J=3.0 Hz).

LC-MS m/z: 393(M+H)$^+$.

Elementary analysis: as $C_{20}H_{20}N_6O_3$

Calculated: C, 61.22; H, 5.14; N, 21.42.

Found: C, 61.01; H, 5.05; N, 21.23.

Example 109

1-[1-(6-Methoxy-3-pyridyl)-5-(2-pyridyl)pyrazole-3-carbonyl]-4-methyl-5-oxo-1,4-diazepane

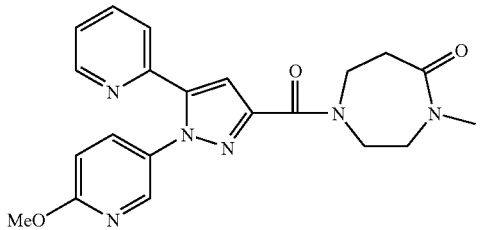

At 0° C., the sodium hydride (washed with pentan and dried, 20.4 mg) was added to a solution of 1-[1-(6-methoxy-3-pyridyl)-5-(2-pyridyl)pyrazole-3-carbonyl]-5-oxo-1,4-diazepane (0.253 g) obtained in Example 108 in N,N-dimethylformamide (5.0 mL), and the mixture was stirred for 15 minutes. To the reaction mixture, methyl iodide (0.0602 mL) was added, and the mixture was stirred at room temperature for 14 hours. The resultant mixture was partitioned between water and chloroform-methanol (5%). The aqueous layer was further extracted with chloroform-methanol (5%), and the organic layers were combined, followed by washing with saturated brine and drying over sodium sulfate anhydrate. After filtration, the solvent was removed under reduced pressure, and the residue was purified through silica gel column chromatography (chloroform-methanol), to thereby give the title compound as an amorphous product (0.231 g, 88%).

$^1$H-NMR (400 MHz, CDCl$_3$) δ: 2.81 (2H, br), 3.00-3.14 (3H, m), 3.51-3.70 (2H, m), 3.90-4.05 (2H, m), 3.95 (3H, s), 4.10-4.27 (2H, m), 6.76 (1H, d, J=8.9 Hz), 7.15 (1H, br d, J=10.0 Hz), 7.22-7.30 (1H, m), 7.45 (1H, br), 7.57 (1H, br), 7.71 (1H, br t, J=7.6 Hz), 8.10 (1H, br), 8.53 (1H, br).

LC-MSm/z: 407(M+H)$^+$.

Example 110

1-[1-(6-Chloro-3-pyridyl)-5-phenylpyrazole-3-carbonyl]-4-methylpiperazine

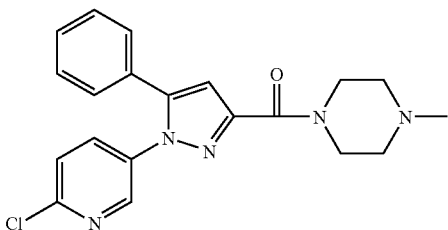

At room temperature, N-methylpiperazine (1.80 mL) was added to a solution of 1-[1-(6-chloro-3-pyridyl)-5-phenylpyrazole-3-carbonyl]-1-succinimide (3.20 g) obtained in Referential Example 124 in chloroform (30 mL), and the mixture was stirred for 2 hours. The reaction mixture was partitioned between water and chloroform. The organic layer was sequentially washed with water, 1N aqueous sodium hydroxide, and water, and then dried over magnesium sulfate anhydrate. After filtration, the solvent was removed under reduced pressure, and the thus-obtained solid was recrystallized from ether-hexane, to thereby give the title compound (2.60 g, 80%).

$^1$H-NMR (400 MHz, CDCl$_3$) δ: 2.34 (3H, s), 2.46-2.52 (4H, m), 3.83-3.86 (2H, m), 4.07-4.12 (2H, m), 6.92 (1H, s), 7.22-7.41 (6H, m), 7.58 (1H, dd, J=9, 3 Hz), 8.35 (1H, d, J=3 Hz).

Elementary analysis: as C$_{20}$H$_{20}$ClN$_5$O
Calculated: C, 62.91%; H, 5.28%; N, 18.34%.
Found: C, 62.67%; H, 5.22%; N, 18.29%.

Example 111

1-[1-(6-Ethoxy-3-pyridyl)-5-phenylpyrazole-3-carbonyl]-4-methylpiperazine hydrochloride

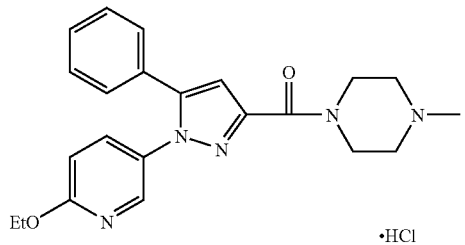

In a manner similar to that employed in Example 110, 1-[1-(6-ethoxy-3-pyridyl)-5-phenylpyrazole-3-carbonyl]-4-methylpiperazine was produced through use of [1-(6-ethoxy-3-pyridyl)-5-phenylpyrazole-3-carbonyl]-1-succinimide (232 mg) obtained in Referential Example 126 and N-methylpiperazine (0.14 mL). The thus-obtained product was dissolved in ethanol, and 1N aqueous hydrochloric acid (0.07 mL) was added thereto, followed by stirring. The solvent was removed under reduced pressure, and the residual solid matter was recrystallized from ether-hexane, to thereby give the title compound (25 mg, 16%).

$^1$H-NMR (400 MHz, CDCl$_3$) δ: 1.40 (3H, t, J=7 Hz), 2.82 (3H, s), 2.80-3.05 (2H, m), 3.45-3.80 (m, 3H), 3.98-4.15 (1H, m), 4.36 (2H, q, J=7 Hz), 4.75-4.99 (1H, m), 5.23-5.52 (1H, m), 6.70 (1H, d, J=9 Hz), 6.99 (1H, s), 7.21-7.43 (6H, m), 8.08 (1H, d, J=3 Hz), 13.49 (1H, br s).

Elementary analysis: as C$_{22}$H$_{26}$ClN$_5$O$_2$.0.25H$_2$O
Calculated: C, 61.11%; H, 6.18%; N, 16.20%.
Found: C, 61.10%; H, 6.15%; N, 16.02%.

Example 112

1-[1-(6-Isopropyloxy-3-pyridyl)-5-phenylpyrazole-3-carbonyl]-4-methylpiperazine hydrochloride

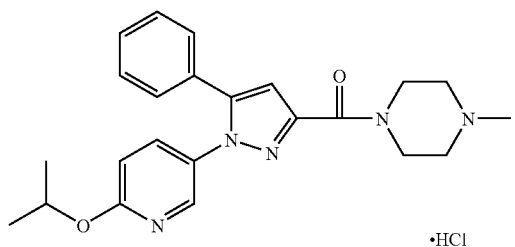

At room temperature, N-methylpiperazine (0.64 mL) was added to a solution of [1-(6-isopropoxy-3-pyridyl)-5-phenylpyrazole-3-carbonyl]-1-succinimide (1.11 g) obtained in Referential Example 128 in methylene chloride (20 mL), and the mixture was stirred overnight. The reaction mixture was partitioned between chloroform and water. The organic layer was sequentially washed with water, 1N aqueous sodium hydroxide, and water, and then dried over magnesium sulfate anhydrate. After filtration, the solvent was removed under reduced pressure. The residue was purified through silica gel column chromatography (chloroform-methanol), and 1-[1-(6-isopropyloxy-3-pyridyl)-5-phenylpyrazole-3-carbonyl]-4-methylpiperazine was produced. The thus-obtained product was dissolved in ethanol, and 1N aqueous hydrochloric acid (2.9 mL) was added thereto, followed by stirring. The solvent was removed under reduced pressure. The thus-obtained solid was recrystallized from ether-ethanol, to thereby give the title compound (25 g, 16%).

$^1$H-NMR (400 MHz, CDCl$_3$) δ: 1.35 (6H, d, J=6 Hz), 2.85 (3H, s), 2.80-3.05 (2H, m), 3.50-3.78 (m, 3H), 4.00-4.15 (1H, m), 4.85-4.95 (1H, m), 5.29 (1H, sep, J=6 Hz), 5.35-5.45 (1H, m), 6.65 (1H, d, J=9 Hz), 6.99 (1H, s), 7.22-7.42 (6H, m), 8.07 (1H, d, J=3 Hz), 13.43 (1H, br s).

Elementary analysis: as C$_{23}$H$_{28}$ClN$_5$O$_2$.0.25H$_2$O
Calculated: C, 61.88%; H, 6.43%; N, 15.69%.
Found: C, 61.98%; H, 6.40%; N, 15.62%.

Example 113

1-[1-(6-Methylamino-3-pyridyl)-5-phenylpyrazole-3-carbonyl]-4-methylpiperazine

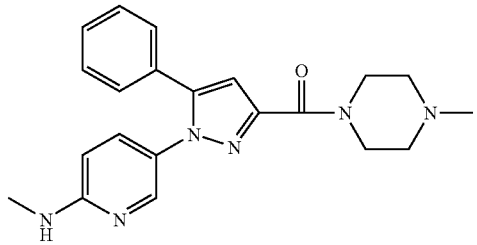

To a solution of 1-[1-(6-chloro-3-pyridyl)-5-phenylpyrazole-3-carbonyl]-4-methylpiperazine (300 mg) obtained in Example 110 in N,N-dimethylformamide (1.5 mL), 40% methylamine-methanol solution (0.6 mL) was added. The mixture was stirred at 85>C for 3 days in a sealed tube, and then cooled in air. The reaction mixture was partitioned between 1N aqueous sodium hydroxide (30 mL) and ethyl acetate. The organic layer was sequentially washed with water, saturated aqueous sodium hydrogencarbonate, and water, and then dried over magnesium sulfate anhydrate. After filtration, the solvent was removed under reduced pressure, and the residue was dissolved in dimethyl sulfoxide (1 mL). The solution was purified through preparative high-performance liquid chromatography (eluent: water acetonitrile), followed by recrystallization from ether-hexane, to thereby give the title compound (11.7 mg, 4%).

$^1$H-NMR (400 MHz, CDCl$_3$) δ: 2.33 (3H, s), 2.47-2.51 (4H, m), 2.93 (3H, d, J=5 Hz), 3.83-3.86 (2H, m), 4.09-4.14 (2H, m), 4.70 (1H, q, J=5 Hz), 6.33 (1H, d, J=9 Hz), 6.89 (1H, s), 7.25-7.34 (6H, m), 8.05 (1H, d, J=3 Hz).

Elementary analysis: as C$_{21}$H$_{24}$N$_6$O.0.25H$_2$O
Calculated: C, 66.21%; H, 6.48%; N, 22.06%.
Found: C, 66.21%; H, 6.39%; N, 21.86%.

Example 114

1-[1-(6-Cyclopropylamino-3-pyridyl)-5-phenylpyrazole-3-carbonyl]-4-methylpiperazine

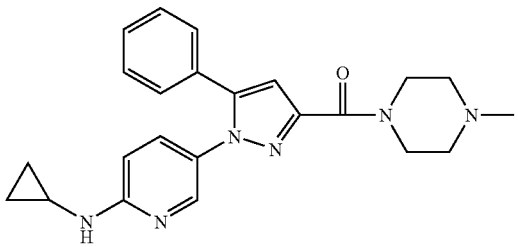

To a solution of 1-[1-(6-chloro-3-pyridyl)-5-phenylpyrazole-3-carbonyl]-4-methylpiperazine (200 mg) obtained in Example 110 in dioxane (1.0 mL), cyclopropylamine (1.0 mL) was added. The mixture was stirred at 100° C. for 3 days in a sealed tube, and then cooled in air. The reaction mixture was partitioned between water and ethyl acetate. The organic layer was sequentially washed with water and saturated aqueous sodium hydrogencarbonate, and then dried over magnesium sulfate anhydrate. After filtration, the solvent was removed under reduced pressure, and the residue was dissolved in dimethyl sulfoxide (1 mL). The solution was purified through preparative high-performance liquid chromatography (eluent: water-acetonitrile), to thereby give the title compound as an oily product (19.6 mg, 9%).

MS (ESI) m/z: 403(M+H)$^+$.

Example 115

1-[1-(6-Methoxy-3-pyridyl)-5-phenylpyrazole-3-carbonyl]-2,2,4-trimethylpiperazine

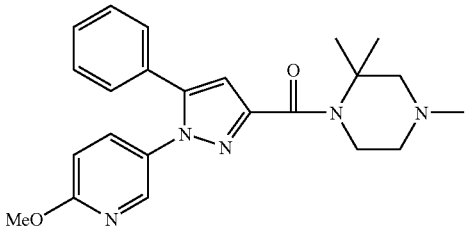

To a solution of 1,3,3-trimethylpiperazine-2,5-dione (162 mg) obtained in Referential Example 130 in tetrahydrofuran (2 mL), a solution of 1.0M borane-tetrahydrofuran complex in tetrahydrofuran (3 mL) was added. The mixture was refluxed under heat for 14 hours, and then cooled in air. The solvent was removed under reduced pressure, and 1N aqueous hydrochloric acid (4 mL) was added to the residue. The resultant mixture was heated at 100° C. for 30 minutes, and then cooled in air. To the reaction mixture, tetrahydrofuran (3 mL) and anion exchange resin (Amberlite, 3.29 g) washed in advance with ethanol were added. The mixture was stirred at room temperature for 8 hours. The reaction mixture was subjected to filtration, and the solvent was removed under reduced pressure, to thereby give a mixture of 1,3,3-trimethylpiperazine and 1-fluorenylmethylpiperidine as an oily product (71.0 mg). The oily mixture and 1-[1-(6-methoxy-3-pyridyl)5-phenylpyrazole-3-carboxy]-1-succinimide (66.4 mg) obtained in Referential Example 129 were dissolved in methylene chloride (2 mL), and diisopropylethylamine (185 µL) was added thereto. The resultant mixture was stirred at room temperature for 48 hours. The reaction mixture was concentrated to 1 mL under reduced pressure, followed by purification through preparative high-performance liquid chromatography (acetonitrile-water (with 0.1% formic acid, 12-50% v/v)), to thereby give the title compound as an oily product (11.8 mg, 15%).

MS (FAB) m/z: 406(M+H)$^+$.

Example 116

4-[1-(6-Methoxy-3-pyridyl)-5-phenylpyrazole-3-carbonyl]-1,2,6-trimethylpiperazine 4-[1-(6-Methoxy-3-pyridyl)-5-phenylpyrazole-3-carbonyl]-2,6-dimethylpiperazine (29.7 mg) obtained in Example 22 was dissolved in ethanol (2.0 mL). To the solution, 35% aqueous formalin solution (0.0325 mL), acetic acid (0.0217 mL), and sodium cyanoborohydride (9.2 mg) were added at room temperature, followed by stirring for 1.5 hours. The reaction mixture was partitioned between aqueous sodium hydrogencarbonate and chloroform at 0° C. The aqueous layer was further extracted with chloroform. The organic layers were combined and washed with saturated brine, followed by drying over sodium sulfate anhydrate. After filtration, the solvent was removed under reduced pressure, and the residue was brought to dryness, to thereby give the title compound (40 mg, quantitative amount).

LC-MSm/z: 406(M+H)$^+$.

Example 117

1-[1-(5-Methoxy-2-pyridyl)-5-phenylpyrazole-3-carbonyl]-4-methylpiperazine

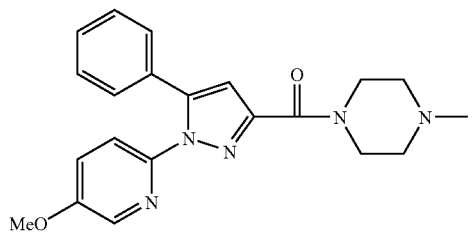

In a manner similar to that employed in step 1) of Example 1, the title compound was obtained as a solid (130 mg, 68%) through use of 1-(5-methoxy-2-pyridyl)-5-phenylpyrazole-3-carboxylic acid (150 mg) obtained in Referential Example 137 and N-methylpiperazine (0.068 mL).

$^1$H-NMR (400 MHz, DMSO-d$_6$) δ: 2.20 (3H, s), 2.35 (4H, br), 3.65 (2H, br), 3.87 (3H, s), 3.92 (2H, br), 6.91 (1H, s), 7.21-7.23 (2H, m), 7.33-7.35 (3H, m), 7.60-7.63 (2H, m), 8.08-8.09 (1H, m).

LC-MSm/z: 378(M+H)$^+$.

Elementary analysis: as C$_{21}$H$_{23}$N$_5$O$_2$
Calculated: C, 66.77; H, 6.15; N, 18.63.
Found: C, 66.83; H, 6.14; N, 18.55.

Example 118

(2S)-1-[1-(5-Methoxy-2-pyridyl)-5-phenylpyrazole-3-carbonyl]pyrrolidine-2-carboxamide

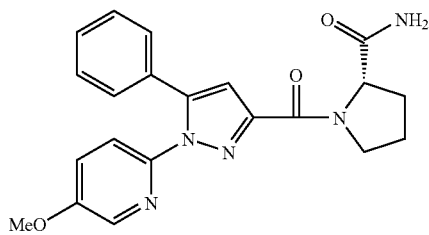

In a manner similar to that employed in step 1) of Example 1, the title compound was obtained as a solid (270 mg, 81%) through use of 1-(5-methoxy-2-pyridyl)-5-phenylpyrazole-3-carboxylic acid (250 mg) obtained in Referential Example 137 and L-prolinamide (116 mg).

$^1$H-NMR (400 MHz, CDCl$_3$) δ: 1.99-2.46 (4H, m), 3.87 (3H, s), 4.13 (1H, m), 4.88 (1H, br), 5.35 (1H, s), 7.04 (1H, s), 7.23-7.48 (7H, m), 7.96 and 8.08 (1H, each s).

FAB-MSm/z: 392(M+H)$^+$.

Example 119

1-[1-(5-Methoxy-2-pyridyl)-5-phenylpyrazole-3-carbonyl]piperidine-2-carboxamide

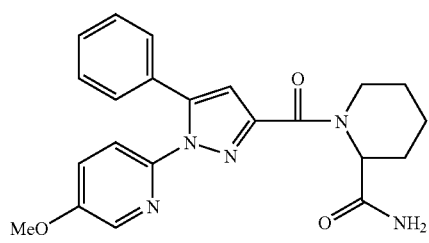

In a manner similar to that employed in step 1) of Example 1, the title compound was obtained as a solid (229 mg, 66%) through use of 1-(5-methoxy-2-pyridyl)-5-phenylpyrazole-3-carboxylic acid (250 mg) obtained in Referential Example 137 and piperidine-2-carboxamide (119 mg) obtained in Referential Example 131.

$^1$H-NMR (400 MHz, CDCl$_3$) δ: 1.62-1.91 (6H, m), 2.28-2.40 (1H, m), 2.81-3.21 (1H, m), 3.88 (3H, s), 4.71-4.80 (1H, m), 5.37 (1H, br s), 5.46 (1H, br s), 6.39 (1H, s), 6.91 (1H, d, J=26.4 Hz), 7.22-7.33 (6H, m), 8.06 (1H, d, J=9.8 Hz).

EI-MSm/z: 405(M$^+$).

Example 120

1-[1-(5-Methoxy-2-pyridyl)-5-(2-pyridyl)pyrazole-3-carbonyl]-4-methylpiperazine

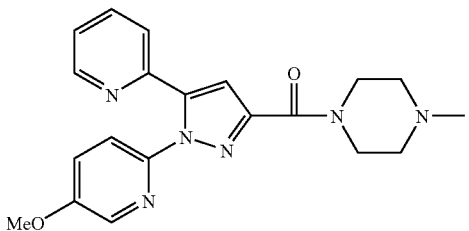

1) The Title Compound

In a manner similar to that employed in step 1) of Example 1, the title compound was obtained as an oily product (264 mg, 69%) through use of 1-(5-methoxy-2-pyridyl)-5-(2-pyridyl)pyrazole-3-carboxylic acid (300 mg) obtained in Referential Example 138 and N-methylpiperazine (0.247 mL).

$^1$H-NMR (400 MHz, CDCl$_3$) δ: 2.31 (3H, s), 2.42-2.51 (4H, m), 3.84 (2H, m), 3.86 (3H, s), 4.08 (2H, m), 7.06 (1H, s), 7.17-7.21 (1H, m), 7.32 (1H, dd, J=8.8, 2.9 Hz), 7.40-7.42 (1H, m), 7.55 (1H, d, J=8.8 Hz), 7.66-7.70 (1H, m), 7.93 (1H, d, J=2.9 Hz), 8.44-8.46 (1H, m).

EI-MSm/z: 378 (M$^+$).

2) Hydrochloric Acid Salt of the Title Compound

In a manner similar to that employed in step 2) of Example 29, a hydrochloric acid salt of the title compound was obtained as a solid (187 mg, 64%) through use of the above-obtained title compound (254 mg).

$^1$H-NMR (400 MHz, DMSO-d$_6$) δ: 2.78 (3H, m), 3.10-3.67 (4H, m), 3.86 (3H, s), 4.60-5.32 (4H, m), 7.18 (1H, s), 7.34-7.37 (1H, m), 7.55-7.60 (2H, m), 7.66-7.68 (1H, m), 7.84-7.88 (1H, m), 7.97 (1H, d, J=2.9 Hz), 8.43 (1H, d, J=4.9 Hz), 11.08 (1H, br s).

EI-MSm/z: 378(M$^+$).

Example 121

4-[1-(6-Methoxy-3-pyridazinyl)-5-(2-pyridyl)pyrazole-3-carbonyl]morpholine

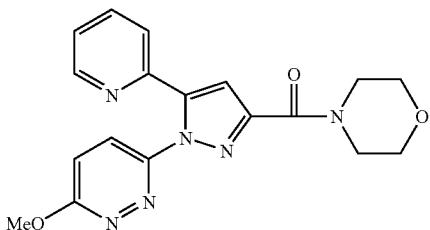

In a manner similar to that employed in step 1) of Example 1, the title compound was obtained as a solid (85 mg, 69%) through use of 1-(6-methoxy-3-pyridazinyl)-5-(2-pyridyl)pyrazole-3-carboxylic acid (100 mg) obtained in Referential Example 139 and morpholine (0.035 mL).

$^1$H-NMR (400 MHz, DMSO-d$_6$) δ: 3.62 (2H, br), 3.66 (4H, br s), 3.96 (2H, br), 4.03 (3H, s), 7.27 (1H, s), 7.32-7.36 (1H, m), 7.47 (1H, d, J=9.3 Hz), 7.79 (1H, d, J=7.8 Hz), 7.89 (1H, dt, J=7.8, 1.5 Hz), 7.99 (1H, d, J=9.3 Hz), 8.37 (1H, d, J=4.0 Hz).

LC-MSm/z: 367(M+H)$^+$.

Elementary analysis: as C$_{18}$H$_{18}$N$_6$O$_3$·0.5H$_2$O
Calculated: C, 58.29; H, 5.03; N, 22.66.
Found: C, 58.59; H, 4.89; N, 22.57.

Example 122

1-[1-(6-Methoxy-3-pyridazinyl)-5-(2-pyridyl) pyrazole-3-carbonyl] piperidine

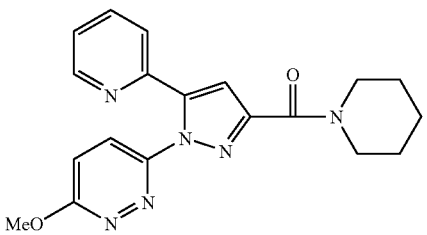

In a manner similar to that employed in step 1) of Example 1, the title compound was obtained as a solid (87 mg, 71%) through use of 1-(6-methoxy-3-pyridazinyl)-5-(2-pyridyl)pyrazole-3-carboxylic acid (100 mg) obtained in Referential Example 139 and piperidine (0.040 mL).

$^1$H-NMR (400 MHz, DMSO-d$_6$) δ: 1.55 (4H, br), 1.65 (2H, br), 3.64 (2H, br), 3.80 (2H, br), 4.03 (3H, s), 7.21 (1H, s), 7.32-7.35 (1H, m), 7.47 (1H, d, J=9.2 Hz), 7.77 (1H, d, J=7.8 Hz), 7.88 (1H, dt, J=7.8, 1.5 Hz), 7.97 (1H, d, J=9.2 Hz), 8.37 (1H, d, J=4.1 Hz).

LC-MSm/z: 365(M+H)$^+$.

Elementary analysis: as C$_{19}$H$_{20}$N$_6$O$_2$
Calculated: C, 62.6.2; H, 5.53; N, 23.06.
Found: C, 62.46; H, 5.43; N, 23.01.

Example 123

4-[1-(6-Methoxy-3-pyridazinyl)-5-phenylpyrazole-3-carbonyl]morpholine

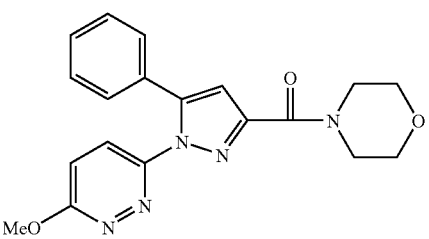

In a manner similar to that employed in step 1) of Example 1, the title compound was obtained as a solid (170 mg, 69%) through use of 1-(6-methoxy-3-pyridazinyl)-5-phenylpyrazole-3-carboxylic acid (200 mg) obtained in Referential Example 43 and morpholine (0.071 mL).

$^1$H-NMR (400 MHz, DMSO-d$_6$) δ: 3.63 (2H, br), 3.67 (4H, br s), 3.96 (2H, br), 4.03 (3H, s), 7.00 (1H, s), 7.29-7.31 (3H, m), 7.36-7.39 (2H, m), 7.49 (1H, d, J=9.2 Hz), 7.99 (1H, d, J=9.2 Hz).

LC-MSm/z: 366(M+H)$^+$.

Example 124

1-[1-(6-Methoxy-3-pyridazinyl)-5-(2-pyridyl)pyrazole-3-carbonyl]-4-methyl-3-oxopiperazine

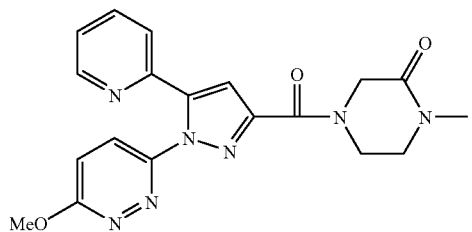

In a manner similar to that employed in step 1) of Example 1, the title compound was obtained as a solid (54 mg, 43%) through use of 1-(6-methoxy-3-pyridazinyl)-5-(2-pyridyl) pyrazole-3-carboxylic acid (90, mg) obtained in Referential Example 139 and 1-methylpiperazin-2-one hydrochloride (57 mg) obtained in Referential Example 157.

$^1$H-NMR (400 MHz, CDCl$_3$) δ: 3.03 (3H, s), 3.47 (2H, t, J=5.8 Hz), 4.07 (1H, m), 4.11 and 4.13 (3H, each s), 4.40 and 4.44 (2H, each brm), 4.87 (1H, br s), 7.14-7.24 (3H, m), 7.59 (1H, d, J=7.8 Hz), 7.70 and 7.86 (1H, each d, J=9.0 Hz), 7.75 (1H, td, J=7.8, 1.7 Hz), 8.40 (1H, s).

ESI-MSm/z: 394(M+H)$^+$.

Example 125

1-[1-(6-Methoxy-3-pyridazinyl)-5-phenylpyrazole-3-carbonyl]-4-methyl-3-oxopiperazine

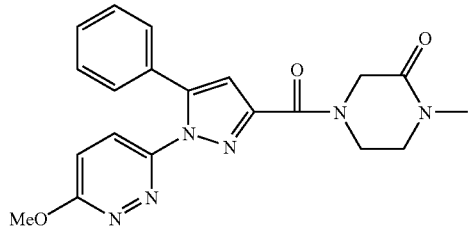

In a manner similar to that employed in step 1) of Example 1, the title compound was obtained as a solid (125 mg, 63%j through use of 1-(6-methoxy-3-pyridazinyl)-5-phenylpyrazole-3-carboxylic acid (151 mg) obtained in Referential Example 43 and 1-methylpiperazin-2-one trifluoroacetic acid salt (128 mg) obtained in Referential Example 91.

$^1$H-NMR (400 MHz, DMSO-d$_6$) δ: 2.89 (3H, s), 3.43 (2H, br s), 3.91 (1H, br), 4.03 (3H, s), 4.21 (2H, br s), 4.62 (1H, br), 7.04 (1H, s), 7.31-7.52 (5H, m), 7.50 (1H, d, J=9.3 Hz), 7.96-8.04 (1H, m).

LC-MSm/z: 393(M+H)$^+$.

Example 126

(2S)-1-[1-(6-Methoxy-3-pyridazinyl)-5-phenylpyrazole-3-carbonyl]-2-hydroxymethylpyrrolidine

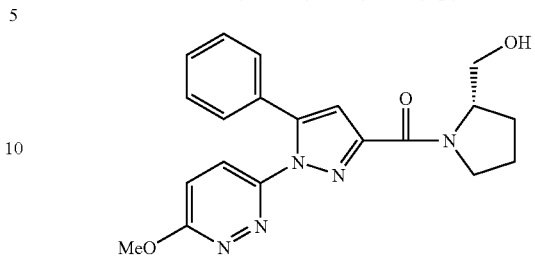

1-[1-(6-Methoxy-3-pyridazinyl)-5-phenylpyrazole-3-carboxylic acid (237 mg) obtained in Referential Example 43 was dissolved in N,N-dimethylformamide (4 mL). To the solution, diphenylphosphodrylazide (0.19 mL), triethylamine (0.245 mL), and (S)-2-pyrrolidinemethanol (0.118 mL) were added, followed by stirring at room temperature for 17 hours. The reaction mixture was partitioned between water and chloroform. The organic layer was washed with saturated aqueous sodium hydrogencarbonate, followed by drying over sodium sulfate anhydrate. After filtration, the solvent was removed under reduced pressure, and the residue was purified through silica gel column chromatography (chloroform-methanol), to thereby give the title compound as a solid (0.166 g, 47%).

$^1$H-NMR (400 MHz, CDCl$_3$) δ: 1.60-2.20 (4H, m), 3.55-4.60 (5H, m), 4.12 (3H, s), 4.83-4.98 (1H, m), 7.03 (1H, s), 7.08 (1H, d, J=9.2 Hz), 7.25-7.42 (5H, m), 7.61 (1H, d, J=9.2 Hz).

ESI-MSm/z: 380(M+H)$^+$.

Example 127

1-[1-(6-Methoxy-3-pyridazinyl)-5-phenylpyrazole-3-carbonyl]piperidine-2-carboxamide

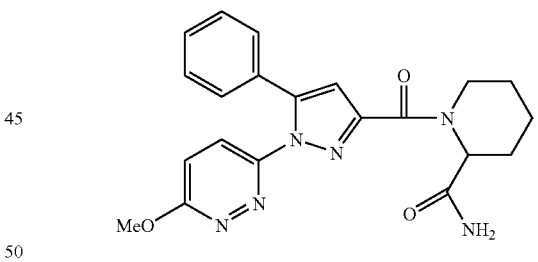

In a manner similar to that employed in step 1) of Example 1, the title compound was obtained as a solid (213 mg, 65%) through use of 1-(6-methoxy-3-pyridazinyl)-5-phenylpyrazole-3-carboxylic acid (151 mg) obtained in Referential Example 43 and piperidine-2-carboxamide (154 mg) obtained in Referential Example 131.

$^1$H-NMR (400 MHz, CDCl$_3$) δ: 1.50-1.87 (6H, m), 2.30-2.43 (1H, m), 2.83-2.92 (½×1H, m), 3.15-3.26 (½×1H, m), 4.13 (3H, s), 4.70-4.78 (1H, m), 5.34-5.50 (1H, m), 5.52 (½×1H, bs), 6.36 (½×1H, bs), 7.05-7.12 (2H, m), 7.26-7.38 (5H, m), 7.50 (½×1H, d, J=9.3 Hz), 7.63 (½×1H, d, J=9.3 Hz).

ESI-MSm/z: 407 (M+H)$^+$.
Elementary analysis: as C$_{21}$H$_{22}$N$_6$O$_3$
Calculated: C, 62.06; H, 5.46; N, 20.68.
Found: C, 62.16; H, 5.52; N, 20.59.

Example 128

1-[1-(6-Methoxy-3-pyridazinyl)-5-(2-pyridyl)pyrazole-3-carbonyl]pyrrolidine

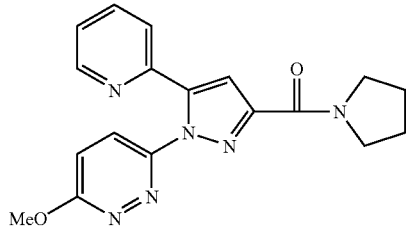

In a manner similar to that employed in step 1) of Example 1, the title compound was obtained as a solid (226 mg, 77%) through use of 1-(6-methoxy-3-pyridazinyl)-5-(2-pyridyl)pyrazole-3-carboxylic acid (250 mg) obtained in Referential Example 139 and pyrrolidine (0.084 mL).

$^1$H-NMR (400 MHz, DMSO-$d_6$) δ: 1.85 (2H, q, J=6.59 Hz), 1.91 (2H, q, J=6.59 Hz), 3.53 (2H, t, J=6.59 Hz), 3.88 (2H, t, J=6.59 Hz), 4.03 (3H, s), 7.30 (1H, s), 7.33 (1H, dt, J=4.27, 1.59 Hz), 7.47 (1H, d, J=9.28 Hz), 7.79 (1H, d, J=7.81 Hz), 7.89 (1H, dt, J=7.81, 1.59 Hz), 7.99 (1H, d, J=9.28 Hz), 8.37 (1H, d, J=4.27 Hz).

FAB-MSm/z: 351(M+H)$^+$.

Elementary analysis: as $C_{18}H_{18}N_6O_2$

Calculated: C, 61.70; H, 5.18; N, 23.99.

Found: C, 61.42; H, 5.01; N, 23.87.

Example 129

4-[1-(6-Methoxy-3-pyridazinyl)-5 (2-pyridyl)pyrazole-3-carbonyl]-1,4-oxazepane

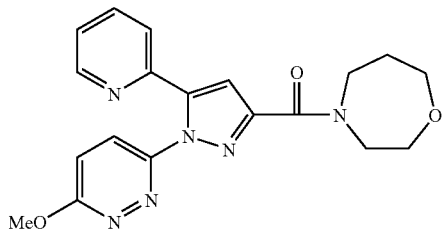

In a manner similar to that employed in step 1) of Example 1, the title compound was obtained as a solid (77.5 mg, 25%) through use of 1-(6-methoxy-3-pyridazinyl)-5-(2-pyridyl)pyrazole-3-carboxylic acid (250 mg) obtained in Referential Example 139 and 1,4-oxazepane hydrochloride (363 mg) obtained in Referential Example 149.

$^1$H-NMR (400 MHz, CDCl$_3$) δ: 2.01-2.11 (2H, m), 3.79-3.91 (6H, m), 4.05-4.15 (2H, m), 4.11 (3H, s), 7.13 (½×1H, s), 7.14 (1H, d, J=9.3 Hz), 7.14 (½×1H, s), 7.20-7.24 (1H, m), 7.59 (1H, d, J=7.8 Hz), 7.73-7.78 (1H, m), 7.79 (1H, d, J=9.3 Hz), 8.40-8.43 (1H, m).

ESI-MSm/z: 381(M+H)$^+$.

Example 130

1-[1-(6-Methoxy-3-pyridazinyl)-5-(2-pyridyl)pyrazole-3-carbonyl]-4-methoxypiperidine

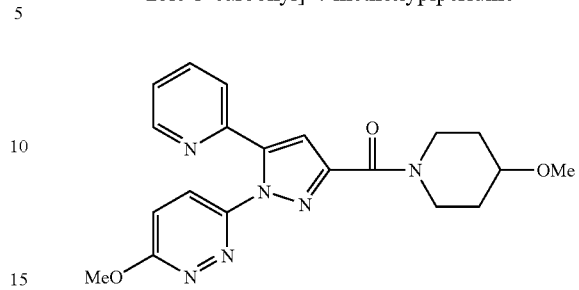

In a manner similar to that employed in step 1) of Example 1, the title compound was obtained as a solid (130 mg, 39%) through use of 1-(6-methoxy-3-pyridazinyl)-5-(2-pyridyl)pyrazole-3-carboxylic acid (250 mg) obtained in Referential Example 139 and 4-methoxypiperidine trifluoroacetic acid salt (386 mg) obtained in Referential Example 151.

$^1$H-NMR (400 MHz, CDCl$_3$) δ: 1.65-1.72 (2H, m), 1.90-1.95 (2H, m), 3.38 (3H, s), 3.48-3.57 (1H, m), 3.69-3.74 (1H, m), 4.11 (3H, s), 4.22-4.24 (1H, m), 7.07 (1H, s), 7.13 (1H, d, J=9.2 Hz), 7.21-7.24 (1H, m), 7.71 (1H, d, J=8.4 Hz), 7.72-7.83 (2H, m), 8.41-8.42 (1H, m).

EI-MSm/z: 394(M$^+$).

Elementary analysis: as $C_{19}H_{20}N_6O_3$

Calculated: C, 60.90; H, 5.62; N, 21.31.

Found: C, 60.72; H, 5.38; N, 21.15.

Example 131

1-[1-(6-Methoxy-3-pyridazinyl)-5-(2-pyridyl)pyrazole-3-carbonyl]-2-methylhexahydropyridazine

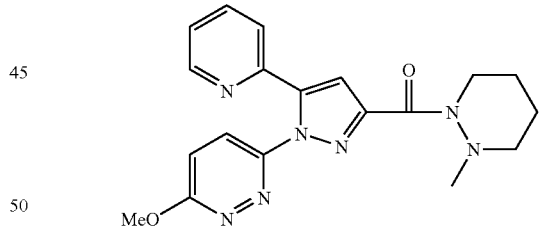

In a manner similar to that employed in step 1) of Example 1, the title compound was obtained as an amorphous product (16.5 mg, 5%) through use of 1-(6-methoxy-3-pyridazinyl)-5-(2-pyridyl)pyrazole-3-carboxylic acid (251 mg) obtained in Referential Example 139 and 1-methylhexahydropyridazine (143 mg) obtained in Referential Example 150.

$^1$H-NMR (400 MHz, CDCl$_3$) δ: 1.35-1.48 (1H, m), 1.65-2.05 (3H, m), 2.75 (3H, s), 2.85-2.95 (1H, m), 3.10-3.23 (1H, m), 4.07 (3H, s), 4.42-4.60 (1H, m), 7.07 (1H, s), 7.12 (1H, d, J=9.3 Hz), 7.17-7.25 (1H, m), 7.52 (1H, d, J=7.8 Hz), 7.72 (1H, dt, J=7.8, 1.9 Hz), 8.03 (1H, d, J=9.3 Hz), 8.46 (1H, d, J=4.7 Hz).

ESI-MSm/z: 380(M+H)$^+$.

Example 132

1-[1-(6-Methoxy-3-pyridazinyl)-5-(2-pyridyl)pyrazole-3-carbonyl]-4-methylpiperazine

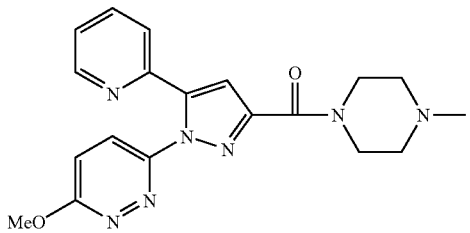

In a manner similar to that employed in step 1) of Example 1, the title compound was obtained as a solid (215 mg, 71%) through use of 1-(6-methoxy-3-pyridazinyl)-5-(2-pyridyl)pyrazole-3-carboxylic acid (238 mg) obtained in Referential Example 139 and N-methylpiperazine (122 mg).

$^1$H-NMR (400 MHz, CDCl$_3$) δ: 2.33 (3H, s), 2.40-2.57 (4H, m), 3.81-3.92 (2H, m), 4.03-4.11 (2H, m), 4.11 (3H, s), 7.10 (1H, s), 7.13 (1H, d, J=9.3 Hz), 7.22 (1H, dd, J=7.8, 4.9 Hz), 7.58 (1H, d, J=7.8 Hz), 7.75 (1H, dt, J=7.8, 1.7 Hz), 7.80 (1H, d, J=9.3 Hz), 8.41 (1H, d, J=4.9 Hz).

ESI-MS m/z: 380(M+H)$^+$.

Elementary analysis: as C$_{19}$H$_{21}$N$_7$O$_2$

Calculated: C, 60.15; H, 5.58; N, 25.84.

Found: C, 59.95; H, 5.40; N, 25.71.

Example 133

1-[1-(6-Methoxy-3-pyridazinyl)-5-(2-pyridyl)pyrazole-3-carbonyl]piperazine

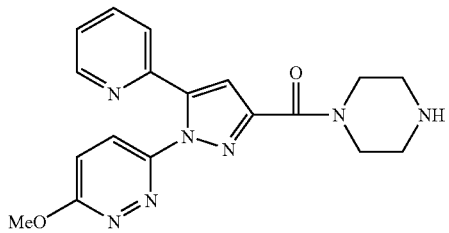

1) 1-[1-(6-Methoxy-3-pyridazinyl)-5-(2-pyridyl)pyrazole-3-carbonyl]piperazine-4-carboxylic acid tert-butyl ester In a manner similar to that employed in step 1) of Example 1, 1-[1-(6-methoxy-3-pyridazinyl)-5-(2-pyridyl)pyrazole-3-carbonyl]piperazine-4-carboxylic acid tert-butyl ester was produced as a solid (349 mg, 94%) through use of 1-(6-methoxy-3-pyridazinyl)-5-(2-pyridyl)pyrazole-3-carboxylic acid (237 mg) obtained in Referential Example 139 and N-tert-butoxycarbonylpiperazine (223 mg).

$^1$H-NMR (400 MHz, CDCl$_3$) δ: 1.48 (9H, s), 1.56 (6H, s), 3.48-3.57 (4H, m), 3.77-3.82 (2H, m), 4.03-4.09 (2H, m), 4.12 (3H, s), 7.13 (1H, s), 7.14 (1H, d, J=9.0 Hz), 7.22 (1H, ddd, J=7.8, 4.9, 1.1 Hz), 7.59 (1H, dt, J=7.8, 1.1 Hz), 7.75 (1H, dt, J=7.8, 1.8 Hz), 7.77 (1H, d, J=9.0 Hz), 8.41 (1H, ddd, J=4.9, 1.8, 1.1 Hz).

ESI-MS m/z: 466(M+H)$^+$.

2) The Title Compound

In a manner similar to that employed in step 2) of Example 16, the title compound was obtained as a solid (242 mg, 88%) through use of the above-obtained product, 1-[1-(6-methoxy-3-pyridazinyl)-5-(2-pyridyl)pyrazole-3-carbonyl]piperazine-4-carboxylic acid tert-butyl ester (349 mg).

$^1$H-NMR (400 MHz, CDCl$_3$) δ: 2.86-3.06 (4H, m), 3.76-3.88 (2H, m), 4.00-4.08 (2H, m), 4.11 (3H, s), 7.10 (1H, s), 7.13 (1H, d, J=9.0 Hz), 7.22 (1H, dd, J=7.8, 4.9 Hz), 7.58 (1H, d, J=7.8 Hz), 7.75 (1H, dt, J=7.8, 1.3 Hz), 7.79 (1H, d, J=9.0 Hz), 8.38-8.45 (1H, m).

ESI-MS m/z: 366(M+H)$^+$.

Example 134

1-[1-(6-Methoxy-3-pyridazinyl)-5-(2-pyridyl)pyrazole-3-carbonyl]-3-oxopiperidine

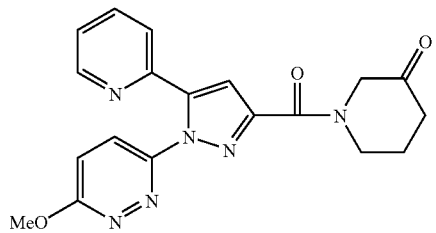

1) Piperidin-3-one hydrochloride

3-Oxopiperidine-1-carboxylic acid tert-butyl ester (400 mg) was dissolved in methylene chloride (5 mL). To the solution, 4N HCl-dioxane solution (3 mL) was added, followed by stirring at room temperature for 3 hours. The reaction solvent was removed under reduced pressure, to thereby give piperidin-3-one hydrochloride.

$^1$H-NMR (400 MHz, CD$_3$OD) δ: 1.85 (2H, m), 3.04 (2H, m), 3.66 (2H, br), 4.88 (2H, br).

2) The Title Compound

In a manner similar to that employed in step 1) of Example 1, the title compound was obtained as a solid (53 mg, 10%) through use of 1-(6-methoxy-3-pyridazinyl)-5-(2-pyridyl)pyrazole-3-carboxylic acid (400 mg) obtained in Referential Example 139 and the above-obtained product, piperidin-3-one hydrochloride (272 mg).

$^1$H-NMR (400 MHz, CDCl$_3$) δ: 2.13 (2H, br), 2.58 (2H, t, J=6.47 Hz), 3.97 (1H, br), 4.12 (3H, br), 4.23 (1H, br), 4.39 (1H, br), 4.74 (1H, br), 7.15 (2H, m), 7.22 (1H, m), 7.59 (1H, d, J=7.81 Hz), 7.79 (2H, m), 8.41 (1H, d, J=3.91 Hz).

FAB-MS m/z: 379(M+H)$^+$.

Example 135

1-[1-(6-Methoxy-3-pyridazinyl)-5-(4-methoxy-2-pyridyl)pyrazole-3-carbonyl]-4-methylpiperazine

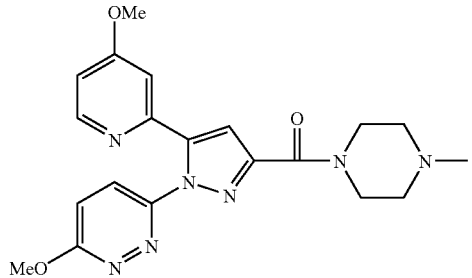

In a manner similar to that employed in step 1) of Example 1, the title compound was obtained as a solid (226 mg, 60%) through use of 1-(6-methoxy-3-pyridazinyl)-5-(4-methoxy-2-pyridyl)pyrazole-3-carboxylic acid (300 mg) obtained in Referential Example 158 and N-methylpiperazine (0.244 mL).

$^1$H-NMR (400 MHz, CDCl$_3$) δ: 2.32 (3H, s), 2.42-2.51 (4H, m), 3.83-3.92 (2H, m), 3.86 (3H, s), 4.06-4.14 (2H, m), 4.10 (3H, s), 6.73 (1H, dd, J=5.9, 2.4 Hz), 7.06 (1H, s), 7.10-7.12 (2H, m), 7.76-7.79 (1H, m), 8.20 (1H, d, J=5.9 Hz).

EI-MSm/z: 409(M$^+$).

Elementary analysis: as C$_{20}$H$_{23}$N$_7$O$_3$.0.25H$_2$O
Calculated: C, 58.03; H, 5.72; N, 23.69.
Found: C, 58.07; H, 5.64; N, 23.47.

Example 136

4-Cyclopropyl-1-[1-(6-methoxy-3-pyridazinyl)-5-(2-pyridyl)pyrazole-3-carbonyl]piperazine

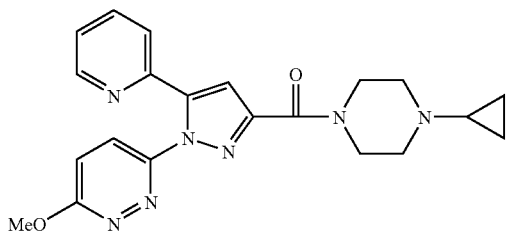

In a manner similar to that employed in step 1) of Example 1, the title compound was obtained as a solid (271 mg, 79%) through use of 1-(6-methoxy-3-pyridazinyl)-5-(2-pyridyl)pyrazole-3-carboxylic acid (250 mg) obtained in Referential Example 139 and 1-cyclopropylpiperazine hydrochloride (284 mg) obtained in Referential Example 99.

$^1$H-NMR (400 MHz, CDCl$_3$) δ: 0.41-0.50 (4H, m), 1.61-1.67 (1H, m), 2.63-2.72 (4H, m), 3.79 (2H, t, J=4.9 Hz), 3.99 (2H, t, J=4.9 Hz), 4.10 (3H, s), 7.08 (1H, s), 7.11-7.13 (1H, m), 7.19-7.23 (1H, m), 7.56-7.58 (1H, m), 7.71-7.81 (2H, m), 8.39-8.41 (1H, m).

EI-MSm/z: 405(M$^+$).

Elementary analysis: as C$_{21}$H$_{23}$N$_7$O$_2$.0.25H$_2$O
Calculated: C, 61.51; H, 5.78; N, 23.92.
Found: C, 61.51; H, 5.54; N, 23.94.

Example 137

4-[1-(6-Methoxy-3-pyridazinyl)-5-(2-pyridyl)pyrazole-3-carbonyl]-1,1-dioxothiomorpholine

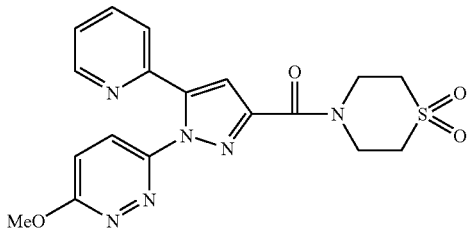

In a manner similar to that employed in step 1) of Example 1, the title compound was obtained as a solid (235 mg, 72%) through use of 1-(6-methoxy-3-pyridazinyl)-5-(2-pyridyl)pyrazole-3-carboxylic acid (250 mg) obtained in Referential Example 139 and thiomorpholine-1,1-dioxide (136 mg).

$^1$H-NMR (400 MHz, DMSO-d$_6$) δ: 3.28 (4H, br), 4.03 (3H, s), 4.07 (2H, br), 4.35 (2H, br), 7.32 (1H, s), 7.34 (1H, dd, J=7.81, 4.88 Hz), 7.47 (1H, d, J=9.28 Hz), 7.77 (1H, d, J=7.81 Hz), 7.89 (1H, dt, J=7.81, 1.59 Hz), 7.99 (1H, d, J=9.28 Hz), 8.37 (1H, d, J=4.88 Hz).

FAB-MSm/z: 415(M+H)$^+$.

Example 138

4-[1-(6-Methoxy-3-pyridazinyl)-5-(2-pyridyl)pyrazole-3-carbonyl] thiomorpholine

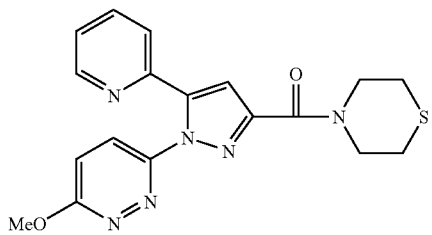

In a manner similar to that employed in step 1) of Example 1, the title compound was obtained as a solid (236 mg, 92%) through use of 1-(6-methoxy-3-pyridazinyl)-5-(2-pyridyl)pyrazole-3-carboxylic acid (200 mg) obtained in Referential Example 139 and thiomorpholine (0.081 mL).

$^1$H-NMR (400 MHz, CDCl$_3$) δ: 2.74 (4H, br), 4.07 (2H, m), 4.11 (3H, s), 4.27 (2H, br), 7.09 (1H, s), 7.14 (1H, d, J=9.16 Hz), 7.23 (1H, ddd, J=7.57, 4.88, 1.10 Hz), 7.58 (1H, d, J=7.81 Hz), 7.74 (1H, dd, J=7.57, 1.71 Hz), 7.78 (1H, d, J=9.16 Hz), 8.41 (1H, d, J=4.88 Hz).

FAB-MSm/z: 383(M+H)$^+$.

Example 139

1-[1-(6-Methoxy-3-pyridazinyl)-5-(2-pyridyl)pyrazole-3-carbonyl]-4,4-difluoropiperidine

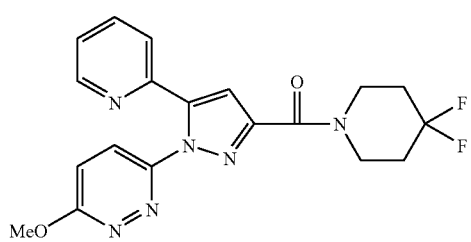

In a manner similar to that employed in step 1) of Example 1, the title compound was obtained as a solid (574 mg, 85%) through use of 1-(6-methoxy-3-pyridazinyl)-5-(2-pyridyl)pyrazole-3-carboxylic acid (500 mg) obtained in Referential Example 139 and 4,4-difluoropiperidine hydrochloride (398 mg) obtained in Referential Example 152.

$^1$H-NMR (400 MHz, CDCl$_3$) δ: 2.07 (4H, m), 3.92 (2H, m), 4.11 (3H, s), 4.17 (2H, m), 7.12-7.15 (2H, m), 7.20-7.23 (1H, m), 7.58 (1H, d, J=7.8 Hz), 7.72-7.77 (2H, m), 8.40 (1H, d, J=4.6 Hz).

EI-MSm/z: 400(M$^+$).

Example 140

1-[1-(6-Methoxy-3-pyridazinyl)-5-(2-pyridyl)pyrazole-3-carbonyl]-3,3-difluoropiperidine

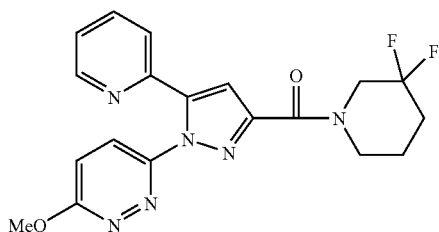

In a manner similar to that employed in step 1) of Example 1, the title compound was obtained as a solid (403 mg, 74%) through use of 1-(6-methoxy-3-pyridazinyl)-5-(2-pyridyl)pyrazole-3-carboxylic acid (400 mg) obtained in Referential Example 139 and 3,3-difluoropiperidine hydrochloride (233 mg) obtained in Referential Example 153.

$^1$H-NMR (400 MHz, CDCl$_3$) δ: 1.88 (2H, m), 2.12-2.09 (2H, m), 3.79 (1H, m), 4.06 (1H, m), 4.11 (3H, s), 4.30-4.36 (1H, m), 7.14-7.26 (3H, m), 7.60-7.61 (1H, m), 7.73-7.84 (2H, m), 8.41 (1H, d, J=3.9 Hz).

EI-MSm/z: 400(M$^+$).

Example 141

1-[1-(6-Methoxy-3-pyridazinyl)-5-(2-pyridyl)pyrazole-3-carbonyl]-4-fluoropiperidine

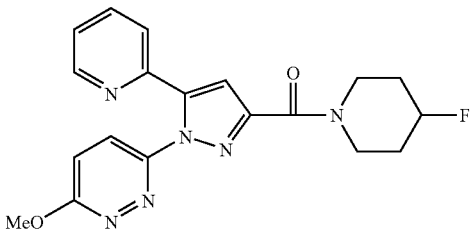

In a manner similar to that employed in step 1) of Example 1, the title compound was obtained as a solid (403 mg, 74%) through use of 1-(6-methoxy-3-pyridazinyl)-5-(2-pyridyl)pyrazole-3-carboxylic acid (400 mg) obtained in Referential Example 139 and 4-fluoropiperidine hydrochloride (207 mg) obtained in Referential Example 154.

$^1$H-NMR (400 MHz, CDCl$_3$) δ: 1.91-2.01 (4H, m), 3.69-3.72 (1H, m), 3.92-4.21 (3H, m), 4.11 (3H, s), 4.86-4.99 (1H, m), 7.10 (1H, s), 7.14 (1H, d, J=9.3 Hz), 7.20-7.24 (1H, m), 7.57-7.59 (1H, m), 7.73-7.80 (2H, m), 8.40-8.42 (1H, m).

FAB-MSm/z: 383(M+H)$^+$.

Elementary analysis: as C$_{19}$H$_{19}$FN$_6$O$_2$

Calculated: C, 59.68; H, 5.01; N, 21.98; F, 4.97.

Found: C, 59.65; H, 4.96; N, 22.04; F, 4.91.

Example 142

1-[1-(6-Methoxy-3-pyridazinyl)-5-(4-dimethylaminophenyl)pyrazole-3-carbonyl]-4-methylpiperazine

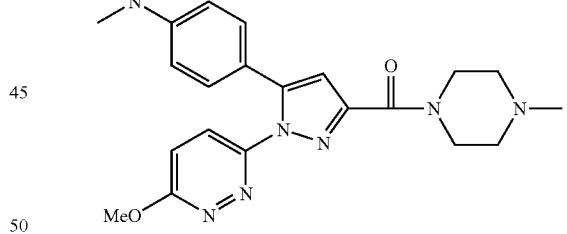

In a manner similar to that employed in Example 20, the title compound was obtained as an amorphous product (200 mg, 76%) through use of 1-(6-methoxy-3-pyridazinyl)-5-(4-dimethylaminophenyl)pyrazole-3-carboxylic acid (203 mg) obtained in Referential Example 140 and N-methylpiperazine (0.067 mL).

$^1$H-NMR (400 MHz, CDCl$_3$) δ: 2.33 (3H, s), 2.43-2.54 (4H, m), 2.96 (6H, s), 3.82-3.88 (2H, m), 4.06-4.12 (2H, m), 4.15 (3H, s), 6.64 (2H, d, J=8.8 Hz), 6.81 (1H, s), 7.02 (1H, d, J=9.3 Hz), 7.16 (2H, d, J=8.8 Hz), 7.47 (1H, d, J=9.3 Hz).

ESI-MSm/z: 422(M+H)$^+$.

Elementary analysis: as C$_{22}$H$_{27}$N$_7$O$_2$·0.75H$_2$O

Calculated: C, 60.74; H, 6.60; N, 22.54.

Found: C, 60.62; H, 6.68; N, 22.54.

Example 143

1-[5-(5-Chloro-2-pyridyl)-1-(6-methoxy-3-pyridazinyl)pyrazole-3-carbonyl]-4-methyl-3-oxopiperazine

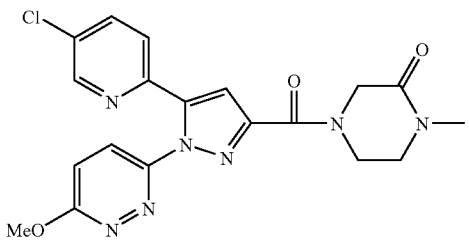

In a manner similar to that employed in Example 20, the title compound was obtained as a solid (45 mg, 7%) through use of 5-(5-chloro-2-pyridyl)-1-(6-methoxy-3-pyridazinyl)pyrazole-3-carboxylic acid (483 mg) obtained in Referential Example 141 and N-methylpiperazin-2-one hydrochloride (440 mg) obtained in Referential Example 157.

$^1$H-NMR (400 MHz, CDCl$_3$) δ: 3.01 (3H, s), 3.45 (3H, m), 4.04 (1H, br), 4.11 (3H, br), 4.36 (1H, br), 4.84 (1H, s), 7.15 (1H, d, J=9.03 Hz), 7.16 (1H, s), 7.53 (1H, d, J=8.30 Hz), 7.71 (1.5H, dd, J=8.30, 2.20 Hz), 7.85 (0.5H, d, J=9.03 Hz), 8.34 (1H, s).

FAB-MS m/z: 428(M+H)$^+$.

Example 144

1-[1-(5-Methoxy-2-pyrazinyl)-5-(2-pyridyl)pyrazole-3-carbonyl]-4-methylpiperazine

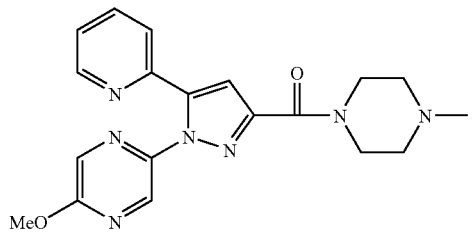

In a manner similar to that employed in step 1) of Example 1, the title compound was obtained as a solid (251 mg, 61%) through use of 1-(5-methoxy-2-pyrazinyl)-5-(2-pyridyl)pyrazole-3-carboxylic acid (320 mg) obtained in Referential Example 142 and N-methylpiperazine (0.179 mL).

$^1$H-NMR (400 MHz, CDCl$_3$) δ: 2.32 (3H, s), 2.44-2.52 (4H, m), 3.85 (2H, m), 4.01 (3H, s), 4.10 (2H, m), 7.12 (1H, s), 7.22-7.19 (1H, m), 7.52-7.54 (1H, m), 7.70-7.75 (1H, m), 7.91 (1H, d, J=1.0 Hz), 8.40-8.41 (2H, m).

EI-MS m/z: 379(M$^+$).

Example 145

1-[1-(5-Methoxy-2-pyrazinyl)-5-(2-pyridyl)pyrazole-3-carbonyl]-4-methyl-3-oxopiperazine

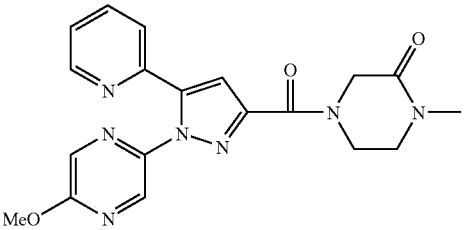

In a manner similar to that employed in step 1) of Example 1, the title compound was obtained as a solid (287 mg, 64%) through use of 1-(5-methoxy-2-pyrazinyl)-5-(2-pyridyl)pyrazole-3-carboxylic acid (329 mg) obtained in Referential Example 142 and 1-methylpiperazin-2-one hydrochloride (333 mg) obtained in Referential Example 157.

$^1$H-NMR (400 MHz, CDCl$_3$) δ: 3.02 (3H, s), 3.47 (2H, m), 4.01-4.03 (4H, m), 4.44 (2H, m), 4.87 (1H, m), 7.16-7.23 (2H, m), 7.52-7.54 (1H, m), 7.73 (1H, m), 7.92 (1H, d, J=8.8 Hz), 8.44-8.38 (2H, m).

FAB-MS m/z: 394(M+H)$^+$.

Elementary analysis: as $C_{19}H_{19}N_7O_3$
Calculated: C, 56.71; H, 5.01; N, 24.36.
Found: C, 56.77; H, 5.16; N, 24.40.

Example 146

1-[1-(6-Methyl-3-pyridyl)-5-(2-pyridyl)pyrazole-3-carbonyl]-4-methylpiperazine

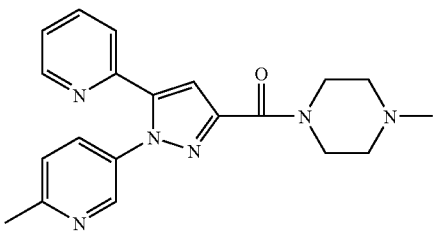

To a solution of 1-(6-Methyl-3-pyridyl)-5-(2-pyridyl)pyrazole-3-carboxylic acid ethyl ester (245 mg) obtained in Referential Example 143 in a mixture of tetrahydrofuran (2 mL), ethanol (0.5 mL), and water (1 mL), lithium hydroxide monohydrate (40.1 mg) was added at room temperature, followed by stirring for 1 hour. 1N Aqueous hydrochloric acid (0.191 mL) was added to the reaction mixture, and the reaction solvent was removed under reduced pressure, to thereby give 1-(6-methyl-3-pyridyl)-5-(2-pyridyl)pyrazole-3-carboxylic acid lithium salt. To a solution of the thus-obtained lithium salt in N,N-dimethylformamide (4.0 mL), 1-hydroxybenzotriazole (153 mg), 1-ethyl-3-(3-dimethylaminopropyl)carbodiimide hydrochloride (238 mg), and N-methylpiperazine (0.265 mL) were added at room temperature, followed by stirring for 3 days. The reaction mixture was partitioned between water and a chloroform-methanol solvent (15:1), and the organic layer was dried over sodium sulfate anhydrate. After filtration, the solvent was removed under reduced pressure, and the residue was purified through silica gel column chromatography (chloroform-methanol), to thereby give the title compound as an amorphous product (66.5 mg, 25%).

$^1$H-NMR (400 MHz, CDCl$_3$) δ: 2.33 (3H, s), 2.45-2.55 (4H, m), 2.59 (3H, s), 3.85 (2H, br), 4.09 (2H, br), 7.12 (1H, s), 7.19 (1H, d, J=8.3 Hz), 7.21-7.27 (1H, m), 7.44 (1H, d like, J=7.8 Hz), 7.62 (1H, dd, J=8.3, 2.7 Hz), 7.72 (1H, t like, J=7.8 Hz), 8.40 (1H, d, J=2.7 Hz), 8.47-8.53 (1H, m).

ESI-MSm/z: 362(M+H)$^+$.

Example 147

1-[1-(6-Methoxy-3-pyridyl)-5-(3-pyridazinyl)pyrazole-3-carbonyl]L-4-methylpiperazine hydrochloride

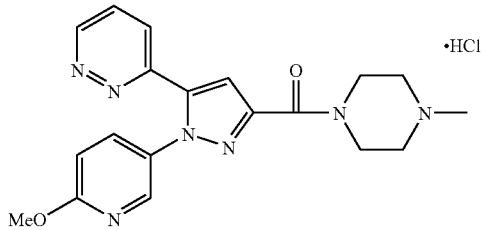

In a manner similar to that employed in step 1) of Example 1, 1-[1-(6-methoxy-3-pyridyl)-5-(3-pyridazinyl)pyrazole-3-carbonyl]-4-methylpiperazine was obtained through use of 1-(6-methoxy-3-pyridyl)-5-(3-pyridazinyl)pyrazole-3-carboxylic acid lithium salt (160 mg) obtained in Referential Example 144 and N-methylpiperazine (0.088 mL). In a manner similar to that employed in step 2) of Example 29, the title compound was obtained as a solid (123 mg, 50%) through use of the above-obtained product.

$^1$H-NMR (400 MHz, DMSO-d$_6$) δ: 2.81 (3H, s), 3.01-3.78 (6H, m), 3.90 (3H, s), 4.57-4.70 (1H, br m), 4.93-5.07 (1H, br m), 6.90 (1H, d, J=8.8 Hz), 7.45 (1H, s), 7.75-7.84 (2H, m), 7.98-8.03 (1H, m), 8.25 (1H, d, J=2.7 Hz), 9.17-9.21 (1H, m), 11.07-11.22 (1H, br).

ESI-MSm/z: 380(M+H)$^+$.

Example 148

1-[1-(6-Methoxy-3-pyridyl)-5-(2-pyrazinyl)pyrazole-3-carbonyl]-4-methylpiperazine

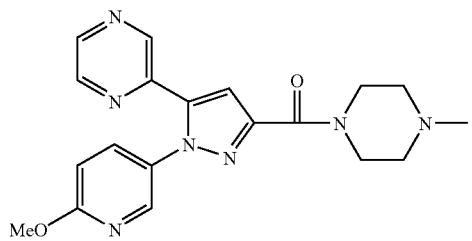

1) 4-(2-Pyrazinyl)-2,4-dioxobutyric acid ethyl ester

In a manner similar to that employed in Referential Example 71, 4-(2-pyrazinyl)-2,4-oxobutyric acid ethyl ester was obtained as a solid (1.83 g, 82%) through use of 1-(2-pyrazinyl)-1-ethanone (1.22 g) and diethyl oxalate (2.05 mL).

The thus-obtained product was subjected to the following reactions, without purification.

2) 1-(6-Methoxy-3-pyridyl)-5-(2-pyrazinyl)pyrazole-3-carboxylic acid ethyl ester In a manner similar to that employed in step 2) of Referential Example 138, 1-(6-methoxy-3-pyridyl)-5-(2-pyrazinyl)pyrazole-3-carboxylic acid ethyl ester was obtained as a solid (1.05 g, 45%) through use of the resultant product, 4-(2-pyrazinyl)-2,4-oxobutyric acid ethyl ester (1.58 g) and 5-hydrazino-2-methoxypyridine hydrochloride (1.50 g) obtained in Referential Example 1.

3) 1-(6-Methoxy-3-pyridyl)-5-(2-pyrazinyl)pyrazole-3-carboxylic acid

In a manner similar to that employed in step 7) of Referential Example 137, 1-(6-methoxy-3-pyridyl)-5-(2-pyrazinyl)pyrazole-3-carboxylic acid was obtained as a solid (0.883 g, 92%) through use of the resultant product, 1-(6-methoxy-3-pyridyl)-5-(2-pyrazinyl)pyrazole-3-carboxylic acid ethyl ester (1.05 g).

4) The Title Compound

In a manner similar to that employed in step 1) of Example 1, the title compound was obtained as a solid (145 mg, 48%) through use of the resultant product, 1-(6-methoxy-3-pyridyl)-5-(2-pyrazinyl)pyrazole-3-carboxylic acid (0.232 g) and N-methylpiperazine (0.156 mL).

$^1$H-NMR (400 MHz, CDCl$_3$) δ: 2.33 (3H, s), 2.45-2.53 (4H, m), 3.84-3.87 (2H, m), 3.97 (3H, s), 4.09-4.12 (2H, m), 6.79 (1H, d, J=8.8 Hz), 7.26 (1H, d, J=2.7 Hz), 7.60 (1H, dd, J=8.8, 2.7 Hz), 8.12 (1H, d, J=2.7 Hz), 8.47 (1H, dd, J=2.4, 1.7 Hz), 8.51 (1H, d, J=2.4 Hz), 8.73 (1H, d, J=1.5 Hz).

ESI-MSm/z: 380(M+H)$^+$.
Elementary analysis: as $C_{19}H_{21}N_7O_2$
Calculated: C, 60.15; H, 5.58; N, 25.83.
Found: C, 60.00; H, 5.52; N, 25.57.

Example 149

(2S)-1-[1-(6-Methoxy-3-pyridyl)-5-(2-pyridyl)pyrazole-3-carbonyl]-2-dimethylaminomethylpyrrolidine

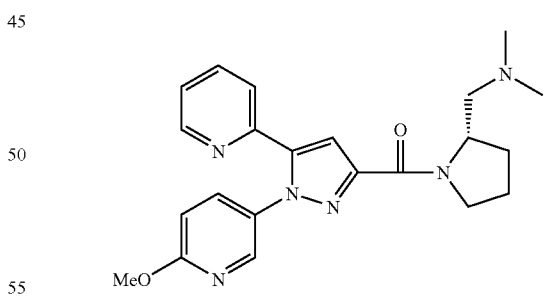

1) (2S)-2-Dimethylaminomethylpyrrolidine

While cooling at −78° C., a solution of sulfuryl chloride (0.409 mL) in methylene chloride (30 mL) was added dropwise to a solution of (2S)-2-pyrrolidinemethanol (0.498 mL) and triethylamine (1.39 mL) in methylene chloride (30 mL) over a period of 10 minutes. The temperature of the resultant mixture was gradually returned to room temperature, followed by stirring of the mixture for 20 hours. The reaction mixture was partitioned between 1N aqueous hydrochloric acid and methylene chloride, and the organic layer was washed with saturated brine, followed by drying over sodium sulfate anhydrate. After filtration, the solvent was removed under reduced pressure, and a solution of 2.0M dimethylamine in tetrahydrofuran (25 mL) was added to the residue, followed by stirring in a sealed tube at an external temperature of. 100° C. for 14 hours and 30 minutes, and then cooled in air. Trifluoroacetic acid (one droplet) was added thereto. The resultant mixture was further stirred in a sealed tube at an external temperature of 100° C. for 21 hours and then cooled in air. The solvent was removed at normal pressure, and 2N aqueous sodium hydroxide (50 mL) was added to the residue, followed by stirring at 100° C. for 15 hours. The resultant mixture was cooled in air. Diethyl ether was added thereto for partitioning the mixture, and the organic layer was dried over sodium sulfate anhydrate. After filtration, the solvent was removed at normal pressure, to thereby give (2S)-2-dimethylaminomethylpyrrolidine.

2) The Title Compound

In a manner similar to that employed in step 1) of Example 1, the title compound was obtained as a solid (116 mg, 5.1%) through use of the resultant product, (2S)-2-dimethylaminomethylpyrrolidine and 1-(6-methoxy-3-pyridyl)-5-(2-pyridyl)pyrazole-3-carboxylic acid (231 mg) obtained in Referential Example 33.

$^1$H-NMR (400 MHz, CDCl$_3$) δ: 2.03-2.11 (2H, m), 2.27-2.37 (1H, m), 2.48-2.55 (1H, m), 2.87-3.08 (7H, m), 3.48 (1H, d, J=12.3 Hz), 3.96-4.04 (4H, m), 4.11-4.17 (1H, m), 4.60-4.65 (1H, m), 6.76 (1H, d, J=8.8 Hz), 7.21 (1H, s), 7.24-7.27 (1H, m), 7.42 (1H, d, J=7.8 Hz), 7.58 (1H, dd, J=8.8, 2.7 Hz), 7.72 (1H, dd, J=7.7, 7.6, 1.7 Hz), 8.12 (1H, d, J=2.5 Hz), 8.52 (1H, d, J=4.2 Hz).

ESI-MSm/z: 407(M+H)$^+$.

Example 150

1-[1-(6-Methoxy-3-pyridyl)-5-(2-pyridyl)pyrazole-3-carbonyl]-3-dimethylaminopyrrolidine

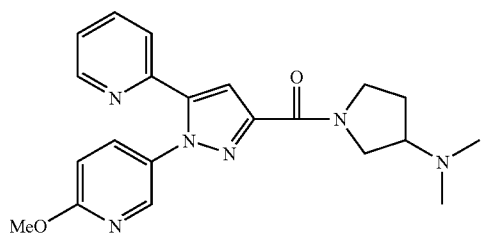

In a manner similar to that employed in step 1) of Example 1, the title compound was obtained as a solid (250 mg, 80%) through use of 1-(6-methoxy-3-pyridyl)-5-(2-pyridyl)pyrazole-3-carboxylic acid (231 mg) obtained in Referential Example 33 and 3-dimethylaminopyrrolidine (0.148 mL).

$^1$H-NMR (400 MHz, CDCl$_3$) δ: 1.77-1.95 (1H, m), 2.11-2.21 (1H, m), 2.29 (3H, s), 2.32 (3H, s), 2.69-2.84 (1H, m), 3.43 (½×1H, dd, J=11.7, 9.0 Hz), 3.59-3.72 (1H, m), 3.88-3.97 (1H, m), 3.96 (3H, s), 4.05 (½×1H, dd, J=12.0, 6.8 Hz), 4.27-4.39 (1H, m), 6.75 (1H, d, J=8.8 Hz), 7.21-7.25 (2H, m), 7.46 (1H, d, J=7.8 Hz), 7.56-7.60 (1H, m), 7.69-7.74 (1H, m), 8.12-8.14 (1H, m), 8.52-8.49 (1H, m).

ESI-MSm/z: 393(M+H)$^+$.

Example 151

1-[1-(6-Methoxy-3-pyridyl)-5-(2-pyridyl)pyrazole-3-carbonyl]-2-methyl-3-oxopyrazolidine

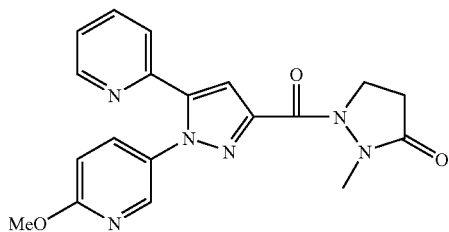

1) 1-[1-(6-Methoxy-3-pyridyl)-5-(2-pyridyl)pyrazole-3-carbonyl]-3-oxopyrazolidine In a manner similar to that employed in step 1) of Example 1, 1-[1-(6-methoxy-3-pyridyl)-5-(2-pyridyl)pyrazole-3-carbonyl]-3-oxopyrazolidine was obtained as a solid (141 mg, 48%) through use of 1-(6-methoxy-3-pyridyl)-5-(2-pyridyl)pyrazole-3-carboxylic acid (231 mg) obtained in Referential Example 33 and 3-oxopyrazolidine hydrochloride (115 mg).

$^1$H-NMR (400 MHz, DMSO-d$_6$) δ: 2.70 (2H, t, J=8.4 Hz), 3.89 (3H, s), 4.48 (2H, br s), 6.89 (1H, d, J=8.8 Hz), 7.33 (1H, s), 7.37 (1H, dd, J=7.6, 4.9 Hz), 7.71-7.75 (2H, m), 7.89 (1H, ddd, J=7.8, 7.8, 1.2 Hz), 8.19 (1H, d, J=2.7 Hz), 8.47 (1H, d, J=4.6 Hz), 11.35 (1H, br s).

ESI-MSm/z: 365(M+H)$^+$.

2) The Title Compound

60% Sodium hydride (142.4 mg) was added to the above-obtained 1-[1-(6-methoxy-3-pyridyl)-5-(2-pyridyl)pyrazole-3-carbonyl]-3-oxopyrazolidine (0.542 g) in N,N-dimethylformamide (5 mL) at room temperature, followed by stirring for 15 minutes. Subsequently, methyl iodide (0.828 mL) was added to the resultant mixture, followed by stirring for 10 days. Potassium carbonate (0.614 g) and methyl iodide (0.276 mL) were added to the reaction mixture. The resultant mixture was stirred at 60° C. for 2 hours, and then cooled in air. The reaction mixture was partitioned between saturated aqueous sodium hydrogencarbonate solution and ethyl acetate. The organic layer was dried over sodium sulfate anhydrate. The mixture was subjected to filtration, and the solvent was removed under reduced pressure. The residue was purified through silica gel column chromatography (ethyl acetate-hexane), to thereby give the title compound as a solid (89.8 mg, 15%).

$^1$H-NMR (400 MHz, CDCl$_3$) δ: 2.93 (2H, t, J=9.6 Hz), 3.94 (3H, s), 3.96 (3H, s), 4.28 (2H, t, J=9.5 Hz), 6.75 (1H, dd, J=8.8, 0.7 Hz), 7.21-7.24 (1H, m), 7.33 (1H, d, J=7.8 Hz), 7.42 (1H, s), 7.65-7.71 (2H, m), 8.11 (1H, d, J=2.7 Hz), 8.55 (1H, d, J=4.2 Hz).

ESI-MSm/z: 379(M+H)$^+$.

Example 152

1-[1-(6-Methoxy-3-pyridyl)-5-phenylpyrazole-3-carbonyl]-4-methylpiperazine-2-carboxamide

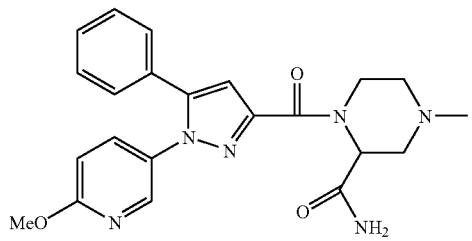

1) 4-tert-Butoxycarbonyl-1-[1-(6-methoxy-3-pyridyl)-5-phenylpyrazole-3-carbonyl]piperazine-2-carboxylic acid ethyl ester In a manner similar to that employed in Example 20, 4-tert-butoxycarbonyl-1-[1-(6-methoxy-3-pyridyl)-5-phenylpyrazole-3-carbonyl]piperazine-2-carboxylic acid ethyl ester (992 mg, 95%) was obtained as an amorphous product through use of 1-(6-methoxy-3-pyridyl)-5-phenylpyrazole-3-carboxylic acid (540 mg) obtained in Referential Example 41 and 4-tert-butoxycarbonylpiperazine-2-carboxylic acid ethyl ester (500 mg) obtained in Referential Example 147.

$^1$H-NMR (400 MHz, CDCl$_3$) δ: 1.23 (½×3H, t, J=7.1 Hz), 1.31 (½×3H, t, J=7.1 Hz), 1.47 (9H, s), 3.94 (½×3H, s), 3.95 (½×3H, s), 6.69-6.74 (1H, m), 6.72 (½×1H, s), 6.74 (½×1H, s), 7.22-7.50 (6H, m), 8.08 (½×1H, d, J=2.7 Hz), 8.13 (½×1H, d, J=2.7 Hz).

FAB-MS m/z: 536(M+H)$^+$.

2) 1-[1-(6-Methoxy-3-pyridyl)-5-phenylpyrazole-3-carbonyl]-4-methylpiperazine-2-carboxylic acid ethyl ester In a manner similar to that employed in step 2) of Example 16, 1-[1-(6-methoxy-3-pyridyl)-5-phenylpyrazole-3-carbonyl]piperazine-2-carboxylic acid ethyl ester was obtained through use of the above-obtained 4-tert-butoxycarbonyl-1-[1-(6-methoxy-3-pyridyl)-5-phenylpyrazole-3-carbonyl]piperazine-2-carboxylic acid ethyl ester (992 mg) and trifluoroacetic acid (2 mL). This compound was dissolved in methylene chloride (27 mL). 37% Aqueous solution of formalin (0.36 mL) and sodium triacetoxyborohydride (1.4 g) were added to the resultant mixture, followed by stirring at room temperature for 1 hour. Subsequently, saturated aqueous sodium hydrogencarbonate solution was added for partitioning the reaction mixture. The organic layer was dried over magnesium sulfate anhydrate. The mixture was subjected to filtration, and the solvent was removed under reduced pressure, and then dried, to thereby give 1-[1-(6-methoxy-3-pyridyl)-5-phenylpyrazole-3-carbonyl]-4-methylpiperazine-2-carboxylic acid ethyl ester as an amorphous product (702 mg, 84%).

$^1$H-NMR (400 MHz, CDCl$_3$) δ: 1.23 (½×3H, t, J=7.1 Hz), 1.30 (½×3H, t, J=7.1 Hz), 2.06-2.19 (1H, m), 2.301 (½×3H, s), 2.304 (½×3H, s), 2.76-2.90 (1H, m), 3.27-3.68 (2H, m), 3.94 (½×3H, s), 3.94 (½×3H, s) 4.20-4.33 (2H, m), 4.58 (½×1H, d, J=13.4 Hz), 4.95 (½×1H, d, J=13.4 Hz), 5.38-5.39 (½×1H, m), 5.85-5.86 (½×1H, m), 6.72 (1H, t, J=8.3 Hz), 6.96 (½×1H, s), 6.99 (½×1H, s), 7.22-7.51 (6H, m), 8.07 (½×1H, d, J=2.7 Hz), 8.14 (½×1H, d, J=2.7 Hz).

EI-MS m/z: 449(M$^+$).

3) The Title Compound

Lithium hydroxide monohydrate (66 mg) was added to the above-obtained 1-[1-(6-methoxy-3-pyridyl)-5-phenylpyrazole-3-carbonyl]-4-methylpiperazine-2-carboxylic acid ethyl ester (702 mg) in a mixture of tetrahydrofuran (33 mL) and water (7 mL), followed by stirring at room temperature for 41 hours. The reaction mixture was neutralized by use of concentrated hydrochloric acid. Subsequently, methylene chloride was added for partitioning the mixture. The organic layer was dried over magnesium sulfate anhydrate, followed by filtration. The solvent was removed under reduced pressure, to thereby give a carboxylic acid compound. Triethylamine (0.5 mL) was added to a mixture of the carboxylic acid compound that was obtained, 1-hydroxybenzotriazole (422 mg), 1-ethyl-3-(3-dimethylaminopropyl)carbodiimide hydrochloride (600 mg), and 28% aqueous solution of ammonia (1.0 mL) in methylene chloride (10 mL), followed by stirring at room temperature for 1 day. Water was added for partitioning the reaction mixture. The organic layer was dried over magnesium sulfate anhydrate. The mixture was subjected to filtration, and the solvent was removed under reduced pressure. The residue was purified through silica gel thin-layer chromatography (methylene chloride-methanol), to thereby give the title compound as an amorphous product (430 mg, 65%).

$^1$H-NMR (400 MHz, CDCl$_3$) δ: 2.10-2.20 (2H, m), 2.33 (3H, s), 2.75-2.93 (1H, m), 3.15-3.60 (2H, m), 3.94 (3H, s), 4.65-5.00 (1H, m), 6.70-6.75 (1H, m), 6.98-7.01 (1H, m), 7.22-7.27 (2H, m), 7.33-7.38 (3H, m), 7.33-7.47 (1H, m), 8.08 (½×1H, br s), 8.14 (½H×1H, br s).

FAB-MS m/z: 421(M+H)$^+$.

Example 153

(3S)-4-[1-(6-Methoxy-3-pyridyl)-5-(2-pyridyl)pyrazole-3-carbonyl]morpholine-3-carboxamide

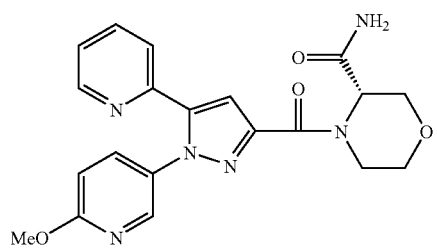

1) (3S)-4-[1-(6-Methoxy-3-pyridyl)-5-(2-pyridyl)pyrazole-3-carbonyl]morpholine-3-carboxylic acid methyl ester In a manner similar to that employed in Example 20, (3S)-4-[1-(6-methoxy-3-pyridyl)-5-(2-pyridyl)pyrazole-3-carbonyl]morpholine-3-carboxylic acid methyl ester was obtained as an amorphous product (387 mg, quantitative amount) through use of 1-(6-methoxy-3-pyridyl)-5 (2-pyridyl)pyrazole-3-carboxylic acid (250 mg) obtained in Referential Example 33 and morpholine-3-carboxylic acid methylester (190 mg) obtained in Referential Example 148.

¹H-NMR (400 MHz, CDCl₃) δ: 3.57-4.02 (5H, m), 3.76 (3H, s), 3.96 (3H, s), 4.45 (1H, d, J=12.09 Hz), 5.00 (0.5H, m), 5.25 (0.2H, s), 5.89 (0.3H, s), 6.74 (1H, d, J=8.79 Hz), 7.23 (1H, d, J=4.52 Hz), 7.27 (1H, d, J=3.78 Hz), 7.46 (1H, m), 7.59 (1H, dd, J=8.79, 2.69 Hz), 7.79 (1H, m), 8.13 (1H, dd, J=5.13, 2.69 Hz), 8.50 (1H, d, J=4.88 Hz).

EI-MSm/z: 424(M+H)⁺.

2) (3S)-4-[1-(6-Methoxy-3-pyridyl)-5-(2-pyridyl) pyrazole-3-carbonyl]morpholine-3-carboxylic acid 1N Aqueous solution of sodium hydroxide (3 mL) was added dropwise to the above-obtained (3S)-4-[1-(6-methoxy-3-pyridyl)-5-(2-pyridyl)pyrazole-3-carbonyl]morpholine-3-carboxylic acid methyl ester (387 mg) in tetrahydrofuran (5 mL) with ice cooling, followed by stirring at room temperature for 3 hours. The reaction mixture was partitioned between 1N aqueous solution of hydrochloric acid (3.5 mL) and chloroform. Subsequently, the organic layer was dried over sodium sulfate anhydrate. The mixture was subjected to filtration, and the solvent was removed under reduced pressure, to thereby give (3S)-4-[1-(6-methoxy-3-pyridyl)-5-(2-pyridyl)pyrazole-3-carbonyl]morpholine-3-carboxylic acid as an amorphous product (338 mg, 90%).

¹H-NMR (400 MHz, CDCl₃) δ: 3.57-3.80 (3H, m), 3.76 (3H, s), 4.45 (1H, d, J=12.09 Hz), 4.93 (0.5H, m), 5.25 (0.2H, s), 5.79 (0.3H, s), 6.76 (1H, m), 7.24-7.78 (5H, m), 8.13 (1H, m), 8.50 (1H, m).

EI-MSm/z: 410(M+H)⁺.

3) The Title Compound

In a manner similar to that employed in Example 20, the title compound was obtained as an amorphous product (58 mg, 17%) through use of the above-obtained (3S)-4-[1-(6-methoxy-3-pyridyl)-5-(2-pyridyl)pyrazole-3-carbonyl]morpholine-3-carboxylic acid (338 mg) and ammonium chloride (221 mg).

¹H-NMR (400 MHz, CDCl₃) δ: 3.23 (0.5H, m), 3.65 (2.5H, m), 3.91 (1H, m), 3.95 (3H, s), 4.61 (1.5H, m), 4.96 (1.5H, m), 5.17 (0.5H, br), 5.46 (1.5H, br), 6.27 (0.5H, br), 6.76 (1.5H, br), 7.26 (2H, m), 7.42 (1H, m), 7.55 (1H, m), 7.73 (1H, m), 8.09 (1H, m), 853 (1H, m). FAB-MSm/z: 409 (M+H)⁺.

Example 154

1-[1-(6-Methoxy-3-pyridyl)-5-(2-pyridyl)pyrazole-3-carbonyl]-3-methyl-4-oxoimidazolidine

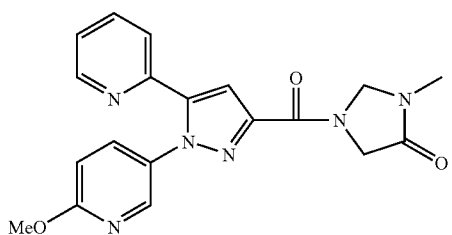

1) 1-[1-(6-Methoxy-3-pyridyl)-5-(2-pyridyl)pyrazole-3-carbonyl]-4-oxoimidazolidine In a manner similar to that employed in step 1) of Example 1, 1-[1-(6-methoxy-3-pyridyl)-5-(2-pyridyl)pyrazole-3-carbonyl]-4-oxoimidazolidine was obtained as a solid (200 mg, 70%) through use of 1-(6-methoxy-3-pyridyl)-5-(2-pyridyl) pyrazole-3-carbonyl (231 mg) obtained in Referential Example 33 and 4-imidazolinone (80.5 mg).

2) The Title Compound

In a manner similar to that employed in step 1) of Referential Example 152, the title compound was obtained as a solid (141 mg, 68%) through use of the above-obtained 1-[1-(6-methoxy-3-pyridyl)-5-(2-pyridyl)pyrazole-3-carbonyl]-4-oxoimidazolidine (200 mg) and methyl iodide (0.052 mL).

¹H-NMR (400 MHz, CDCl₃) δ: 2.98 (1H, s), 3.02 (2H, s), 3.97 (2H, s), 3.98 (1H, s), 4.29 (2/3H, s), 4.71 (4/3H, s), 5.09 (4/3H, s), 5.45 (2/3H, s), 6.76-6.80 (1H, m), 7.24-7.27 (1H, m), 7.32 (2/3H, s), 7.33 (1/3H, s), 7.43-7.48 (1H, m), 7.55 (1/3H, dd, J=8.9, 2.8 Hz), 7.62 (2/3H, dd, J=8.9, 2.8 Hz), 7.71-7.76 (1H, m), 8.08 (2/3H, d, J=2.7 Hz), 8.19 (1/3H, d, J=2.4 Hz), 8.50-8.54 (1H, m).

ESI-MSm/z: 379(M+H)⁺.

Example 155

(3R)-1-[1-(6-Methoxy-3-pyridyl)-5-(2-pyridyl)pyrazole-3-carbonyl]-3-methoxypyrrolidine

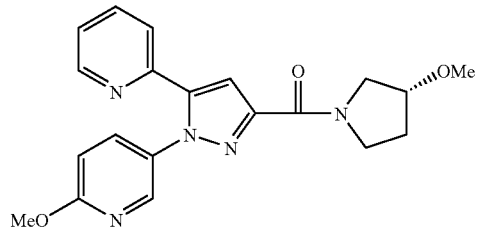

1) (3R)-3-Methoxypyrrolidine hydrochloride

4N Solution of HCl-dioxane (10 mL) was added to (3R)-3-methoxypyrrolidine-1-carboxylic acid tert-butyl ester (899 mg) obtained in Referential Example 155, followed by stirring at room temperature for 18.5 hours. The reaction mixture was treated under reduced pressure, to thereby give (3R)-3-methoxypyrrolidine hydrochloride (0.637 g, quantitative amount).

2) The Title Compound

In a manner similar to that employed in step 1) of Example 1, the title compound was obtained as an oily substance (267 mg, 88%) through use of the above-obtained (3R)-3-methoxypyrrolidine hydrochloride (0.20 g) and 1-(6-methoxy-3-pyridyl)-5-(2-pyridyl)pyrazole-3-carboxylic acid (0.231 g) obtained in Referential Example 33.

¹H-NMR (400 MHz, CDCl₃) δ: 1.95-2.18 (2H, m), 3.34 (3H, s), 3.37 (3H, s), 3.71-4.08 (4H, m), 3.96 (3H, s), 4.15-4.25 (1H, m), 6.75 (1H, d, J=8.8 Hz), 7.21-7.27 (2H, m), 7.44-7.48 (1H, m), 7.57-7.61 (1H, m), 7.69-7.74 (1H, m), 8.13-8.15 (1H, m), 8.50 (1H, d, J=3.7 Hz).

ESI-MSm/z: 380(M+H)⁺.

Elementary analysis: as $C_{20}H_{21}N_5O_3 \cdot 0.5H_2O$

Calculated: C, 61.84; H, 5.71; N, 18.03.

Found: C, 61.69; H, 5.60; N, 17.74.

Example 156

1-[1-(6-Methoxy-3-pyridyl)-5-(4-methyl-2-pyridyl)pyrazole-3-carbonyl]-4-methylpiperazine

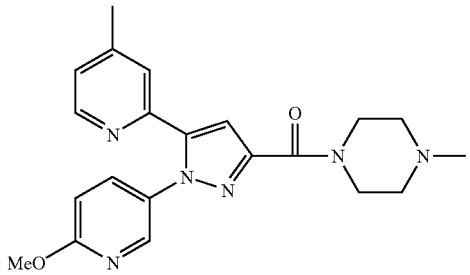

In a manner similar to that employed in step 1) of Example 1, the title compound was obtained as a solid (265 mg, 82%) through use of 1-(6-methoxy-3-pyridyl)-5-(4-methyl-2-pyridyl)pyrazole-3-carboxylic acid (250 mg) obtained in Referential Example 145 and N-methylpiperazine (0.0983 mL).

$^1$H-NMR (400 MHz, CDCl$_3$) δ: 2.33 (3H, s), 2.36 (3H, s), 2.46-2.51 (4H, m), 3.85 (2H, m), 3.95 (3H, s), 4.09 (2H, m), 6.73-6.75 (1H, m), 7.05-7.07 (1H, m), 7.08 (1H, s), 7.27-7.28 (1H, m), 7.57-7.60 (1H, m), 8.11 (1H, d, J=2.4 Hz), 8.36 (1H, d, J=4.8 Hz).

EI-MSm/z: 392(M$^+$).

Elementary analysis: as C$_{21}$H$_{24}$N$_6$O$_2$·0.5H$_2$O
Calculated: C, 62.83; H, 6.28; N, 20.93.
Found: C, 63.09; H, 6.18; N, 20.67.

Example 157

1-[1-(6-Methoxy-3-pyridyl)-5-(4-methyl-2-pyridyl)pyrazole-3-carbonyl]-4-methyl-3-oxopiperazine

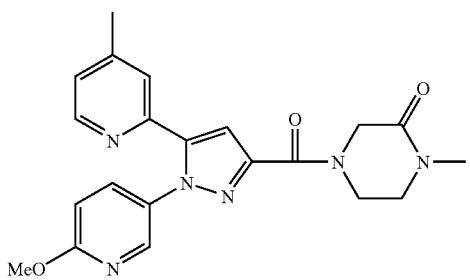

In a manner similar to that employed in step 1) of Example 1, the title compound was obtained as a solid (204 mg, 57%) through use of 1-(6-methoxy-3-pyridyl)-5-(4-methyl-2-pyridyl)pyrazole-3-carboxylic acid (250 mg) obtained in Referential Example 145 and N-methylpiperazin-2-one trifluoroacetic acid salt (313 mg) obtained in Referential Example 91.

$^1$H-NMR (400 MHz, CDCl$_3$) δ: 2.37 (3H, s), 3.03 (3H, s), 3.48 (2H, m), 3.96 (3H, s), 4.05 (1H, m), 4.44 (2H, m), 4.85 (1H, m), 6.76 (1H, d, J=8.0 Hz), 7.07 (1H, m), 7.16 (1H, m), 7.27-7.30 (1H, m), 7.56-7.62 (1H, m), 8.02-8.14 (1H, m), 8.35 (1H, d, J=4.8 Hz).

EI-MSm/z: 406(M$^+$).

Elementary analysis: as C$_{21}$H$_{22}$N$_6$O$_3$·0.5H$_2$O
Calculated: C, 60.71; H, 5.58; N, 20.23.
Found: C, 60.83; H, 5.55; N, 20.19.

Example 158

1-[1-(6-Methoxy-3-pyridyl)-5-(2-pyridyl)pyrazole-3-carbonyl]piperidine-2-carboxamide

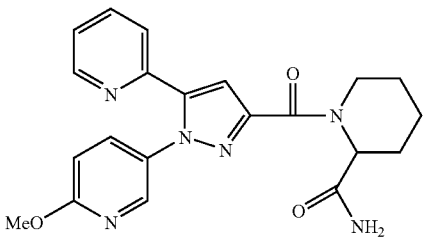

In a manner similar to that employed in step 1) of Example 1, the title compound was obtained as a solid (198 mg, 59%) through use of 1-(6-methoxy-3-pyridyl)-5-(2-pyridyl)pyrazole-3-carboxylic acid (231 mg) obtained in Referential Example 33 and piperidine-2-carboxamide (150 mg) obtained in Referential Example 131.

$^1$H-NMR (400 MHz, CDCl$_3$) δ: 1.49-1.88 (5H, m), 2.36 (1H, dd, J=30.0, 13.6 Hz), 2.80-2.87 (½×1H, m), 3.15-3.22 (½×1H, m), 3.96 (3H, s), 4.70-4.79 (1H, m), 5.33-5.44 (2H, m), 6.37 (½×1H, br s), 6.76 (1H, dd, J=8.6, 4.9 Hz), 7.12 (½×1H, br s), 7.15 (1H, d, J=15.7 Hz), 7.24-7.27 (1H, m), 7.42 (1H, dd, J=12.0, 7.8 Hz), 7.56 (1H, dd, J=25.6, 8.7 Hz), 7.70-7.75 (1H, m), 8.11 (1H, d, J=17.4 Hz), 8.54 (1H, s).

ESI-MSm/z: 407(M+H)$^+$.

Example 159

1-[1-(6-Methoxy-3-pyridyl)-5-(5-methyl-2-pyridyl)pyrazole-3-carbonyl]-4-methyl-3-oxopiperazine

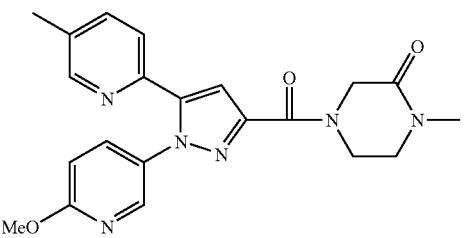

In a manner similar to that employed in step 1) of Example 1, the title compound was obtained as a solid (156 mg, 46%) through use of 1-(6-methoxy-3-pyridyl)-5-(5-methyl-2-pyridyl)pyrazole-3-carboxylic acid (250 mg) obtained in Referential Example 146 and N-methylpiperazin-2-one trifluoroacetic acid salt (313 mg) obtained in Referential Example 91.

$^1$H-NMR (400 MHz, CDCl$_3$) δ: 2.34 (3H, s), 3.02 (3H, s), 3.47 (2H, m), 3.96 (3H, s), 4.04 (1H, m), 4.43 (2H, m), 4.84 (1H, m), 6.76 (1H, d, J=8.8 Hz), 7.15 (1H, m), 7.27 (1H, m), 7.51-7.62 (2H, m), 8.08-8.13 (1H, m), 8.35 (1H, m).

EI-MSm/z: 406(M$^+$).

Example 160

4-[1-(6-Methoxy-3-pyridyl)-5-(2-pyridyl)pyrazole-3-carbonyl]-1,4-oxazepane

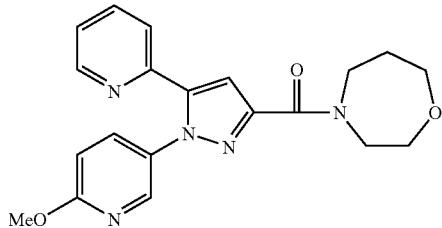

In a manner similar to that employed in Example 20, the title compound was obtained as a solid (215 mg, 66%) through use of 1-(6-methoxy-3-pyridyl)-5-(2-pyridyl)pyrazole-3-carboxylic acid (250 mg) obtained in Referential Example 33 and 1,4-oxazepane hydrochloride (173 mg) obtained in Referential Example 149.

$^1$H-NMR (400 MHz, DMSO-d$_6$) δ: 1.86 (2H, br), 3.70 (6H, m), 3.87 (3H, s), 3.96 (2H, m), 6.87 (1H, d, J=8.67 Hz), 7.19 (1H, s), 7.35 (1H, m), 7.68 (2H, m), 7.87 (1H, t, J=7.81 Hz), 8.15 (1H, s), 8.45 (1H, d, J=4.64 Hz).

FAB-MSm/z: 380(M+H)$^+$.

Elementary analysis: as C$_{20}$H$_{21}$N$_5$O$_3$.0.5H$_2$O

Calculated: C, 61.84; H, 5.71; N, 18.03.

Found: C, 62.12; H, 5.49; N, 17.89.

Example 161

1-[1-(6-Methoxy-3-pyridyl)-5-(4-methoxy-2-pyridyl)pyrazole-3-carbonyl]-4-methylhomopiperazine

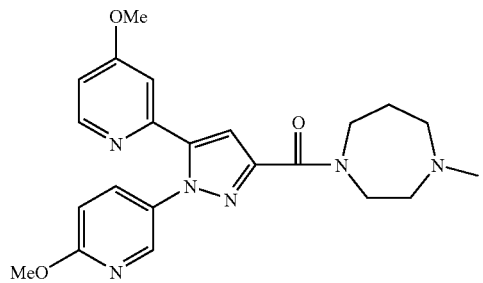

1) The Title Compound

In a manner similar to that employed in step 1) of Example 1, the title compound was obtained as a solid (136 mg, 42%) through use of 1-(6-methoxy-3-pyridyl)-5-(4-methoxy-2-pyridyl)pyrazole-3-carboxylic acid (250 mg) obtained in Referential Example 158 and N-methylhomopiperazine (0.105 mL).

$^1$H-NMR (400 MHz, CDCl$_3$) δ: 1.99-2.07 (2H, m), 2.39 (½×3H, s), 2.41 (½×3H, s), 2.61-2.67 (2H, m), 2.76-2.77 (2H, m), 3.80-4.10 (10H, m), 6.73-6.77 (2H, m), 6.96-6.99 (1H, m), 7.09 (½×1H, s), 7.11 (½×1H, s), 7.55-7.60 (1H, m), 8.13 (1H, d, J=2.8 Hz), 8.32-8.34 (1H, m).

EI-MSm/z: 422(M$^+$).

2) Hydrochloric Acid Salt of the Title Compound

In a manner similar to that employed in step 2) of Example 29, a hydrochloric acid salt of the title compound was obtained as a solid (140 mg, 82%) through use of the above-obtained title compound (132 mg).

$^1$H-NMR (400 MHz, DMSO-d$_6$) δ: 2.14-2.34 (2H, m), 2.78-2.80 (3H, m), 3.18-3.26 (1.5H, m), 3.35-3.95 (5H, m), 3.88 (3H, s), 4.06-4.19 (1H, m), 4.50-4.54 (0.5H, m), 6.87 (1H, dd, J=8.9, 3.5 Hz), 7.04-7.06 (1H, m), 7.28-7.33 (2H, m), 7.70-7.72 (1H, m), 8.20 (1H, dd, J=17.1, 2.7 Hz), 8.33-8.36 (1H, m).

EI-MSm/z: 422(M$^+$).

Example 162

1-[1-(6-Methoxy-3-pyridyl)-5-(2-pyridyl)pyrazole-3-carbonyl]hexahydropyridazine

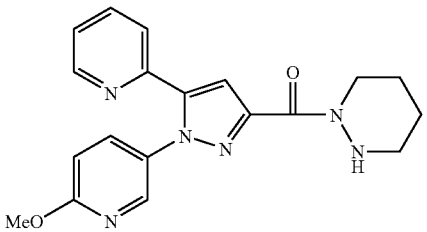

In a manner similar to that employed in step 1) of Example 1, the title compound was obtained as an amorphous product (1.61 g, 87%) through use of 1-(6-methoxy-3-pyridyl)-5-(2-pyridyl)pyrazole-3-carboxylic acid (1.495 g) obtained in Referential Example 33 and hexahydropyridazine (0.629 g) obtained in Referential Example 156.

$^1$H-NMR (400 MHz, CDCl$_3$) δ: 1.60-1.90 (4H, m), 2.95-3.10 (2H, m), 3.80-3.90 (⅓×1H, m), 3.95 (⅔×3H, s), 3.97 (⅓×3H, s), 4.20-4.27 (⅔×1H, m), 6.75 (1H, d, J=8.8 Hz), 7.17 (1H, s), 7.20-7.75 (5H, m), 8.12 (1H, br), 8.5 (1H, br).

FAB-MSm/z: 365(M+H)$^+$.

Example 163

1-[1-(6-Methoxy-3-pyridyl)-5-(2-pyridyl)pyrazole-3-carbonyl]-2-acetylhexahydropyridazine

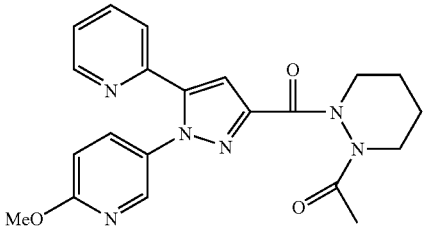

Triethylamine (0.210 mL), acetyl chloride (0.0807 mL) and 4-dimethylaminopyridine (13.5 mg) were added to 1-[1-(6-methoxy-3-pyridyl)-5-(2-pyridyl)pyrazole-3-carbonyl]hexahydropyridazine (0.275 g) obtained in Example 162 in methylene chloride (6.0 mL) at room temperature, followed by stirring for 20 minutes. The mixture was partitioned between water and chloroform. The organic layer was washed with saturated brine, and then dried over sodium sulfate anhydrate. The mixture was subjected to filtration, and the solvent was removed under reduced pressure. The residue was purified through silica gel column chromatography (chloroform-methanol), to thereby give the title compound as an amorphous product (0.149 g, 59%).

$^1$H-NMR (400 MHz, CDCl$_3$) δ: 1.65-1.90 (3H, m), 2.13 (3H, s), 2.52 (1H, br), 2.84-3.02 (2H, m), 3.93 (3H, s), 4.60-4.85 (⅞×2H, m), 5.20-5.40 (⅛×2H, m), 6.76 (1H, d, J=8.8 Hz), 7.15-7.80 (5H, m), 8.02 (1H, br), 8.53 (1H, br).

ESI-MSm/z: 407(M+H)$^+$.

Example 164

1-[1-(6-Methoxy-3-pyridyl)-5-(2-pyridyl)pyrazole-3-carbonyl]hexahydropyridazine-2-carboxamide

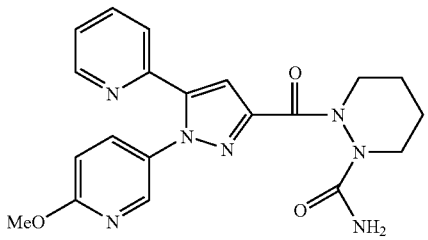

Trimethylsilyl isocyanide (0.920 mL) was added to 1-[1-(6-methoxy-3-pyridyl)-5-(2-pyridyl)pyrazole-3-carbonyl]hexahydropyridazine (0.397 g) obtained in Example 162 in 1,4-dioxane (3 mL) at room temperature, followed by stirring at an external temperature of 110° C. in a sealed tube for 4 days. Subsequently, the mixture was cooled in air. After methanol was added to the reaction mixture, the reaction solvent was removed under reduced pressure. The residue was partitioned between saturated aqueous solution of sodium hydrogencarbonate and a mixture solvent of chloroform-methanol (20:1). The organic layer was washed with saturated brine, and then dried over sodium sulfate anhydrate. The mixture was subjected to filtration, and the solvent was removed under reduced pressure. The residue was purified through silica gel column chromatography (chloroform-methanol), to thereby give the title compound as a solid (0.122 g, 25%).

$^1$H-NMR (400 MHz, CDCl$_3$) δ: 1.60-1.90 (4H, m), 2.84-3.13 (2H, m), 3.93 (3H, s), 4.42 (1H, d like, J=12.4 Hz), 4.62-4.73 (1H, br), 5.51 (2H, br), 6.73 (1H, d, J=8.7 Hz), 7.08 (1H, s), 7.20-7.26 (1H, m), 7.33 (1H, d like, J=7.8 Hz), 7.62 (1H, dd, J=8.8, 2.7 Hz), 7.65-7.72 (1H, m), 8.06 (1H, d, J=2.4 Hz), 8.48-8.54 (1H, m).

ESI-MSm/z: 408(M+H)$^+$.

Example 165

1-[1-(6-Methoxy-3-pyridazinyl)-5-(2-pyridyl)pyrazole-3-carbonyl]-4-formylpiperazine

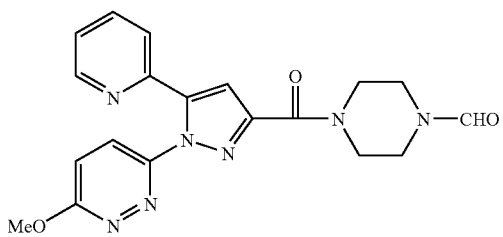

In a manner similar to that employed in Example 20, the title compound was obtained as a solid (0.249 g, 77%) through use of 1-(6-methoxy-3-pyridazinyl)-5-(2-pyridyl)pyrazole-3-carboxylic acid (0.246 g) obtained in Referential Example 139 and N-formylpiperazine (0.185 mL).

$^1$H-NMR (400 MHz, CDCl$_3$) δ: 3.42-3.55 (2H, m), 3.61-3.72 (2H, m), 3.80-3.90 (2H, m), 4.10-4.24 (2H, m), 4.12 (3H, s), 7.12-7.27 (3H, m), 7.59 (1H, d, J=8.1 Hz), 7.70-7.81 (2H, m), 8.13 (1H, br), 8.40 (1H, d, J=4.6 Hz).

ESI-MSm/z: 394(M+H)$^+$.

Example 166

1-[1-(6-Methoxy-3-pyridyl)-5-(2-pyridyl)pyrazole-3-carbonyl]-2-formylhexahydropyridazine

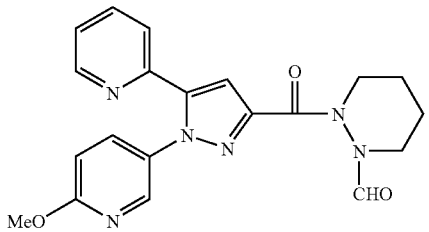

4-Dimethylaminopyridine (0.142 g) and trifluoromethane sulfonic acid anhydride (0.140 mL) were added to 1-[1-(6-methoxy-3-pyridyl)-5-(2-pyridyl)pyrazole-3-carbonyl]hexahydropyridazine (0.203 g) obtained in Example 162 in N,N-dimethylformamide (4.0 mL) at 0° C., followed by stirring for 20 minutes. The reaction mixture was partitioned between saturated aqueous solution of sodium hydrogencarbonate and ethyl acetate. The organic layer was washed with saturated brine, and then dried over sodium sulfate anhydrate. The mixture was subjected to filtration, and the solvent was removed under reduced pressure. The residue was purified through silica gel column chromatography (chloroform-methanol), to thereby give the title compound as a solid (65.5 mg, 30%).

$^1$H-NMR (400 MHz, CDCl$_3$) δ: 1.65-2.00 (4H, m), 2.86-3.10 (1H, m), 3.94 (3H, s), 4.41-4.51 (1H, br), 4.85 (1H, br), 6.76 (1H, d, J=8.8 Hz), 7.12-7.30 (2H, m), 7.47 (1H, d, J=8.8 Hz), 7.52-7.63 (1H, m), 7.67-7.76 (1H, m), 8.02 (1H, br), 8.34 (1H, br), 8.50-8.55 (1H, m).

FAB-MSm/z: 393(M+H)$^+$.

Example 167

1-[1-(6-Methoxy-3-pyridyl)-5-(pyrrol-2-yl)pyrazole-3-carbonyl]-4-methylpiperazine

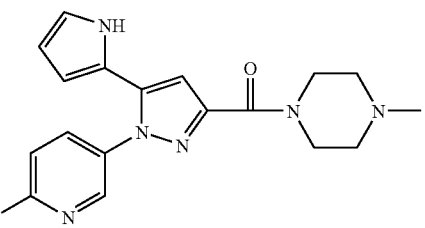

In a manner similar to that employed in step 1) of Example 1, the title compound was obtained as a solid (218 mg, 76%)

through use of 1-(6-methoxy-3-pyridyl)-5-(pyrrol-2-yl)pyrazole-3-carboxylic acid (222 mg) obtained in Referential Example 159 and N-methylpiperazine (0.156 mL).

$^1$H-NMR (400 MHz, CDCl$_3$) δ: 2.33 (3H, s), 2.44-2.52 (4H, m), 3.83-3.85 (2H, m), 3.99 (3H, s), 4.11-4.14 (2H, m), 5.91-5.93 (1H, m), 6.15-6.17 (1H, m), 6.80 (1H, d, J=8.8 Hz), 6.82-6.84 (1H, m), 6.93 (1H, s), 7.57 (1H, dd, J=8.8, 2.7 Hz), 8.26 (1H, d, J=2.7 Hz), 8.66 (1H, br s).

ESI-MSm/z: 367(M+H)$^+$.

Elementary analysis: as C$_{19}$H$_{22}$N$_6$O$_2$

Calculated: C, 62.28; H, 6.05; N, 22.94.

Found: C, 62.08; H, 6.08; N, 22.73.

Example 168

4-[1-(6-Methoxy-3-pyridyl)-5-(pyrrol-2-yl)pyrazole-3-carbonyl]morpholine

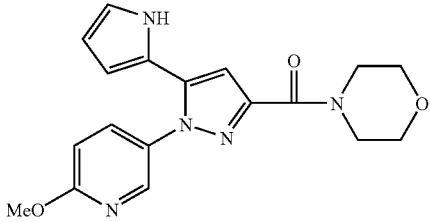

In a manner similar to that employed in step 1) of Example 1, the title compound was obtained as a solid (212 mg, 76%) through use of 1-(6-methoxy-3-pyridyl)-5-(pyrrol-2-yl)pyrazole-3-carboxylic acid (222 mg) obtained in Referential Example 159 and morpholine (0.123 mL).

$^1$H-NMR (400 MHz, CDCl$_3$) δ: 3.72-3.75 (2H, m), 3.79-3.83 (4H, m), 3.99 (3H, s), 4.16-4.19 (2H, m), 5.92-5.94 (1H, m), 6.16-6.18 (1H, m), 6.81 (1H, d, J=8.8 Hz), 6.82-6.84 (1H, m), 6.94 (1H, s), 7.56 (1H, dd, J=8.8, 2.7 Hz), 8.25 (1H, d, J=2.4 Hz), 8.50 (1H, br s).

ESI-MSm/z: 354(M+H)$^+$.

Example 169

4-[1-(6-Methoxy-3-pyridyl)-5-(2-pyrazinyl)pyrazole-3-carbonyl]morpholine

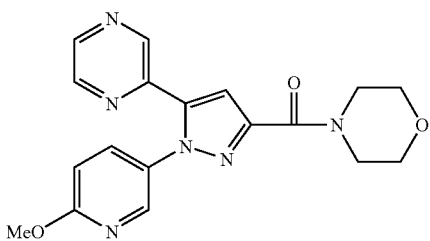

In a manner similar to that employed in step 1) of Example 1, the title compound was obtained as a solid (1.41 mg, 55%) through use of 1-(6-methoxy-3-pyridyl)-5-(2-pyrazinyl)pyrazole-3-carboxylic acid (195 mg) obtained in step 3) of Example 148 and morpholine (0.123 mL).

$^1$H-NMR (400 MHz, CDCl$_3$) δ: 3.73-3.76 (2H, m), 3.79-3.86 (4H, m), 3.97 (3H, s), 4.15-4.17 (2H, m), 6.79 (1H, d, J=8.8 Hz), 7.29 (1H, s), 7.59 (1H, dd, J=8.9, 2.8 Hz), 8.12 (1H, d, J=2.7 Hz), 8.47-8.48 (1H, m), 8.51 (1H, d, J=2.4 Hz), 8.73 (1H, d, J=1.5 Hz).

ESI-MSm/z: 367(M+H)$^+$.

Example 170

1-[1-(6-Methoxy-3-pyridyl)-5-(1-methylpyrrol-2-yl)pyrazole-3-carbonyl]-4-methylpiperazine

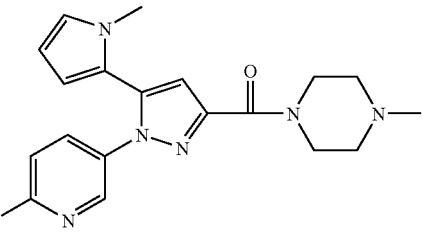

In a manner similar to that employed in step 1) of Example 1, the title compound was obtained as a viscous substance (258 mg, 81%) through use of 1-(6-methoxy-3-pyridyl)-5-(1-methylpyrrol-2-yl)pyrazole-3-carboxylic acid (232 mg) obtained in Referential Example 161 and N-methylpiperazine (0.156 mL).

$^1$H-NMR (400 MHz, CDCl$_3$) δ: 2.34 (3H, s), 2.47-2.53 (4H, m), 3.39 (3H, s), 3.84-3.86 (2H, m), 3.94 (3H, s), 4.13-4.16 (2H, m), 6.07 (1H, dd, J=3.7, 1.7 Hz), 6.14 (1H, dd, J=3.7, 2.9 Hz), 6.69-6.71 (2H, m), 6.88 (1H, s), 7.42 (1H, dd, J=8.8, 2.7 Hz), 8.13 (1H, d, J=2.7 Hz).

ESI-MSm/z: 381(M+H)$^+$.

Test Example 1

Platelet Aggregation-Inhibiting Action

Human blood was collected in the presence of 3.13% sodium citrate as an anticoagulant in a volume 1/10 the blood volume. The collected blood was centrifuged at 180 g for 10 minutes so as to separate the upper layer; i.e., platelet rich plasma (PRP) from the blood. The remaining lower layer was further centrifuged at 1600 g for 10 minutes, and platelet poor plasma (PPP); i.e., the thus-obtained upper layer, was collected. A solution (1 μL) of the inventive compound was added to PRP (200 μL), and the mixture was allowed to stand at 37° C. for 2 minutes. Subsequently, collagen (2 μL) was added to the resultant mixture so as to induce platelet aggregation. Percent platelet aggregation was measured by means of PAM-12C(SSR Engineering). Optical transmittance of PPP was employed as the value reflecting the state in which 100% coagulation occurred. Percent platelet aggregation values of PRP were determined at a series of concentrations of each Example compound. From the determined values, IC$_{50}$ with respect to each compound was calculated. Table 1 shows the results.

Test Example 2

Inhibitory effects on cyclooxygenase-1 (COX-1) and cyclooxygenase-2 (COX-2)

Inhibitory activity against COX-1 and COX-2 of the compounds produced in the Examples was measured using a COX Inhibitor Screening Assay Kit (product of Cayman Chemical Company, Catalog Nos. 560101 and 560121).

Before starting the measurement, reaction buffer, heme, arachidonic acid, $SnCl_2$, EIA buffer, washing buffer, prostaglandin (PG) screening EIA standard, PG screening acetylcholine esterase (AchE), tracer (chromogenic enzyme HRP conjugate), and PG screening EIA antiserum were prepared ready for use.

(1) Production of $PGF_2\alpha$ in the Presence of COX-1 or COX-2

A reaction mixture containing the compound of the Examples (50 μM) and COX-1 or COX-2 was incubated at 37° C. for 10 minutes. Arachidonic acid (10 μL) was added thereto, and the resultant mixture was further incubated at 37° C. for 2 minutes. 1N-Hydrochloric acid (50 μL) was added to the reaction mixture, to thereby stop the reaction. $SnCl_2$ solution (100 μL) was added thereto, and the resultant mixture was kept at room temperature for 5 minutes.

(2) Quantitative Determination of $PGF_2\alpha$ through ELISA

Antiserum (rabbit anti-$PGF_2\alpha$antibody, 50 μL) was added to the wells of 96 well plate that had been coated with mouse anti-rabbit IgG. A solution of $PGF_2\alpha$-containing mixture obtained above (2000-fold dilution, 50 μL) and AchE tracer (50 μL) were added to the well in this order, and the mixture was incubated at room temperature for 18 hours. The wells were washed 5 times with the washing buffer to remove an excessive AchE tracer, and Ellman reagent (200 μL) was added. After keeping the plate in a dark room for 60 minutes, absorbance at 405 nm was measured.

(3) Calculation of Inhibitory Activity of the Compound of the Examples

A calibration curve was obtained by use of the PG screening EIA standard, and the production amount of $PGF_2\alpha$ was determined from the absorbance. Percent inhibition of COX-1 or COX-2 activity at 50 μM of the compound of the Examples was calculated. Table 1 shows the results.

Notably, the amount of produced $PGF_2\alpha$ in a reaction mixture containing no compound was regarded as 100% in calculation of percent inhibition.

TABLE 1

| Compound | Inhibition of collagen-induced platelet aggregation, $IC_{50}$ (μM) | Inhibitory effect against COX-1 at 50 μM (% inhibition) | Inhibitory effect against COX-2 at 50 μM (% inhibition) |
| --- | --- | --- | --- |
| 23 | 0.17 | −1.2 | 3.4 |
| 27 | 0.27 | 0.5 | −0.1 |
| 36 | 0.14 | ND | ND |
| 55 | 0.035 | ND | ND |
| 62 | 0.12 | −2.4 | −2.6 |
| 70 | 0.26 | ND | ND |
| 122 | 0.75 | 1 | 4.5 |
| 132 | 0.4 | 2.7 | 10.5 |
| 139 | 0.042 | 7.6 | 3.4 |
| 140 | 0.11 | ND | ND |
| 144 | 0.44 | 9.7 | 8.8 |
| 148 | 0.09 | ND | ND |
| 160 | 0.17 | ND | ND |
| 163 | 0.09 | ND | ND |
| 167 | 0.029 | ND | ND |
| 168 | 0.017 | ND | ND |

ND: Not Determined

As is clear from Table 1, the compounds (I) and (II) of the present invention, a salt thereof or a solvate thereof, or a solvate of the salt exhibited strong platelet aggregation inhibitory activity, without inhibiting neither COX-1 nor COX-2.

The invention claimed is:

1. A compound represented by formula (I), or a salt of the compound:

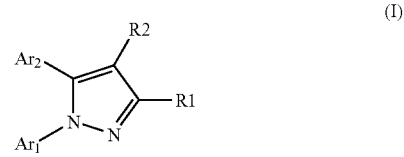

wherein $Ar_1$ represents
a pyridyl group having 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl)amino groups, or
a pyridazinyl group having 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl) amino groups,
$Ar_2$ represents
a pyridyl group which may have 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl)amino groups, or
a pyridazinyl group which may have 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl)amino groups,
wherein is one of $Ar_1$ and $Ar_2$ is pyridazine which may be substituted as defined herein and the other one of $Ar_1$ and $Ar_2$ is pyridine which may be substituted as defined herein,
R1 is a group represented by formula (1):

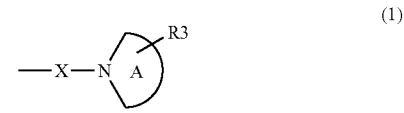

wherein ring structure A represents an azetidine ring, pyrrolidine ring, imidazolidine ring, pyrazolidine ring, piperidine ring, piperazine ring, morpholine ring, thiomorpholine ring, hexahydropyridazine ring, hexahydropyrimidine ring, homopiperazine ring, or oxazepane ring;
X represents a carbonyl group; R3 represents 1 to 4 groups on ring structure A, R3 being selected from the group consisting of a hydrogen atom, a halogeno group, a hydroxyl group, a $C_{1-6}$ alkoxy group, a $C_{1-6}$ alkoxycarbonyl group, a carboxyl group, a sulfo group, a $C_{1-6}$ alkylsulfonyl group, a $C_{1-6}$ alkyl group which may have 1 or 2 substituents, an amino group which may have 1 or 2 substituents, a carbamoyl group which may have 1 or 2 substituents, a $C_{1-6}$ acyl group, an aminosulfonyl group which may have 1 or 2 substituents, an oxo group, a hydroxyiminocarbonyl group, a $C_{1-6}$ alkoxyiminocarbonyl group, and a substituted or non-substituted 3- to 6-membered spiro alicyclic alkyl group; and R2 represents a hydrogen atom, a halogeno group, or a $C_{1-6}$ alkyl group which may have 1 or 2 substituents.

2. The compound as described in claim 1, or a salt of the compound, wherein $Ar_1$ is a pyridyl group having 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl)amino groups or a pyridazinyl group having 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl)amino groups.

3. The compound as described in claim 1, or a salt of the compound, wherein $Ar_2$ is a pyridyl group which may have 1 to 3 substituents wherein the substituents are selected from the group consisting of $C_{1-6}$ alkyl, halogeno, $C_{1-6}$ alkoxy, $C_{1-6}$ alkylamino, and di($C_{1-6}$ alkyl)amino groups.

4. The compound as described in claim 1, or a salt of the compound, wherein the moiety represented by the following formula:

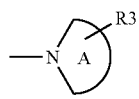

is a group selected from a 3-dimethylaminoazetidin-1-yl group, a 2,2-dimethyl-3-dimethylaminoazetidin-1-yl group, a 2-hydroxymethylazetidin-1-yl group, a 2-carbamoylazetidin-1-yl group, a 2-oxopyrrolidino group, a 2-hydroxymethylpyrrolidino group, a 2-carbamoylpyrrolidino group, a 2-hydroxymethylpiperidino group, a 2-carbamoylpiperidino group, a 2-methylcarbamoylpiperidino group, a 2-dimethylcarbamoylpiperidino group, a 3-oxo-4-methylpiperazino group, a 4-methylpiperazino group, a 4-ethylpiperazino group, a 4-isopropylpiperazino group, a 4-cyclopropylpiperazino group, a 2,4-dimethylpiperazino group, a 3,4-dimethylpiperazino group, a 3-cyclopropyl-4-methylpiperazino group, a 3,4,5-trimethylpiperazino group, a 2,2,4-trimethylpiperazino group, a 3,3,4-trimethylpiperazino group, a 2-cyclopropanespiro-4-methylpiperazino group, a morpholino group, a 3-carbamoylmorpholino group, a 1,1-dioxothiomorpholino group, a 2-methylhexahydropyridazin-1-yl group, a 3-methylhexahydropyridazin-1-yl group, a 3-oxo-4-methylhomopiperazino group, a 5-oxo-4-methylhomopiperazino group, a 4-methylhomopiperazino group, a 4-ethylhomopiperazino group, a 4-cyclopropylhomopiperazino group, a piperidino group, a 4-methoxypiperazino group, a thiomorpholino group, a 4,4-difluoropiperazino group, a 3,3-difluoropiperazino group, a 4-fluoropiperazino group, a 2-dimethylaminoethylpyrrolidino group, a 3-dimethylaminopyrrolidino group, a 3-methyl-4-oxoimidazolidin-1-yl group, a 3-methoxypyrrolidino group, a 2-acetylhexahydropyridazin-1-yl group, and a 2-carbamoylhexahydropyridazin-1-yl group.

5. A compound or a salt of the compound, the compound being selected from the group consisting of:

(7)

(8)

(9)

and

(10)

6. 1-[1-(6-Methoxy-3-pyridazinyl)-5-(2-pyridyl)pyrazole-3-carbonyl)-4-methylpiperazine, or a salt of the compound.

7. A pharmaceutical composition comprising a compound as described in claim 1, or a salt of the compound, and a pharmacologically acceptable carrier therefor.

8. A pharmaceutical composition comprising a compound as described in claim 2, or a salt of the compound, and a pharmacologically acceptable carrier therefor.

9. A pharmaceutical composition comprising a compound as described in claim 3, or a salt of the compound, and a pharmacologically acceptable carrier therefor.

10. A pharmaceutical composition comprising a compound as described in claim 4, or a salt of the compound, and a pharmacologically acceptable carrier therefor.

11. A pharmaceutical composition comprising a compound as described in claim 5, or a salt of the compound, and a pharmacologically acceptable carrier therefor.

12. A pharmaceutical composition comprising a compound as described in claim 6, or a salt of the compound, and a pharmacologically acceptable carrier therefor.

* * * * *